United States Patent
Rajagopalan et al.

(10) Patent No.: US 10,610,663 B2
(45) Date of Patent: *Apr. 7, 2020

(54) SYSTEMS, DEVICES AND METHODS FOR PERFORMING MEDICAL PROCEDURES IN THE INTESTINE

(71) Applicant: Fractyl Laboratories, Inc., Lexington, MA (US)

(72) Inventors: Harith Rajagopalan, Wellesley Hills, MA (US); Jay Caplan, Belmont, MA (US); Craig M. Gardner, Belmont, MA (US); J. Christopher Flaherty, Auburndale, FL (US)

(73) Assignee: Fractyl Laboratories, Inc., Lexington, MA (US)

( * ) Notice: Subject to any disclaimer, the term of this patent is extended or adjusted under 35 U.S.C. 154(b) by 173 days.

This patent is subject to a terminal disclaimer.

(21) Appl. No.: 15/683,713

(22) Filed: Aug. 22, 2017

(65) Prior Publication Data

US 2018/0193590 A1 Jul. 12, 2018

Related U.S. Application Data

(63) Continuation of application No. 15/274,764, filed on Sep. 23, 2016, now Pat. No. 9,757,535, which is a
(Continued)

(51) Int. Cl.
*A61B 18/14* (2006.01)
*A61M 25/00* (2006.01)
(Continued)

(52) U.S. Cl.
CPC ........... *A61M 25/00* (2013.01); *A61B 5/0084* (2013.01); *A61B 5/4255* (2013.01);
(Continued)

(58) Field of Classification Search
CPC ...... A61B 18/1492; A61B 2018/00494; A61B 2018/00529; A61B 2018/00535; A61B 2018/00642
(Continued)

(56) References Cited

U.S. PATENT DOCUMENTS

| | | |
|---|---|---|
| 5,084,044 A | 1/1992 | Quint |
| 5,190,540 A | 3/1993 | Lee |

(Continued)

FOREIGN PATENT DOCUMENTS

| | | |
|---|---|---|
| CA | 2666661 C | 1/2015 |
| CN | 1771888 A | 5/2006 |

(Continued)

OTHER PUBLICATIONS

European Search Report and Search Opinion dated Aug. 7, 2017 for European Patent Application No. EP14864511.2.
(Continued)

*Primary Examiner* — Thomas A Giuliani
(74) *Attorney, Agent, or Firm* — Wilson Sonsini Goodrich & Rosati

(57) ABSTRACT

A method for performing a medical procedure in an intestine of a patient is provided. The method comprises providing a system comprising: a catheter for insertion into the intestine, the catheter comprising: an elongate shaft comprising a distal portion; and a functional assembly positioned on the shaft distal portion and comprising at least one treatment element. The catheter is introduced into the patient, and target tissue is treated with the at least one treatment element. The target tissue comprises mucosal tissue of the small intestine, and the medical procedure can be configured to treat at least one of non-alcoholic fatty liver disease (NAFLD) or non-alcoholic steatohepatitis (NASH).

30 Claims, 47 Drawing Sheets

Related U.S. Application Data continuation-in-part of application No. PCT/US2016/040512, filed on Jun. 30, 2016, and a continuation-in-part of application No. PCT/US2015/040775, filed on Jul. 16, 2015.

(60) Provisional application No. 62/187,594, filed on Jul. 1, 2015, provisional application No. 62/025,307, filed on Jul. 16, 2014, provisional application No. 62/273,015, filed on Dec. 30, 2015.

(51) Int. Cl.

| | | |
|---|---|---|
| *A61B 18/02* | (2006.01) | |
| *A61F 5/00* | (2006.01) | |
| *A61B 5/00* | (2006.01) | |
| *A61B 17/00* | (2006.01) | |
| *A61B 18/08* | (2006.01) | |
| *A61B 18/18* | (2006.01) | |
| *A61M 25/04* | (2006.01) | |
| *A61N 7/00* | (2006.01) | |
| *A61B 18/00* | (2006.01) | |
| *A61B 18/06* | (2006.01) | |
| *A61B 18/04* | (2006.01) | |
| *A61N 7/02* | (2006.01) | |
| *A61B 17/02* | (2006.01) | |
| *A61B 90/00* | (2016.01) | |
| *A61B 5/055* | (2006.01) | |
| *A61B 17/34* | (2006.01) | |
| *A61B 17/30* | (2006.01) | |
| *A61B 18/24* | (2006.01) | |

(52) U.S. Cl.
CPC .......... *A61B 5/4836* (2013.01); *A61B 5/6852* (2013.01); *A61B 5/6885* (2013.01); *A61B 17/00234* (2013.01); *A61B 18/02* (2013.01); *A61B 18/082* (2013.01); *A61B 18/1492* (2013.01); *A61B 18/1815* (2013.01); *A61F 5/0069* (2013.01); *A61F 5/0079* (2013.01); *A61M 25/04* (2013.01); *A61N 7/00* (2013.01); *A61B 5/0066* (2013.01); *A61B 5/055* (2013.01); *A61B 17/00491* (2013.01); *A61B 17/0218* (2013.01); *A61B 17/3478* (2013.01); *A61B 18/06* (2013.01); *A61B 18/24* (2013.01); *A61B 2017/00004* (2013.01); *A61B 2017/00022* (2013.01); *A61B 2017/00199* (2013.01); *A61B 2017/00269* (2013.01); *A61B 2017/00818* (2013.01); *A61B 2017/306* (2013.01); *A61B 2018/00005* (2013.01); *A61B 2018/00011* (2013.01); *A61B 2018/00017* (2013.01); *A61B 2018/0022* (2013.01); *A61B 2018/00029* (2013.01); *A61B 2018/00041* (2013.01); *A61B 2018/00255* (2013.01); *A61B 2018/00285* (2013.01); *A61B 2018/00291* (2013.01); *A61B 2018/00494* (2013.01); *A61B 2018/00559* (2013.01); *A61B 2018/00577* (2013.01); *A61B 2018/00642* (2013.01); *A61B 2018/00672* (2013.01); *A61B 2018/00678* (2013.01); *A61B 2018/00744* (2013.01); *A61B 2018/00791* (2013.01); *A61B 2018/00809* (2013.01); *A61B 2018/00815* (2013.01); *A61B 2018/00821* (2013.01); *A61B 2018/00839* (2013.01); *A61B 2018/00863* (2013.01); *A61B 2018/00875* (2013.01); *A61B 2018/00982* (2013.01); *A61B 2018/0212* (2013.01); *A61B 2018/046* (2013.01); *A61B 2018/1861* (2013.01); *A61B 2090/395* (2016.02); *A61B 2090/3908* (2016.02); *A61B 2090/3933* (2016.02); *A61B 2218/002* (2013.01); *A61B 2505/05* (2013.01); *A61B 2560/0431* (2013.01); *A61B 2562/227* (2013.01); *A61M 25/0082* (2013.01); *A61M 2210/1053* (2013.01); *A61M 2210/1057* (2013.01); *A61M 2210/1071* (2013.01); *A61M 2210/1408* (2013.01); *A61N 7/022* (2013.01)

(58) Field of Classification Search
USPC .......................................................... 606/41
See application file for complete search history.

(56) References Cited

U.S. PATENT DOCUMENTS

| | | |
|---|---|---|
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,871,525 A | 2/1999 | Edwards et al. |
| 5,879,347 A | 3/1999 | Saadat |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | McGuckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 * | 6/2005 | Ellman .............. A61B 18/0218 606/41 |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |

(56) References Cited

U.S. PATENT DOCUMENTS

| | | |
|---|---|---|
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 * | 9/2017 | Rajagopalan ............ A61B 18/02 |
| 2002/0013581 A1 | 1/2002 | Edwards et al. |
| 2002/0115992 A1 | 8/2002 | Utley et al. |
| 2003/0093072 A1 | 5/2003 | Friedman |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0203489 A1 | 9/2005 | Saadat et al. |
| 2005/0222558 A1 | 10/2005 | Baxter et al. |
| 2005/0251116 A1 | 11/2005 | Steinke et al. |
| 2005/0273090 A1 | 12/2005 | Nieman et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van et al. |
| 2008/0207994 A1 | 8/2008 | Gonon |
| 2008/0243112 A1 | 10/2008 | De |
| 2008/0275445 A1 | 11/2008 | Kelly et al. |
| 2009/0012512 A1 * | 1/2009 | Utley ............... A61B 18/0218 606/21 |
| 2009/0012518 A1 | 1/2009 | Utley et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0319809 A1 | 12/2011 | Smith |
| 2012/0004654 A1 | 1/2012 | Jackson et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 * | 7/2013 | Azamian ........ A61B 17/00234 607/33 |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 * | 6/2014 | Goldsmith ....... A61B 17/00491 623/1.11 |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0081745 A1 | 3/2016 | Rajagopalan et al. |
| 2016/0256663 A1 | 9/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2018/0193078 A1 | 7/2018 | Rajagopalan et al. |
| 2018/0221622 A1 | 8/2018 | Rajagopalan et al. |

FOREIGN PATENT DOCUMENTS

| | | | |
|---|---|---|---|
| CN | 101212932 A | 7/2008 | |
| EP | 1698296 A1 | 9/2006 | |
| EP | 1886634 A1 | 2/2008 | |
| EP | 3071286 A1 | 9/2016 | |
| JP | 2002503512 A | 2/2002 | |
| JP | 2003520068 A | 7/2003 | |
| JP | 2004500184 A | 1/2004 | |
| JP | 2006509536 A | 3/2006 | |
| JP | 2006136726 A | 6/2006 | |
| JP | 2007502690 A | 2/2007 | |
| JP | 2008515464 A | 5/2008 | |
| JP | 2010142661 A | 7/2010 | |
| JP | 2010533036 A | 10/2010 | |
| JP | 2011517599 A | 6/2011 | |
| JP | 2013543423 A | 12/2013 | |
| JP | 2014503256 A | 2/2014 | |
| KR | 20080013945 A | 2/2008 | |
| WO | WO-9912489 A2 | 3/1999 | |
| WO | WO-0207628 A2 | 1/2002 | |
| WO | WO-02058577 A1 | 8/2002 | |
| WO | WO-02102453 A2 | 12/2002 | |
| WO | WO-03033045 A2 | 4/2003 | |
| WO | WO-03092609 A2 | 11/2003 | |
| WO | WO-2006020370 A2 | 2/2006 | |
| WO | WO-2007044244 A2 | 4/2007 | |
| WO | WO-2008002654 A2 | 1/2008 | |
| WO | WO-2010042461 A1 | 4/2010 | |
| WO | WO-2010125570 A1 | 11/2010 | |
| WO | WO-2011060301 A1 | 5/2011 | |
| WO | WO-2012009486 A2 | 1/2012 | |
| WO | WO 2012/099974 A2 * | 7/2012 | ............ A61B 17/32 |
| WO | WO-2012099974 A2 | 7/2012 | |
| WO | WO-2013130655 A1 | 9/2013 | |
| WO | WO-2013134541 A2 | 9/2013 | |
| WO | WO-2013159066 A1 | 10/2013 | |
| WO | WO-2014022436 A1 | 2/2014 | |
| WO | WO-2014026055 A1 | 2/2014 | |
| WO | WO-2014055997 A1 | 4/2014 | |

(56) References Cited

FOREIGN PATENT DOCUMENTS

| WO | WO-2014070136 A1 | 5/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |
| WO | WO-2019018362 A1 | 1/2019 |

OTHER PUBLICATIONS

European Search Report and Search Opinion dated Aug. 7, 2017 for European Patent Application No. EP15768945.6.
European search report with written opinion dated Feb. 1, 2018 for EP Application No. 15822378.
European search report with written opinion dated Dec. 2, 2016 for EP Application No. 14807116.
International search report with written opinion dated Jan. 9, 2018 for PCT/US2017/061074.
"Office Action dated Jul. 11, 2018 for U.S. Appl. No. 14/917,243."
"Office Action dated Aug. 9, 2018 for U.S. Appl. No. 14/673,565."
Office action dated Jan. 8, 2018 for U.S. Appl. No. 14/609,334.
Office action dated Mar. 19, 2018 for U.S. Appl. No. 14/470,503.
Office action dated Apr. 4, 2018 for U.S. Appl. No. 15/156,585.
Office action dated May 18, 2018 for U.S. Appl. No. 14/956,710.
"Office action dated Sep. 7, 2018 for U.S. Appl. No. 14/609,332."
Office action dated Nov. 16, 2017 for U.S. Appl. No. 14/609,332.
Office action dated Nov. 30, 2017 for U.S. Appl. No. 14/673,565.
Office action dated Dec. 18, 2017 for U.S. Appl. No. 14/515,324.
Office action dated Dec. 19, 2017 for U.S. Appl. No. 13/945,138.
"Office action dated Oct. 4, 2018 for U.S. Appl. No. 14/515,324."
"Office action dated Nov. 2, 2018 for U.S. Appl. No. 14/609,334".
Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European search report and search opinion dated Nov. 25, 2015 for EP Application No. 13777572.2.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
Miyawaki, et al. Inhibition of gastric inhibitory polypeptide signaling prevents obesity. Nat Med. Jul. 2002;8(7):738-42. Epub Jun. 17, 2002.
Office action dated Feb. 29, 2016 for U.S. Appl. No. 14/609,334.
Office Action dated Mar. 7, 2017 for U.S. Appl. No. 15/274,809.
Office action dated Mar. 12, 2015 for U.S. Appl. No. 13/945,138.
Office Action dated Mar. 23, 2017 for U.S. Appl. No. 13/945,138.
Office action dated Mar. 28, 2016 for U.S. Appl. No. 14/673,565.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office Action dated Sep. 23, 2016 for U.S. Appl. No. 14/515,324.
Office Action dated Oct. 7, 2016 for U.S. Appl. No. 13/945,138.
Office action dated Nov. 30, 2015 for U.S. Appl. No. 13/945,138.
Office action dated Dec. 17, 2015 for U.S. Appl. No. 14/515,324.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Tomizawa, et al. Clinical Outcome of Endoscopic Mucosal Resection (EMR) of Sporadic, Non-Ampullary Duodenal Adenoma (SNADA) : Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
"Office action dated Dec. 18, 2018 for U.S. Appl. No. 14/470,503."
Co-pending U.S. Appl. No. 15/406,572, filed Jan. 13, 2017.
International Search Report and Written Opinion dated Sep. 22, 2016 for International PCT Patent Application No. PCT/US2016/040512.
Notice of Allowance dated Jul. 7, 2017 for U.S. Appl. No. 15/274,764.
Notice of Allowance dated Sep. 14, 2017 for U.S. Appl. No. 15/274,809.
Office Action dated Jan. 13, 2017 for U.S. Appl. No. 14/609,332.
Office Action dated Mar. 7, 2017 for U.S. Appl. No. 15/274,764.
Office Action dated May 31, 2017 for U.S. Appl. No. 15/274,764.
Office Action dated Nov. 2, 2017 for U.S. Appl. No. 15/156,585.
Office Action dated Nov. 15, 2016 for U.S. Appl. No. 14/609,334.
"Office action dated Mar. 7, 2019 for U.S. Appl. No. 13/945,138."
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Office action dated Mar. 7, 2019 for U.S. Appl. No. 14/673,565.
Office action dated May 16, 2019 for U.S. Appl. No. 14/515,324.
Tolman, et al. Spectrum of liver disease in type 2 diabetes and management of patients with diabetes and liver disease. Diabetes care 30.3 (2007): 734-743.
U.S. Appl. No. 15/274,948 Office Action dated Nov. 20, 2018.
U.S. Appl. No. 15/406,572 Office Action dated Feb. 7, 2019.

(56) References Cited

OTHER PUBLICATIONS

U.S. Appl. No. 13/945,138 Office Action dated Dec. 10, 2019.
U.S. Appl. No. 16/267,771 Office Action dated Feb. 6, 2020.

* cited by examiner

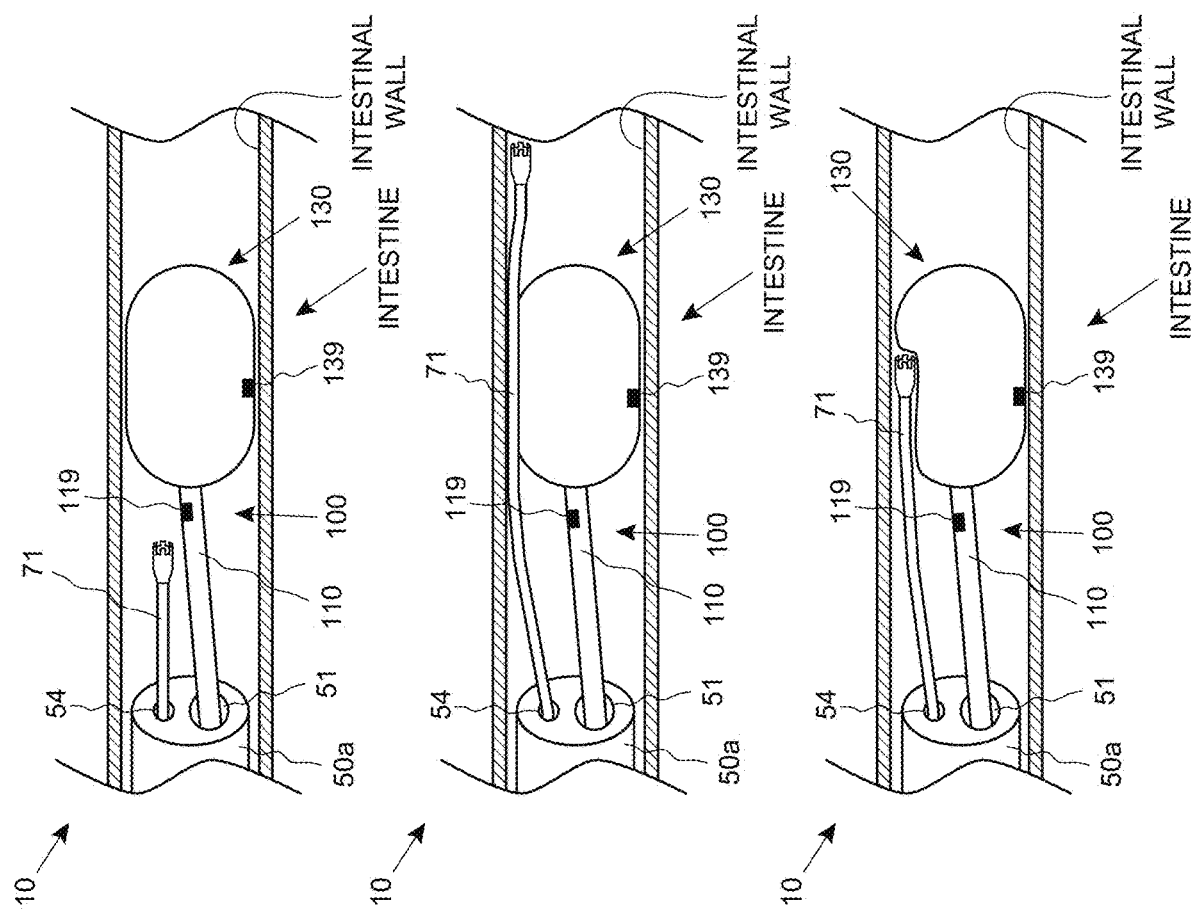

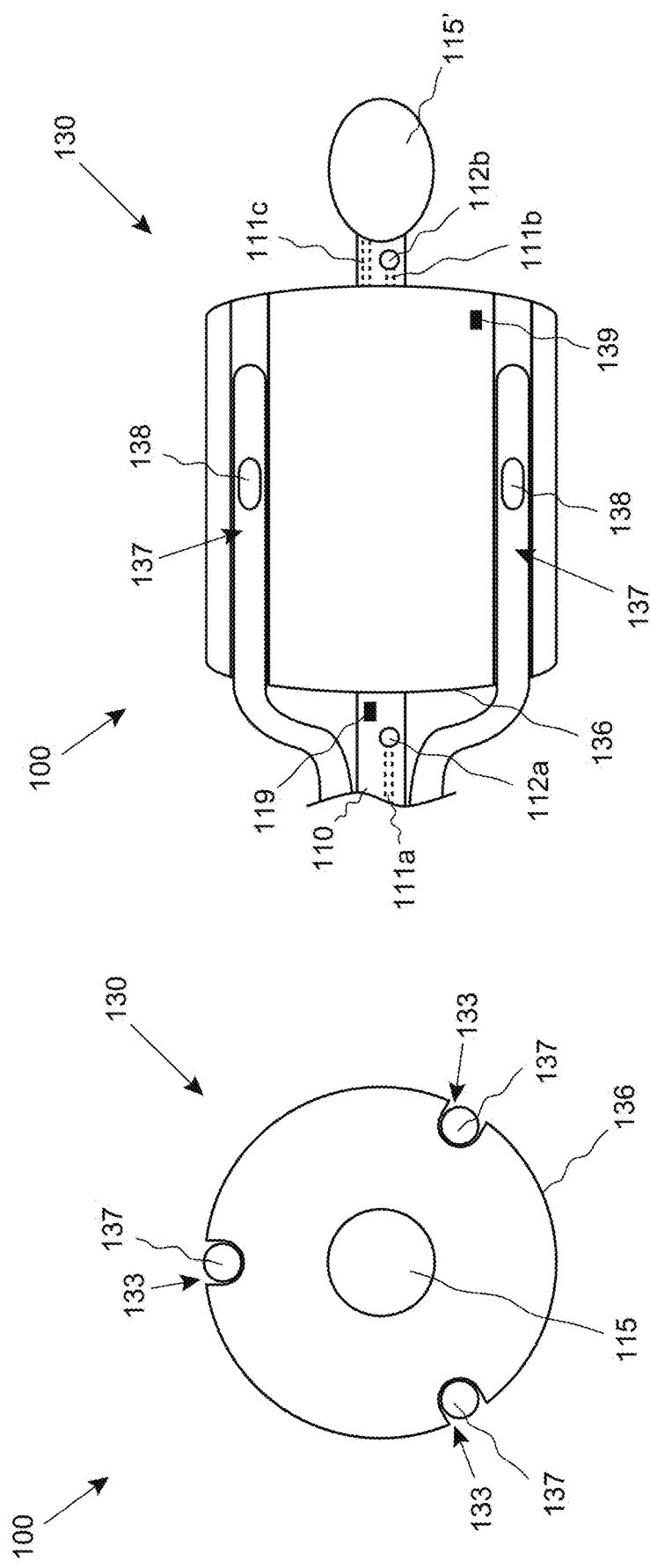

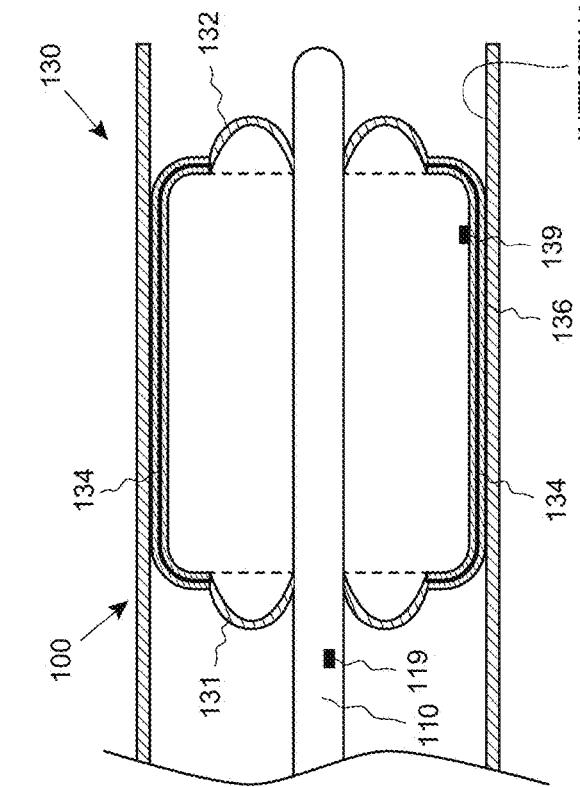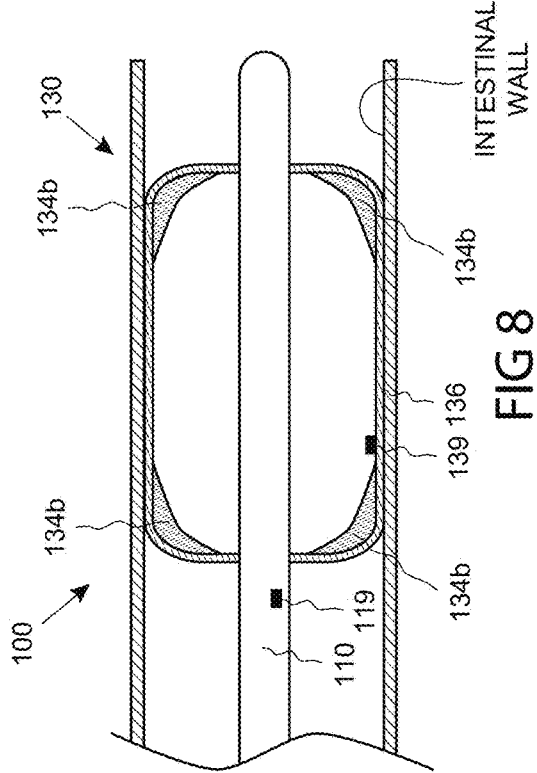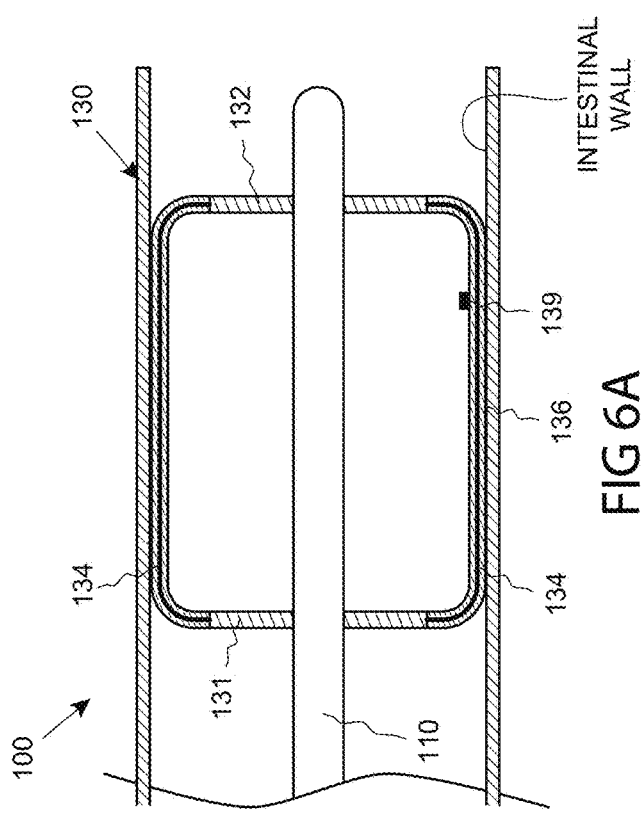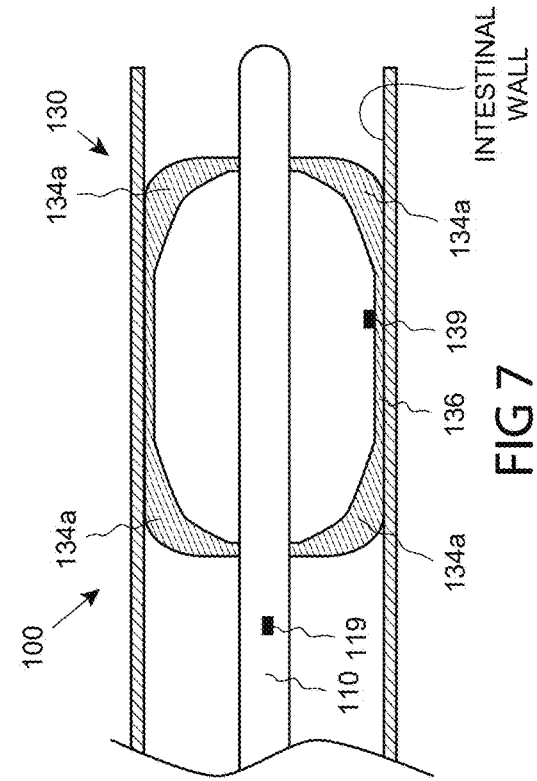

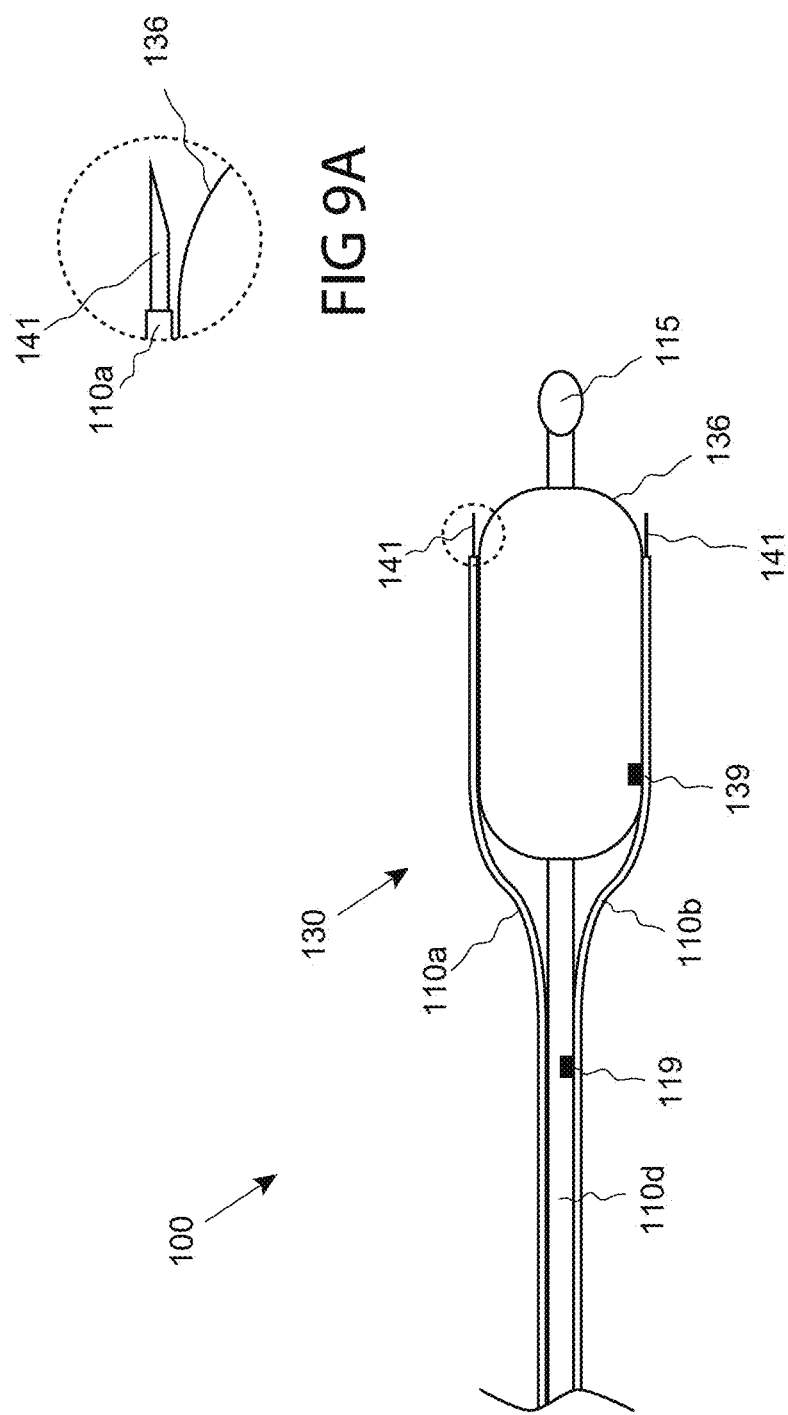

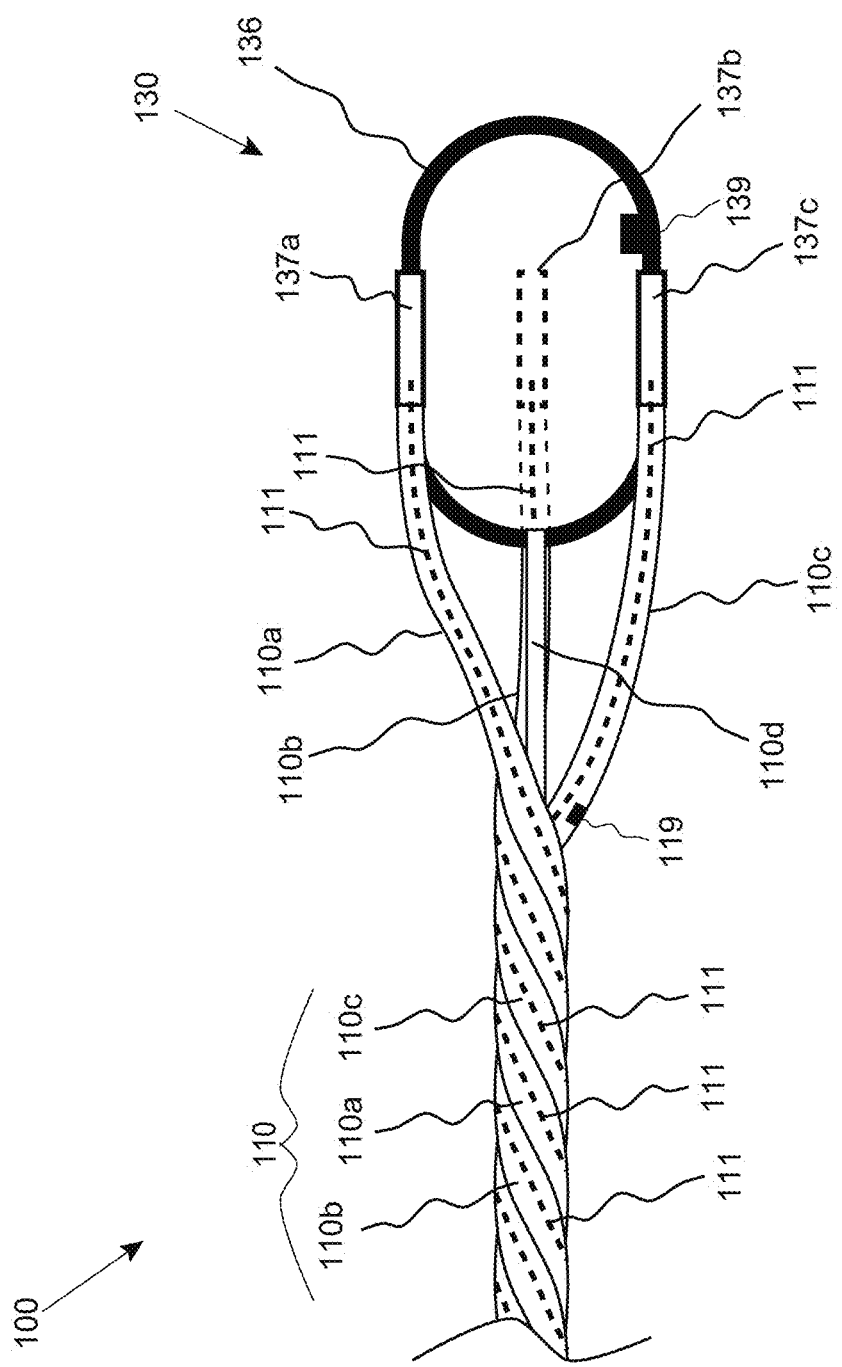

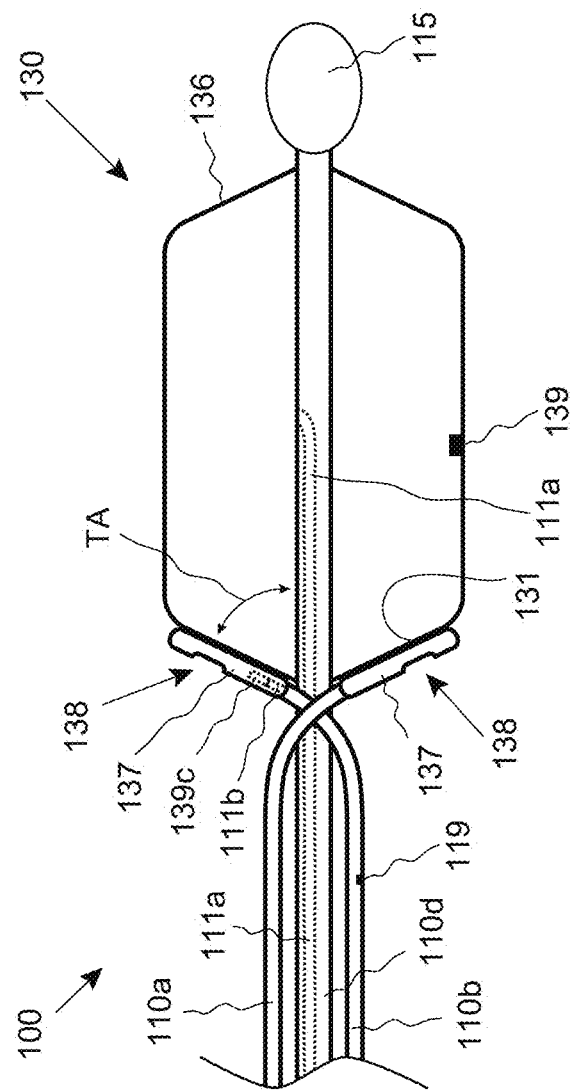

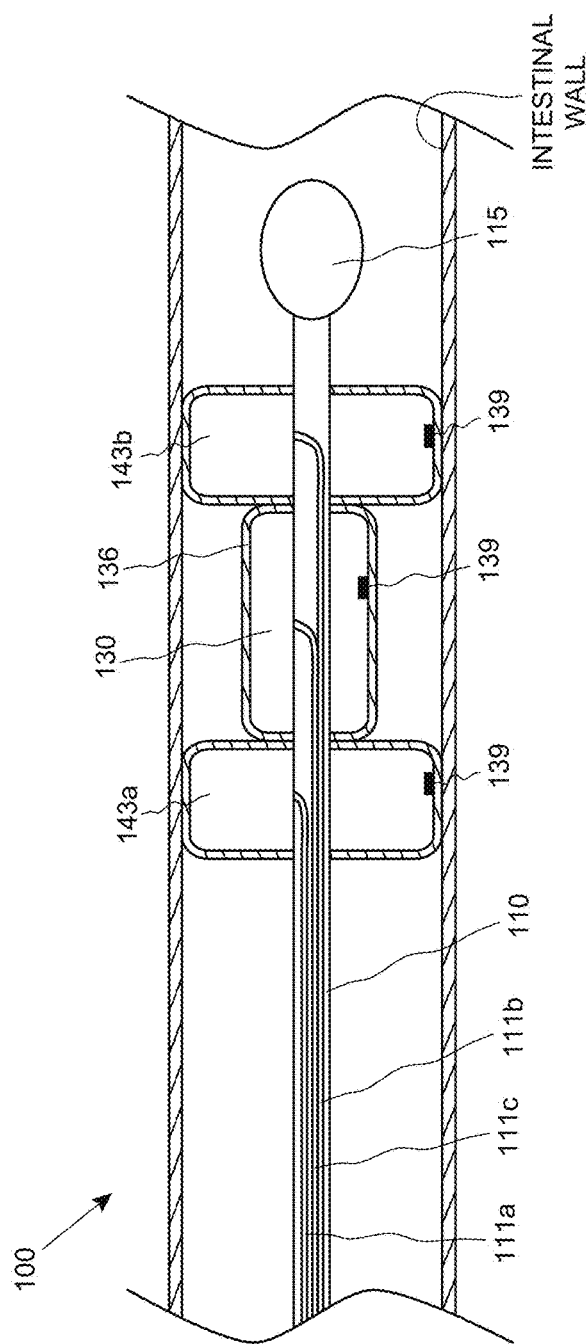
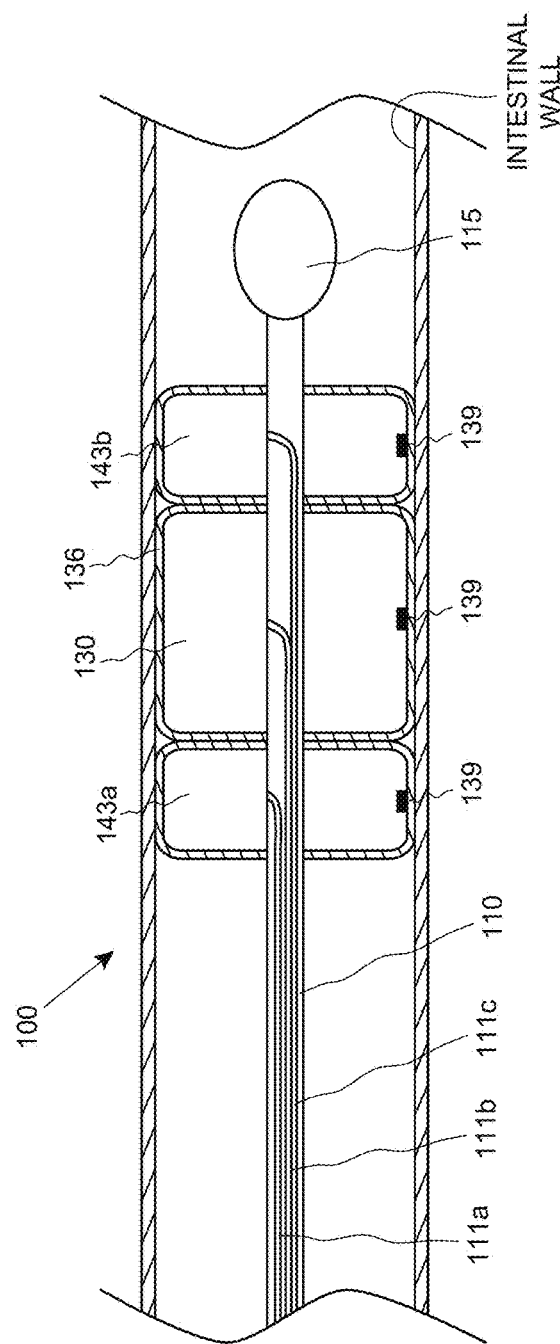

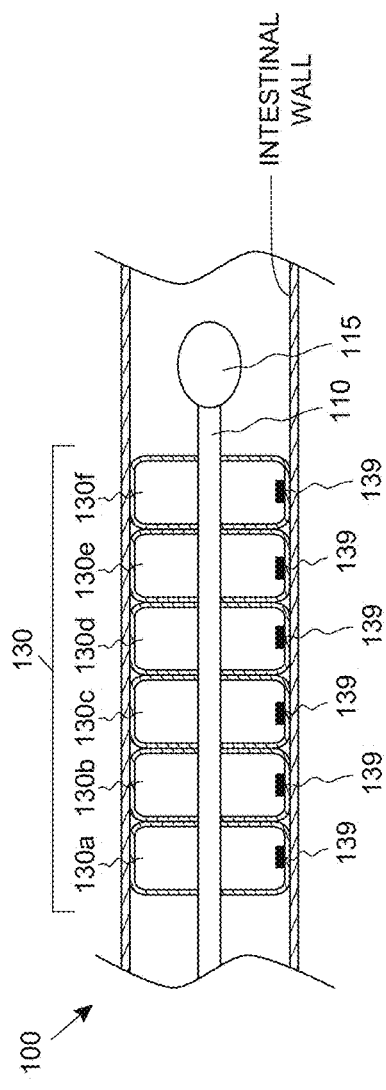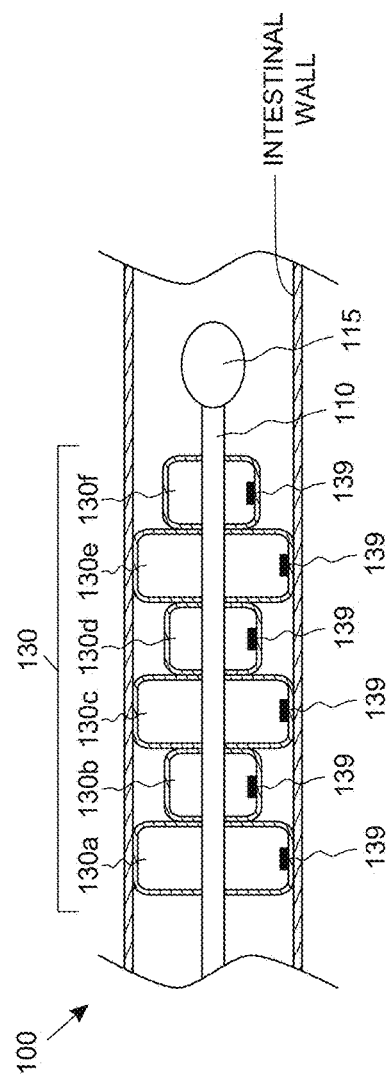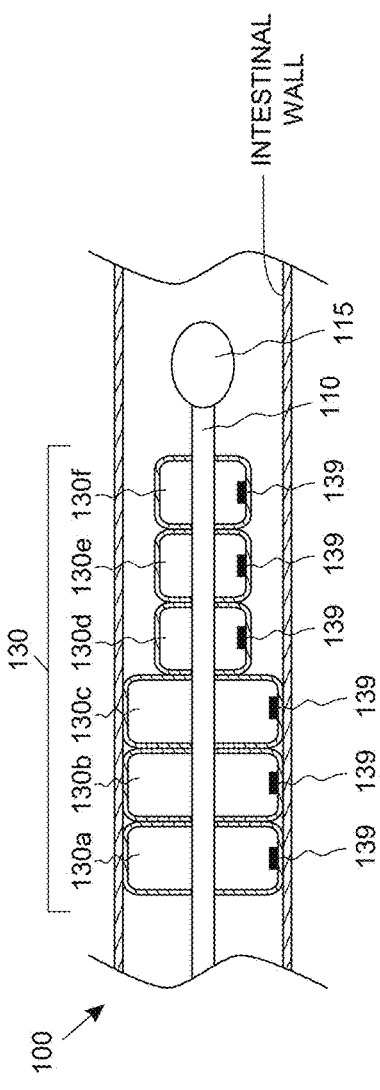

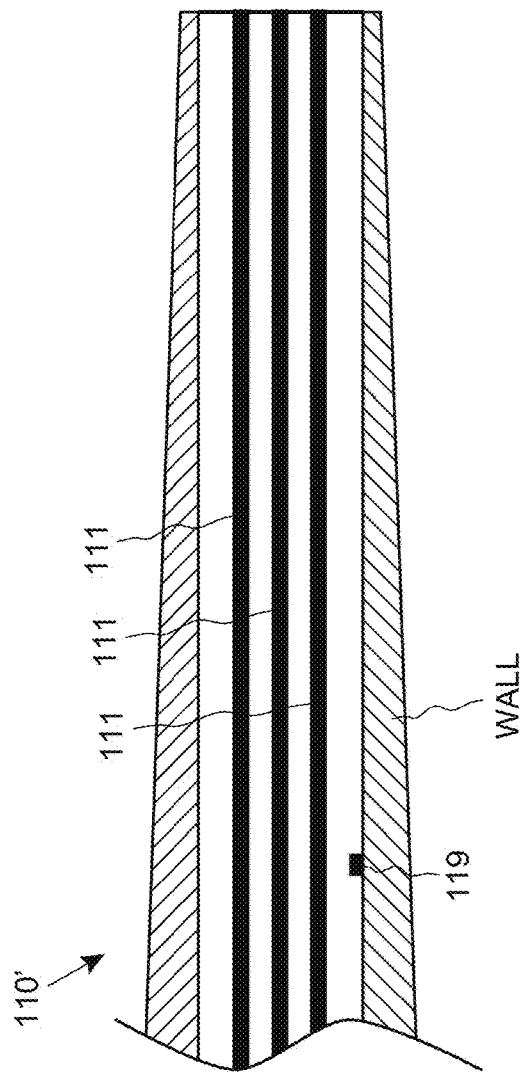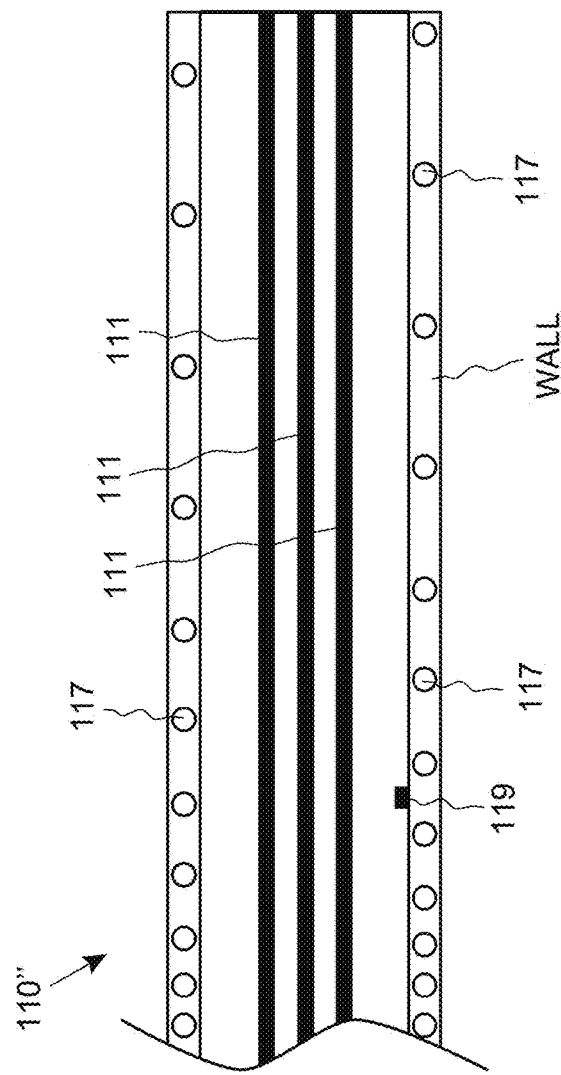
FIG 27
FIG 28

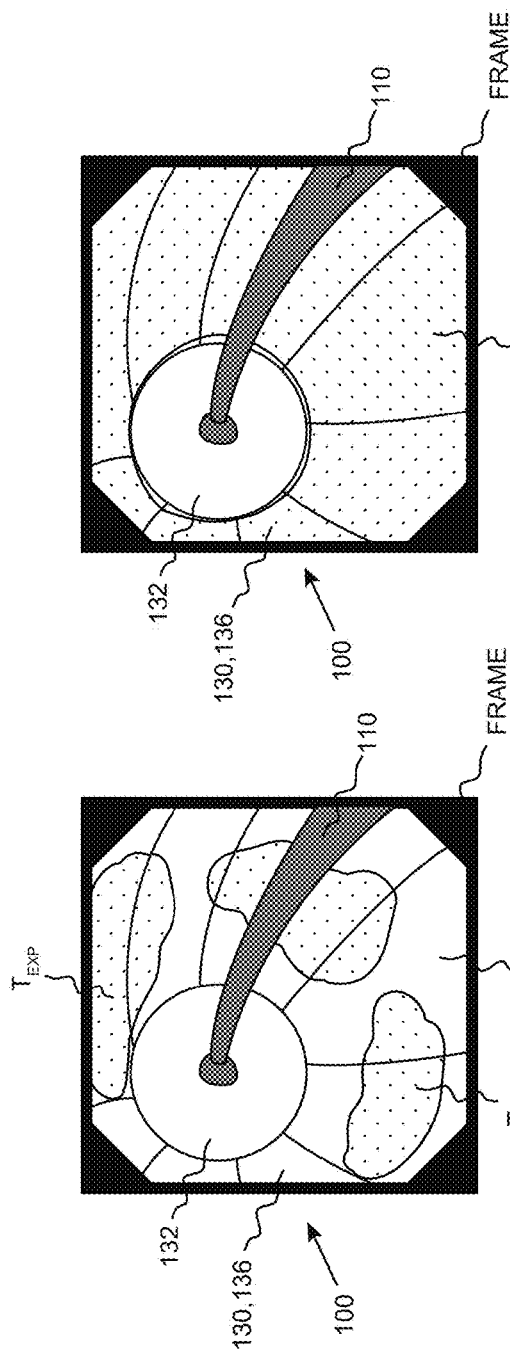
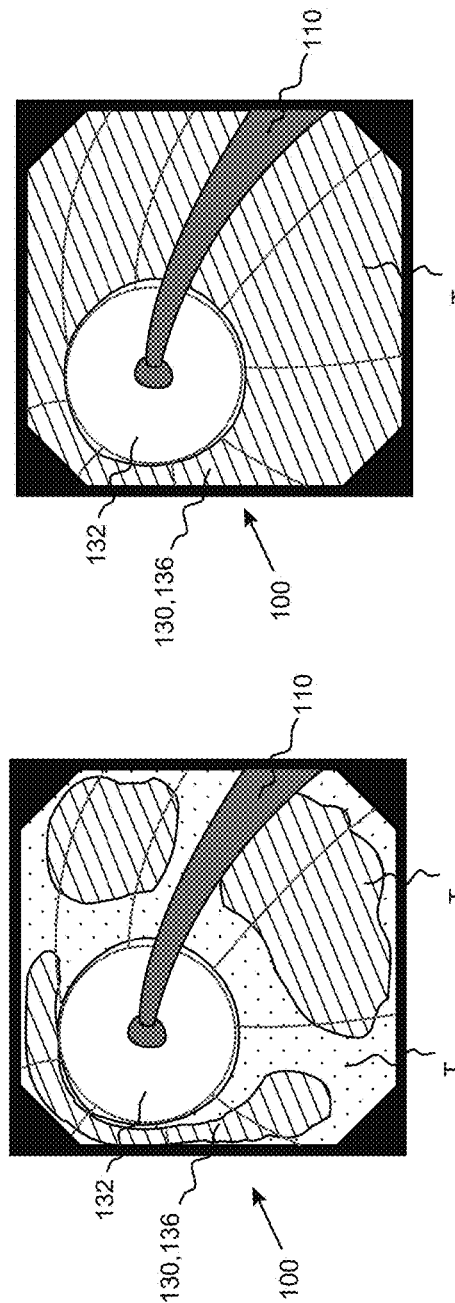
FIG 29A
FIG 29B
FIG 29C
FIG 29D

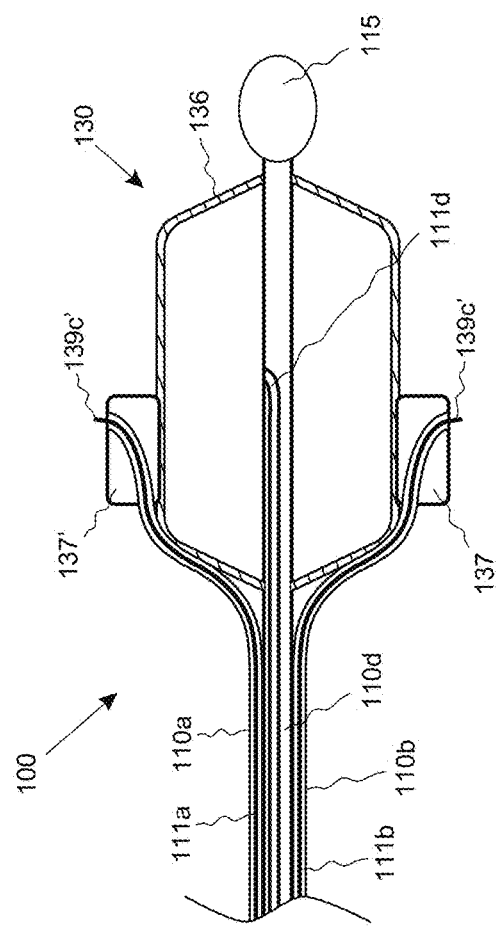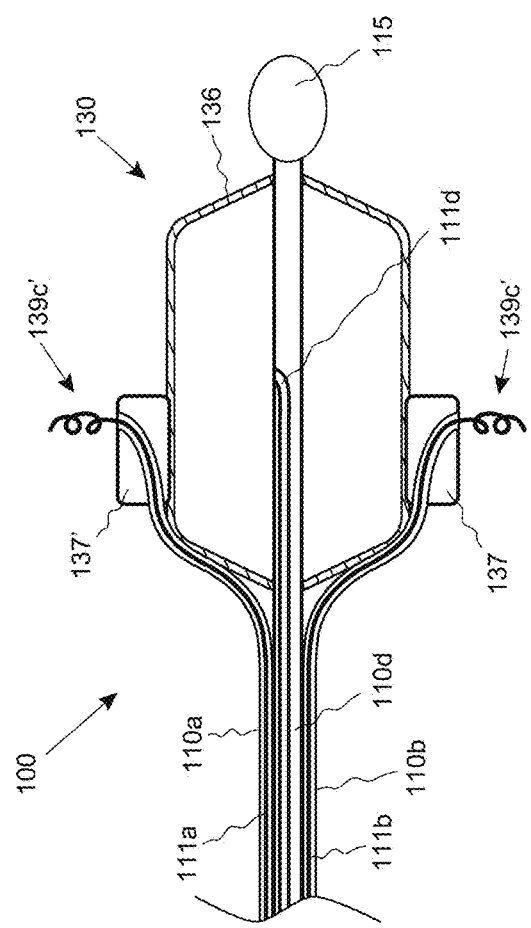

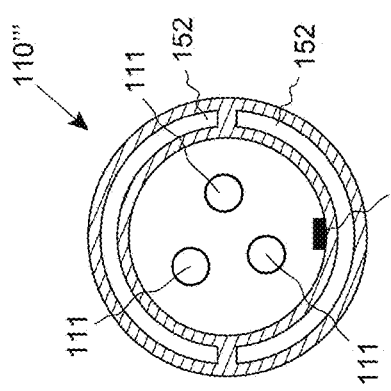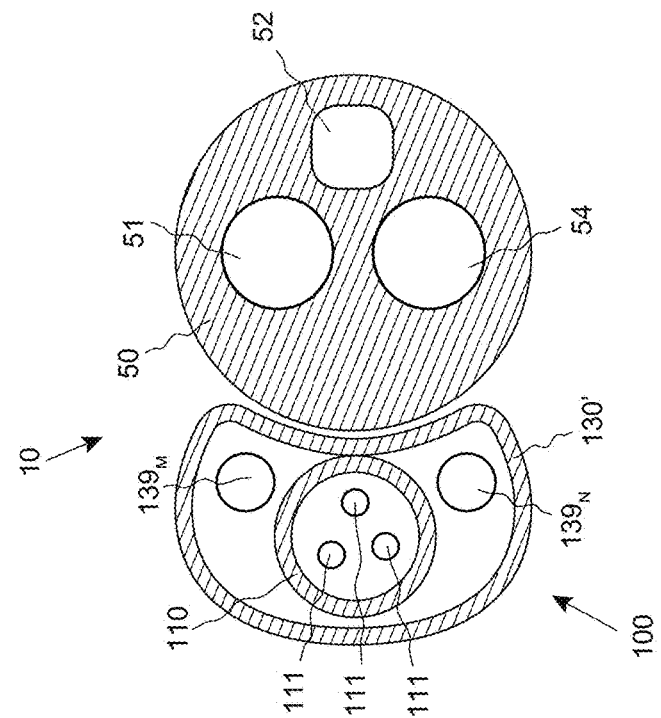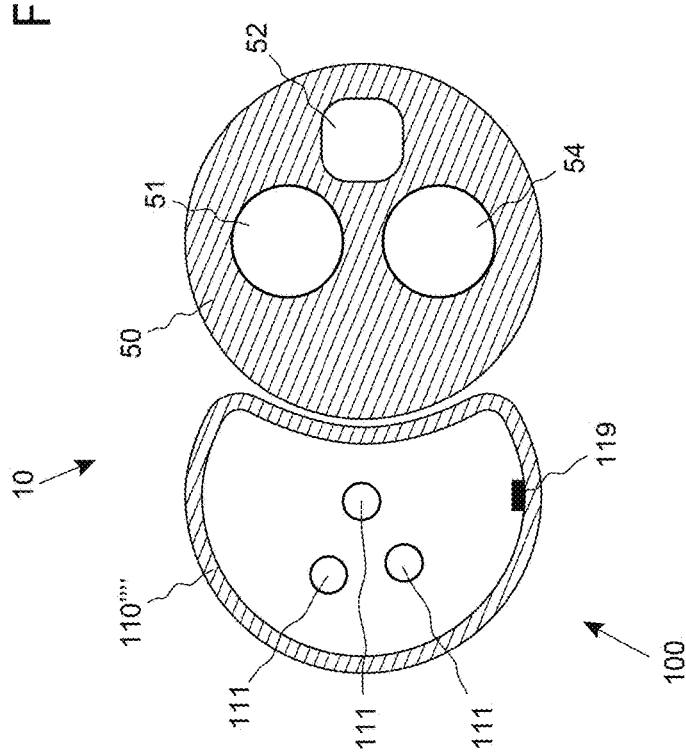

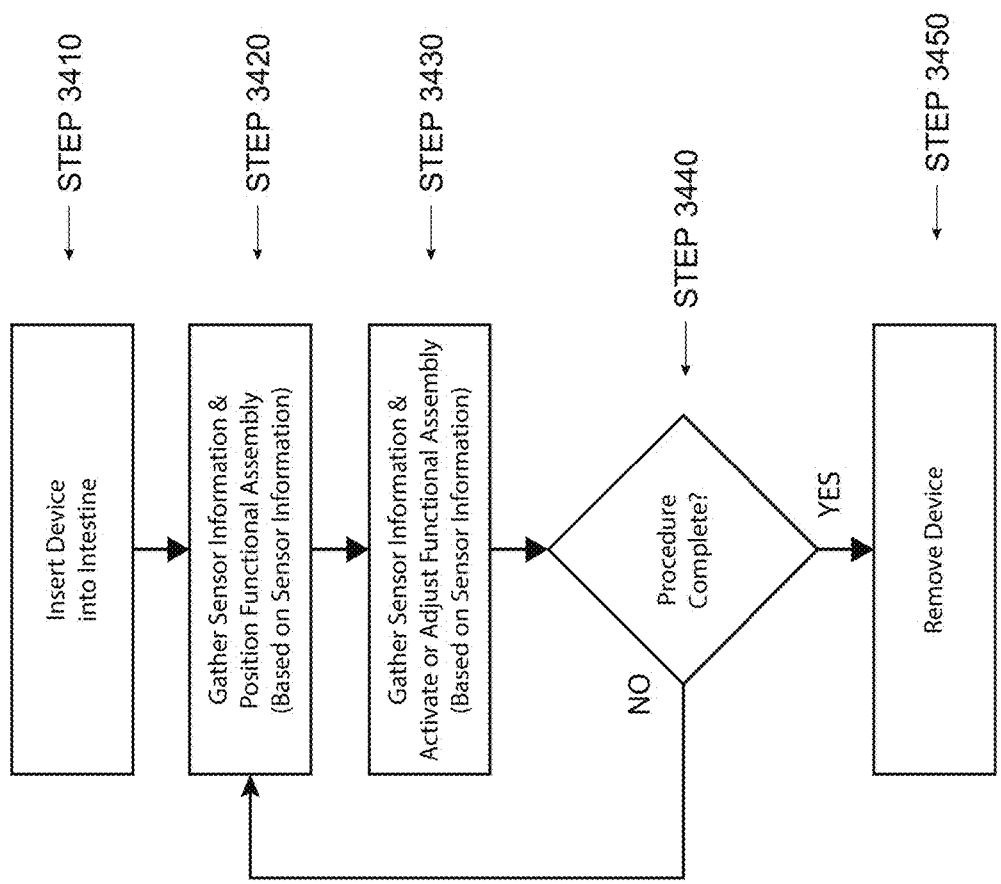

Red = < 3 ablations
Blue = 3+ ablations

SYSTEMS, DEVICES AND METHODS FOR PERFORMING MEDICAL PROCEDURES IN THE INTESTINE

CROSS-REFERENCE TO RELATED APPLICATIONS

This application is a continuation of U.S. patent application Ser. No. 15/274,764, filed Sep. 23, 2016 (now U.S. Pat. No. 9,757,535), which is a continuation-in-part of (1) International Patent Application No. PCT/US2016/040512, filed Jun. 30, 2016, which claims priority to Provisional No. 62/187,594, filed Jul. 1, 2015, and (2) International Patent Application Serial Number PCT/US2015/040775, entitled "Methods and Systems for Treating Diabetes and Related Diseases and Disorders", filed Jul. 16, 2015, which claims priority to Provisional No. 62/025,307, filed Jul. 16, 2014, the entire content of each of which are incorporated herein by reference in their entity; this application also claims the benefit of U.S. Provisional Application No. 62/273,015, entitled "Methods and Systems for Treating Diabetes, Non-Alcoholic Fatty Liver Disease, Non-Alcoholic Steatohepatitis and Related Diseases and Disorders", filed Dec. 30, 2015, the entire content of which is incorporated herein by reference in its entity.

This application is related to: U.S. patent application Ser. No. 13/945,138, entitled "Devices and Methods for the Treatment of Tissue", filed Jul. 18, 2013; U.S. patent application Ser. No. 14/470,503, entitled "Heat Ablation Systems, Devices and Methods for the Treatment of Tissue", filed Aug. 27, 2014; U.S. patent application Ser. No. 14/515,324, entitled "Tissue Expansion Devices, Systems and Methods", filed Oct. 15, 2014; U.S. patent application Ser. No. 14/609,332, entitled "Electrical Energy Ablation Systems, Devices and Methods for the Treatment of Tissue", filed Jan. 29, 2015; U.S. patent application Ser. No. 14/609,334, entitled "Ablation Systems, Devices and Methods for the Treatment of Tissue", filed Jan. 29, 2015; U.S. patent application Ser. No. 14/673,565, entitled "Methods, Systems and Devices for Performing Multiple Treatments on a Patient", filed Mar. 30, 2015; U.S. patent application Ser. No. 14/956,710, entitled "Methods, Systems and Devices for Reducing the Luminal Surface Area of the Gastrointestinal Tract", filed Dec. 2, 2015; U.S. patent application Ser. No. 14/917,243, entitled "Systems, Methods and Devices for Treatment of Target Tissue", filed Mar. 7, 2016; U.S. patent application Ser. No. 15/156,585, entitled "Systems, Devices and Methods for the Creation of a Therapeutic Restriction in the Gastrointestinal Tract", filed May 17, 2016; International Patent Application Serial Number PCT/US2015/022293, entitled "Injectate Delivery Devices, Systems and Methods", filed Mar. 24, 2015, the entire contents of each of which are incorporated herein by reference in their entirety for all purposes.

TECHNICAL FIELD

The embodiments disclosed herein relate generally to systems, devices and methods for performing medical procedures in the intestine of a patient.

BACKGROUND OF THE INVENTION

Numerous diagnostic and therapeutic procedures are performed in the small and large intestine, as well as other locations of the gastrointestinal tract. Devices used in these procedures can be difficult to maneuver and otherwise operate, and have limited functionality There is a need for improved systems and devices for treating and diagnosing tissue of the intestine, as well as a need for methods of treating intestinal tissue as a new or improved therapy for various diseases and disorders.

BRIEF SUMMARY OF THE INVENTION

According to one aspect of the present inventive concepts, a method for performing a medical procedure in an intestine of a patient, comprising: providing a system comprising: a catheter for insertion into the intestine, the catheter comprising: an elongate shaft comprising a distal portion; and a functional assembly positioned on the shaft distal portion and comprising at least one treatment element; introducing the catheter into the patient; and treating target tissue with the at least one treatment element, wherein the target tissue comprises mucosal tissue of the small intestine; wherein the medical procedure is configured to treat at least one of non-alcoholic fatty liver disease (NAFLD) or non-alcoholic steatohepatitis (NASH).

In some embodiments, the medical procedure is further configured to treat insulin resistance.

In some embodiments, the medical procedure is further configured to treat a disease or disorder selected from the group consisting of: Type 2 diabetes; Type 1 diabetes; "Double diabetes"; gestational diabetes; hyperglycemia; pre-diabetes; impaired glucose tolerance; insulin resistance; and combinations thereof.

In some embodiments, the system further comprises a console operably attached to the functional assembly, and wherein the console comprises one or more variable console parameters used to control the functional assembly.

In some embodiments, the system further comprises at least one sensor constructed and arranged to produce a sensor signal, and wherein the method further comprises adjusting at least one variable console parameter based on the sensor signal. The console can be configured to perform closed-loop energy delivery to the functional assembly based on the sensor signal.

In some embodiments, the treating target tissue modifies at least one of nutrient absorption by the target tissue or hormonal signaling from the target tissue.

In some embodiments, the treating target tissue modifies secretions of the target tissue.

In some embodiments, the treating target tissue comprises treating mucosal tissue within 15 cm of the ampulla of Vater.

In some embodiments, the method comprises avoiding treating tissue between a first location proximate the ampulla of Vater and a second location 0.5 cm distal to the ampulla of Vater.

In some embodiments, at least 6 cm, or at least 9 cm of length of duodenum are treated.

In some embodiments, the treating target tissue comprises treating at least a first axial segment and a second axial segment of the intestine. The treating target tissue can comprise treating between two and six axial segments of the intestine to treat at least 6 cm of axial length of intestine.

In some embodiments, the treating target tissue comprises treating an amount of tissue that is based on the severity of the patient's NAFLD and/or NASH.

In some embodiments, the method further comprises identifying non-target tissue. The non-target tissue can be identified by marking tissue selected from the group consisting of: ampulla of Vater; tissue proximate the ampulla of Vater; pylorus; tissue proximate the pylorus; and combinations thereof.

In some embodiments, the treating target tissue comprises a series of tissue ablation steps, each comprising ablation of an axial length of intestinal tissue, wherein each ablation step is preceded by a tissue expansion step. The method can further comprise preventing axial motion of the functional assembly between the tissue expansion and the tissue treatment steps. The method can further comprise applying vacuum to tissue during the tissue expansion step. The tissue expansion can comprise delivering injectate into submucosal tissue, and the injectate can comprise visualizable material.

In some embodiments, the treating target tissue comprises a series of tissue ablation steps, each ablation step comprising ablation of an axial length of intestinal tissue, wherein each ablation step is followed by a tissue neutralizing step. Each ablation step can comprise a heat ablation of tissue, and each neutralizing step can comprise a cooling of tissue. The method can further comprise performing a separate tissue neutralizing step prior to each ablation step. Each ablation step can comprise a heat ablation of tissue, and each separate neutralizing step can comprise a cooling of tissue.

In some embodiments, the method further comprises maintaining the functional assembly at or below a target diameter.

In some embodiments, the method further comprises maintaining the functional assembly at or below a target pressure.

In some embodiments, the method further comprises maintaining the functional assembly at or below a target volume.

In some embodiments, the method further comprises delivering an anti-peristaltic agent.

In some embodiments, the method further comprises modifying the pressure of a segment of intestine that is proximate the target tissue being treated.

In some embodiments, the functional assembly includes a tissue contacting portion comprising a surface area between 500 mm$^2$ and 3500 mm$^2$.

In some embodiments, the functional assembly comprises an expanded diameter between 19 mm and 28 mm.

In some embodiments, the functional assembly comprises at least one fluid delivery element.

In some embodiments, the functional assembly further comprises at least one recess. The functional assembly can further comprise a vacuum port positioned in the at least one recess.

In some embodiments, the catheter further comprises a fluid removal port configured to remove fluid from a segment of the intestine.

According to one aspect of the present inventive concepts, a system for performing a medical procedure in an intestine of a patient comprises a first catheter for insertion into the intestine, the first catheter comprising an elongate shaft comprising a distal portion, and a functional assembly positioned on the shaft distal portion and comprising at least one functional element. The system further comprises a console operably attachable to the first catheter functional assembly and comprising one or more variable console settings used to control the functional assembly, and at least one sensor constructed and arranged to produce a sensor signal, and at least one console setting is configured to be adjusted based on the sensor signal.

In some embodiments, the sensor signal is related to a physiologic parameter of the intestine. The sensor signal can be related to the anatomical geometry of a portion of the intestine. The sensor signal can be related to force applied to tissue of the intestine. The sensor signal can be related to pressure applied to tissue of the intestine. The sensor signal can be related to temperature of tissue of the intestine.

In some embodiments, the sensor signal is related to a parameter of the functional assembly. The sensor signal can be related to pressure within the functional assembly. The sensor signal can be related to force applied to a portion of the functional assembly. The sensor signal can be related to the temperature of at least a portion of the functional assembly. The sensor signal can be related to the temperature of fluid within the functional assembly.

In some embodiments, the system is configured to maintain pressure within the functional assembly relative to a threshold based on the sensor signal. The system can be configured to maintain pressure within the functional assembly below a pressure threshold, above a pressure threshold and/or within a range of pressures based on the sensor signal. The system can be configured to maintain the pressure relative to a threshold during a tissue ablation procedure. The system can be configured to maintain the pressure relative to a threshold during a tissue expansion procedure. The system can be configured to inflate the functional assembly to a first pressure, deliver injectate into tissue, and reduce the pressure in the functional assembly when the pressure in the functional assembly reaches a threshold. The first pressure can comprise a pressure of approximately 0.7 psi and the threshold can comprise a pressure of approximately 0.9 psi.

In some embodiments, the console settings comprise a parameter selected from the group consisting of: delivery rate of fluid into the functional assembly; withdrawal rate of fluid from the functional assembly; delivery rate of fluid into tissue; rate of energy delivered into tissue; peak energy level delivered into tissue; average energy delivery rate delivered into tissue; amount of energy delivered into tissue during a time period; temperature of an ablative fluid; temperature of a neutralizing fluid; temperature of functional assembly; pressure of functional assembly; pressure of fluid delivered into functional assembly; pressure of fluid delivered into tissue; duration of energy delivery; time of energy delivery (e.g. time of day of or relative time compared to another step); translation rate; translation rate of the functional assembly; rotation rate; rotation rate of the functional assembly; a flow rate; a recirculation rate; a heating rate; a heating temperature; a cooling rate; a cooling temperature; a sampling rate; a sensor sampling rate; and combinations thereof.

In some embodiments, the console settings comprise a system parameter selected from the group consisting of: pressure and/or volume of a fluid delivered to the elongate shaft; pressure and/or volume of a fluid delivered to and/or extracted from the functional assembly; pressure and/or volume of a fluid delivered to one or more conduits of the elongate shaft; pressure and/or volume of a fluid within one or more conduits of the elongate shaft; level of a vacuum within a conduit of the elongate shaft; a force used to advance and/or retract one or more conduits of the elongate shaft; a force used to advance and/or retract one or more fluid delivery elements of the first catheter; and combinations thereof.

In some embodiments, the console settings comprise a system parameter selected from the group consisting of: temperature, flow rate, pressure and/or duration of fluid delivered to the first catheter and/or the functional assembly; temperature, flow rate, pressure and/or duration of fluid contained within the functional assembly and/or recirculating to and/or from the functional assembly: and combinations thereof.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 4A, 4B and 4C are anatomical, side sectional views of a series of steps for performing a medical procedure, consistent with the present inventive concepts.

FIGS. 5A and 5B are end and side views of the distal portion of a catheter including recessed ports, shaft-located vacuum ports, and an inflatable distal tip, consistent with the present inventive concepts.

FIGS. 6A and 6B are anatomical, side sectional views of the distal end of a catheter comprising a functional assembly configured to expand to multiple geometric configurations, consistent with the present inventive concepts.

FIG. 7 is an anatomical, side sectional view of the distal end of a catheter comprising a functional assembly including a balloon with varied wall thickness, consistent with the present inventive concepts.

FIG. 8 is an anatomical, side sectional view of the distal end of a catheter comprising a functional assembly including an insulating element, consistent with the present inventive concepts.

FIG. 9 is a side view of a catheter comprising a tissue dissecting assembly, consistent with the present inventive concepts.

FIG. 9A is a magnified view of one of the tools of FIG. 9, consistent with the present inventive concepts.

FIG. 11 is a side view of the distal portion of a catheter including multiple shafts arranged in a helix, consistent with the present inventive concepts.

FIG. 12 is a side view of a distal portion of a catheter comprising ports mounted on a tapered proximal portion of a functional assembly, consistent with the present inventive concepts.

FIGS. 17A-B are two anatomical, side sectional views of a distal portion of a catheter comprising a functional assembly and at least one stabilizing assembly, consistent with the present inventive concepts.

FIGS. 25A-C are anatomical, side sectional views of the distal portion of a multiple expandable assembly catheter in a series of steps, consistent with the present inventive concepts.

FIG. 27 is a medical device shaft comprising a tapered profile, consistent with the present inventive concepts.

FIG. 28 is a medical device shaft comprising a varied pitch braid, consistent with the present inventive concepts.

FIGS. 29A-D is a camera view of a series of steps for expanding tissue and treating target tissue at a single axial segment, consistent with the present inventive concepts.

FIGS. 30A-B are side sectional views of a distal portion of a catheter comprising a tissue-engaging fluid delivery element, consistent with the present inventive concepts.

FIG. 31 is a medical device shaft comprising one or more insulating elements, consistent with the present inventive concepts.

FIG. 32 is an end sectional view of a system comprising a catheter with a non-circular cross section and a body introduction device with a circular cross section, consistent with the present inventive concepts.

FIG. 33 is an end sectional view of a system comprising a catheter with a functional assembly comprising a non-circular unexpanded cross section and a body introduction device with a circular cross section, consistent with the present inventive concepts.

FIG. 34 is a flowchart of a method of performing a medical procedure including gathering sensor information, consistent with the present inventive concepts.

DETAILED DESCRIPTION OF THE DRAWINGS

Figure 1:
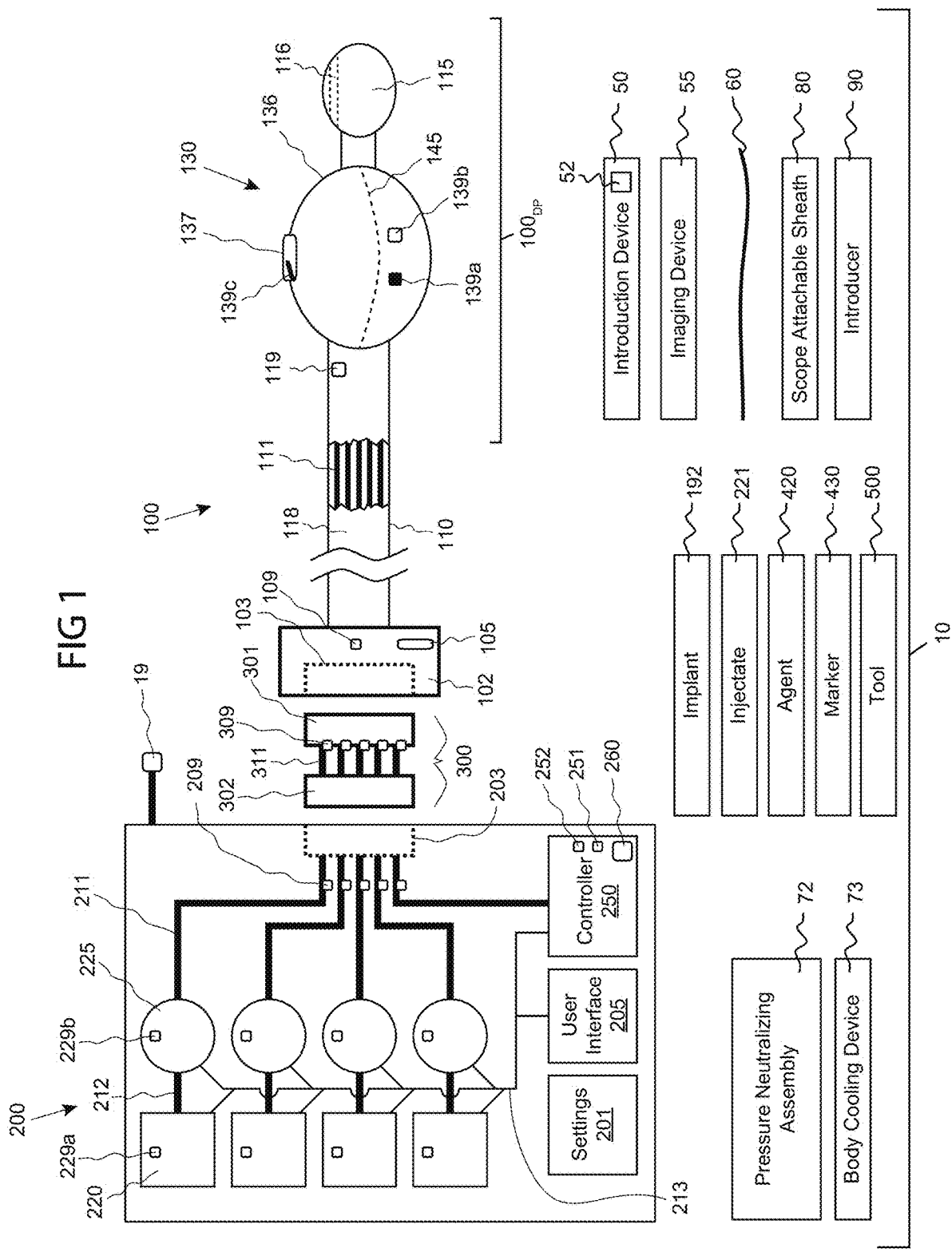
FIG. 1 is a schematic view of a system for performing a medical procedure in the intestine of a patient, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove. As used herein, the term "vacuum level" refers to a measure of a vacuum wherein the lower the pressure, the greater the vacuum level.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

As used herein, the term "ablative temperature" refers to a temperature at which tissue necrosis or other desired tissue treatment occurs (e.g. a temperature sufficiently hot or sufficiently cold to cause tissue necrosis). As used herein, the term "ablative fluid" refers to one or more liquids, gases, gels or other fluids whose thermal properties cause tissue necrosis and/or another desired tissue treatment (e.g. one or more fluids at an ablative temperature). Alternatively or additionally, "ablative fluid" refers to one or more fluids whose chemical properties (at room temperature, body temperature or otherwise) cause tissue necrosis or another desired tissue treatment. A tissue treatment element (e.g. a functional element) of the present inventive concepts can comprise one or more ablative fluids.

As used herein, the term "threshold" refers to a maximum level, a minimum level and/or range of values. In some embodiments, a system parameter is maintained above a threshold, below a threshold and/or within a threshold, to cause a desired effect (e.g. efficacious therapy) and/or to prevent or otherwise reduce (hereinafter "prevent") an undesired event (e.g. a device or clinical adverse event). In some embodiments, a system parameter is maintained above a first threshold (e.g. above a first temperature threshold) and below a second threshold (e.g. below a second temperature threshold). In some embodiments, a threshold value is determined to include a safety margin, such as to cause a desired effect and/or prevent an undesired event as the system parameter slightly crosses the threshold (e.g. to account for patient variability, system variability, tolerances, and the like).

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

As used herein, the term "functional element" is to be taken to include one or more elements constructed and arranged to perform a function. In some embodiments, a functional element is configured to deliver energy and/or otherwise treat tissue (e.g. a functional element configured as a treatment element). Alternatively or additionally, a functional element can be configured to record one or more parameters, such as a patient physiologic parameter; a patient anatomical parameter (e.g. a tissue geometry parameter); a patient environment parameter; and/or a system parameter. In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a patient anatomical parameter; and combinations of one or more of these. A functional element can comprise a fluid, such as an ablative fluid (as described hereabove) comprising a liquid or gas configured to ablate or otherwise treat tissue. A functional element can comprise a reservoir, such as an expandable balloon configured to receive an ablative fluid. A "functional assembly" can comprise an assembly constructed and arranged to perform a function, such as is described hereabove. In some embodiments, a functional assembly is configured to deliver energy and/or otherwise treat tissue (e.g. a functional assembly configured as a treatment assembly). Alternatively or additionally, a functional assembly can be configured to record one or more parameters, such as a patient physiologic parameter; a patient anatomical parameter; a patient environment parameter; and/or a system parameter. A functional assembly can comprise an expandable assembly. A functional assembly can comprise one or more functional elements.

As used herein, the term "transducer" is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal. Alternatively or additionally, a transducer can convert a physical quantity (e.g. variations in a physical quantity) into an electrical signal. A transducer can include any component that delivers energy and/or an agent to tissue, such as a transducer configured to deliver one or more of: heat energy to tissue; cryogenic energy to tissue; electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these. Alternatively or additionally, a transducer can comprise a mechanism, such as a valve, a grasping element; an anchoring mechanism; an electrically-activated mechanism, a mechanically-activated mechanism and/or a thermally activated mechanism As used herein, the term "tissue contacting surface" refers to a surface of a system or device component that makes physical contact with tissue, such as a portion of an external surface of an expandable component (e.g. a portion of a balloon's surface) which contacts tissue once expanded. In some embodiments, tissue contacting a tissue contacting surface directly receives energy from the tissue contacting surface of the expandable components, however tissue in proximity (e.g. below or alongside) also receives energy (e.g. via conduction of the delivered energy and/or a resultant heat energy).

It is an object of the present inventive concepts to provide systems, methods and devices for safely and effectively treating and/or diagnosing a volume of tissue (the "target tissue"), such as to treat and/or diagnose a patient disease or disorder. Target tissue can comprise one or more target tissue segments or other target tissue portions, such as target tissue located in the intestine of a patient. Clinical procedures in the duodenum and other locations of the small intestine are challenging for a number of reasons, such as those caused by the long distance between the mouth and the intestine and the complexities of the gastrointestinal passageway encountered (including passage through the stomach) during device (e.g. catheter) insertion and operation. Intestinal diameter varies along its length, and effective devices must accommodate this variation. The intestine is quite distensible in the longitudinal and radial directions, further complicating device (e.g. catheter) manipulation and operation (e.g. delivery of energy to tissue). Mobility of intestinal mucosa relative to muscularis is present, as well as mobility of the full wall, but can result in undesired stretching, compression and intussusception. The duodenum is normally closed, and requires insufflation to open (e.g. for visualization). The insufflation medium (e.g. gas) moves through the intestine, so more must be delivered, while excess gas causes discomfort or other adverse effect for the patient. Duodenal and other intestinal tissue tends to stretch or compress as a device is advanced or retracted, respectively, such as to cause retrograde expulsion of devices if a stabilization force is not maintained. It is difficult to manipulate and control devices that include treatment and other elements positioned in the small intestine. The small intestine wraps around the pancreas, and the curvature is quite variable from patient to patient. The length of the intestine along an outer curve is longer than that along an inner curve. In many procedures, there is a desire to avoid damage to the ampulla of Vater (e.g. to avoid restricting bile and/or pancreatic fluid), tissue which can be difficult to visualize or otherwise identify. There are relatively few endoscopically visualizable landmarks in the intestine, making it difficult to know where in the intestine a portion (e.g. a distal portion) of a device is positioned. Access to the intestine through the stomach via an over-the-wire catheter loses one-to-one motion between a proximal handle and a distal portion of the device, as slack can accumulate in the stomach during advancement and slack can be relieved from the stomach during withdrawal. Accessing the intestine can include entering the intestine through the pylorus, a small sphincter, from the stomach, and in obese patients, large stretchable stomachs make it difficult to direct a device to the pylorus. The intestinal mucosa has a very irregular surface due to plicae circulares and mucosal villi, and performing a treatment (e.g. an ablation treatment) of the intestinal mucosa is quite different from a treatment procedure performed in the stomach or esophagus, because of this irregularity. Peristalsis present in the small intestine is dynamic and unpredictable and can alter functional element, functional assembly and/or other device component position and/or contact level with tissue. The intestine is not only thin-walled, but the thickness of the wall is highly variable, even within small axial segments of the small intestine, thus complicating preferential ablation of inner layers versus outer layers of the small intestine. The muscularis is innervated and scars and/or stenoses easily, and as such, even minimal trauma to the muscularis should be avoided.

Target tissue can comprise one or more layers of a portion of tubular or non-tubular tissue, such as tissue of an organ or tissue of the gastrointestinal (GI) tract of a patient, such as tissue of the small intestine or large intestine. The systems and devices of the present inventive concepts can include one or more functional assemblies and/or functional elements configured to treat target tissue, such as a treatment element comprising fluid at an ablative temperature delivered to a balloon (ablative temperature fluid and/or balloon filled with ablative fluid each referred to singly or collectively as a "functional element" or a "treatment element" of the present inventive concepts). One or more functional elements can be provided in, on and/or within an expandable functional assembly or other radially deployable mechanism. Functional assemblies and/or functional elements can be configured to treat target tissue (e.g. deliver energy to target tissue), such as to modify target tissue (e.g. to modify the secretions from the target tissue and/or absorption of the target tissue), ablate target tissue (e.g. to cause the replacement of the target tissue with "new tissue") and/or to cause a reduction in the surface area of target tissue (e.g. the luminal surface area of an inner wall of tubular tissue) at and/or proximate to one or more locations where the treatment was performed (e.g. at and/or proximate the location where energy was delivered). The luminal or other tissue treatment can occur acutely and/or it can take place over time, such as days, weeks or months. A tissue surface area reduction can correspond to a reduction in mucosal surface area available to function in an absorptive, neuronal signaling, and/or a hormonal secretory capacity. A target tissue treatment can result in the replacement of target tissue with new tissue with different absorptive and/or secretory capacity and/or other desirable effect related to replacement and/or modification of target tissue. The treatment of target tissue with the systems, devices and methods of the present inventive concepts can provide a therapeutic benefit to the patient, such as to treat one or more diseases or disorders of the patient, as described in detail herebelow.

Each functional assembly (e.g. treatment assembly) can comprise at least one functional element (e.g. tissue treatment element) such as a tissue treatment element selected from the group consisting of: ablative fluid delivered to a balloon or other expandable fluid reservoir; energy delivery element mounted to an expandable functional assembly such as an electrode or other energy delivery element configured to deliver radiofrequency (RF) energy and/or microwave energy; light delivery element configured to deliver laser or other light energy; fluid delivery element (e.g. needle or nozzle) configured to deliver ablative fluid directly onto and/or into tissue; sound delivery element such as an ultrasonic and/or subsonic sound delivery element; and combinations of one or more of these. Numerous forms of functional assemblies and/or functional elements can be included. In some embodiments, the functional assemblies and/or the one or more functional elements contained therein are configured as described in: applicant's co-pending U.S. patent application Ser. No. 13/945,138, entitled "Devices and Methods for the Treatment of Tissue", filed Jul. 18, 2013; applicant's co-pending U.S. patent application Ser. No. 14/470,503, entitled "Heat Ablation Systems, Devices and Methods for the Treatment of Tissue", filed Aug. 27, 2014; applicant's co-pending U.S. patent application Ser. No. 14/609,332, entitled "Electrical Energy Ablation Systems, Devices and Methods for the Treatment of Tissue", filed Jan. 29, 2015; and/or applicant's co-pending U.S. patent application Ser. No. 14/609,334, entitled "Ablation Systems, Devices and Methods for the Treatment of Tissue", filed Jan. 29, 2015; the content of each of which is incorporated herein by reference in its entirety for all purposes.

The treatment assemblies and/or treatment elements of the present inventive concepts can be constructed and arranged to deliver one or more treatments (e.g. deliver energy, deliver a chemically ablative fluid, mechanically abrade and/or otherwise treat tissue) directly to a particular area of tissue, the "delivery zone". During a single delivery of treatment, a treatment element can be constructed and arranged to deliver treatment to a relatively continuous surface of tissue (e.g. a continuous surface of tissue in contact with a balloon filled with ablative fluid or a surface of tissue onto which a chemically ablative fluid is sprayed, coated or otherwise delivered). In these continuous-surface treatment delivery embodiments, the delivery zone comprises the continuous surface of tissue receiving the treatment directly. Alternatively, a treatment element can be constructed and arranged to deliver treatment to multiple discrete portions of a tissue surface, with one or more tissue surface portions in-between other surface portions that do not directly receive energy or other treatment from the treatment element. In these segmented-surface treatment delivery embodiments, the delivery zone is defined by a periphery of the multiple tissue surface area portions receiving treatment, similar to a "convex hull" or "convex envelope" used in mathematics to define an area including a number of discrete locations that define a periphery. A delivery zone can comprise two or more contiguous or non-contiguous delivery zones, and multiple delivery zones can be treated sequentially and/or simultaneously.

For example, in embodiments where the treatment element is hot fluid (e.g. ablative fluid at a sufficiently high temperature to cause tissue necrosis) positioned within a balloon, the delivery zone comprises all tissue surfaces contacted by the balloon that directly receive ablative thermal energy from the ablative fluid through the balloon. In embodiments where the treatment element is a balloon filled with cold fluid (e.g. ablative fluid at a sufficiently low temperature to cause tissue necrosis), the delivery zone can comprise all tissue surfaces contacted by the balloon that have heat directly extracted from them by the cold fluid (e.g. at a sufficient cold temperature to treat the tissue). In embodiments where the treatment element is an array of electrodes configured to deliver electrical energy (e.g. RF energy) to tissue, the delivery zone can comprise an area defined by the electrodes on the periphery of the array (e.g. a convex hull as described above), such as when the electrodes are positioned and energy is delivered to treat relatively the entire surface of tissue within the periphery. In embodiments where the treatment element comprises one or more fluid delivery elements delivering ablative fluid directly onto tissue (e.g. an ablative fluid whose chemical nature modifies tissue, at body temperature or otherwise), the delivery zone can comprise a surface defined by the periphery of tissue locations receiving the ablative fluid, such as when the ablative fluid is delivered (e.g. sprayed or otherwise applied, such as via a sponge) to relatively the entire surface within the periphery. In embodiments where the treatment element comprises one or more light delivery elements such as those that deliver laser energy to tissue, the delivery zone can comprise a surface area defined by the periphery of tissue locations receiving the light energy, such as when light is delivered at a set of locations and with a magnitude of energy configured to treat relatively the entire surface of tissue within the periphery. In these embodiments, light can be delivered to relatively the entire energy delivery zone, or to a large number (e.g. greater than 100) of tissue locations within the periphery of the delivery zone (e g making up less than 50%, less than 20% or less than 10% of the total surface area of the delivery zone). In embodiments where the treatment element comprises one or more sound delivery elements such as those that deliver sub-sonic and/or ultrasonic sound energy to tissue, the delivery zone can comprise a surface area defined by the periphery of tissue locations receiving the sound energy, such as when ablative sound energy is delivered at a set of locations and with a magnitude of energy configured to treat relatively the entire surface of tissue within the periphery. In embodiments in which the treatment element comprises a mechanical cutter or other abrasion element, the delivery zone can comprise a surface defined by all tissue dissected, cut, mechanically disrupted and/or otherwise modified during a single abrading step of the mechanical abrader.

A delivery zone can comprise a cumulative set of delivery zones that receive treatment simultaneously and/or sequentially, by one or more tissue treatment elements, such as those described herein. A delivery zone can comprise a first delivery zone defined when a treatment element treats target tissue in a first treatment delivery, plus a second delivery zone defined when the treatment element treats target tissue in a second treatment delivery, and so on. In these embodiments, the treatment element can be translated, rotated and/or otherwise repositioned between treatments (e.g. energy delivery), where each delivery zone is associated with the position of the treatment element during each treatment. Multiple delivery zones can receive treatment in a single procedure, such as within a period of less than twenty-four hours. A delivery zone can comprise a set of multiple delivery zones treated by two or more treatment elements.

Target tissue treated by each energy delivery and/or other treatment delivery comprises the tissue directly receiving treatment (i.e. the tissue defined by the delivery zone) plus "neighboring tissue" which is also modified by the associated treatment delivery. The neighboring tissue can comprise tissue alongside, below (e.g. in a deeper tissue layer) and/or otherwise proximate the delivery zone tissue. The neighboring tissue treatment can be due to one or more of: conduction and/or convection of heat or cold from the delivery zone; flow of ablative fluid from the delivery zone; flow of toxins or other agents that occur during cell degradation and/or cell death; radiation; luminescence, light dissipation; and other energy and/or chemical propagation mechanisms. In some embodiments, an area (i.e. the delivery zone) comprising an inner surface of mucosal tissue directly receives treatment from one or more treatment elements (e.g. an ablative fluid contained within a balloon), and the total volume of target tissue treated by that single treatment delivery includes: the delivery zone tissue (i.e. surface mucosal tissue directly receiving energy and/or other treatment from the treatment element); surface mucosal tissue in close proximity (e.g. adjacent) to the delivery zone tissue; and mucosal and potentially submucosal tissue layers beneath (deeper than) the delivery zone tissue and the treated adjacent surface mucosal tissue.

In some embodiments, a "treatment neutralizing" procedure is performed after one or more treatments (e.g. energy deliveries), such as a treatment neutralizing cooling procedure performed after one or more treatment elements deliver heat to treat target tissue, or a treatment neutralizing warming procedure performed after one or more treatment elements deliver cryogenic energy to treat target tissue. In these embodiments, the treatment neutralizing cooling or warming fluid can be delivered to the same functional assembly (e.g. an expandable functional assembly comprising a balloon) delivering the heat or cryogenic treatment, respectively, and/or the neutralizing fluid can be delivered directly to tissue by the same or different functional assembly or functional element. In some embodiments, a functional element delivers an ablating agent to target tissue (e.g. a chemical or other agent configured to cause target tissue necrosis or otherwise treat target tissue), and a treatment neutralizing procedure comprises delivery of a neutralizing agent (by the same or different functional element) to target and/or non-target tissue to reduce continued ablation due to the delivered caustic ablative fluid (e.g. a base to neutralize a delivered acid or an acid to neutralize a delivered base).

Each functional assembly and/or functional element of the present inventive concepts can be configured to be positioned in one or more intestinal and/or other locations of the patient, such as to perform a function (e.g. perform a treatment, deliver fluid and/or record data) at one or more contiguous or discontiguous tissue locations. Target tissue to be treated (e.g. ablated) comprises a three dimensional volume of tissue, and can include a first portion, a treatment portion, whose treatment has a therapeutic benefit to a patient; as well as a second portion, a "safety-margin" portion, whose treatment has minimal or no adverse effects to the patient. "Non-target tissue" can be identified (e.g. prior to and/or during the medical procedure), wherein the non-target tissue comprises tissue whose treatment by the treatment assembly and/or treatment element should be reduced or avoided such as to reduce or prevent an undesired effect to the patient.

The target tissue treatment can cause one or more modifications of the target tissue such as a modification selected from the group consisting of: modification of cellular function; cell death; apoptosis; instant cell death; cell necrosis; denaturing of cells; removal of cells; and combinations of one or more of these. In some embodiments, the target tissue treatment is configured to create scar tissue. Target tissue can be selected such that after treatment the treated target tissue and/or the tissue that replaces the target tissue functions differently than the pre-treated target tissue, such as to have a therapeutic benefit for the patient. The modified and/or replacement tissue (singly or collectively "treated tissue") can exhibit different properties than the pre-treated target tissue, such as different properties that are used to treat a patient disease or disorder. The treated tissue can have different secretions and/or quantities of secretions than the pre-treated target tissue, such as to treat diabetes, hypercholesterolemia and/or another patient disease or disorder. The treated tissue can have different absorptive properties than the target tissue, such as to treat diabetes, hypercholesterolemia and/or another patient disease or disorder. The treated tissue can have a different surface topography than the target tissue, such as a modification of the topography of the inner wall of the GI tract that includes a smoothing or flattening of its inner surface, such as a modification in which the luminal surface area of one or more segments of the GI tract is reduced after treatment. The effect of the treatment (e.g. the effect on the target tissue) can occur acutely, such as within twenty-four hours, or after longer periods of time, such as greater than twenty-four hours or greater than one week.

Target tissue to be treated can comprise two or more discrete tissue segments, such as two or more axial segments of the GI tract. Each tissue segment can comprise a full (e.g. approximately 360°) or partial circumferential segment of the tissue segment. Multiple tissue segments can be treated with the same or different functional elements (e.g. treatment elements), and they can be treated simultaneously or in sequential steps (e.g. sequential energy delivery steps that deliver energy to multiple delivery zones). Multiple tissue segments can be treated in the same or different clinical procedures (e.g. procedures performed on different days). In some embodiments, a series of tissue segments comprising a series of axial segments of the GI tract are treated in a single clinical procedure. The first and second tissue segments can be directly adjacent, they can contain overlapping portions of tissue, and there can be gaps between the segments. Dissimilarities in treatment elements can include type and/or amount of energy to be delivered by an energy delivery based treatment element. Dissimilarities in target tissue treatments can include: target tissue area treated; target tissue volume treated; target tissue length treated; target tissue depth treated; target tissue circumferential portion treated; ablative fluid type, volume and/or temperature delivered to a reservoir such as a balloon; ablative fluid type, volume and/or temperature delivered directly to tissue; energy delivery type; energy delivery rate and/or amount; peak energy delivered; average temperature of target tissue achieved during target tissue treatment; maximum temperature achieved during target tissue treatment; temperature profile of target tissue treatment; duration of target tissue treatment; surface area reduction achieved by target tissue treatment; and combinations of one or more of these.

Target tissue can include tissue of the duodenum, such as tissue including substantially all or a portion of the mucosal layer of one or more axial segments of the duodenum (e.g. including all or a portion of the plicae circulares), such as to treat diabetes, hypercholesterolemia and/or another patient disease or disorder, such as while leaving the duodenum anatomically connected after treatment. Target tissue can include one or more portions of a tissue layer selected from the group consisting of: mucosa; mucosa through superficial submucosa; mucosa through mid-submucosa; mucosa through deep-submucosa; and combinations of one or more of these. Replacement tissue can comprise cells that have migrated from one or more of: gastric mucosa; jejunal mucosa; an untreated portion of the duodenum whose mucosal tissue functions differently than the treated mucosal tissue functions prior to treatment; and combinations of one or more of these. Replacement tissue can include one or more tissue types selected from the group consisting of: scar tissue; normal intestinal mucosa; gastric mucosa; and combinations of one or more of these. In some embodiments, replacement tissue comprises tissue that has been delivered onto and/or into tissue by a catheter of the present inventive concepts. In some embodiments, target tissue includes a treatment portion comprising the mucosal layer of the duodenum, and a safety-margin portion comprising a near-full or partial layer of the submucosal layer of the duodenum. In some embodiments, the target tissue comprises nearly the entire mucosal layer of the duodenum, and can include a portion of the pylorus contiguous with the duodenal mucosa and/or a portion of the jejunum contiguous with the duodenal mucosa. In some embodiments, the target tissue comprises all or a portion of the duodenal mucosa distal to the ampulla of Vater (e.g. avoiding tissue within at least 0.5 cm, 1.0 cm or 1.5 cm from the ampulla of Vater while including tissue within 5 cm, 10 cm or 15 cm distal to the ampulla of Vater). In these embodiments, the target tissue can comprise at least 10%, at least 15%, at least 25%, at least 30% or at least 50% of the duodenal mucosa distal to the ampulla of Vater. Alternatively or additionally, the target tissue can comprise no more than 70% or no more than 90% of the duodenal mucosa distal to the ampulla of Vater. In these embodiments, tissue proximal to and/or proximate the ampulla of Vater can comprise non-target tissue (i.e. tissue whose treatment is avoided or at least reduced).

In some embodiments, the target tissue comprises at least a portion of duodenal mucosal tissue, and the systems, methods and devices of the present inventive concepts are configured to counteract duodenal mucosal changes that cause an intestinal hormonal impairment leading to insulin resistance in patients. In these embodiments, the therapy provided can improve the body's ability to process sugar and dramatically improve glycemic control for patients with insulin resistance and/or Type 2 diabetes. In some embodiments, target tissue is treated to prevent and/or reduce cognitive decline (e.g. Alzheimer's Disease), such as by improving sugar metabolism in the brain, overcoming insulin resistance in the brain, reducing toxicity of beta amyloid, reducing oxidative stress, and/or reducing inflammation in the brain associated with neuronal death. In some embodiments, target tissue is treated to: prevent liver fibrosis and/or cirrhosis (e.g. non-alcoholic fatty liver disease NAFLD or non-alcoholic steatohepatitis NASH); reduce liver fat; reduce oxidative stress; and/or reduce inflammation in the liver associated with liver fibrosis and toxicity.

Hormones released from the intestinal mucosa play an important role in modulating glucose homeostasis, and different axial segments of the intestinal mucosa release different hormones in the fasting and post-prandial state, in order to modulate blood glucose in the fasting and post-prandial states, respectively. After a meal, the proximal intestinal mucosa senses the intestine for ingested glucose and releases a collection of hormones in response to this signal. These hormones initiate the process of insulin release into the bloodstream after a meal, but they also induce some insulin resistance to prevent the released insulin from causing hypoglycemia before the body has a chance to absorb the ingested glucose. One such hormone that plays a role in this is GIP. Distal gut hormones (produced in the jejunum or a more distal location), on the contrary, allow the release of more insulin but also play a role in helping the body now become sensitive to its circulating insulin. Teleologically, the explanation for this difference in the type of gut hormones produced by different segments of the intestine is that enough glucose will have been absorbed by the time nutrients reach the distal intestine to allow the insulin to begin to function to reduce blood glucose levels. Releasing different hormones at different times (e.g. from different segments of the intestine) enables the body to absorb and process glucose in such a way as to avoid hypoglycemia (blood sugars that are too low) and hyperglycemia (blood sugars that are too high). In this way, intestinal hormonal signaling is important for whole body glucose homeostasis in the fasting and post-prandial states. The treatment can also lead to weight loss through decreased absorption of nutrients, increased sensation of satiety, altered food preferences, increased energy expenditure, and combinations of one or more of these.

In patients with Type 2 Diabetes, a lifetime of exposure to fat and sugar can lead to intestinal changes that occur in regions with the highest exposure to these nutrients, predominantly in the proximal intestine. These changes are characterized by an excess proximal intestinal mucosa's hormonal contribution to the fasting and post-prandial glucose homeostasis. The net result of these intestinal changes is to create a condition of insulin resistance and impaired glucose tolerance. Treatment of duodenal mucosal tissue with the systems, devices and methods of the present inventive concepts can be performed to alter the intestinal mucosal hormone production from the region of treated tissue. The treated tissue can then have an altered hormonal secretion pattern that affects blood glucose levels in the fasting and post-prandial states. The tissue treatment of the present inventive concepts can be performed to effect duodenal mucosal tissue secretion of GIP and/or GLP-1. The tissue treatment can lead to changes in the blood levels of GIP and/or GLP-1 (and other gut hormones) that can lead to changes in glucose homeostasis in the fasting and/or post-prandial states. The treatment can lead to changes in insulin and/or glucagon secretion from the pancreas and/or insulin and/or glucagon levels in the bloodstream. The treatment can lead to changes in pancreatic beta cell function and/or health through direct hormonal consequences of the treated duodenal tissue and/or indirectly through improved blood glucose levels. In some embodiments, the treatment of the present inventive concepts is configured to at least one of reduce a blood glucose level and/or reduce a lipoprotein level.

Treatment of intestinal tissue (e.g. duodenal mucosal tissue) can be performed to treat a disease and/or disorder selected from the group consisting of: diabetes; pre-diabetes; impaired glucose tolerance; insulin resistance; obesity or otherwise being overweight; a metabolic disorder and/or disease; and combinations of one or more of these. In some embodiments, treatment of intestinal tissue (e.g. at least duodenal mucosal tissue) using the systems, devices and/or methods of the present inventive concepts can be performed to treat one or more disease and/or disorder selected from the group consisting of: Type 2 diabetes; Type 1 diabetes; "Double diabetes"; gestational diabetes; hyperglycemia; pre-diabetes; impaired glucose tolerance; insulin resistance; non-alcoholic fatty liver disease (NAFLD); non-alcoholic steatohepatitis (NASH); obesity; obesity-related disorder; polycystic ovarian syndrome (PCOS); hypertriglyceridemia; hypercholesterolemia; psoriasis; GERD; coronary artery disease (e.g. as a secondary prevention); stroke; TIA; cognitive decline; dementia; Alzheimer's; neuropathy; diabetic nephropathy; retinopathy; heart disease; diabetic heart disease; heart failure; diabetic heart failure; and combinations of one or more of these. A near full circumferential portion (e.g. approximately) 360° of the mucosal layer of one or more axial segments of GI tissue can be treated. In some embodiments, less than 360° of one or more axial segments of tubular tissue is treated, such as one or more circumferential portions less than 350°, or between 300° and 350°, such as to prevent a full circumferential scar from being created at the one or more axial segment locations.

Target tissue can be selected to treat two or more patient diseases or disorders, such as two or more patient diseases or disorders as described herein.

Target tissue can comprise tissue of the terminal ileum, such as to treat hypercholesterolemia and/or diabetes. In these embodiments, the target tissue can extend into the proximal ileum and/or the colon.

Target tissue can comprise gastric mucosal tissue, such as tissue regions that produce ghrelin and/or other appetite regulating hormones, such as to treat obesity and/or an appetite disorder.

Target tissue can comprise tissue selected from the group consisting of: large and/or flat colonic polyps; margin tissue remaining after a polypectomy; and combinations of one or more of these. These tissue locations can be treated to treat residual cancer cells.

Target tissue can comprise at least a portion of the intestinal tract afflicted with inflammatory bowel disease, such that Crohn's disease and/or ulcerative colitis can be treated.

Target tissue can comprise GI tissue selected to treat Celiac disease and/or to improve intestinal barrier function.

The functional assemblies, functional elements, systems, devices and methods of the present inventive concepts can be configured to avoid ablating or otherwise adversely affecting certain tissue, termed "non-target tissue" herein. Depending on the location of tissue intended for treatment (i.e. target tissue), different non-target tissue can be applicable. In certain embodiments, non-target tissue can comprise tissue selected from the group consisting of: gastrointestinal adventitia; duodenal adventitia; the tunica serosa; the tunica muscularis; the outermost partial layer of the submucosa; ampulla of Vater (also known as the papilla); pancreas; bile duct; pylorus; and combinations of one or more of these.

In some embodiments, two or more clinical procedures are performed in which one or more volumes of target tissue are treated in each clinical procedure, such as is described in applicant's co-pending U.S. patent application Ser. No. 14/673,565, entitled "Methods, Systems and Devices for Performing Multiple Treatments on a Patient", filed Mar. 30, 2015. For example, a second clinical procedure can be performed at least twenty-four hours after the first clinical procedure, such as a second clinical procedure performed within 6 months of a first clinical procedure or a clinical procedure performed after at least 6 months after the first clinical procedure. The first and second clinical procedures can be performed using similar or dissimilar methods, and they can be performed using similar or dissimilar systems and/or devices (e.g. performed with similar or dissimilar treatment and/or other functional elements). The first and second clinical procedures can treat similar or dissimilar volumes of target tissue (e.g. similar or dissimilar amounts of tissue treated and/or locations of tissue treated), and they can deliver energy to similar or dissimilar sets of multiple delivery zones. In some embodiments, the first and second clinical procedures can include treating and/or delivering energy to contiguous and/or overlapping regions of the GI tract either in the circumferential and/or axial dimensions. In other embodiments, the first and second clinical procedures can include the treatment of disparate regions of the GI tract (such as disparate regions of the duodenum, ileum, and/or stomach). The first and second clinical procedures can be performed using similar or dissimilar devices (e.g. catheters). The first and second clinical procedures can comprise similar or dissimilar deliveries of energy to treat the target tissue. The first and second clinical procedures can be performed at similar or dissimilar temperatures. The second clinical procedure can be performed based on diagnostic results collected after the first clinical procedure has been performed, such as when the diagnostic results are based on a biopsy of mucosal tissue.

The functional assemblies, treatment assemblies, treatment elements and other functional elements of the present inventive concepts can comprise an expandable element or otherwise be configured to automatically and/or manually expand or traverse in at least one radial direction. Typical expandable elements include but are not limited to: an inflatable balloon; a radially expandable cage or stent; one or more radially deployable arms; an expandable helix; an unfurlable compacted coiled structure; an unfurlable sheet; an unfoldable compacted structure; and combinations of one or more of these. In some embodiments, an expandable element can comprise a radially expandable tube, such as a sheet of material resiliently biased in a radially expanded condition that can be compacted through a furling operation, or a sheet of material resiliently biased in a radially compact condition that can be expanded through an unfurling operation. An expandable element can comprise a foldable sheet, such as a sheet configured to be folded to be radially compacted and/or to be unfolded to radially expand. In some embodiments, an expandable element expands to contact tissue, such as to expand to a diameter similar to the diameter of the luminal wall tissue into which the expandable element has been placed. In some embodiments, an expandable element expands to be closer to wall tissue, but remain at a distance (e.g. a fixed or pre-determined distance) from the tissue surface, such as when the tissue is subsequently brought into contact with all or a portion of an expanded functional assembly or functional element (e.g. using insufflation fluid withdrawal techniques). In some embodiments, an expandable element expands to be larger than the diameter of the luminal wall tissue into which the expandable element has been placed, such as to improve the quality of the apposition of the expandable element against the uneven surface of the tissue. In these embodiments, the fully expanded diameter of an expandable element would be configured to avoid a diameter large enough to cause lasting mechanical damage to the apposed tissue and/or to tissue proximate the apposed tissue. In some embodiments, the expansion of an expandable element (e.g. the expansion of an expandable functional assembly) is monitored and/or varied (e.g. decreased and/or increased), such as to accommodate or otherwise compensate for peristalsis or other muscle contractions that occur in the GI tract (e.g. contractions that occur when a foreign body is present in the GI tract) and/or varied to accommodate changes in GI lumen diameter imposed by aspects of the procedure itself.

Any device (e.g. catheter) of the present inventive concepts can include one or more functional elements comprising one or more treatment elements configured to deliver energy to one or more delivery zones, to treat at least a portion of target tissue. Any device can include one or more functional elements comprising one or more fluid delivery elements, such as one or more nozzles or needles configured to deliver fluid toward and/or into tissue. The fluid delivery elements can be constructed and arranged to deliver fluid to perform a function selected from the group consisting of: expanding one or more tissue layers; warming or cooling tissue; removing debris or other substance from a tissue surface; delivering energy to a delivery zone comprising a continuous or segmented surface; treating target tissue; and combinations of one or more of these. Any of the expandable functional assemblies of the present inventive concepts can include one or more other functional elements, such as are described herein. The treatment elements and/or other functional elements (e.g. fluid delivery elements) can be mounted on, within (e.g. within the wall) and/or inside of an expandable element such as a balloon or expandable cage. In some embodiments, one or more functional elements is not mounted to an expandable element, such as those attached to a shaft or other non-expandable catheter component.

In some embodiments, a catheter comprises at least one functional element configured to deliver energy to a delivery zone such as to ablate target tissue. Examples of ablation-based functional elements include but are not limited to: ablative fluids, such as hot or cold ablative fluids delivered to a balloon and/or directly to target tissue; one or more fluid delivery elements configured to deliver ablative fluid directly to target tissue; an RF and/or microwave energy delivery element such as one or more electrodes; an ultrasonic and/or subsonic transducer such as one or more piezo crystals configured to ablate tissue with ultrasonic or subsonic energy, respectively, sound waves; a laser energy delivery element such as one or more optical fibers, laser diodes, prisms and/or lenses; a rotating ablation element; a circumferential array of ablation elements; and combinations of one or more of these.

The expandable elements comprising balloons of the present inventive concepts can be divided into two general categories: those that are composed of a substantially elastic material, such as silicone, latex, low-durometer polyurethane, and the like; and those that are composed of a substantially inelastic material, such as polyethylene terephthalate (PET), nylon, high-durometer polyurethane and the like. A third category includes balloons which include both elastic and inelastic portions. Within the category of elastic balloons, two subcategories exist: a first sub-category wherein a combination of material properties and/or wall thickness can be combined to produce a balloon that exhibits a measurable pressure-threshold for inflation (i.e. the balloon becomes inflated only after a minimum fluidic pressure is applied to the interior of the balloon); and a second sub-category, wherein the balloon expands elastically until an elastic limit is reached which effectively restricts the balloon diameter to a maximum value. The individual properties of the balloons in each of these categories can be applied to one or more advantages in the specific embodiments disclosed herein, these properties integrated singly or in combination. By way of example only, one or more of the following configurations can be employed: a highly elastic balloon can be used to achieve a wide range of operating diameters during treatment (e.g. during operation a desired balloon diameter can be achieved by adjustment of a combination of fluid temperature and pressure); a substantially inelastic balloon or a balloon that reaches its elastic limit within a diameter approximating a target tissue diameter (e.g. a duodenal mucosal diameter) can be used to achieve a relatively constant operating diameter that will be substantially independent of operating pressure and temperature; a balloon with a pressure-threshold for inflation can be used to maintain an uninflated diameter during relatively low pressure conditions of fluid flow and then achieve a larger operating diameter at higher pressure conditions of flow. Pressure-thresholded balloons can be configured in numerous ways. In one embodiment, a balloon is configured to have a relatively thick wall in its uninflated state, such as to maximize an electrically and/or thermally insulating effect while the balloon is maintained in this uninflated state. The balloon can be further configured such that its wall thickness decreases during radial expansion (e.g. to decrease an electrically and/or thermally insulating effect). In another embodiment, a balloon is configured to have a relatively small diameter in its uninflated state (e.g. a diameter that is small relative to the inner diameter of tubular target tissue such as the diameter of the mucosal layer of duodenal wall tissue), such as to minimize or completely eliminate apposition between the balloon and the surrounding tissue to minimize heat, RF and/or other energy transfer into the surrounding tissue until the balloon is fully inflated. In another embodiment, a balloon and an ablation system or catheter are configured to circulate a flow of fluid through the balloon (e.g. an elastic balloon or an inelastic balloon) at a sufficiently low enough pressure to prevent apposition of the balloon or other catheter component with target tissue, such as to pre-heat one or more surfaces of the ablation system or ablation device that are in fluid communication with the balloon. In this configuration, when the balloon or other ablation element is positioned to deliver energy to target tissue, the temperature of the balloon or other ablation element will be at a desired level or it will rapidly and efficiently reach the desired level for treatment (i.e. minimal heat loss to the fluid path components due to the pre-heating or pre-cooling). These configurations provide a method of delivering energy to tissue with an ablative fluid filled balloon. A "thermal priming" procedure can be performed prior to one or more target tissue treatments, such as to improve thermal response time of one or more portions of the catheter. Ablative fluid filled balloon catheters as well as thermal priming devices and methods can be configured as is described in applicant's co-pending U.S. patent application Ser. No. 14/470,503, entitled "Heat Ablation Systems, Devices and Methods for the Treatment of Tissue", filed Aug. 27, 2014, the content of which is incorporated herein by reference in its entirety for all purposes.

A fluid evacuation procedure can be performed on one or more internal locations of the catheters, functional assemblies and/or functional elements of the present inventive concepts, such as when a negative pressure is applied to purge or otherwise evacuate fluid from one or more locations. A fluid evacuation procedure can be performed prior to a thermal priming procedure and/or prior to delivering ablative fluid to a treatment element.

At times during target tissue treatment when it is desirable to initiate, increase and/or otherwise modify the treatment of tissue by one or more treatment elements (e.g. a fluid delivery element delivering ablative fluid, a mechanically abrasive element, a hot or cold fluid balloon delivering a thermal energy to tissue and/or an electrode delivering RF energy), the diameter of the treatment assembly and/or treatment element (e.g. the diameter of a balloon, deployable cage, expandable tube or other expandable assembly) can be increased in situ to move a treatment element closer to target tissue and/or to change the contact force between the treatment element and the target tissue. At times during treatment when it is desirable to stop or otherwise decrease the amount of tissue treatment, the diameter of the treatment assembly and/or treatment element can be reduced in situ, such as to prevent or otherwise reduce delivery of energy or other treatment to the target tissue by eliminating or reducing tissue contact of one or more treatment elements (e.g. electrodes, abrasive surfaces or ablative fluid-filled balloons). For those cases where the native diameter of the target tissue varies substantially within a delivery zone, then a highly elastic or compliant balloon or other expandable element can be employed, such as a balloon or deployable cage which can be adjusted to achieve a wide range of operating diameters.

Alternatively or additionally, to initiate, increase and/or otherwise modify the treatment of tissue by one or more functional elements (e.g. a fluid delivery element delivering ablative fluid, a mechanically abrasive element, a hot or cold fluid balloon delivering thermal energy to or from tissue and/or an electrode delivering RF energy), the diameter of the target tissue can be decreased in situ to move target tissue closer to a treatment element and/or to change the contact force between the target tissue and the treatment element. To stop or otherwise decrease ablation of tissue, the diameter of tissue neighboring a treatment element can be increased in situ, such as to prevent or otherwise reduce delivery of energy or other treatment to the target tissue by eliminating or reducing tissue contact of one or more treatment elements (e.g. electrodes, abrasive surfaces or ablative fluid filled balloons). The diameter of the tissue proximate a functional assembly can be increased or decreased, independent of the functional assembly diameter, by means of delivering and/or withdrawing a fluid, to and/or from a body lumen (e.g. a lumen of a segment of the intestine) surrounded by target tissue, such as by using standard GI insufflation techniques. Typical insufflation fluids include but are not limited to: gases such as carbon dioxide or air; liquids such as water or saline solution; and combinations of one or more of these. The insufflation fluids can be introduced through a catheter, through an endoscope such as an endoscope through which the catheter is inserted, and/or via another device placed proximate the target tissue. Delivery of insufflation fluids can be performed to move target tissue away from one or more functional elements, such as to stop transfer of energy to target tissue at the end of a treatment of target tissue as described hereabove. Alternatively or additionally, delivery of insufflation fluids can be performed to manipulate tissue, such as to distend and/or elongate tissue. Extraction of these insufflation fluids and/or the application of a vacuum or other negative pressure can be used to decrease the diameter of the target tissue, such as to bring the target tissue in closer proximity to one or more functional elements and/or to increase the contact force between target tissue and one or more functional elements, also as described hereabove. In this tissue diameter controlled approach, a functional assembly including a balloon that can be maintained at a substantially constant diameter can be desirable, such as a substantially inelastic balloon such as a balloon with an elastic-limit.

The systems of the present inventive concepts can include one or more tissue expansion catheters that comprise one or more functional elements configured as fluid delivery elements. In these embodiments, the one or more functional elements can comprise one or more needles, nozzles and/or fluid jets configured to deliver one or more fluids or other injectates to tissue, such as to expand target tissue and/or tissue proximate the target tissue (e.g. safety margin tissue) prior to treatment of target tissue by a tissue treatment element. The expanded tissue layer acts as a safety volume of tissue, reducing the specificity of the treatment (e.g. ablation) required and/or the need to protect the underlying non-target tissue from damage. In some embodiments, a vacuum pressure can be used to manipulate tissue and/or to maintain proximity between a portion of a tissue expansion device and tissue. The vacuum can be provided by one or more vacuum sources, such as via one or more operator adjustable vacuum sources.

Referring now to FIG. 1, a schematic view of a system and device for performing a medical procedure on a patient is illustrated, consistent with the present inventive concepts. The medical procedure can comprise a diagnostic procedure, a therapeutic procedure or a combined diagnostic and therapeutic procedure. System 10 comprises one or more catheters 100 (e.g. a catheter, flexible probe, or other elongate device for insertion into a patient, hereinafter "catheter"), and console 200 which operably attaches to the one or more catheters 100 (e.g. two, three or more catheters 100). Catheter 100 comprises an elongate shaft, shaft 110, comprising one or more shafts. In some embodiments, shaft 110 comprises multiple shafts in a spiraled configuration (e.g. helical configuration) such as is described herebelow in reference to FIG. 11. In some embodiments, shaft 110 comprises a non-circular cross section, such as the non-circular cross section of shaft 110 described herebelow in reference to FIG. 32 (e.g. to "hug" a second device such as an endoscope simultaneously inserted into the patient). In some embodiments, shaft 110 comprises one or more of: a braided portion; a tapered portion; an insertable stiffening mandrel; a variable stiffness portion; and combinations of one or more of these, as described herebelow.

Catheter 100 comprises functional assembly 130, which can be configured to radially expand and contract. Functional assembly 130 can be positioned on a distal portion of catheter 100 (e.g. on the distal end or a distal portion of shaft 110). In some embodiments, functional assembly 130 comprises a non-circular cross section, such as the non-circular cross section of functional assembly 130 described herebelow in reference to FIG. 33 (e.g. to "hug" a second device such as an endoscope simultaneously inserted into the patient). Functional assembly 130 can comprise one or more tissue-contacting portions, as described hereabove (e.g. side walls of functional assembly 130 that contact inner wall tissue of the intestine or other GI lumen). Functional assembly 130 can comprise a tissue-contacting surface area (e.g. when expanded) of between 500 $mm^2$ to 3500 $mm^2$, such as a tissue contacting surface area of approximately between 1000 $mm^2$ and 2000 $mm^2$, or approximately between 1250 $mm^2$ and 1750 $mm^2$, or approximately 1500 $mm^2$. In some embodiments, functional assembly 130 comprises an expanded diameter of approximately 19 mm, 22 mm, 25 mm or 28 mm. In some embodiments, functional assembly 130 comprises a tissue-contacting length (e.g. when expanded) of between 10 mm and 40 mm, such as a length of approximately 15 mm, 20 mm, 25 mm or 30 mm. In some embodiments, system 10 includes a first catheter 100 comprising a functional assembly 130a with a first geometry, and a second catheter 100 comprising a functional assembly 130b with a second geometry different than the first geometry (e.g. a different length, expanded diameter; and/or tissue contacting surface area).

Figure 2:
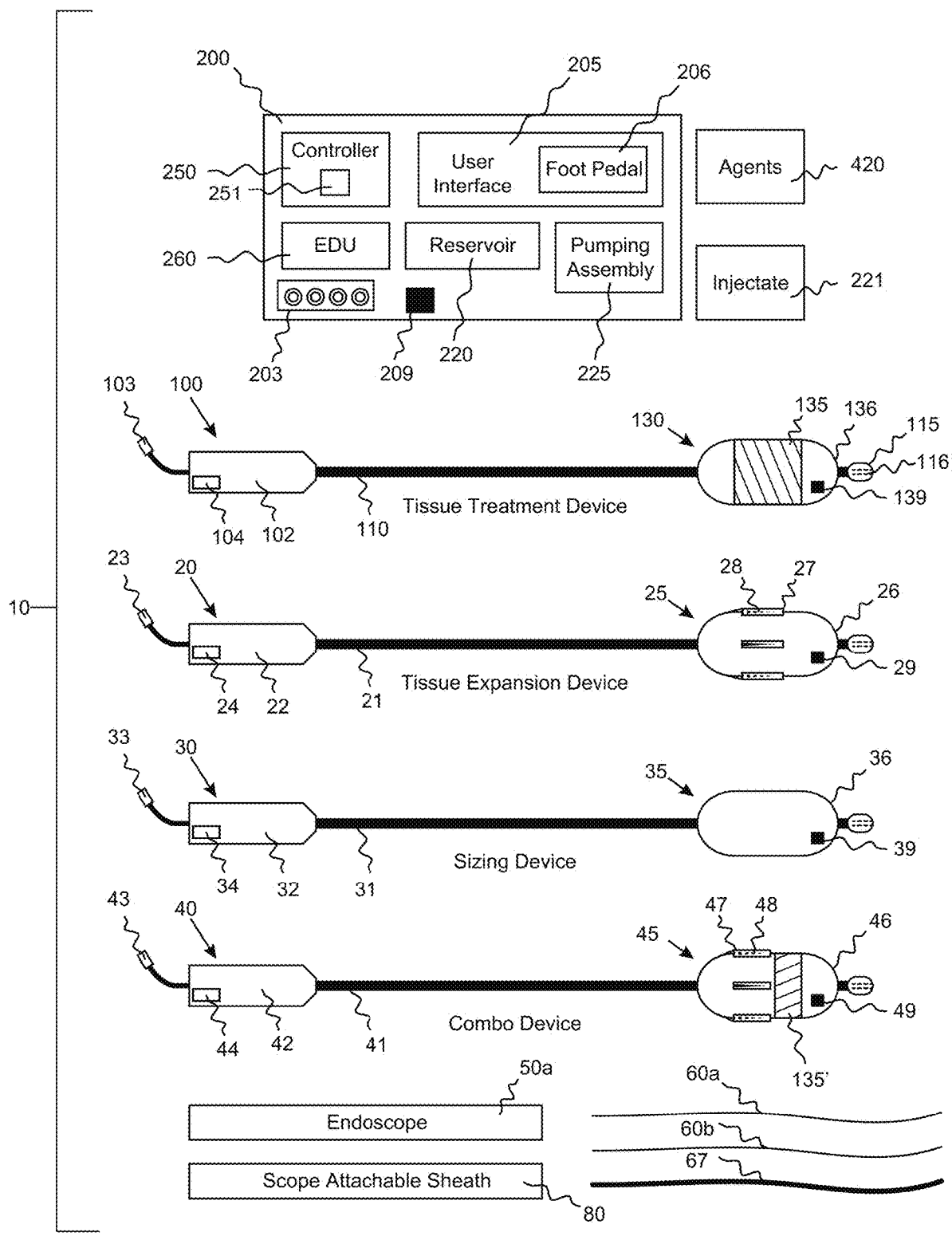
FIG. 2 is a schematic view of a system and device for performing a medical procedure on the small intestine of a patient, consistent with the present inventive concepts.

Catheter 100 can comprise one or more catheters of similar construction and arrangement (e.g. and include similar components) as one or more of devices 100, 20, 30 and/or 40 of FIG. 2, each described in detail herebelow. Catheter 100 can be constructed and arranged to perform a medical procedure in an intestine of the patient, such as a procedure in the small intestine (e.g. in the duodenum) and/or in the large intestine. In some embodiments, system 10 further comprises connecting assembly 300 which can be constructed and arranged to operably attach (e.g. fluidly, mechanically, electrically and/or optically connect) catheter 100 to console 200. In alternate embodiments, catheter 100 can operably attach directly to console 200, without connecting assembly 300. Console 200 can be of similar construction and arrangement as console 200 of FIG. 2, also described in detail herebelow.

System 10 can further comprise body introduction device 50, one or more guidewires 60, a sheath 80 (e.g. an endoscope-attachable sheath), injectate 221 and/or agent 420, each of which can be of similar construction and arrangement to the similar components described in detail herebelow in reference to FIG. 2. In some embodiments, guidewire 60 comprises a guidewire of similar construction and arrangement to that described herebelow in reference to FIG. 26 or 26A. Body introduction device 50 can comprise an endoscope, a laparoscopic port and/or a vascular introducer. Body introduction device 50 can comprise a camera, such as camera 52, and a display, not shown but such as a display of console 200 and/or another display used to display an image (i.e. camera view) provided by camera 52.

In some embodiments, system 10 further comprises imaging device 55, which can comprise an imaging device constructed and arranged to provide an image of the patient's anatomy (e.g. inner wall or any part of the intestine of the patient) and/or an image of all or part of catheter 100 or other portion of system 10, as described in detail herein. Imaging device 55 can comprise an imaging device selected from the group consisting of: endoscope camera; visible light camera; infrared camera; X-ray imager; fluoroscope; Ct Scanner; MRI; PET Scanner; ultrasound imaging device; and combinations of one or more of these. In some embodiments, a patient image is used to set, confirm and/or adjust one or more system 10 parameters, such as is described herebelow in reference to FIG. 41, such as when imaging device 55 comprises a sensor of the present inventive concepts configured to produce a signal.

In some embodiments, system 10 further comprises functional element 19 comprising a sensor, transducer or other functional element. Functional element 19 can be operably attached to console 200 or another component of system 10. Functional element 19 can comprise a sensor configured to produce a signal, which can be used to modify a parameter of system 10, as described in detail herein. In some embodiments, functional element 19 comprises a sensor configured to measure a patient parameter, such as a patient parameter selected from the group consisting of: a patient physiologic parameter; blood pressure; heart rate; pulse distention; glucose level; blood glucose level; blood C-peptide level; blood glucagon level; blood insulin level; blood gas level; hormone level; GLP-1 level; GIP level; EEG; LFP; respiration rate; breath distention; perspiration rate; temperature; gastric emptying rate; peristaltic frequency; peristaltic amplitude; a patient anatomical parameter such as tissue geometry information; a patient environment parameter such as room pressure or room temperature; and combinations of one or more of these.

In some embodiments, system 10 further comprises tool 500, such as a tool 500 described herebelow.

In some embodiments, system 10 comprises one or more sensors, such as when one or more functional elements of system 10 are configured as a sensor, such as functional elements 109, 119, 139, 229 and/or 309 described in detail herebelow. Each of the system 10 sensors can be configured to produce a signal related to a patient parameter and/or a system 10 parameter. For purposes herein, a signal "related" to a parameter shall include signals that directly represent the parameter, as well as signals that provide information that can be correlated to or in any way relate to the parameter. For example, a sensor (e.g. a temperature or pressure sensor) placed proximate tissue or a component of system 10 can directly represent a parameter (e.g. the temperature or pressure, respectively) of or within that tissue or component. Alternatively, a sensor placed at one location (e.g. one location within system 10), can provide a signal that can be analyzed to produce information representing a parameter at a different location (e.g. a different location within system 10 or a location within the patient). For example, a temperature or pressure measured at one location (e.g. within console 200, connecting assembly 300 and/or a proximal portion of catheter 100) can correlate to a temperature or pressure at a different location (e.g. proximate and/or within functional assembly 130). Correlation of signals provided by a sensor of system 10 to a parameter at a location distant from the sensor can be accomplished by one or more algorithms of system 10, such as algorithm 251 described herebelow.

In some embodiments, a system 10 sensor is configured to produce a signal related to an anatomic and/or physiologic parameter of the patient, such as a parameter selected from the group consisting of: a parameter of the intestine; a parameter related to the anatomical geometry of a portion of the intestine; a parameter related to force and/or pressure applied to tissue (e.g. tissue of the intestine); a parameter related to a pressure within tissue (e.g. tissue within the luminal surface of the intestine); a parameter related to temperature of tissue (e.g. tissue of the intestine); and combinations of one or more of these. In some embodiments, one or more sensors of system 10 comprise a camera configured to provide an image, and the signal provided by the sensor comprises the image or an analysis of the image. The signal provided by the sensor can relate to a patient parameter (e.g. a patient physiologic or anatomical parameter) or a system 10 parameter (e.g. a functional assembly 130 parameter).

In some embodiments, a system 10 sensor is configured to produce a signal related to a parameter of one or more components of system 10, such as a component of console 200, connecting assembly 300 and/or catheter 100. For example, the signal produced by one or more sensors of system 10 can be related to a functional assembly 130 parameter, such as a parameter selected from the group consisting of: pressure within functional assembly 130; force applied to and/or by a portion of functional assembly 130; temperature of at least a portion of functional assembly 130; temperature of fluid within functional assembly 130; state of expansion of functional assembly 130; position of functional assembly 130 (e.g. position of functional assembly 130 relative to the patient's anatomy): and combinations of one or more of these.

In some embodiments, system 10 is configured to perform a therapeutic procedure selected from the group consisting of: a tissue removal procedure such as a tissue removal procedure in which mucosal intestinal tissue is removed; a tissue ablation procedure such as a tissue ablation procedure in which at least intestinal mucosal tissue is removed; a tissue expansion procedure such as a tissue expansion procedure configured to create a safety margin of tissue and/or a tissue expansion procedure configured to create a therapeutic restriction; and combinations of one or more of these. In some embodiments, system 10 is configured to treat one or more patient diseases and/or disorders, such as are described hereabove. For example, system 10 can be configured to treat diabetes, such as Type 2 diabetes, Type 1 diabetes, "Double diabetes" and/or gestational diabetes. In some embodiments, system 10 is configured to treat hypercholesterolemia, such as when target tissue treated by functional assembly 130 includes tissue of the terminal ileum. In some embodiments, system 10 is configured to treat both diabetes and hypercholesterolemia. In some embodiments, system 10 is configured such that functional assembly 130 treats a part of the intestine exhibiting inflammatory bowel disease, ulcerative colitis and/or chronic ulcers. System 10 can be constructed and arranged to cause functional assembly 130 to expand one or more layers of tissue (e.g. submucosal tissue), and/or to treat target tissue (e.g. target tissue comprising mucosal tissue of the duodenum or other intestinal mucosa). System 10 can be further constructed and arranged to avoid adversely affecting non-target tissue, as described in detail herein and in applicant's co-pending application Ser. No. 13/945,138, entitled "Devices and Methods for the Treatment of Tissue", filed Jul. 18, 2013, the content of which is incorporated herein by reference in its entirety for all purposes.

In some embodiments, system 10 is constructed and arranged to alter intestinal microbiota, such as to perform a treatment that affects a patient's gut flora in a way that leads to an improvement in weight and/or metabolic status (e.g. to treat Type 2 diabetes). Catheter 100 and functional assembly 130 can be configured to treat target tissue including intestinal mucosa such as to destroy local bacteria and/or modify the microbiome in the treated tissue area. Target tissue can include tissue regions where the microbiota contribute to the incidence or maintenance of metabolic disease.

In some embodiments, system 10 is constructed and arranged to reduce or otherwise alter the surface area of intestinal mucosa, such as is described in applicant's co-pending U.S. patent application Ser. No. 14/956,710, entitled "Methods, Systems and Devices for Reducing the Luminal Surface Area of the Gastrointestinal Tract", filed Dec. 2, 2015, the content of which is incorporated herein by reference in its entirety for all purposes. In some embodiments, system 10 is configured to reduce or otherwise alter the surface area of intestinal mucosa as a treatment for diabetes, a metabolic disease, obesity and/or hypercholesterolemia. In these embodiments, treatment of target tissue comprising mucosal folds and/or other mucosal tissue results in intestinal mucosa with reduced plicae circulares and delayed recovery or regrowth of intestinal villi. The treatment provided by system 10 can comprise a durable treatment effect that reduces the total absorptive surface area of the treated region. Alternatively or additionally, the treatment provided by system 10 can reduce enteroendocrine cell and/or absorptive cell quantities in the intestine by reducing the geometric complexity of the intestinal surface, such as by a target tissue treatment comprising ablation of intestinal tissue to a certain depth (mucosa alone; mucosa and superficial submucosa; mucosa through mid submucosa; or mucosa through deep submucosa) that induces the healing response that leads to elimination of plicae circulares and blunting of villi for a prolonged period of time (at least 2 weeks, at least 6 weeks, at least 6 months or at least one year).

In some embodiments, system 10 is configured to treat sufficient duodenal mucosa to provide an improvement in a patient's diabetes, such as is described in applicant's co-pending International Patent Application Serial Number PCT/US2015/040775, entitled "Methods and Systems for Treating Diabetes and Related Diseases and Disorders", filed Jul. 16, 2015, the content of which is incorporated herein by reference in its entirety for all purposes.

In some embodiments, system 10 is configured to create a therapeutic restriction in a patient, such as is described in applicant's co-pending U.S. patent application Ser. No. 15/156,585, entitled "Systems, Devices and Methods for the Creation of a Therapeutic Restriction in the Gastrointestinal Tract", filed May 17, 2016, the content of which is incorporated herein by reference in its entirety for all purposes. In some embodiments, the therapeutic restriction is created at a location selected from the group consisting of: within mucosal tissue; within submucosal tissue; between mucosal and submucosal tissue; and combinations thereof. In some embodiments, the therapeutic restriction is created at a location selected from the group consisting of: lower stomach; pylorus; proximal small intestine; duodenum; proximal jejunum; distal small intestine; distal jejunum; ileum; and combinations thereof. In some embodiments, the therapeutic restriction is created in a location selected from the group consisting of: colon; rectum; anal sphincter and combinations thereof. In some embodiments, the therapeutic restriction is created by injecting (e.g. via one or more fluid delivery elements 139c) a volume of injectate 221 of at least 1.0 mL. The therapeutic restriction can be created by injecting a volume of injectate 221 of at least 3.0 mL, or at least 4.0 mL. In some embodiments, the therapeutic restriction is created by injecting a volume of injectate 221 of no more than 20.0 mL. The therapeutic restriction can be created by injecting a volume of injectate 221 of no more than 10.0 mL, or no more than 8.0 mL. In some embodiments, the therapeutic restriction comprises an axial length between 1 mm and 100 mm. The therapeutic restriction can comprise an axial length between 1 mm and 20 mm. In some embodiments, the therapeutic restriction comprises an inner diameter (e.g. diameter of its open portion) that is less than or equal to 10 mm. The therapeutic restriction can comprise an inner diameter less than or equal to 5 mm, 4 mm, 3 mm, 2 mm or 1 mm. In some embodiments, the therapeutic restriction comprises an inner diameter that is between 1% and 50% (e.g. 99% to 50% narrowing, respectively) of the inner diameter of the luminal segment prior to creation of the therapeutic restriction. The therapeutic restriction can comprise an inner diameter that is between 1% and 20% of the inner diameter of the luminal segment prior to creation of the therapeutic restriction. The inner diameter of the therapeutic restriction can increase over time, such as via the therapeutic restriction volume decreasing over time such as via absorption, migration or other reduction of the delivered injectate 221. The inner diameter of the therapeutic restriction can increase to an inner diameter that is between 11% and 20% of the inner diameter of the luminal segment prior to creation of the therapeutic restriction. The therapeutic restriction can comprise an inner diameter that is between 1% and 10% of the inner diameter of the luminal segment prior to creation of the therapeutic restriction. The therapeutic restriction can comprise an inner diameter that is between 1% and 5% of the inner diameter of the luminal segment prior to creation of the therapeutic restriction.

System 10 can be constructed and arranged to perform one or more diagnostic procedures. In some embodiments, system 10 is constructed and arranged to perform a lumen sizing procedure, such as a procedure in which one or more diameters of one or more lumen locations in the intestine are determined (e.g. estimated). In these embodiments, the relative location at which the diameter is determined can be maintained at a pressure at or near room pressure (e.g. via one or more lumens of catheter 100 and/or body introduction device 50. System 10 can be constructed and arranged to perform a patient imaging procedure, such as a procedure in which a patient image is collected, such as a patient image that includes functional assembly 130 positioned in a segment of the intestine. System 10 can be constructed and arranged to perform a tissue sampling procedure, such as in a biopsy procedure. In some embodiments, system 10 is constructed and arranged to perform a diagnostic and/or other procedure selected from the group consisting of: assessment of mucosal thickness and/or hypertrophy, such as while using OCT or similar imaging technologies; assessment of wall thickness, such as via endoscopic ultrasound or similar imaging technologies; visualization of enteroendocrine cell populations, such as via molecular imaging techniques or antibody labeling; assessment of the location of the ampulla of Vater, such as via bile acid labeling; and combinations of one or more of these. In some embodiments, system 10 is constructed and arranged to perform a therapeutic and/or other procedure selected from the group consisting of: an obesity treatment procedure, such as an endoluminal implant of a balloon or other volume reducing and/or restricting device in the stomach or small intestine, a suturing or anastomosing procedure to reduce and/or restrict gastrointestinal volume, and/or an intestinal bypass; a procedure including the injection of sclerosing material configured to induce scar formation; a procedure including the injection of material to create a therapeutic restriction; a procedure including the injection of drugs or other agents into the submucosal space; a microbial transplantation procedure, such as to alter gut microbial populations; and combinations of one or more of these.

In some embodiments, system 10 is constructed and arranged to perform a patient assessment, such as a patient screening to determine if an intestinal tissue ablation (e.g. a duodenal mucosa ablation) would benefit the patient. In these embodiments, system 10 and/or the methods of the present inventive concepts can be configured to compare glucagon administered orally (PO) versus glucagon administered intravenously (IV). Data gathered can include the difference in the patient's ability to suppress glucagon after a meal. Patient's whose ability to suppress glucagon falls below a threshold can be selected to receive a treatment of the present inventive concepts (e.g. an ablation or other treatment to at least the duodenal mucosa). Alternatively or additionally, analysis of fasting and/or postprandial glucagon can be compared to a threshold, and patients whose level is above the threshold can be selected to receive a treatment of the present inventive concepts (e.g. a treatment to at least the duodenal mucosa).

Catheter 100 of system 10 includes shaft 110, typically a flexible shaft comprising one or more lumens. In some embodiments, shaft 110 comprises varied flexibility along its length, such as is described herebelow in reference to FIG. 27. Positioned on the distal end of catheter 100 is bulbous tip 115. Bulbous tip 115 can comprise a diameter of at least 4 mm and/or a diameter less than or equal to 15 mm. In some embodiments, bulbous tip 115 comprises an inflatable bulbous tip as described herebelow in reference to FIG. 5B. An operator graspable handle, handle 102 is positioned on the proximal end of shaft 110. Handle 102 can comprise a user interface 105, such as user interface 105 shown. User interface 105 can comprise one or more user input components and/or user output components. User interface 105 can comprise one or more user input components configured to allow an operator to modify one or more console settings 201, such as an operator-based modification based on information provided via a signal produced by a sensor of system 10. User interface 105 can comprise a control (e.g. control 104 described herebelow in reference to FIG. 2) or other user input component selected from the group consisting of: switch; keyboard; membrane keypad; knob; lever; touchscreen; and combinations of one or more of these. User interface 105 can comprise a user output component selected from the group consisting of: light such as an LED; display; touchscreen; audio transducer such as a buzzer or speaker; tactile transducer such as an eccentric rotational element; and combinations of one or more of these.

Catheter 100 further includes functional assembly 130, which can be positioned on a distal portion 100$_{DP}$ of catheter 100 as shown. Functional assembly 130 can be constructed and arranged to perform a patient diagnosis and/or perform a patient treatment, such as a diagnosis or treatment performed on tissue of the intestine. In some embodiments, functional assembly 130 comprises an expandable assembly constructed and arranged to radially expand as determined by an operator of system 10. Functional assembly 130 can comprise an expandable element selected from the group consisting of: an inflatable balloon (e.g. balloon 136 as shown); a radially expandable cage or stent; one or more radially deployable arms; an expandable helix; an unfurlable compacted coiled structure; an unfurlable sheet; an unfoldable compacted structure; and combinations of one or more of these. Functional assembly 130 is shown in a radially expanded state in FIG. 1. Balloon 136 can comprise a compliant balloon, a non-compliant balloon and/or a balloon with compliant and non-compliant sections, as described hereabove. Balloon 136 can comprise a pressure-thresholded balloon, also as described hereabove. Balloon 136 can comprise a multi-layer construction, such as a construction with different materials positioned in different layers of balloon 136. In some embodiments, at least the distal portion of catheter 100, distal portion 100$_{DP}$, is constructed and arranged to be: inserted through an endoscope such as body introduction device 50; inserted alongside an endoscope; inserted over a guidewire such as guidewire 60; inserted through a sheath such as scope attachable sheath 80; inserted through an introducer such as sheath 90 (e.g. an introducer sheath); and combinations of one or more of these.

Positioned within shaft 110 are one or more conduits or lumens, conduits 111. Conduits 111 can comprise a conduit selected from the group consisting of: a fluid transport conduit (e.g. a tube or lumen configured to deliver fluids to functional assembly 130 and/or extract fluids from functional assembly 130); a tube comprising a lumen; a tube comprising a translatable rod; a hydraulic tube; a pneumatic tube; a tube configured to provide a vacuum (e.g. provide a vacuum to port 137); a lumen of shaft 110; an inflation lumen; a lumen configured to provide a vacuum (e.g. provide a vacuum to port 137); a fluid delivery lumen; a wire such as an electrically conductive wire; a linkage; a rod; a flexible filament; an optical fiber; and combinations of one or more of these. One or more conduits 111 can be configured to: transport fluid (e.g. deliver fluid and/or extract fluid); extract fluid; provide a positive pressure; provide a vacuum; and combinations of one or more of these. One or more conduits 111 can comprise a hollow tube, such as a tube comprising polyimide and/or a tube comprising a braid, such as a braided polyimide tube. One or more conduits 111 can be configured to allow the transport of: power, signals and/or materials such as fluids. A conduit 111 can be configured to slidingly receive a guidewire (e.g. guidewire 60), such as for over-the-wire delivery of catheter 100, such as when a conduit 111 is operably connected to guidewire lumen 116 of bulbous tip 115. Alternatively, guidewire lumen 116 can both enter and exit bulbous tip 115 (as shown in FIG. 1), such as for rapid-exchange manipulation of catheter 100 over a guidewire. In some embodiments, one or more conduits 111 can be translated within shaft 110 (e.g. advanced and/or retracted), such as to change the position of a distal end of a conduit 111 (e.g. to change the position of an outflow tube or inflow tube within functional assembly 130).

Shaft 110 can comprise one or more functional elements, such as functional element 119 shown. Functional element 119 can be positioned on (e.g. on the outer surface of), in (e.g. within the wall of) and/or within (e.g. within a lumen of) shaft 110. Functional element 119 can be positioned proximate (e.g. nearby, on, in and/or within) one or more conduits 111, such as when functional element 119 comprises a valve, heating element and/or cooling element configured to exert a force and/or alter the temperature of one or more fluids passing within a conduit 111.

Functional assembly 130 can comprise one or more functional elements 139, such as treatment element 139a, sensor 139b and/or fluid delivery element 139c. Each functional element 139 can comprise a sensor, a transducer and/or other functional element, as described in detail herein.

In some embodiments, one or more functional elements 139 are constructed and arranged as a tissue treatment element of the present inventive concepts, as described herein, such as when treatment element 139a comprises an energy delivery element configured to treat target tissue of the intestine. Treatment element 139a can be of similar construction and arrangement as treatment element 135 described herebelow in reference to FIG. 2. Treatment element 139a can comprise a treatment element selected from the group consisting of: an ablative fluid (e.g. an ablative fluid to be maintained within balloon 136 and/or an ablative fluid to be delivered onto tissue such as via a fluid delivery element 139c); an electrode configured to deliver radiofrequency (RF) or other electrical energy to tissue; an optical element (e.g. a lens or a prism) configured to deliver light energy to tissue; a sound energy delivery element such as a piezo crystal configured to deliver ultrasound or subsonic sound energy to tissue; an agent delivery element such as a needle, nozzle or other fluid delivery element configured to deliver an ablative or other agent onto and/or into tissue; and combinations of one or more of these. In some embodiments, treatment element 139a comprises fluid at an ablative temperature. In these embodiments, treatment element 139a can comprise fluid whose temperature changes, such as when system 10 is configured to introduce a fluid both at an ablative temperature and fluid at a neutralizing temperature, such as when fluid at a neutralizing temperature is delivered within functional assembly 130 before and/or after fluid at an ablative temperature is delivered within functional assembly 130, as described in detail herein.

In some embodiments, one or more functional elements 139 are constructed and arranged to perform a diagnosis, such as when sensor 139b comprises a sensor configured to sense a physiologic parameter of intestinal tissue. Sensor 139b can comprise one or more sensors, such as are described in detail herebelow.

In some embodiments, one or more functional elements 139 are constructed and arranged to expand tissue, such as when fluid delivery element 139c comprises one or more of: a needle, nozzle, fluid jet, iontophoretic fluid delivery element, an opening in functional assembly 130 (e.g. an opening in balloon 136) and/or other fluid delivery element configured to deliver fluid into and/or onto tissue. In some embodiments, fluid delivery element 139c comprises an element (e.g. a needle or fluid jet) configured to deliver fluid into tissue, such as submucosal tissue, to expand the tissue receiving the injected fluid. Alternatively or additionally, fluid delivery element 139c can comprise an element (e.g. a nozzle) configured to deliver fluid onto tissue, such as ablative fluid delivered onto tissue to ablate and/or remove tissue or neutralizing fluid configured to reduce tissue trauma. Fluid delivery element 139c can comprise a needle selected from the group consisting of: a straight needle; a curved needle; a single lumen needle; a multiple lumen needle; and combinations of one or more of these. In some embodiments, one or more fluid delivery elements 139c comprise a tissue-engaging fluid delivery element, such as is described herebelow in reference to FIG. 30A or 30B. Fluid delivery element 139c can be positioned proximate and/or within a port, such as port 137 shown. Port 137 can be placed on top of balloon 136 and/or recessed into balloon 136 (e.g. positioned within a recess of balloon 136 or other component of functional assembly 130). Port 137 can be engaged between layers of balloon 136, such as when balloon 136 comprises multiple layers including an outer layer (e.g. a layer of PET) that surrounds at least a portion of port 137. In some embodiments, port 137 comprises an insulating element, such as an insulating element configured to prevent full circumferential ablation of an axial segment of intestine, as described herebelow in reference to FIG. 20. Port 137 can be positioned on a tissue-contacting portion of balloon 136 as shown. Port 137 can be attached to a source of vacuum, such as vacuum provided by a conduit 111, such that port 137 can engage with the tissue. Port 137 can be constructed and arranged such that tissue can be drawn into port 137, such as when tissue is drawn into port 137 prior to delivery of fluid by fluid delivery element 139c into tissue, as described herein. In some embodiments, catheter 100 comprises multiple ports 137 and multiple corresponding fluid delivery elements 139c, such as two, three or more pairs of ports 137 and fluid delivery elements 139c (e.g. equally spaced about a circumference of balloon 136). One or more functional elements 139 can be attached to one or more conduits 111 and can be configured to be translated (e.g. translated within a port 137). Translation of a fluid delivery element 139c can be limited by one or more mechanical stops constructed and arranged to limit advancement and/or retraction of fluid delivery element 139c. One or more fluid delivery elements 139c and a fluidly attached conduit 111 can be biased by one or more springs, such as one or more springs positioned in handle 102. Fluid delivery element 139c and an associated functional assembly 130 can be of similar construction and arrangement as those described herebelow in reference to catheter 20 and/or catheter 40 of FIG. 2, or as described in applicant's co-pending application Serial Number PCT/US2015/022293, entitled "Injectate Delivery Devices, Systems and Methods", filed Mar. 24, 2015, the content of which is incorporated herein by reference in its entirety for all purposes. One or more fluid delivery element 139c can comprise a straight or a curved needle. One or more fluid delivery elements 139c can be constructed and arranged to enter tissue at an angle between 0° and 90°, such as at an angle between 30° and 60°.

Functional assembly 130 can be configured to treat target tissue, such as when functional element 139 comprises ablative fluid introduced into balloon 136 or when functional element 139 comprises one or more energy delivery elements as described herein. Functional assembly 130 can be constructed and arranged to treat a full or partial circumferential axial segment of intestinal tissue (e.g. intestinal mucosa). System 10 can be configured to treat multiple axial segments of tissue, such as multiple relatively contiguous or discontiguous segments of mucosal tissue treated simultaneously and/or sequentially. The multiple segments can comprise overlapping and/or non-overlapping borders.

Catheter 100 is configured to operably attach to console 200. In some embodiments, catheter 100 attaches directly to console 200. In other embodiments, attachment assembly 300 is positioned and operably attached between catheter 100 and console 200, such as to transfer materials (such as injectate 221, agent 420, hydraulic and/or pneumatic fluid, ablative fluids and/or other fluids), energy (such as ablative fluids and/or electromagnetic energy), and/or data between catheter 100 and console 200. Attachment assembly 300 comprises end 301 which attaches to catheter 100 via port 103 of handle 102. Attachment assembly 300 further comprises end 302 which attaches to console 200 via port 203 of console 200. Conduits 311 of attachment assembly 300 operably attach conduits 111 of catheter 100 to conduits 211 of console 200. Attachment assembly 300 can comprise a cassette configuration configured to operably attach to console 200. Attachment assembly 300 can comprise one or more flexible portions (e.g. coiled tubes and/or filaments) that allow movement of catheter 100 relative to console 200, such as to extend catheter 100 away from console 200 and toward a table onto which a patient is positioned. Attachment assembly 300 can comprise one or more functional elements 309, such as an array of functional elements 309, each positioned proximate a conduit 311. Each functional elements 309 can comprise a sensor, transducer and/or other functional element as described in detail herein.

Console 200 is configured to operably control and/or otherwise interface with catheter 100. In some embodiments, console 200 comprises one or more pumping assemblies 225 (four shown in FIG. 1), which can each be attached to a reservoir 220 via one or more conduits 212. Each reservoir 220 can be constructed and arranged to store and supply fluids to catheter 100 and/or to extract fluids from catheter 100, such as is described herebelow in reference to system 10 of FIG. 2. An ablative fluid, a neutralizing fluid, agent 420 and/or injectate 221 can be placed or otherwise positioned within one or more reservoirs 220, such as to be transported by one or more pumping assemblies 225 into one or more conduits 111 of catheter 100 (e.g. via conduits 211 of console 200 and optionally via conduits 311 of connecting assembly 300). In some embodiments, console 200 is constructed and arranged to deliver a neutralizing fluid (e.g. a cooling fluid or warming fluid contained within a reservoir 220), then an ablative fluid (e.g. a hot fluid and/or a cryogenic fluid, respectively, contained within one or more reservoirs 220). In these embodiments, console 200 can be further constructed and arranged to subsequently deliver (i.e. after the ablation step), the same or a different neutralizing fluid (e.g. a cooling fluid contained within a reservoir 200). In some embodiments, a first reservoir 220 provides an ablative fluid comprising a hot fluid at a temperature above 44° C., such as above 65° C., above 75° C., above 85° C. or above 95° C., and a second reservoir 220 provides a neutralizing fluid comprising a cooling fluid below 37° C., such as below 20° C. or below 15° C. In some embodiments, a first reservoir 220 provides an ablative fluid comprising a cryogenic fluid, and a second reservoir 220 provides a neutralizing fluid comprising a warming fluid at or above 37° C.

Alternatively or additionally, console 200 can be configured to provide RF and/or light energy to functional assembly 130 to ablate or otherwise treat tissue, and a cooling step can be performed (e.g. via a neutralizing fluid provided by a reservoir 220 comprising fluid below 37° C.) prior to and/or after the delivery of the RF and/or light energy. In some embodiments, system 10 comprises two return paths, one for recovery of ablative fluid (e.g. hot fluid), and one for recovery of neutralizing fluid (e.g. cooling fluid), such as via separate conduits 111, 311 and/or 211. In these embodiments, two separate pumping assemblies 225 can be fluidly attached to the separate return paths.

Console 200 comprises one or more console settings 201 that can be varied, such as a change made manually (e.g. by a clinician or other operator of system 10), and/or automatically by system 10. Controller 250 can comprise one or more signal processors, such as signal processor 252 shown. Signal processor 252 can be configured to analyze one or more sensor signals, such as to modify one or more settings 201 of console 200. Controller 250 and/or signal processor 252 can comprise algorithm 251 which can be configured to perform one or more mathematical or other functions, such as to compare one or more sensor signals (e.g. compare the signal itself or a mathematical derivation of the signal) to a threshold. Console settings 201 can comprise one or more parameters (e.g. system parameters as also referred to herein) of catheter 100, console 200 and/or any component of system 10. Console settings 201 can comprise one or more parameters selected from the group consisting of: delivery rate of fluid into functional assembly 130; withdrawal rate of fluid from functional assembly 130; delivery rate of fluid into tissue; rate of energy delivered into tissue; peak energy level delivered into tissue; average energy delivery rate delivered into tissue; amount of energy delivered into tissue during a time period; temperature of an ablative fluid (e.g. temperature of an ablative fluid in reservoir 220, console 200, functional assembly 130 and/or catheter 100); temperature of a neutralizing fluid (e.g. temperature of a neutralizing fluid in reservoir 220, console 200, functional assembly 130 and/or catheter 100); temperature of functional assembly 130; pressure of functional assembly 130; pressure of fluid delivered into functional assembly 130; pressure of fluid delivered into tissue; duration of energy delivery; time of energy delivery (e.g. time of day of or relative time compared to another step); translation rate such as translation rate of a functional assembly 130; rotation rate such as rotation rate of a functional assembly 130; a flow rate; a recirculation rate; a heating rate or temperature; a cooling rate or temperature; a sampling rate (e.g. a sampling rate of a sensor); and combinations of one or more of these. In some embodiments, one or more console settings 201 comprise a setting related to a system 10 parameter selected from the group consisting of: pressure and/or volume of a fluid delivered to shaft 110 to change the stiffness of shaft 110 (e.g. to modify pushability and/or trackability); pressure and/or volume of a fluid delivered to and/or extracted from functional assembly 130 for inflation and/or deflation (e.g. to obtain apposition of ports 137 and/or to anchor functional assembly 130 in the intestine); pressure and/or volume of a fluid delivered to one or more conduits 111, each configured as a fluid transport tube to provide injectate 221 to one or more fluid delivery elements 139c (described herebelow) such as to advance and/or retract one or more fluid delivery elements 139c and/or to deliver injectate 221 into tissue (e.g. submucosal tissue); pressure and/or volume of a fluid within one or more conduits 111, each configured to provide a vacuum to one or more ports 137 to engage the one or more ports 137 with tissue and/or to cause a fluid delivery element to engage (e.g. penetrate) tissue; a force used to advance and/or retract one or more conduits 111 and/or one or more fluid delivery elements 139c; and combinations of one or more of these. In some embodiments, one or more console settings 201 comprise a setting related to a system 10 parameter selected from the group consisting of: temperature, flow rate, pressure and/or duration of fluid delivered to catheter 100 and/or functional assembly 130; temperature, flow rate, pressure and/or duration of fluid contained within functional assembly 130 and/or circulating loops (e.g. conduits 111, 211 and/or 311) of system 10: and combinations of one or more of these. System 10 can be configured to adjust one or more console settings 201 based on one or more signals produced by one or more sensors of system 10. Based on the one or more sensor signals, system 10 can be configured to modify a console setting 201 to cause: stopping delivery of fluid and/or energy to and/or by functional assembly 130; delivering additional fluid into functional assembly 130 and/or into tissue (e.g. adjust fluid delivery rate); delivering neutralizing and/or other additional fluid into functional assembly 130 and/or into tissue; adjusting the pressure of functional assembly 130; adjusting the volume of functional assembly 130; and combinations of one or more of these. In some embodiments, algorithm 251 is configured to determine an injectate delivery parameter, such as the amount (e.g. volume and/or mass) of injectate 221 to be delivered by catheter 100.

In some embodiments, system 10 adjusts a functional assembly 130 parameter based on a signal of a sensor of system 10. In these embodiments, a functional assembly 130 parameter can be adjusted during performance of a procedural step, such as an ablation step or a tissue expansion step. The functional assembly 130 parameter adjusted can comprise a parameter selected from the group consisting of: volume of functional assembly 130; diameter of functional assembly 130; pressure of functional assembly 130; force applied to tissue by functional assembly 130; and combinations of one or more of these. The functional assembly 130 parameter can be adjusted to prevent excessive force being applied to the intestinal wall or to maintain a minimum apposition level of functional assembly 130 with tissue of the intestine.

In some embodiments, console 200 comprises a first reservoir 220 containing hot fluid for ablation, a second reservoir 220 comprising cooling fluid at a first temperature (e.g. a temperature less than 37° C. but more than 10° C.), and a third reservoir 220 comprising fluid at a second temperature cooler than the first temperature (e.g. a temperature less than 6° C., such as a temperature between 2° C. and 4° C.). Fluid from the third reservoir 220 can be delivered into the second reservoir 220 (e.g. after one or more steps including cooling and ablation of tissue have been performed).

In some embodiments, console 200 comprises a first reservoir 220 containing hot fluid for ablation at a first temperature (e.g. approximately 55° C.), and a second reservoir 220 comprising hot fluid for ablation at a second temperature (e.g. approximately 95° C.). Fluid from the first reservoir 220 and the second reservoir 220 can be delivered to functional assembly 130 for equal time periods. In these embodiments, console 200 can further comprise a third reservoir 220 comprising cooling fluid, such as when console 200 is configured to deliver hot fluid from the first reservoir 220, followed by hot fluid from the second reservoir 220, followed by cooling fluid from the third reservoir 220. Console 200 can be further configured to deliver the cooling fluid prior to the delivery of the hot fluid from the first reservoir 220. In some embodiments, fluid from a reservoir 220 is delivered for a time period determined based on the temperature of fluid in that reservoir and/or based on the temperature of fluid in a separate reservoir 220, as described herebelow. For example, the amount of ablative fluid delivered by a reservoir 220 containing hot fluid can be adjusted based on the temperature of cooling fluid in a different reservoir 220.

In some embodiments, console 200 comprises two functional elements 209, a first functional element 209 comprising a heating element and a second functional element 209 comprising a cooling element. In these embodiments, connecting assembly 300 can comprise a tubeset configured to be engaged with console 200 to allow the first functional element 209 to transfer heat into fluid within connecting assembly 300 and the second functional element 209 to extract heat from (i.e. cool) fluid within connecting assembly 300. In these embodiments, system 10 can avoid the need for heated and/or cooled reservoirs 220, such as when console 200 further comprises a disposable fluid supply fluidly attached to connecting assembly 300. Connecting assembly 300 can comprise a reusable tubing set. Connecting assembly 300 can comprise a tubing set comprising multiple lumens (e.g. multiple tubes each with one or more lumens, or a single tube with multiple lumens), such as at least a first lumen configured to deliver inflation fluid (e.g. deliver inflation fluid to functional assembly 130 to perform a tissue expansion procedure and/or a tissue sizing procedure), and at least two lumens configured to deliver a recirculating fluid (e.g. to recirculate ablative hot or cold fluid within functional assembly 130 during a tissue ablation procedure).

Console 200 can comprise controller 250. Controller 250 can comprise user interface 205 which can deliver commands to controller 250 and receive information (e.g. to be displayed) from controller 250. In some embodiments, console 200 comprises energy delivery unit (EDU) 260, such as an energy delivery unit configured to provide one or more of: thermal energy such as heat energy or cryogenic energy; electromagnetic energy such as radiofrequency (RF) energy; light energy such as light energy provided by a laser; sound energy such as subsonic energy or ultrasonic energy; chemical energy; and combinations of one or more of these. EDU 260 can be of similar construction and arrangement as EDU 260 described herebelow in reference to FIG. 2. Console 200 can further comprise conduits 211 which can be operably connected to catheter 100 (e.g. operably connected to one or more conduits 111 or other components of catheter 100). Conduits 211 can comprise one or more fluid transport tubes fluidly attached to pumping assemblies 225 and/or any filament bundle operably attached to controller 250 and comprising one or more filaments selected from the group consisting of: a tube comprising a lumen; a tube comprising a translatable rod; a hydraulic tube; a pneumatic tube; a tube configured to provide a vacuum (e.g. provide a vacuum to port 137); a lumen of shaft 110; an inflation lumen; a fluid delivery lumen; a wire such as an electrically conductive wire; a linkage; a rod; a flexible filament; an optical fiber; and combinations of one or more of these. Controller 250 can be operably connected to one or more of reservoirs 220, pumping assemblies 225 and/or user interface 205 via bus 213. Bus 213 can comprise one or more wires, optical fibers or other conduits configured to provide power, transmit data and/or receive data.

In some embodiments, console 200 is configured to operably expand functional assembly 130, such as with a liquid or gas provided by a reservoir 220 and propelled by an associated pumping assembly 225. In some embodiments, console 200 is configured to deliver fluid to tissue via one or more fluid delivery elements 139c, such as with a fluid (e.g. injectate 221) provided by a reservoir 220 and propelled by an associated pumping assembly 225. In some embodiments, console 200 is configured to deliver ablative fluid to functional assembly 130, such as ablative fluid provided by a reservoir 220 and propelled by an associated pumping assembly 225. In these embodiments, ablative fluid can be recirculated to and from functional assembly 130 by console 200. In some embodiments, console 200 is configured to deliver energy, such as electromagnetic or other energy, to functional assembly 130, such as via controller 250. Each of these embodiments is described in detail herebelow in reference to system 10 of FIG. 2.

One or more reservoirs 220 can each comprise one more functional elements 229a and/or one or more pumping assemblies 225 can each comprise one or functional elements 229b. Each functional elements 229a and/or 229b (singly or collectively functional element 229) can comprise a sensor, a transducer or other functional element. In some embodiments, one or more functional elements 229 comprise a heating element or a chilling element configured to heat or chill fluid within a reservoir 220 and/or a pumping assembly 225. Alternatively or additionally, one or more functional elements 229 comprise a sensor, such as a temperature sensor, pressure sensor and/or a flow rate sensor configured to measure the temperature, pressure and/or flow rate, respectively, of fluid within a reservoir 220 and/or pumping assembly 225.

In some embodiments, controller 250 comprises one or more algorithms, such as algorithm 251 configured to operatively adjust one or more operating parameters of console 200 and/or catheter 100 (generally console settings 201), such as an algorithm that analyzes data provided by one or more sensors of system 10. Algorithm 251 can be configured to correlate a signal received by one or more sensors of system 10 positioned at a first location, to a parameter of system 10 or the patient at a second location distant from the first location (e.g. a second location proximal or distal to the first location). For example, a measured temperature or pressure within console 200 (e.g. via functional element 229*a* or 229*b*), connecting assembly 300 (e.g. via functional element 309) or catheter 100 (e.g. via functional element 119), can provide a signal related to a parameter at a remote location, such as a parameter of functional assembly 130 or the patient. Algorithm 251 can be configured to analyze a signal received from a first location, and produce parameter information correlating to a second location.

In some embodiments, console 200 is constructed and arranged to operably attach and control multiple catheters 100, such as two or more catheters 100 of similar construction and arrangement to devices 100, 20, 30 and/or 40 described herebelow in reference to FIG. 2.

In some embodiments, injectate 221 comprises a material selected from the group consisting of: water; saline; a gel; a hydrogel; a protein hydrogel; a cross-linked hydrogel; a cross-linked polyalkyleneimine hydrogel; autologous fat; collagen; bovine collagen; human cadaveric dermis; hyaluronic acid; calcium hydroxylapatite; polylactic acid; semi-permanent PMMA; dermal filler; gelatin; mesna (sodium 2-sulfanylethanesulfonate); and combinations of one or more of these. In some embodiments, injectate 221 comprises beads (e.g. pyrolytic carbon-coated beads) suspended in a carrier (e.g. a water-based carrier gel). In some embodiments, injectate 221 comprises a solid silicone elastomer (e.g. heat-vulcanized polydimethylsiloxane) suspended in a carrier, such as a bio-excretable polyvinylpyrrolidone (PVP) carrier gel. In some embodiments, injectate 221 has an adjustable degradation rate, such as an injectate 221 comprising one or more cross linkers in combination with polyalkyleneimines at specific concentrations that result in hydrogels with adjustable degradation properties. In some embodiments, injectate 221 and/or agent 420 comprises living cells, such as living cells injected into the mucosa or submucosa of the intestine to provide a therapeutic benefit.

In some embodiments, injectate 221 comprises a visualizable and/or otherwise detectable (e.g. magnetic) material (e.g. in addition to one or more materials of above) selected from the group consisting of: a dye; a visible dye; indigo carmine; methylene blue; India ink; SPOT™ dye; a visualizable media; radiopaque material; radiopaque powder; tantalum; tantalum powder; ultrasonically reflective material; magnetic material; ferrous material; and combinations of one or more of these.

In some embodiments, injectate 221 comprises a material selected from the group consisting of: a peptide polymer (e.g. a peptide polymer configured to stimulate fibroblasts to produce collagen); polylactic acid; polymethylmethacrylate (PMMA); a hydrogel; ethylene vinyl alcohol (EVOH); a material configured to polymerize EVOH; dimethyl sulfoxide (DMSO); saline; material harvested from a mammalian body; autologous material; fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; a sclerosant; an adhesive; cyanoacrylate; a pharmaceutical agent; a visualizable material; a radiopaque material; a visible dye; ultrasonically reflective material; and combinations of one or more of these. As described herein, in some embodiments, a volume of injectate 221 is delivered into tissue to create a therapeutic restriction (e.g. a therapeutic restriction with an axial length between 1 mm and 20 mm), as described herein, or as is described in applicant's co-pending U.S. patent application Ser. No. 15/156,585, entitled "Systems, Devices and Methods for the Creation of a Therapeutic Restriction in the Gastrointestinal Tract", filed May 17, 2016, the content of which is incorporated herein by reference in its entirety for all purposes. In some embodiments, a volume of injectate 221 is delivered into tissue to create a safety margin of tissue prior to an ablation procedure, as is described herein.

In some embodiments, injectate 221 comprises a fluorescent-labeled material or other biomarker configured to identify the presence of a biological substance, such as to identify diseased tissue and/or other tissue for treatment by functional assembly 130 (e.g. to identify target tissue). For example, injectate 221 can comprise a material configured to be identified by imaging device 55 (e.g. identify a visualizable change to injectate 221 that occurs after contacting one or more biological substances). In these embodiments, imaging device 55 can comprise a molecular imaging device, such as when imaging device 55 comprises a molecular imaging probe and injectate 221 comprises an associated molecular imaging contrast agent. In these embodiments, injectate 221 can be configured to identify diseased tissue and/or to identify a particular level of one or more of pH, tissue oxygenation, blood flow, and the like. Injectate 221 can be configured to be delivered onto the inner surface of intestinal or other tissue, and/or to be delivered into tissue (i.e. beneath the surface).

In some embodiments, agent 420 comprises a material selected from the group consisting of: anti-peristaltic agent, such as L-menthol (i.e. oil of peppermint); glucagon; buscopan; hycosine; somatostatin; a diabetic medication; an analgesic agent; an opioid agent; a chemotherapeutic agent; a hormone; and combinations of one or more of these.

In some embodiments, agent 420 comprises cells delivered into the intestine, such as living cells delivered into intestinal mucosa or submucosa via a fluid delivery element 139*c*.

System 10 comprises one or more sensors, transducers and/or other functional elements, such as functional element 109, functional element 119 and/or functional element 139 (e.g. 139*a*, 139*b* and/or 139*c*) of catheter 100 and/or functional element 209 and/or functional element 229 (e.g. 229*a* and/or 229*b*) of console 200. In some embodiments, system 10 comprises connecting assembly 300 which can include one or more functional elements 309.

In some embodiments, one or more functional elements 109, 119, 139, 209, 229 and/or 309 comprise a transducer selected from the group consisting of: an energy converting transducer; a heating element; a cooling element such as a Peltier cooling element; a drug delivery element such as an iontophoretic drug delivery element; a magnetic transducer; a magnetic field generator; a sound generator; an ultrasound wave generator such as a piezo crystal; a light producing element such as a visible and/or infrared light emitting diode; a motor; a pressure transducer; a vibrational transducer; a solenoid; a fluid agitating element; and combinations of one or more of these.

In some embodiments, one or more functional elements 109, 119, 139, 209, 229 and/or 309 comprise a visualizable element, such as an element selected from the group consisting of: a radiopaque marker; an ultrasonically visible marker; an infrared marker; a marker visualizable by a camera such as an endoscopic camera; a marker visualizable by an MRI, a chemical marker; and combinations of one or more of these.

In some embodiments, one or more of functional elements 109, 119, 139, 209, 229 and/or 309 comprise a sensor configured to produce a signal, the sensor selected from the group consisting of: physiologic sensor; blood glucose sensor; blood gas sensor; blood sensor; respiration sensor; EKG sensor; EEG sensor; neuronal activity sensor; blood pressure sensor; flow sensor such as a flow rate sensor; volume sensor (e.g. a volume sensor used to detect a volume of injectate 221 not delivered into tissue); pressure sensor; force sensor; sound sensor such as an ultrasound sensor; electromagnetic sensor such as an electromagnetic field sensor or an electrode; gas bubble detector such as an ultrasonic gas bubble detector; strain gauge; magnetic sensor; ultrasonic sensor; optical sensor such as a light sensor; chemical sensor; visual sensor such as a camera; temperature sensor such as a thermocouple, thermistor, resistance temperature detector or optical temperature sensor; impedance sensor such as a tissue impedance sensor; and combinations of one or more of these. Each sensor can be configured to produce a signal that directly correlates to or is otherwise related to a patient parameter or a system 10 parameter. One or more console settings 201 can be manually adjusted (e.g. by a clinician or other operator of system 10) and/or automatically (e.g. by an algorithm of system 10) based on the sensor signal.

In some embodiments, one or more of functional elements 109, 119, 139, 209, 229 and/or 309 comprise a pressure sensor that produces a signal related to one or more of: pressure within functional assembly 130; the level of apposition of functional assembly 130 with the intestine; the diameter of the intestine proximate functional assembly 130; muscular contraction of the intestine; pressure within a reservoir 220; pressure within connecting assembly 300; pressure within a lumen of shaft 110; and combinations of one or more of these. One or more console settings 201 can be adjusted (e g manually or automatically) based on the pressure sensor signal. In some embodiments, a pressure sensor produces a signal related to the pressure within functional assembly 130, console 200 delivers and/or extracts fluids to and/or from functional assembly 130 via one or more conduits 111, and console 200 adjusts the volume of functional assembly 130 to maintain pressure in functional assembly 130 below a threshold.

In some embodiments, one or more of functional elements 109, 119, 139, 209, 229 and/or 309 comprise a temperature sensor that produces a signal related to one or more of: temperature of fluid in console 200 (e.g. in one or reservoirs 220); temperature of elongate shaft 110; temperature of fluid within elongate shaft 110; temperature of functional assembly 130; temperature of fluid within functional assembly 130; temperature of an ablative fluid; temperature of a neutralizing fluid; temperature of tissue proximate the functional assembly; temperature of target tissue; temperature of non-target tissue; and combinations of one or more of these. One or more console settings 201 can be adjusted (e g manually or automatically) based on the temperature sensor signal.

In some embodiments, system 10 comprises a sensor (e.g. a functional element 109, 119, 139, 209, 229 and/or 309 comprising a sensor) configured to detect a parameter related to a level of treatment of tissue, such as a parameter selected from the group consisting of: color, density and/or saturation of tissue (e.g. a color change to tissue that occurs during ablation or to an injectate 221 present in the tissue during ablation or other treatment); temperature of local tissue and/or temperature of other body tissue; texture, length and/or diameter of villi or other mucosal feature (e.g. as detected via a camera-based sensor, such as when ablation causes a blunting and/or drooping of villi or other intestinal tissue); electrical resistance, impedance and/or capacitance of tissue (e.g. as altered by ablation of tissue); pressure and/or force of peristaltic contractions (e.g. as altered by ablation of tissue); compliance of tissue and/or the entire duodenum in radial and/or axial directions (e.g. as altered by ablation of tissue); chemical composition of film adhered to mucosal tissue (e.g. as altered by ablation); types, quantities and/or locations of bacterial colonies present (e.g. as altered by ablation); and combinations of one or more of these.

In some embodiments, system 10 comprises a sensor (e.g. a functional element 109, 119, 139, 209, 229 and/or 309 comprising a sensor) configured to detect a parameter related to a level of tissue expansion, such as a parameter selected from the group consisting of: color, density and/or saturation related to injected dye or particles which alter tissue appearance (e.g. as determined via a camera-based sensor); temperature of tissue (e.g. that can be altered briefly due to delivery of injectate 221 and/or inflammation response due to injectate 221 delivery); texture, length and/or diameter of villi or mucosal features (e.g. as determined via a camera-based sensor) such as spacing between villi or other intestinal tissue features that can change (e.g. increased spacing, disappearance or reduction of plicae, blebs of injectate 221 present) due to submucosal tissue expansion; electrical resistance, impedance and/or capacitance of tissue (e.g. as altered by delivery of injectate 221); pressure and/or force of peristaltic contractions (e.g. as altered by delivery of injectate 221); compliance of tissue and/or the entire duodenum in radial and/or axial directions (e.g. as altered by injectate 221, such as to make tissue more compliant until the muscularis layer is contacted); chemical composition of film adhered to mucosa (e.g. as altered by injectate 221, such as when injectate 221 creates a biologic response that is detectable); types, quantities and/or locations of bacterial colonies present; and combinations of one or more of these.

In some embodiments, system 10 comprises a sensor (e.g. a functional element 109, 119, 139, 209, 229 and/or 309 comprising a sensor) configured to assess engagement of port 137 with tissue (e.g. to determine if adequate engagement is present during a tissue expansion or tissue ablation step in which vacuum is applied to port 137 to engage port 137 with tissue). In some embodiments, a sensor is positioned to detect injectate in a conduit 111 of catheter 100 in which the vacuum is applied. In these embodiments, detection of sufficient injectate can correlate to inadequate engagement with tissue. The detector can comprise an optical sensor, and/or a window which is visualizable by an operator (e.g. to see injectate that is recovered), such as when the injectate comprises visible material.

In some embodiments, one or more functional elements 109, 119, 139, 209, 229 and/or 309 comprises one or more temperature sensors that produces a signal related to a first temperature representing the temperature of ablative fluid delivered to functional assembly 130 and a second temperature related to the temperature of fluid extracted from functional assembly 130. In these embodiments, system 10 can be configured to assess (e.g. via algorithm 251) the effect (e.g. quantity) of tissue treated (e.g. depth of tissue ablated), such as by analyzing the first temperature and the second temperature (e.g. a comparison of the two). In some embodiments, the first and/or second temperature is measured by one or more sensors of connecting assembly 300 (e.g. two or more functional elements 309 comprising thermistors or other temperature sensors) and/or one or more sensors of catheter 100 (e.g. two or more functional elements 109, 119 and/or 139 comprising thermistors or other temperature sensors).

In some embodiments, one or more of functional elements 109, 119, 139, 209, 229 and/or 309 comprise a sensor configured to provide a signal related to lumen diameter information. In these embodiments, the sensor can comprise a sensor selected from the group consisting of: pressure sensor; optical sensor; sound sensor; ultrasound sensor; strain gauge; electromagnetic sensor; an imaging device such as a camera; and combinations of one or more of these. One or more console settings 201 can be adjusted (e g manually or automatically) based on the lumen diameter information.

In some embodiments, one or more of functional elements 109, 119, 139, 209, 229 and/or 309 comprise a sensor including an imaging device configured to provide a signal related to image information. The imaging device can comprise a device selected from the group consisting of: visible light camera; infrared camera; endoscope camera; MRI; Ct Scanner; X-ray camera; PET Scanner; ultrasound imaging device; and combinations of one or more of these. In these embodiments, controller 250 or another assembly of system 10 can comprise signal processor 252 and/or algorithm 251, each of which can be configured to analyze the image information provided by the imaging device. One or more console settings 201 can be adjusted (e.g. manually or automatically) based on the image information. Based on the image information, system 10 can be configured to modify a console setting 201 to cause an event selected from the group consisting of: stopping delivery of fluid and/or energy to functional assembly 130; delivering additional fluid into functional assembly 130 and/or into tissue; delivering neutralizing fluid into functional assembly 130 and/or into tissue; adjusting the pressure of functional assembly 130; adjusting the volume of functional assembly 130; and combinations of one or more of these.

In some embodiments, functional assembly 130 comprises a biasing member, such as biasing member 145 shown. Biasing member 145 is constructed and arranged to apply a force to functional assembly 130, such as to place functional assembly 130 in tension along the axis of shaft 110 proximate functional assembly 130, such as when functional assembly 130 is in an unexpanded state. Biasing member 145 can be constructed and arranged to bend as functional assembly 130 expands. Biasing member 145 can comprise an element selected from the group consisting of: spring; coil spring; leaf spring; flexible filament; flexible sheet; nickel titanium alloy component; and combinations of one or more of these. In some embodiments, functional assembly 130 comprises balloon 136, and biasing member 145 is configured to avoid contacting balloon 136 when functional assembly is in its unexpanded state.

In some embodiments, shaft 110 passes through all or a portion of functional assembly 130. In other embodiments, functional assembly 130 is positioned on a distal end of shaft 110.

Figure 18:
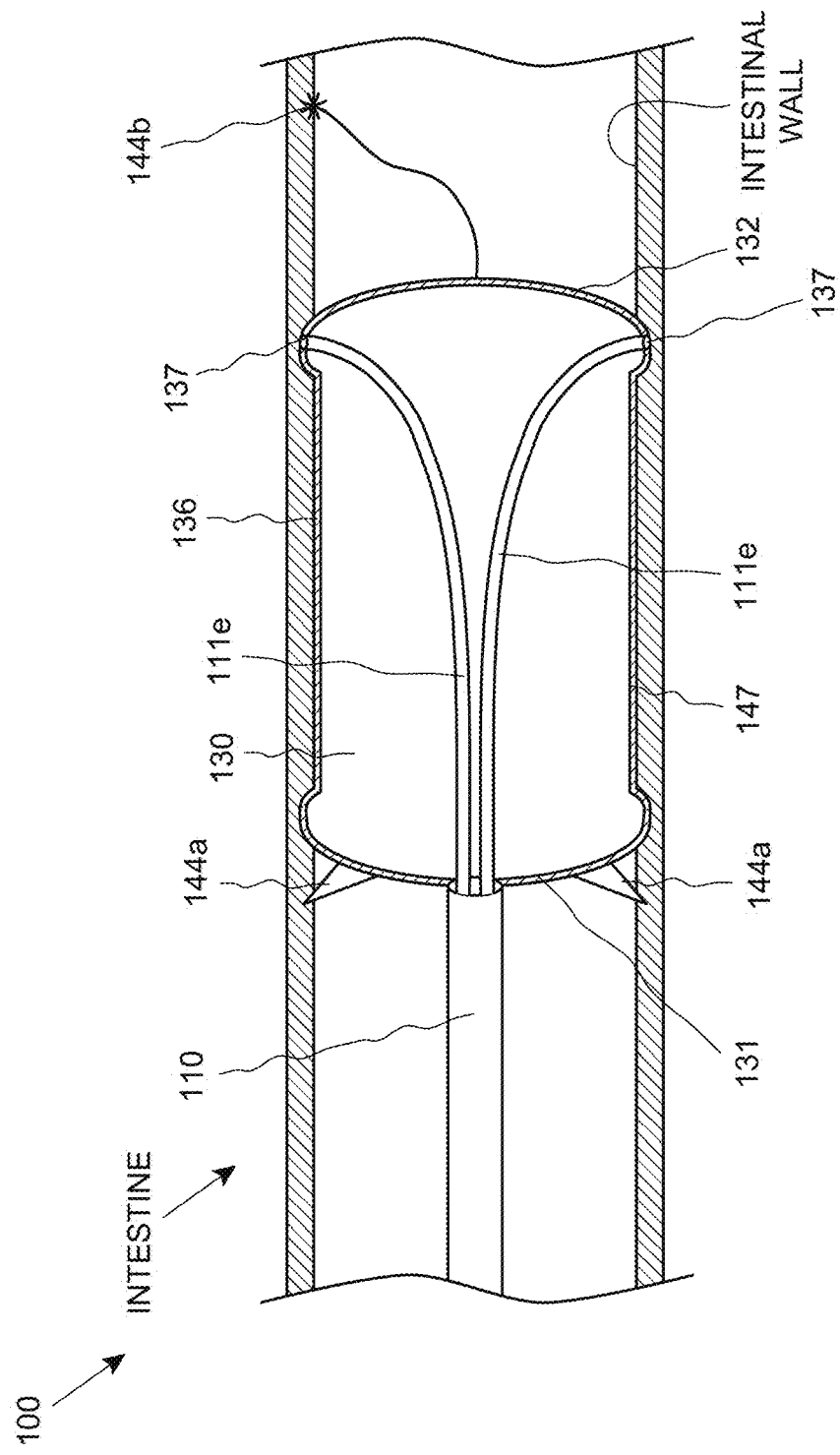
FIG. 18 is an anatomical, side sectional view of a distal portion of a catheter comprising a functional assembly configured to avoid unintended translation within the intestine, consistent with the present inventive concepts.

In some embodiments, functional assembly 130 comprises a shape constructed and arranged to prevent or otherwise reduce migration of functional assembly 130, such as is described herebelow in reference to FIG. 18. In some embodiments, functional assembly 130 is constructed and arranged to perform a first procedure (e.g. a tissue expansion procedure), anchor in tissue (e.g. anchoring performed prior to the first procedure, during the first procedure and/or after the first procedure), and perform a second procedure (e.g. a tissue ablation procedure), such as is described herebelow in reference to FIG. 35.

In some embodiments, functional assembly 130 and/or other components of catheter 100, connecting assembly 300 and/or console 200 are configured to enhance mixing of one or more fluids within functional assembly 130 (e.g. one or more functional element 139 comprising a fluid mixing element). In some embodiments, one or more functional elements 139 within functional assembly 130 comprise a baffle configured to improve fluid mixing and/or occupy a volume (e.g. a baffle positioned within functional assembly 130). In some embodiments, one or more functional elements 139 comprise an expandable and/or compressible baffle. These baffles can be configured to "take up" volume within functional assembly 130, such as to decrease the amount of fluid (e.g. ablative fluid) delivered into functional assembly 130 during a tissue ablation and/or tissue expansion procedure. The baffles can be configured to reduce rise times or fall times of temperatures associated with functional assembly 130 (e.g. reduce rise times or fall times to or from ablative temperatures, respectively, during a tissue ablation procedure). The baffles can be configured to take up volume in between two or more ports 137, such as to minimize the overall diameter of a catheter 100 configured as a tissue expansion device.

In some embodiments, a first conduit 111 can comprise an inflow tube configured to at least deliver fluid to functional assembly 130. A second conduit 111 can surround the first conduit 111, and an opening on the proximal end of the second (outer) conduit 111 can be closed off (e.g. a proximal end of second conduit 111 positioned near the proximal end of functional assembly 130). The distal end of the second conduit 111 can extend past the midpoint of functional assembly 130 but terminate proximal to the distal end of functional assembly 130, forming a collar around the inner first conduit 111 that channels the flow from the first conduit 111 to the distal portion of functional assembly 130, and improving mixing within all of the internal volume of functional assembly 130.

In some embodiments, catheter 100 comprises one or more insulating elements configured to avoid transfer of energy from shaft 110 to tissue, such as an insulating element comprising a full or partial layer of shaft 110 that comprises thermally insulating material and/or an insulating element comprising one or more conduits 111 which contain circulating fluid configured to dissipate heat from shaft 110.

Shaft 110 of catheter 100 can comprise one or more coatings 118, along all or a portion of its outer and/or inner surfaces. In some embodiments, coating 118 is positioned on at least a portion of the outer surface of shaft 110, and is configured to prevent or otherwise reduce inadvertent translation of catheter 100 through the intestine (e.g. an anti-migration coating configured to reduce undesired translation and/or rotation of catheter 100). Alternatively or additionally (e.g. on a different portion), coating 118 can comprise a lubricous coating. In some embodiments, coating 118 is positioned on one or more lumens of shaft 110, such as a lubricous coating configured to assist in the translation of one or more filaments within the lumen. In some embodiments, coating 118 comprises a coating positioned on at least a portion of shaft 110 and selected from the group consisting of: a hydrophilic coating (e.g. to improve lubricity); a coating comprising bumps (e.g. atraumatic projections configured to roughen a surface to reduce friction); a coating comprising a surface exposed to grit blasting (e.g. to roughen a surface to reduce friction); an insulative coating: parylene; PTFE; PEEK; a coating comprising a colorant (e.g. to improve or otherwise improve visibility of shaft 110 in-vivo); and combinations of one or more of these. In some embodiments, coating 118 comprises a coating positioned on at least a portion of functional assembly 130 (e.g. on at least a portion of a balloon 136) and selected from the group consisting of: a lubricous coating; a surface roughening coating; a silicone coating; an insulative coating; and combinations of one or more of these.

In some embodiments, one or more functional elements 109, 119, 139, 209, 229 and/or 309 comprise a filter (e.g. a hydrophobic filter) positioned in a fluid pathway of system 10. The filter can be positioned between a sensor and the fluid pathway. In these embodiments, the associated functional element 109, 119, 139, 209, 229 and/or 309 can further comprise a valve, such as a valve configured to vent the fluid pathway proximate the filter.

In some embodiments, system 10 can be configured to deliver injectate 221 to tissue to cause tissue expansion via a body fluid (e.g. via osmotic pressure). For example, injectate 221 can comprise a salt solution delivered by one or more fluid delivery elements 139*c* that cause water or other fluid to migrate from submucosal capillaries into the submucosa.

In some embodiments, one or more of functional elements 109, 119, 139, 209, 229 and/or 309 comprise a sensor configured to detect gas-bubbles, such as a gas bubble present in one or more of conduits 111, 211, 212 and/or 311 and/or a gas bubble present in functional assembly 130. In some embodiments, one or more de-gassing procedures are performed on one or more components of system 10, and the one or more gas-bubble detector based functional elements 109, 119, 139, 209, 229 and/or 309 are used to confirm that the de-gassing procedure is adequately completed and/or to indicate a de-gassing procedure should be performed.

In some embodiments, multiple conduits 111 are in fluid communication with functional assembly 130 (e.g. to simultaneously or sequentially inflate and/or deflate functional assembly 130) and/or port 137 (e.g. to simultaneously or sequentially provide a vacuum to port 137). In these embodiments, simultaneous and/or redundant delivery or extraction of fluids (e.g. application of a vacuum) can be initiated based on the signal provided by one or more sensors of system 10. For example, if a sensor detects a first conduit 111 is fully or partially occluded, the second conduit 111 can be used to additionally or alternatively deliver and/or extract fluids.

In some embodiments, system 10 is configured to maintain the pressure of functional assembly 130 relative to a threshold (e.g. pressure is maintained below a pressure threshold, above a pressure threshold, and/or within a threshold comprising a range of pressures), such as during treatment and/or diagnosis of target tissue of the intestine (e.g. during a tissue expansion and/or tissue ablation procedure). Functional assembly 130 can comprise a balloon 136 comprising a compliant balloon; a non-compliant balloon; a pressure-thresholded balloon; and/or a balloon comprising compliant and non-compliant portions, as described herein. Pressure can be maintained at a particular pressure or within a particular range of pressures by monitoring one or more sensors of system 10, such as sensor 139*b* and/or a sensor-based functional element 119, 109, 209 and/or 229. A lower pressure threshold can comprise a pressure of 0.3 psi, 0.5 psi or 0.7 psi. A lower pressure threshold can be selected to ensure sufficient contact of functional assembly 130 with tissue. An upper pressure threshold can comprise a pressure of 1.0 psi, 1.2 psi, 2.5 psi or 4.0 psi. An upper pressure threshold can be selected to avoid damage to tissue, such as damage to an outer layer of intestinal tissue (e.g. a serosal layer of the intestine). Pressure can be monitored such that console 200 can modulate or otherwise control one or more inflow and/or outflow rates of fluid delivered to and/or extracted from functional assembly 130. Pressure can be monitored to maintain flow rates to or from functional assembly 130 to a minimum rate of at least 250 ml/min, 500 ml/min, 700 ml/min or 750 ml/min. In some embodiments, pressure is determined by a sensor positioned outside of balloon 136, such as when pressure is maintained in functional assembly within a narrow range of pressures, such as at a pressure of between 1.05 psi and 0.55 psi. In these embodiments, a luminal sizing step can be avoided. In some embodiments, system 10 comprises one or more catheters 100 and/or one or more functional assemblies 130, such as to provide an array of functional assemblies 130 with different lengths and/or diameters. In these embodiments, the upper and/or lower pressure thresholds can be independent of functional assembly 130 size.

In some embodiments, conduits 111 comprise an inflow tube and an outflow tube fluidly connected to functional assembly 130. Fluid can be delivered to functional assembly 130 by console 200 via one or more conduits 111 at various flow rates, such as flow rates up to 500 ml/min, 1000 ml/min, 1500 ml/min, 2000 ml/min and/or 2500 ml/min. Fluid can be extracted from functional assembly 130 by console 200 via one or more conduits 111 at various flow rates, such as flow rates up to 500 ml/min, 750 ml/min, or 1000 ml/min.

In some embodiments, treatment element 139*a* can comprise fluid at a sufficiently high temperature to ablate tissue (such as liquid above 60° C. or steam). Delivery of superheated fluid through a conduit 111 can be performed, such as when functional element 119 comprises an orifice configured to cause the superheated fluid to boil upon entering functional assembly 130, providing steam at 100° C. Delivery of cooled fluids through a conduit 111 can be performed. In some embodiments, a fluid (cooled or otherwise) is introduced through a conduit 111 and through a functional element 119 comprising a valve, such that expansion of the fluid into functional assembly 130 results in a cooling effect.

In some embodiments, system 10 and catheter 100 are constructed and arranged to fill functional assembly 130 with neutralizing (e.g. chilled) fluid, and then thermally prime a first conduit 111 with ablative (e.g. hot) fluid, when the first conduit is positioned in a retracted state (e.g. preventing or otherwise reducing heating of functional assembly 130). Subsequently, the first conduit 111 is advanced (i.e. first conduit 111 is constructed and arranged as a translatable conduit) and ablative fluid is introduced into functional assembly 130, allowing functional assembly 130 to be in a fully or partially expanded state prior to fluid at an ablative temperature residing in functional assembly 130 and avoiding undesired "partial ablative contact" of functional assembly 130 with tissue. Another advantage of this configuration is that functional assembly 130 can be checked for leaks with non-ablative fluid prior to one or more subsequent steps (e.g. each ablation step).

In some embodiments, functional assembly 130 is constructed and arranged to both expand tissue (e.g. expand submucosal tissue) and treat target tissue (e.g. treat duodenal mucosal tissue), such as is described herebelow in reference to multi-function catheter 40 of FIG. 2. For example, functional assembly 130 can comprise fluid delivery element 139c which can be positioned to deliver fluid into tissue that has been drawn into (e.g. upon application of a vacuum) port 137, to expand one or more layers of tissue (e.g. one or more layers of submucosal tissue). Functional assembly 130 can further comprise treatment element 139a which can comprise ablative fluid which can be introduced into functional assembly 130 and/or an energy delivery element configured to deliver energy to tissue (e.g. RF energy, light energy, sound energy, chemical energy, thermal energy and/or electromagnetic energy), each configured to perform a therapeutic treatment on target tissue.

In some embodiments, system 10 and catheter 100 are configured to both expand tissue (e.g. expand submucosal tissue of the intestine) and treat target tissue (e.g. treat mucosal tissue of the intestine proximate the expanded submucosal tissue). Catheter 100 can comprise a single catheter 100 comprising one or more functional elements 139 configured to collectively expand tissue and treat target tissue, or a first catheter 100a configured to expand tissue and a second catheter 100b configured to treat target tissue. In these embodiments, injectate 221 can comprise a material configured to enhance or otherwise modify a target treatment step. For example, injectate 221 can comprise a conductive fluid (e.g. an electrically conductive fluid), such as saline configured to modify a subsequent target tissue treatment by treatment element 139a in which RF or other electrical energy is delivered to target tissue (e.g. when treatment element 139a comprises an array of electrodes). Similarly, injectate 221 can comprise a chromophore or other light absorbing material and/or a light scattering material configured to modify a subsequent target tissue treatment by treatment element 139a in which light energy is delivered to target tissue (e.g. when treatment element 139a comprises a lens, one or more conduits 111 comprise an optical fiber, and controller 250 comprises an energy delivery unit EDU 260 comprising a laser).

In some embodiments, fluid delivery element 139c comprises a needle with two separate lumens (e.g. two lumens each fluidly connected to a different conduit 111), such that two different materials can be injected into tissue without the two fluids mixing prior to entering the tissue. Alternatively, fluid delivery element 139c can comprise two different needles directed toward a similar area. Injectate 221 can comprise a first material and a second material which form a hydrogel when mixed (e.g. the two materials crosslink to form an absorbable hydrogel). Alternatively or additionally, injectate 221 can comprise water soluble PEG reactive end groups and an amino acid with reactive end groups.

In some embodiments, injectate 221 comprises a material selected from the group consisting of: autologous fat; collagen; bovine collagen; human cadaveric dermis; hyaluronic acid; calcium hydroxylapatite; polylactic acid; semi-permanent PMMA; dermal filler; gelatin; and combinations of one or more of these. In some embodiments, injectate 221 comprises a material whose viscosity changes (e.g. increases) after delivery into tissue, such as a fluid whose viscosity increases as it is heated to body temperature.

In some embodiments, injectate 221 comprises a material including hollow materials and a carrier material, such as when system 10 is constructed and arranged to deliver injectate 221 to create a therapeutic restriction. In these embodiments, injectate 221 can comprise a material as described in US Patent Application US20080107744 or US Patent Application US20110091564, the contents of each of which is incorporated herein by reference in its entirety for all purposes. In some embodiments, injectate 221 comprises inorganic fibers and a carrier material. The inorganic fibers can be constructed and arranged to prevent or otherwise reduce their migration within tissue. The carrier material can be constructed and arranged to allow the inorganic fibers to be injectable (e.g. to pass through fluid delivery element 139c). In these embodiments, injectate 221 can comprise a material as described in US Patent Application US20140255458, the contents of which is incorporated herein by reference in its entirety for all purposes.

In some embodiments, system 10, console 200 and/or catheter 100 is constructed and arranged to reduce risk during injection of material into the wall of the duodenum. In some embodiments, a pre-determined volume of polymer or other material is injected using catheter 100 or a standard endoscopic needle device. A volume of at least 1 ml or 2.5 ml of a first material (e.g. a relatively inert material such as sterile saline), is injected into the wall first, creating a first expanded tissue volume, a "bleb" of expanded tissue and the saline. Subsequently, a second material, such as a pharmaceutical agent, a durable material (e.g. to create a therapeutic restriction as described herein), or other active material is injected into the first expanded tissue volume to further expand the tissue.

In some embodiments, system 10 includes a tool 500 comprising a vacuum applying tool such as an endoscopic cap. Catheter 100 or a standard endoscopic needle device can inject a material into the wall of the duodenum while the endoscopic cap applies suction to the intestinal mucosa. A needle or other fluid delivery element of catheter 100 (e.g. fluid delivery element 139c) or a needle of a standard endoscopic needle device is delivered into intestinal tissue while the mucosa of the intestine is lifted by tool 500.

In some embodiments, injectate 221 comprises a system 10 or operator detectable material such as a visualizable material, magnetic material or other detectable material. In some embodiments, injectate 221 comprises one or more materials (e.g. a biocompatible polymer or copolymer such as ethylene vinyl alcohol), and can further include a detectable material selected from the group consisting of: a radiopaque material; barium sulfate; tantalum; ultrasonically reflecting material; magnetic material; a visible dye; and combinations of one or more of these. In these embodiments, system 10 can comprise a fluid extraction assembly comprising one or more ports 137 that are constructed and arranged to withdraw fluids from within the intestine, such as via one or more conduits 111 and one or more pumping assemblies 225. One or more functional elements 109, 119, 139, 229 and/or 309 can comprise a sensor configured to produce a signal related to the quantity of injectate 221 recovered via the one or more ports 137, such as a sensor configured to detect a volume, mass, flow rate and/or other parameter of injectate 221. Signal processor 252 can be configured to assess tissue expansion based on an analysis of the recovered injectate 221.

In some embodiments, injectate 221 comprises one or more materials such as ethylene vinyl alcohol (EVOH) which is provided in a liquid solvent such as dimethyl sulfoxide (DMSO). In these embodiments, a visualizable material such as a radiopaque material (e.g. tantalum) can be further included. In these embodiments, catheter 100 can be configured to deliver this injectate 221 into tissue (e.g. via one or more fluid delivery elements 139c), after which the one or more materials, and the visualizable material if included, precipitate from the solution to form a spongy implant, which can remain in proximity to the injection site for a prolonged period of time.

In some embodiments, algorithm 251 is configured to determine an expanded size for functional assembly 130, such as when system 10 comprises multiple catheters 100 with different expanded diameters for functional assembly 130 and/or when the expanded diameter of functional assembly 130 can be varied by system 10 (e.g. by varying pressure and/or volume of fluid within functional assembly 130). In these embodiments, algorithm 251 can comprise a bias, such as a bias which tends toward lower diameters (e.g. rounds down to the next smaller size of a functional assembly 130 available after calculating a target value). In some embodiments, algorithm 251 is configured to select one catheter 100 for use in a patient, by selecting one a kit of multiple catheters 100 comprising one or more different parameters (e.g. one or more functional assembly 130 parameters). In these embodiments, algorithm 251 can also include a bias, such as a bias toward choosing a smaller functional assembly 130 (e.g. smaller length or smaller expanded diameter).

In some embodiments, algorithm 251 of console 200 comprises an image analysis algorithm configured to analyze one or more patient and/or system 10 images. For example, a tissue location can be analyzed prior to, during and/or after a desufflation (e.g. aspiration) step, such as to confirm adequate apposition of a functional assembly 130 with tissue of an axial segment of tubular tissue (e.g. an axial segment of the intestine). Algorithm 251 can comprise one or more image analysis algorithms configured to assess various conditions including but not limited to: apposition of functional assembly 130 with tissue (e.g. intestinal wall tissue); effectiveness of a desufflation procedure; effectiveness of an insufflation procedure; sufficiency of a tissue expansion procedure; sufficiency of a tissue ablation procedure; and combinations of one or more of these.

In some embodiments, one or more reservoirs 220 and/or one or more pumping assemblies 225 are constructed and arranged to provide a cryogenic gas or other cryogenic fluid to functional assembly 130, such as to perform a cryogenic ablation of target tissue and/or to cool target tissue that has been heated above body temperature. Cryogenic gas can be delivered through smaller diameter conduits 111 than would be required to sufficiently accommodate a liquid ablative or neutralizing fluid, which correlates to a reduced diameter of shaft 110. Balloon 136 can comprise a compliant balloon (e.g. a highly compliant balloon). Balloon 136 can be fluidly connected to multiple fluid transport conduits 111, singly or collectively providing inflow (i.e. delivery) and/or outflow (i.e. extraction) of the cryogenic gas. System 10 can be configured to control the pressure within balloon 136, such as at a pressure sufficient, but not much greater than that which would be required to simply inflate balloon 136. A highly compliant balloon 136 can be configured to reduce or avoid the need for a luminal sizing step to be performed. Temperature seen by the target tissue is driven by the temperature of the fluid in balloon 136. During treatment (i.e. cryogenic ablation) the pressure in balloon 136 can be maintained at a pressure at or below 20 inHg, such as below 18 inHg, 15 inHg or 10 inHg.

In some embodiments, system 10 comprises a first catheter 100 with a functional assembly with a first diameter, and a second catheter 100 with a functional assembly with a second diameter (e.g. a smaller expanded diameter than the first diameter). In these embodiments, system 10 can be constructed and arranged such that an operator (e.g. a clinician) inserts the first catheter 100 into the intestine of a patient and performs a first function, such as a function selected from the group consisting of: size (e.g. determine the diameter) of one or more axial locations of intestine; perform or at least attempt to perform a tissue expansion procedure in one or more axial segments of intestine; perform or at least attempt to perform a tissue treatment (e.g. tissue ablation) at one or more axial segments of intestine; and combinations of one or more of these. In some embodiments, during and/or after performance of the first function, a decision can be made to switch to the second catheter 100 with a different functional assembly 130, such as when it is determined the functional assembly 130 of the first catheter 100 is too large. In these embodiments, the first catheter 100 and the second catheter 100 can each be configured to perform both a tissue expansion procedure and an ablation procedure. In some embodiments, the functional assembly 130 of the first catheter 100 comprises an expanded diameter between 21 mm and 29 mm, such as a diameter between 23 mm and 27 mm, such as a diameter of approximately 25 mm. In some embodiments, algorithm 251 is configured to select the first catheter 100 and/or the second catheter 100 for use (e.g. use in the patient). Alternatively, the functional assembly 130 of the first catheter 100 can comprise an expanded diameter smaller than the expanded diameter of the functional assembly 130 of the second catheter 100, wherein the second catheter 100 is introduced into the patient if it is determined that the expanded diameter of the functional assembly 130 of the first catheter 100 is too small In some embodiments, pumping assembly 225 comprises at least two pumping assemblies 225 configured to propel fluid out of (i.e. extract fluid from) functional assembly 130 and/or another component of catheter 100, such as two pumping assemblies 225 which operate simultaneously during the performance of a functional assembly 130 drawdown procedure (e.g. an emergency radial contraction of functional assembly 130 that is initiated during an undesired situation, such as an emergency drawdown procedure initiated when a leak is detected). In some embodiments, two pumping assemblies 225 are configured to deliver fluid to functional assembly 130 (e.g. to balloon 136 and/or one or more fluid delivery elements 139c) or other component of catheter 100. In these embodiments, simultaneous fluid delivery can also be performed when a leak is detected, such as to simultaneously deliver a neutralizing fluid to tissue being undesirably exposed to ablative fluid. Alternatively or additionally, a second pumping assembly 225 can be configured to begin fluid delivery and/or fluid extraction when the failure of a first pumping assembly 225 is detected. Two or more pumping assemblies 225 can be fluidly attached to one or more fluid transport conduits 211.

In some embodiments, console 200 is constructed and arranged to maintain a minimum volume (e.g. "level") of one or more reservoirs 220. In some embodiments, console 200 is constructed and arranged to disable a pump 225 if an undesired condition is detected, such as by a signal recorded by a functional element 229a and/or 229b that comprises a sensor configured to monitor one or more system parameters (e.g. temperature, pressure, flow rate, and the like).

In some embodiments, console 200 is constructed and arranged to limit a treatment time or to limit another treatment parameter. In these embodiments, the treatment parameter can be limited by software, such as software of algorithm 251 and/or controller 250. Alternatively, the treatment parameter can be limited by hardware (e.g. a hardware-based algorithm 251), such as hardware of controller 250 such as a temperature controlled functional element which turns off a pumping assembly 225 and/or otherwise prevents or reverses energy being delivered by a functional assembly 130 of catheter 100.

In some embodiments, system 10 is constructed and arranged (e.g. via algorithm 251) to adjust one or more treatment parameters, such as an adjustment based on the expanded size of a functional assembly 130, such as when system 10 comprises multiple catheters 100, each comprising a different expanded size of its functional assembly 130. In these embodiments, system 10 can be constructed and arranged to adjust one or more treatment parameters selected from the group consisting of: temperature of ablative fluid; volume of ablative fluid; pressure of ablative fluid; amount of energy delivered such as peak amount of energy delivered and/or cumulative amount of energy delivered; duration of treatment; amount of fluid delivered into tissue (e.g. during a tissue expansion procedure or a tissue ablation procedure); and combinations of one or more of these.

In some embodiments, console 200 is constructed and arranged to provide a first fluid at an ablative temperature, and a second fluid at a neutralizing temperature. For example, a first fluid can be provided by a first reservoir 220 such that the first fluid enters functional assembly 130 at a sufficiently high temperature to ablate tissue, such as at a temperature above 44° C. or above 60° C. A second fluid can be provided by a second reservoir 220 such that the second fluid enters functional assembly 130 at a neutralizing temperature below body temperature, such as a temperature between room temperature and body temperature, or a temperature below room temperature. Alternatively, an ablative fluid can comprise a fluid of sufficiently low temperature to ablate tissue (e.g. below 5° C.), and an associated neutralizing fluid can comprise a warmer fluid configured to reduce the tissue damaging effects of the ablative fluid, as described herein. In some embodiments, a neutralizing fluid is provided to functional assembly 130 prior to and/or after delivery of ablative fluid to functional assembly 130, as described in detail herebelow.

An ablative fluid and a neutralizing fluid can be transported to functional assembly 130 via the same or different conduits 111. Fluid can be extracted from functional assembly 130 via the same or different conduits used to deliver the first fluid and/or the second fluid. In some embodiments, conduits 111 used to deliver and/or extract an ablative fluid or a neutralizing fluid are configured to be translated (e.g. advanced and/or retracted), such that their distal end position within or otherwise relative to functional assembly 130 can be varied. In some embodiments, one or more conduits 111 and/or functional assembly 130 can be thermally primed prior to treating target tissue. In some embodiments, ablative fluid and/or neutralizing fluid is provided to functional assembly 130 in a recirculating manner. Alternatively, ablative fluid and/or neutralizing fluid can be provided to functional assembly 130 as a bolus (non-circulating volume of fluid). In some embodiments, functional element 119 comprises one or more valves constructed and arranged to control the flow of fluid through one or more conduits 111. In recirculating fluid embodiments, a conduit 111 supplying fluid can be manually or automatically changed to a fluid extraction conduit, such as when a separate conduit 111 is configured to normally extract fluid from functional assembly 130 becomes occluded, when a conduit 111 or functional assembly 130 begins to leak, or otherwise when it is desired to radially compact functional assembly 130 at an accelerated rate.

In some embodiments, at least a first conduit 111a provides ablative fluid to functional assembly 130 while at least a separate conduit 111b simultaneously withdraws ablative fluid from functional assembly 130, such as to recirculate ablative fluid within functional assembly 130. In these embodiments, functional assembly can be radially expanded (e.g. initially or after a radial compacting step), by filling functional assembly 130 (e.g. with ablative fluid, neutralizing fluid and/or other fluid) by using both first conduit 111a and second conduit 111b.

In some embodiments, treatment element 139a comprises an energy delivery element including multiple layers of electrical conductors (e.g. conductors and/or semiconductors) configured to generate heat when electricity passes through one or more of the conductors. In these embodiments, functional element 139 can be electrically connected to one or more conduits 111 comprising one or more electrical wires. Functional assembly 130 can comprise a compliant or non-compliant balloon onto which functional element 139 is positioned. Treatment element 139a can comprise electrical conductors created by depositing one or more coatings on one or more substrates. When electricity is passed through the coating, heat is generated. The heat can be effectively transferred across the whole surface of functional element 139 mainly through conduction, but also via radiation and convection and into target tissue.

In some embodiments, balloon 136 comprises at least a porous portion or a portion otherwise constructed and arranged to allow material contained within balloon 136 to pass through at least a portion of balloon 136. In these embodiments, injectate 221 can comprise a material configured to pass through at least a portion of balloon 136, such as a conductive gel material configured to modify energy delivery, such as when treatment element 139a comprises one or more electrodes configured to delivery RF energy to target tissue. In other embodiments, agent 420 comprises one or more agents configured to be delivered into balloon 136 and to pass through at least a portion of balloon 136 and into the intestine.

In some embodiments, system 10 is constructed and arranged to deliver fluid into functional assembly 130 at a flow rate of at least 500 ml/min, at least 1000 ml/min, at least 2000 ml/min, or at least 2500 ml/min. In some embodiments, system 10 is constructed and arranged to extract fluid from functional assembly at a flow rate of at least 500 ml/min, at least 750 ml/min, or at least 1000 ml/min. In some embodiments, system 10 is constructed and arranged to remove and extract fluids at approximately the same flow rate. In some embodiments, fluid in console 200 is provided to catheter 100 at a temperature of at least 60° C., 70° C. or 80° C. In some embodiments, system 10 is configured to treat at least three axial segments of intestinal tissue, such as at least three axial segments of tissue treated with a heat ablation and at least one cooling step (e.g. a cooling step performed prior to and/or after the heat ablation step).

In some embodiments, tool 500 comprises an insufflation and/or desufflation tool, such as a catheter comprising a port (e.g. a distal opening) for delivering and/or extracting fluids from the intestine. Tool 500 can be insertable through the working channel of an introduction device 50 (e.g. through an endoscope). Delivery of insufflation fluids can be performed to move tissue away from functional assembly 130 and/or move tissue away from one or more functional elements 139 or other parts of catheter 100. In some embodiments, insufflation is performed to stop or limit a transfer of energy to tissue (e.g. in an emergency or insufflation-controlled ablation step).

In some embodiments, tool 500, catheter 100, introduction device 50 and/or another component of system 10 comprises a pressure-neutralizing assembly constructed and arranged to modify the pressure within a luminal segment of the intestine (e.g. a luminal segment proximate functional assembly 130). In these embodiments, tool 500 and/or catheter 100 can comprise one or more openings or other elements configured as vents, such as to vent the luminal segment to room pressure (e.g. clinical procedure room pressure) or otherwise maintain the pressure in a segment of the intestine below a threshold. In some embodiments, introduction device 50 comprises an endoscope comprising a biopsy port configured to vent the luminal segment to room pressure. The pressure-neutralizing assembly can be configured to extract gas from the intestinal segment, and/or to maintain the pressure within the intestinal segment below a threshold. In some embodiments, venting is activated automatically, such as when a pressure (e.g. as measured by a sensor of the present inventive concepts) reaches a threshold (e.g. as determined by algorithm 251).

In some embodiments, algorithm 251 comprises a pressure algorithm configured to modify a system parameter based on a measured pressure, such as a modification made based on the pressure within a luminal segment of the intestine in which functional assembly 130 is positioned or otherwise proximate (e.g. as measured or otherwise determined by analysis of a signal provided by a sensor of catheter 100, body introduction device 50 or another sensor of system 10 as described herein. In these embodiments, system 10 can be configured to modify the volume of fluid within functional assembly 130 and/or modify the pressure of functional assembly 130 based on the luminal segment pressure.

In some embodiments, functional assembly 130 is positioned in an axial segment of intestine, expanded to a diameter less than the average diameter of the axial segment, and activated (e.g. to deliver energy to tissue and/or fluids to tissue) during a contraction of the intestine. In these embodiments, the contraction of the intestine can be one or more of: a (natural) peristaltic contraction; a contraction caused by stimulation (e.g. electrical or chemical stimulation by catheter 100 and/or tool 500); a contraction caused during a desufflation procedure; and combinations of one or more of these. Contraction of the intestine can comprise a desufflation procedure performed by a device selected from the group consisting of: catheter 100; an endoscope or other body introduction device 50; a second catheter inserted into the intestine; and combinations of one or more of these.

In some embodiments, tool 500 comprises a diagnostic tool, such as a diagnostic tool comprising a sensor. Tool 500 can be configured to perform a diagnostic test of the patient and/or a diagnostic test of all or a portion of system 10. Tool 500 can comprise a body-insertable tool. Tool 500 can be constructed and arranged to gather data (e.g. via an included sensor) related to a patient physiologic parameter selected from the group consisting of: blood pressure; heart rate; pulse distention; glucose level; blood glucose level; blood gas level; hormone level; GLP-1 level; GIP Level; EEG; LFP; respiration rate; breath distention; perspiration rate; temperature; gastric emptying rate; peristaltic frequency; peristaltic amplitude; and combinations of one or more of these.

Alternatively or additionally, tool 500 can comprise a tissue marking tool, such as a tissue marking tool configured to be deployed through introduction device 50 (e.g. an endoscope). In some embodiments, system 10 comprises marker 430, which can comprise a dye or other visualizable media configured to mark tissue (e.g. using a needle-based tool 500), and/or a visualizable temporary implant used to mark tissue, such as a small, temporary anchor configured to be attached to tissue by tool 500 and removed at the end of the procedure (e.g. by tool 500) or otherwise passed by the natural digestive process of the patient shortly after procedure completion. Tissue marker 430 can be deposited or deployed in reference to (e.g. to allow an operator to identify) non-target tissue (e.g. a marker positioned proximate the ampulla of Vater to be visualized by an operator to avoid damage to the ampulla of Vater), and/or to identify target tissue (e.g. tissue to be ablated). In some embodiments, tissue marker 430 is deposited or deployed in reference to tissue selected from the group consisting of: gastrointestinal adventitia; duodenal adventitia; the tunica serosa; the tunica muscularis; the outermost partial layer of the submucosa; ampulla of Vater; pancreas; bile duct; pylorus; and combinations of one or more of these. In some embodiments, tissue marking is performed as described herebelow in reference to FIG. 43.

In some embodiments, port 137 can be configured to engage tissue (e.g. when a vacuum is applied to port 137 via one or more conduits 111), after which target tissue can be treated by treatment element 139a. Engagement of tissue by port 137 can be used to stretch or otherwise manipulate tissue such that a safe and effective treatment of target tissue can be performed by treatment element 139a, such as when treatment element 139a comprises fluid at an ablative temperature or an array of electrodes configured to deliver RF energy. In these embodiments, catheter 100 can be configured to treat target tissue without performing an associated tissue expansion procedure (e.g. without expanding tissue in proximity to the target tissue to be treated).

Functional assembly 130 can be configured to perform a medical procedure (e.g. a tissue expansion procedure and/or a tissue ablation or other tissue treatment procedure) on multiple axial segments of intestinal tissue. Two or more of the multiple axial segments can be treated sequentially and/or simultaneously. The two or more of the multiple axial segments can be relatively proximate each other, such as to share common boundaries or avoid significant gaps in untreated tissue. The multiple axial segments can comprise partial or full circumferential segments of intestinal tissue. The multiple axial segments can cumulatively comprise at least 3 cm in length or at least 6 cm in length, such as when between 1 and 6 treatments (e.g. between 2 and 6 treatments) are performed (e.g. functional assembly 130 is repositioned between 1 and 5 times). The multiple axial segments can cumulatively comprise a length of at least 9 cm, such as when between 2 and 9 treatments are performed (e.g. functional assembly 130 is repositioned between 1 and 8 times). In these embodiments, system 10 can be configured to treat diabetes, such as Type 2 diabetes. In some embodiments, system 10 is constructed and arranged to treat diabetes as described in applicant's co-pending International Patent Application Serial Number PCT/US2015/040775, entitled "Methods and Systems for Treating Diabetes and Related Diseases and Disorders", filed Jul. 16, 2015, the content of which is incorporated herein by reference in its entirety for all purposes.

In some embodiments, system 10 is configured to initially expand functional assembly 130, with a fluid at a non-ablative temperature (e.g. a fluid configured to cool tissue without ablating it), after which a fluid at an ablative temperature can be introduced into functional assembly 130 (e.g. a fluid at sufficiently high temperature to ablate tissue).

In some embodiments, catheter 100 and/or another device of system 10 comprises an anchoring element, such as when port 137 is configured to anchoringly engage tissue when a vacuum is applied to port 137 (e.g. via one or more conduits 111). Alternatively or additionally, inflation of balloon 136 can be used to anchor functional assembly 130 at a particular intestinal location. One or more functional elements 139 can comprise an anchor element, such as a high friction coating or surface treatment, or an extendable barb.

In some embodiments, system 10 is constructed and arranged to allow an operator to position the functional assembly within an axial segment of the intestine and perform a first procedure on intestinal tissue with functional assembly 130. System 10 is further constructed and arranged to anchor functional assembly 130 (prior to, during and/or after the first procedure). Subsequent to the performance of the first procedure and the anchoring of functional assembly 130, a second procedure is performed. The first procedure can comprise a tissue expansion procedure. The second procedure can comprise a tissue ablation procedure, such as a tissue ablation procedure which ablates mucosal tissue within or otherwise proximate previously expanded submucosal tissue. Repeating of the three steps (i.e. the first procedure, the anchoring of functional assembly 130, and the second procedure) can be performed at additional locations within the intestine.

As described herein, in some embodiments, catheter 100 or another device of system 10 such as catheter 30 of system 10 of FIG. 2, is constructed and arranged to perform a luminal sizing measurement (e.g. a measurement in which diameter and/or other cross sectional geometry is quantified), and produce luminal size information. In these embodiments, system 10 can include multiple catheters 100, one of which is selected and/or adjusted based on the luminal size information. Alternatively or additionally, system 10 can be configured to adjust one or more system parameters based on the luminal size information, such as a console setting 201 selected from the group consisting of: volume of fluid delivered into functional assembly 130; flow rate of fluid delivered into functional assembly 130; temperature of fluid delivered into functional assembly 130; pressure of functional assembly 130; and combinations of one or more of these.

In some embodiments, console 200 and system 10 are constructed and arranged to maintain functional assembly 130 of catheter 100 at or below a target level of a functional assembly 130 parameter, such as at or below a target diameter, pressure and/or volume for functional assembly 130. In some embodiments, functional assembly 130 is maintained below a target pressure of 0.9 psi (e.g. during a tissue expansion, tissue ablation and/or other tissue treatment step).

In some embodiments, catheter 100 and system 10 are constructed and arranged to compensate for muscle contraction of the intestine (e.g. peristalsis within the intestine). For example, algorithm 251 can be configured to actively regulate a functional assembly 130 parameter (e.g. diameter, pressure within and/or flowrate to and/or from), such as when algorithm 251 anticipates, recognizes and/or compensates for muscular contraction of the intestine. In some embodiments, expansion of functional assembly 130 can be timed to occur during the bottom (lower range) of a muscular contraction (e.g. peristalsis) cycle.

In some embodiments, catheter 100 and system 10 are constructed and arranged to perform a medical procedure in the intestine that is synchronized with one or more muscular contractions of the intestine, such as one or more peristaltic contractions used to contact intestinal wall tissue with an expanded or partially expanded functional assembly 130.

In some embodiments, system 10 is constructed and arranged to size a lumen of a first axial segment of the intestine. System 10 can be further constructed an arranged to subsequently perform a tissue expansion of a portion of the first axial segment (e.g. a full or partial circumferential segment of the submucosa of the axial segment), by injecting fluid (e.g. a fixed volume of fluid) into tissue within or proximate the first axial segment. System 10 can be further constructed and arranged to subsequently perform a luminal sizing measurement of the first axial segment. System 10 can be further constructed and arranged to subsequently perform a target tissue treatment of the first axial segment (e.g. a treatment of a full or partial circumferential segment of the mucosal tissue of the first axial segment). The treatment performed by system 10 can comprise one or more treatment parameters (e.g. one or more ablation parameters) that are based on the luminal sizing measurement performed after tissue expansion, and determined via algorithm 251.

In some embodiments, system 10 comprises one or more first catheters 100a, each with a first functional assembly 130a of a particular size and configured to treat target tissue. System 10 further comprises one or more second catheters 100b, each with a functional assembly 130b and configured to perform a tissue expansion procedure. System 10 can be constructed and arranged to size a lumen of one or more axial segments of intestine (e.g. using a catheter 100 or other luminal sizing device as described herein) to determine the diameter at a relatively narrow (e.g. the smallest diameter) location within the one or more axial segments to be treated. System 10 is further constructed and arranged to select a first catheter 100a based on the luminal sizing information (e.g. using algorithm 251). System 10 can be constructed and arranged to inflate or otherwise expand the functional assembly 130a of a catheter 100a (e.g. with an ablative fluid) to a diameter related to the smallest diameter location. System 10 can be constructed and arranged to inflate or otherwise expand the functional assembly 130b of a catheter 100b (e.g. with a gas) to a diameter corresponding to the expanded diameter of the selected catheter 100a (e.g. a diameter less than the proximate axial segment lumen size and/or to a diameter related to the smallest diameter location). System 10 can be constructed and arranged to apply a vacuum to one or more ports 137 of catheter 100b to engage neighboring tissue. System 10 can be further constructed and arranged to inject fluid into tissue (e.g. submucosal tissue) until the pressure within the associated functional assembly 130b exceeds a threshold, such as a threshold of 0.3 psi, 0.5 psi or 0.7 psi (e.g. but below a second threshold of 2.0 psi or 4.0 psi). System 10 can be constructed and arranged to subsequently disengage functional assembly 130b from the tissue (e.g. by removal of the vacuum from each port 137), and radially collapse balloon 136 (e.g. via extraction of fluid from balloon 136 via one or more conduits 111 of catheter 100b). System 10 can be constructed and arranged to similarly expand tissue at one or more other axial segments of the intestine. System 10 can be constructed and arranged to treat target tissue of the one or more axial segments (with expanded tissue) using the particular first catheter 100a whose expanded diameter was chosen based on the minimum diameter of the one or more axial segments. In some embodiments, multiple tissue expansion procedures are performed by catheter 100b sequentially, after which a series of target tissue treatments (e.g. tissue ablations) are performed by catheter 100a sequentially. Alternatively, a pattern of alternating between one or more tissue expansions and one or more tissue treatments can be performed.

In some embodiments, system 10 comprises one or more first catheters 100a, each with a first functional assembly 130a of a particular size and configured to treat target tissue. System 10 can further comprise one or more second catheters 100b, each with a functional assembly 130b and configured to perform a tissue expansion procedure. System 10 can be constructed and arranged to size a lumen of one or more axial segments of intestine (e.g. using a catheter 100 or other luminal sizing device as described herein) to determine the diameter at a relatively narrow (e.g. the smallest diameter) location within the one or more axial segments. System 10 can be further constructed and arranged to select a first catheter 100a based on the luminal sizing information (e.g. using algorithm 251). System 10 is further constructed and arranged to inflate the functional assembly 130b of a catheter 100b (e.g. with a gas) to a pressure sufficient to correlate to sufficient apposition with the axial segment luminal wall. System 10 can be further constructed and arranged to apply a vacuum to one or more ports 137 of catheter 100b to engage neighboring tissue. System 10 can be further constructed and arranged to inject fluid into tissue (e.g. submucosal tissue) until the pressure within the associated functional assembly 130b exceeds a threshold, at which time fluid (e.g. air) can be exhausted from functional assembly 130b and fluid delivery by fluid delivery element 139c continues until the volume of functional assembly 130b reaches a pre-determined lower limit.

As described hereabove, system 10 can be constructed and arranged to ablate or otherwise treat tissue with an expanded functional assembly 130 that is smaller than the native lumen diameter of an axial segment of intestine. The amount of fluid injected to expand tissue (e.g. submucosal tissue) can be determined in a closed-loop manner to achieve a post-expansion lumen size with a specific diameter along one or more axial segments of the intestine (e.g. the duodenum). System 10 can comprise a single functional assembly 130 configured to treat (e.g. ablate) multiple axial segments of intestine, each with a pre-expanded tissue layer (e.g. submucosal tissue layer expanded to a diameter approximating or otherwise related to the diameter of the expanded functional assembly 130). System 10 can comprise a functional assembly 130 configured to treat (e.g. ablate) multiple axial segments of intestine that are selected prior to the performance of tissue layer expansion, such as to reduce overall procedure time and/or time between tissue expansion and tissue treatment. System 10 can be constructed and arranged such that the difference between the native intestinal lumen diameter and the post-tissue expansion lumen diameter is known, such as to confirm acceptability of the tissue expansion step(s) prior to an ablation step being performed. System 10 can be constructed and arranged to eliminate one or more sizing steps, as described hereabove.

In some embodiments, system 10 is constructed and arranged to perform a medical procedure comprising a tissue treatment procedure for treating a patient disease or disorder, and the amount of tissue treated is based on the severity of the patient's disease or disorder (e.g. amount of tissue treated is proportional to the severity). In some embodiments, the disease treated is diabetes, and the severity is determined by measuring one or more of: HbA1c level; fasting glucose level; and combinations of one or more of these. In some embodiments, algorithm 251 is configured to determine the amount of tissue to be treated based on the severity of the patient's disease or disorder.

In some embodiments, system 10 is constructed and arranged to (e.g. via algorithm 251) to introduce fluid into functional assembly 130 (e.g. into a balloon 136 of functional assembly 130) until sufficient apposition against an intestinal wall is achieved (e.g. as determined by a pressure measurement and/or image analysis provided by a sensor of the present inventive concepts). Subsequently, fluid is extracted from functional assembly 130 (e.g. until a second, lesser volume of fluid resides within functional assembly 130), after which the intestinal wall is contracted (e.g. via desufflation as described herein) such that the intestinal wall again contacts functional assembly 130. In these embodiments, system 10 can operate as described herebelow in reference to FIG. 38 or 40.

In some embodiments, desufflation is accomplished by applying vacuum to a port (e.g. one or more ports configured to remove fluid from the intestine, such as port 137, one or more ports of shaft 110 proximal or distal to functional assembly 130 (e.g. port 112a and/or 112b described herebelow in reference to FIG. 5B) and/or a lumen of an endoscope or other introduction device 50).

In some embodiments, functional assembly 130 is anchored to the intestine (e.g. by expanding functional assembly 130 and/or by having port 137 engage tissue). In these embodiments, a tissue expansion procedure can be performed, such as by advancing at least one fluid delivery element 139c (e.g. at least three fluid delivery elements 139c) into tissue and delivering injectate 221 (e.g. into submucosal tissue). Alternatively or additionally, a tissue ablation procedure can be performed.

In some embodiments, system 10 is configured to deliver injectate 221 into tissue, such as via one or more fluid delivery elements 139c, each of which can be positioned in a port 137. The delivery of injectate 221 into tissue can produce a therapeutic restriction, occlude one or more body conduits (e.g. blood vessels), deliver a (single) bolus of drug or other agent into blood or other tissue, create a drug or other agent "depot" in tissue, and combinations of one or more of these. Injectate 221 can be configured to expand after delivery into tissue. Injectate 221 can be configured to remain relatively "in place" within tissue proximate the injection site for at least 1 month, 3 months, 6 months, or 1 year. Injectate 221 can be delivered into tissue (e.g. via fluid delivery element 139c) in a location selected from the group consisting of: lower stomach; pylorus; proximal small intestine; distal small intestine; duodenum; jejunum; terminal ileum; bowel; and combinations of one or more of these. In some embodiments, injectate 221 comprises a hydrogel, such as to create a hydrogel prosthesis within one or more tissue layers of the intestine (e.g. one or more submucosal tissue layers).

Injectate 221 can be delivered into tissue to create a therapeutic restriction, as described herein, such as to create a space occupying obstruction as a treatment for obesity; type 2 diabetes; hypercholesterolemia, hypertension; non-alcoholic fatty liver disease; non-alcoholic steatohepatitis; and/or other metabolic disease. Injectate 221 can be delivered to one or more tissue locations to create a sense of satiety, reduce chime throughput and/or reduce obesity. Injectate 221 can be injected into the gastric varices, such as when injectate 221 comprises an occlusive agent such as an adhesive such as cyanoacrylate. System 10 can be constructed and arranged such that delivery of injectate 221 into one or more tissue locations alters nutrient absorption and/or hormonal signaling from the mucosa. System 10 can be constructed and arranged to deliver injectate 221 into colon tissue (e.g. to expand colon submucosal tissue), such as to treat fecal incontinence.

As described above, system 10 can be constructed and arranged to deliver injectate 221 into tissue to deliver a bolus of medication and/or to create a drug or other agent depot within tissue of the patient, such as within mucosal tissue and/or submucosal tissue of the intestine. In some embodiments, an injectate 221 positioned within tissue is activated based on one or more signals produced by a sensor, such as a bioactive glucose sensor that responds to the detection of an analyte and leads to (e.g. via one or more components of system 10) release or other activation of injectate 221. For example, injectate 221 can comprise an anti-diabetic agent, such as insulin, and a sensor (e.g. implant 192 configured as a sensor) can comprise a glucose sensor that detects a glucose change, such as the higher glucose levels that occur after a meal. Injectate 221 can comprise a drug or other agent selected from the group consisting of: a steroid; an anti-inflammatory agent; a chemotherapeutic; a proton pump inhibitor; a sclerosant agent; a differentiation factor such as trans-retinoic acid; an anti-hyperglycemic agent such as GLP-1 analogue or others; an anti-obesity agent; an anti-hypertensive agent; an anti-cholesterol agent such as a statin or others; and combinations of one or more of these. In some embodiments, injectate 221 comprises a steroid or other anti-inflammatory agent delivered to a therapeutic restriction of the present inventive concepts (e.g. delivered into an existing restriction or to create a restriction). In some embodiments, injectate 221 comprises one or more steroids and/or other anti-inflammatory agents delivered to the site of chronic inflammation, such as a site of ulcerative colitis or Crohn's disease. In some embodiments, injectate 221 comprises one or more steroids or other anti-inflammatory agents delivered at the site of celiac disease (e.g. the proximal small intestine) and/or otherwise delivered to treat celiac disease. In some embodiments, injectate 221 comprises one or more chemotherapeutic agents delivered to the site of a cancerous or pre-cancerous lesion.

Injectate 221 can be injected into tissue in a single procedure or multiple procedures. System 10 can be configured to determine an injectate 221 delivery parameter (e.g. determined by algorithm 251), such as by performing an analysis based on a patient demographic parameter and/or a patient physiologic parameter, such as age, weight, HbA1c level and cholesterol level. The injectate delivery parameter can comprise a parameter selected from the group consisting of: volume of injectate 221 delivered; length and/or area of a tissue layer receiving injectate 221; type of material included in injectate 221; viscosity of injectate 221; titration result of injectate 221; and combinations of one or more of these.

In some embodiments, system 10 is constructed and arranged to both deliver a durable injectate 221 (e.g. injectate 221 remains in place for at least 1 month), as well as treat target tissue (e.g. a treatment comprising ablating duodenal and/or other intestinal mucosa). The two procedures can be performed on the same day or on different days.

In some embodiments, injectate 221 comprises a radiographic material, such as tantalum, such as to be used in combination with X-ray or fluoroscopy to assess tissue expansion (e.g. submucosal tissue expansion), as described herein. Alternatively or additionally, injectate 221 can comprise a material that is visualizable under other imaging modalities (e.g. an imaging modality provided by imaging device 55), such as magnetic material; ferrous material; ultrasonically reflective material; and combinations of one or more of these.

In some embodiments, sensor 139*b* comprises a sensor configured to provide an impedance measurement, such as an impedance measurement used by algorithm 251 to enable closed-loop or otherwise adjust delivery of RF energy from treatment element 139*a*. In some embodiments, injectate 221 comprises a conductive substance, such as a conductive substance configured to enhance an impedance measurement recorded by sensor 139*b*. In these embodiments, injectate 221 can comprise one or more substances that are both conductive and visualizable (e.g. visualizable by imaging device 55 as described hereabove), such as tantalum.

In some embodiments, injectate 221 comprises a pharmaceutical drug or other agent (e.g. injectate 221 comprises agent 420) configured to provide a therapeutic benefit when delivered by one or more fluid delivery elements 139*c* into intestinal or other tissue. In these embodiments, injectate 221 can be injected into mucosal tissue and/or tissue proximate mucosal tissue (e.g. submucosal tissue). A major function of the mucosa is to bind or absorb certain molecules, and prevent or otherwise reduce the passage of all other molecules. Thus, insertion of injectate 221 directly into the submucosa can bypass the mucosal barrier, enabling the delivery of therapeutic large molecules that otherwise would be passed through the body completely or largely unabsorbed. This procedure also provides more precise dosage control, since the amount of absorption through the mucosa can be variable. Injectate 221 (e.g. injectate 221 comprising agent 420) can comprise any therapeutic biologic or biochemical entity. The entity of injectate 221 can have therapeutic effect by itself or it can be externally triggered, such as when injectate 221 comprises trigger materials, such as magnetic nanoparticles triggered by magnetic fields, gold nanoparticles triggered by light, optical or other fields, particles activated by light such as ultraviolet light or infrared light, and/or particles activated by heating or chilling. In some embodiments, tool 500 is configured to provide the triggering event, such as by generating a magnetic field, delivering light, and/or by delivering or extracting heat.

Local administration of drugs with high systemic toxicity and/or propensity for resistance by catheter 100 is advantageous, as much higher local concentrations of the drug and/or much lower systemic bioavailability can be achieved. Avoidance of skin-penetrating injections can be beneficial (e.g. avoiding associated pain, cosmetic issues and likely trauma to injection site). Catheter 100 can be used to deliver depot formulations of drugs or other agents to intestinal tissue (e.g. the intestinal submucosa) for the treatment of various GI or systemic illnesses. Submucosal delivery via catheter 100 can avoid the limitations associated with the mucosal barrier as described hereabove, and the limited bioavailability that is created. Submucosal delivery via catheter 100 can also allow the delivered drug to avoid chemical reactions or other adverse effects that result from interaction with various microbiological and pH environments in the patient's gut. In some embodiments, injectate 221 comprises an anti-reflux medication and/or an anti-acid medication, such as when injectate 221 is delivered into the mucosa or submucosa of the esophagus, intestine and/or stomach.

Systemic pharmaceutical therapy including immunomodulators to treat inflammatory bowel disease has issues with toxicity associated with immune suppression. This systemic therapy can also have limited efficacy once an individual develops antibodies against the monoclonal antibody therapies. In both cases, high systemic concentrations of the drugs limit the ability to achieve sufficiently effective doses in the GI tract itself, where the therapy needs to be most effective. A catheter 100 comprising one or more fluid delivery elements 139c can be used as a tool to perform site-specific delivery of drugs and other agents to treat GI illnesses, such as celiac disease and inflammatory bowel disease.

In some embodiments, system 10 comprises an implantable device, such as implant 192 shown. Implant 192 can comprise a medical device, such as a drug delivery depot or other drug delivery device. Implant 192 can comprise a sensor or sensing device. In some embodiments, system 10 is configured to deliver implant 192 via a functional element 139, such as fluid delivery element 139c (e.g. when fluid delivery element 139c comprises a needle comprising a lumen through which a sensor-based implant 192 can be deployed into tissue such as mucosal tissue, submucosal tissue, other intestinal tissue and/or other tissue of the patient). In some embodiments, system 10 is constructed and arranged to deliver one or more implants 192 into tissue that is not proximate to a significant number of pain-sensing nerves. In some embodiments, implant 192 can comprise a sensor configured to measure a physiologic parameter selected from the group consisting of: blood pressure; heart rate; pulse distention; glucose level; blood glucose level; blood gas level; hormone level; GLP-1 level; GIP Level; EEG; LFP; respiration rate; breath distention; perspiration rate; temperature; gastric emptying rate; peristaltic frequency; peristaltic amplitude; and combinations of one or more of these.

In some embodiments, implant 192 comprises a sensor, such as a sensor configured to be implanted in the submucosal tissue of the intestine. In some embodiments, catheter 100 is configured to implant 192 into tissue via a fluid delivery element 139c and/or another functional element of catheter 100. Implant 192 can comprise a sensor configured to produce a signal related to a physiologic parameter related to the concentration of a material selected from the group consisting of: fat, sugar (e.g. glucose or fructose); protein; one or more amino acids; and combinations of one or more of these. In some embodiments, implant 192 comprises a wireless communication element, such as an RF or infrared element configured to transmit information (e.g. to a receiving component of system 10). System 10 can be configured to analyze the received information, such as an analysis performed by algorithm 251 used to manage obesity, insulin resistance and/or Type 2 diabetes.

In some embodiments, system 10 is constructed and arranged to expand tissue by delivering injectate 221 into tissue (e.g. submucosal tissue of the intestine) with fluid delivery element 139c. System 10 can be constructed and arranged to deliver injectate 221 at a constant or varied rate, in open loop or closed loop delivery configurations. In some embodiments, system 10 is configured to deliver fluid at an elevated flow rate and/or at an elevated pressure, such as with a flow rate and/or pressure which decreases over time. System 10 can be constructed and arranged to monitor one or more pressures achieved during delivery of injectate 221 into tissue. System 10 can be configured to measure a pressure using a pressure sensor-based functional element 109, 119, 139, 209, 229 and/or 309. Alternatively or additionally, system 10 can comprise a sensor positioned in tissue proximate the tissue to be expanded. In some embodiments, catheter 100 comprises multiple fluid delivery elements 139c, such as an array of three fluid delivery elements 139c equally spaced about functional assembly 130. In these embodiments, injectate 221 can be delivered into tissue by the multiple fluid delivery elements 139c simultaneously or sequentially. Pressure measured by system 10 can correlate to the quality of tissue expansion, or other tissue expansion parameter. In some embodiments, system 10 regulates delivery of injectate 221 (e.g. by regulation of one or more pumps 225 delivering injectate 221), and/or detects an undesired state in the delivery of injectate 221, based on pressure measured by system 10. System 10 can be configured to confirm that during delivery of injectate 221, a proper pressure increase occurs in the expanded tissue, within functional assembly 130 and/or at another system 10 location. The pressure at a first location can be measured directly (e.g. via a pressure sensor-based functional element located proximate the first location, or indirectly such as via a pressure sensor-based functional element located at a second location whose pressure can be correlated to the pressure at the first location, as described herein for measurement of pressure, temperature and/or any system 10 parameter). System 10 can prevent a pressure threshold from being surpassed at one or more locations, such as to prevent an undesired event such as an amount and/or location of expansion of tissue that can have a deleterious effect, such as expansion of serosal tissue of the intestine. In some embodiments, pressure information is processed (e.g. via algorithm 251), such that cumulative pressure information (e.g. time at pressure, pressure change rates, and the like) can be compared to one or more thresholds. In these embodiments, pressure information and/or processed pressure information (herein "pressure information") can be used to confirm size or geometric shape of expanded tissue, such as to confirm full circumferentiality of a tissue expansion. In some embodiments, system 10 correlates one or more pressure readings below a threshold to an adverse event selected from the group consisting of: fluid delivery element 139c not delivering fluid into the appropriate tissue (e.g. fluid delivery element 139c has not properly penetrated tissue); failure of a functional element such as failure of a functional element comprising a valve; leak in a conduit such as a leak in a conduit 111, 211, 212 and/or 311; and combinations of one or more of these.

In some embodiments, functional assembly 130 is expanded with fluid at a first pressure (e.g. a pressure of approximately 0.5 psi, 0.7, psi or 0.9 psi), and fluid is delivered into tissue by one or more fluid delivery elements 139c (e.g. three fluid delivery elements 139c). During fluid injection, system 10 can monitor pressure (e.g. a sensor of the present inventive concepts monitors pressure within functional assembly 130 and/or within a conduit in fluid communication with functional assembly 130), and if the pressure exceeds a second pressure (e.g. a pressure of at least 0.7 psi, 0.9 psi 1.1 psi, or other pressure greater than the first pressure), system 10 can reduce the pressure within the functional assembly 130 (e.g. reduce the pressure to the first pressure).

In some embodiments, system 10, console 200 and/or catheter 100 are constructed and arranged to perform partial circumferential tissue expansion of one or more axial segments of the GI tract (e.g. less than 360° expansion of submucosal tissue of one or more axial segments of the intestine). In some embodiments, injectate 221 comprises a relatively viscous material and catheter 100 delivers injectate 221 to create focal (i.e. partial circumferential) or multi-focal expansions of tissue (e.g. multiple partial circumferential expansions of submucosal tissue). In some embodiments, a therapeutic restriction or other tissue expansion of the present inventive concepts can comprise two or more focal restrictions created around the circumference of an axial segment of tubular tissue that block more than 50% or more than 75% of the luminal diameter. In some embodiments, a full or near-full circumferential expansion of tissue is created by first expanding (e.g. inflating) a functional assembly 130 and creating one or more focal expansions, subsequently compacting (e.g. deflating) the functional assembly 130, re-expanding (e.g. re-inflating) the functional assembly 130 and creating additional focal expansions between the previously expanded areas to create a substantially circumferential expansion. Prior to re-expanding, functional assembly 130 can be repositioned (e.g. rotated). The compacting and re-expanding can be configured to allow multiple fluid delivery elements 139c to self-reposition during contact with the peaks of the focal expansions (e.g. reposition into valleys in between the focal expansions). Alternatively, the functional assembly 130 (e.g. shaft 110 of the catheter 100) can be rotated and/or otherwise repositioned (e.g. automatically and/or manually) after the initial focal expansions.

In some embodiments, functional assembly 130 comprises an expanded diameter of a magnitude (e.g. a small enough diameter) configured to accommodate a range of luminal diameters of the small intestine. Desufflation of the duodenum (e.g. using body introduction device 50 and desufflation techniques known to those of skill in the art) can be performed to collapse the inner wall of the intestine onto a fully expanded functional assembly 130. Functional assembly 130 can comprise one or more ports 137 configured to desufflate to collapse the inner wall of the intestine onto functional assembly 130. In some embodiments, shaft 110 or another component of catheter 100 comprises one or more ports configured to perform desufflation, such as ports 112a and/or 112b described herebelow in reference to FIG. 5B. In some embodiments, system 10 comprises a separate desufflation tool (e.g. aspiration tool), such as tool 500 constructed and arranged to extract fluid from a segment of intestine, such as a segment comprising functional assembly 130. In these embodiments, tool 500 can comprise one or more holes, slots, slits or other openings (e.g. positioned in a distal portion of tool 500) that are configured to aspirate fluids from the intestine, such as to collapse the inner wall of the intestine onto a fully expanded functional assembly 130.

In some embodiments, system 10 is configured to work in combination with a patient care practice, such as a patient diet that is maintained prior to and/or after performance of a medical device or diagnostic procedure performed using system 10. For example, a patient diet or other patient practice can be included prior to and/or after a tissue treatment procedure performed by system 10 to slow down healing (e.g. mucosal healing) and/or provide another enhancement to the therapy achieved. In some embodiments, mucosal healing is slowed down by a functional element 139, tool 500 and/or other component of system 10. In some embodiments, regrowth of treated mucosal tissue is enhanced by a pre-procedural and/or post-procedural patient diet. The diet can include: a liquid diet for at least one day; a low sugar diet and/or a low fat diet for at least one week; a standardized diabetic diet for at least 1 week; and/or nutritional counseling for at least 1 week.

In some embodiments, injectate 221 comprises an injectate configured to cause inflammation of tissue. In these embodiments, one or more fluid delivery elements 139c can be configured to deliver the injectate 221 to tissue to cause an inflammatory response in the tissue. The inflammatory response can result in a tissue layer that functions as a protective layer during a subsequent tissue treatment procedure (e.g. tissue ablation procedure) performed by a functional assembly 130 of catheter 100.

In some embodiments, system 10 includes a tool 500 comprising a mucus removal assembly constructed and arranged to remove mucus from one or more intestinal wall locations (e.g. a full or partial circumferential segment of intestine), such as to remove mucus prior to a tissue treatment performed by functional assembly 130. Alternatively or additionally, functional assembly 130, one or more functional elements 139 and/or one or more other components of catheter 100 can be constructed and arranged to similarly remove mucus. In some embodiments, mucus is removed mechanically. Alternatively or additionally, mucus is removed by delivery (e.g. via one or more fluid delivery elements 139c) of agent 420 to a tissue surface (e.g. when agent 420 comprises a mucolytic agent).

In some embodiments, system 10 comprises one or more materials or devices configured to modify tissue healing, such as when catheter 100 is constructed and arranged to treat intestinal mucosa (e.g. duodenal mucosa). For example, injectate 221, or implant 192 can be delivered in and/or proximate target tissue, such as at a time prior to, during and/or after target tissue treatment. In these embodiments, for example, injectate 221, agent 420 and/or implant 192 that is delivered (e.g. by fluid delivery element 139c or another component of catheter 100) can be configured to delay healing of treated tissue in the intestine, such as to provide enhanced therapeutic benefit to the patient and/or prolong the benefit (e.g. enhance or prolong HbA1c reduction). In some embodiments, injectate 221, agent 420 and/or implant 192 comprises a material selected from the group consisting of: a chemotherapeutic agent; a cytotoxic agent; 5Fluorouracil; Mitomycin-c; Tretinoin topical (Retin-A, Retin-A Micro, Renova); Bleomycin; Doxorubicin (Adriamycin); Tamoxifen; Tacrolimus; Verapamil (Isoptin, Calan, Verelan PM); Interferon alfa-2b; Interferon beta 1a (Avonex, Rebif); Interferon alfa-n3 (Alferon N); Triamcinolone (Aristospan, Kenalog-10); Imiquimod (Aldara, Zyclara); and combinations of one or more of these.

In some embodiments, system 10 includes pressure neutralizing assembly 72, which can be constructed and arranged to monitor and/or adjust (e.g. automatically or semi-automatically) the pressure within a segment of the intestine, such as to allow one or more therapeutic or diagnostic procedures to be performed by functional assembly 130 at a particular pressure or within a particular range of pressures. Pressure neutralizing assembly 72 can be configured to deliver or extract fluids from a segment of the intestine, such as to perform an insufflation procedure, a desufflation procedure, or to otherwise modify the pressure within the segment of the intestine proximate functional assembly 130.

In some embodiments, system 10 includes body core cooling device 73, which can be constructed and arranged to cool the patient's body temperature (e.g. core body temperature). For example, body core cooling device 73 can be configured to cool one or more portions of the patient during a tissue ablation or other procedure performed by catheter 100 as described herein. Body cooling device 73 can be constructed and arranged to cool the patient's blood (e.g. via an external blood circulation circuit), intestine, and/or other body location, such as by extracting heat from one or more body locations. Body cooling device 73 can comprise an elongate shaft for positioning in the esophagus. In some embodiments, body cooling device 73 is used to reduce the patient's core body temperature prior to performance of one or more ablation procedures performed by functional assembly 130 of catheter 100.

In some embodiments, system 10 is constructed and arranged to produce an image (e.g. an image produced by an imaging device and/or other sensor of the present inventive concepts), such as is described herebelow in reference to FIG. 19 and FIGS. 29A-D. Algorithm 251 can be configured to analyze one or more images of tissue that are visualized through one or more portions of functional assembly 130, such as to determine the level of tissue expansion and/or a level of tissue ablation, such as to assess completion adequacy of one or more steps of a medical procedure.

Referring now to FIG. 2, a schematic view of a system and device for performing a medical procedure on the small intestine of a patient is illustrated, consistent with the present inventive concepts. System 10 can comprise one or more components of similar construction and arrangement to similar components of system 10 of FIG. 1 described hereabove. System 10 comprises catheter 100 and console 200. Catheter 100 is constructed and arranged to treat target tissue, such as via the delivery of energy and/or an ablating agent to target tissue. Catheter 100 includes port 103 which operably attaches to port 203 of console 200. In some embodiments, system 10 further comprises tissue expansion catheter 20 which is constructed and arranged to expand one or more layers of tissue, such as one or more layers of target tissue and/or one or more layers of tissue proximate target tissue (e.g. one or more layers of safety-margin tissue as described herein). In some embodiments, system 10 further comprises lumen diameter sizing catheter 30 which is constructed and arranged to collect information correlated to the diameter of a portion of tubular tissue (e.g. one, two or more diameters of a GI lumen within and/or proximate target tissue). In some embodiments, system 10 comprises multi-function catheter 40, which is constructed and arranged to perform two or more functions selected from the group consisting of: tissue treatment (e.g. tissue ablation); tissue expansion; luminal diameter sizing; and combinations of one or more of these. In some embodiments, system 10 comprises multi-function catheter 40, and does not include one or more of: catheter 100, tissue expansion catheter 20 and/or sizing catheter 30.

System 10 can further comprise a body introduction device, such as a vascular introducer, laparoscopic port, and/or endoscope 50a. System 10 can further comprise one or more guidewires, such as guidewires 60a and 60b (singly or collectively guidewire 60). In some embodiments, one or more guidewires 60 comprise a guidewire selected from the group consisting of: a Savary-Gilliard® 400 cm guidewire, a Dreamwire™ guidewire; a super stiff Jagwire™ guidewire; and/or a similar guidewire. In some embodiments, system 10 includes scope attached sheath 80. Sheath 80 can comprise an elongate hollow tube which attaches (e.g. in a side-by-side manner) at one or more points along endoscope 50a. Sheath 80 can attach to endoscope 50a along a majority of its length. In some embodiments, sheath 80 comprises the Reach® overtube manufactured by U.S. Endoscopy, or similar.

Catheter 100, tissue expansion catheter 20, lumen diameter sizing catheter 30 and multi-function catheter 40 comprise handles 102, 22, 32 and 42, respectively. Handles 102, 22, 32 and 42 each comprise one or more controls, controls 104, 24, 34 and 44, respectively. Controls 104, 24, 34 and 44 are configured to allow an operator to control one or more functions of the associated device, such as a function selected from the group consisting of: inflate or otherwise expand a functional assembly (e.g. functional assembly 130); deliver energy; modify energy delivery; deliver an insufflation fluid; insufflate a portion of the GI tract; desufflate a portion of the GI tract; deliver an injectate (e.g. into tissue and/or onto the surface of tissue); deliver a tissue expanding fluid (e.g. into tissue); steer the distal portion of a shaft; translate a control cable or control rod (hereinafter "control rod"); activate a sensor (e.g. record a signal); activate a transducer; and combinations of one or more of these. In some embodiments, handles 102, 22, 32 and/or 42 can comprise a user interface configured to control one or more components of system 10, such as controls 104, 24, 34 and/or 44, respectively, each of which can be constructed and arranged to control operation of one or more of: catheter 100, catheter 20, catheter 30, catheter 40 and/or console 200. In some embodiments, controls 104, 24, 34 and/or 44 can comprise one or more user input and/or user output components, such as a component selected from the group consisting of: screen; touchscreen; light; audible transducer such as a beeper or speaker; tactical transducer such as a vibratory motor assembly; a keyboard; a membrane keypad; a switch; a safety-switch 206 such as a foot-activated switch; a mouse; a microphone; and combinations of one or more of these.

Handles 102, 22, 32 and 42 each attach to the proximal end of shafts 110, 21, 31 and 41, respectively. Shafts 110, 21, 31 and 41 each typically comprise a relatively flexible shaft comprising one or more internal lumens or other passageways. Shafts 110, 21, 31 and/or 41 can comprise a lumen, such as lumen 116 of shaft 110 shown, that is sized and configured to perform a function selected from the group consisting of: provide for the delivery or extraction of one or more fluids such as ablation fluids, cooling fluids, insufflation fluids, pneumatic fluids, hydraulic fluids and/or balloon expanding fluids; allow over the guidewire delivery of the associated device; surround an electrical wire providing electrical energy and/or signals; slidingly receive a control shaft or other control filament such as a control filament used to expand or contract a functional assembly (e.g. functional assembly 130) or otherwise modify the shape of a portion of the device; and combinations of one or more of these. Shafts 110, 21, 31 and/or 41 can comprise a braided or otherwise reinforced shaft or they can include one or more portions which are reinforced. Shafts 110, 21, 31 and/or 41 can comprise a multi-layer construction, such as a construction including a braid, a friction-reduced (e.g. PTFE) liner, a thermally insulating layer and/or an electrically insulating layer. Shafts 110, 21, 31 and/or 41 can include a bulbous distal end, such as bulbous end 115 of shaft 110 shown, a circular or elliptical shaped enlarged end configured to improve traversing the innermost tissue of the duodenum or other luminal tissue of the GI tract (e.g. to smoothly advance within a lumen whose walls include villi and/or one or more folds). As described hereabove, shafts 110, 21, 31 and/or 41 can include a guidewire lumen, such as lumen 116 of shaft 110.

Positioned on the distal end or on a distal portion of shafts 110, 21, 31 and 41 is an expandable functional assembly, functional assemblies 130, 25, 35 and 45, respectively. Functional assemblies 130, 25, 35 and 45 are each constructed and arranged to be radially expanded and subsequently radially compacted (each shown in their radially expanded state in FIG. 2), one or more times during use. Each of functional assemblies 130, 25, 35 and 45 can include an expandable element selected from the group consisting of: an inflatable balloon; a radially expandable cage or stent; one or more radially deployable arms; an expandable helix; an unfurlable compacted coiled structure; an unfurlable sheet; an unfoldable compacted structure; and combinations of one or more of these. Functional assembly 130 can comprise a functional element, such as treatment element 135 shown, configured to treat target tissue. Treatment element 135 can be similar to one or more functional elements 139 described hereabove in reference to catheter 100 of FIG. 1.

In some embodiments, catheter 100, tissue expansion catheter 20, lumen diameter sizing catheter 30 and/or multi-function catheter 40, with their functional assemblies 130, 25, 35 and 45 (respectively) in their radially compacted state, are sized and configured to be inserted through a working channel of endoscope 50*a* and/or sheath 80, after endoscope 50*a* and/or sheath 80 have been inserted into a patient (e.g. through the mouth and advanced such that their distal end resides in the duodenum or other GI tract location). In some embodiments, catheter 100, tissue expansion catheter 20, sizing catheter 30 and/or multi-function catheter 40 are sized and configured to be inserted through the mouth and into a patient's GI tract alongside endoscope 50*a*. In some embodiments, catheter 100, tissue expansion catheter 20, lumen diameter sizing catheter 30 and/or multi-function catheter 40 are sized and configured to be inserted into a patient over one or more guidewires 60. For insertion over a guidewire, the shafts 110, 21, 31 and/or 41 and the distal portions of the associated catheter 100, 20, 30 and/or 40 can comprise sufficient flexibility to traverse the pylorus and enter the duodenum, while having sufficient column and torsional strength to be advanced through the duodenum. In some embodiments, one or more portions of the shafts 110, 21, 31 and 41 have variable stiffness (e.g. stiffer in a proximal portion of the shaft) and/or include a lumen configured to accept a stiffening wire or other stiffening mandrel (e.g. a tapered mandrel), such as stiffening wire 67. Alternatively or additionally, stiffening wire 67 can be inserted into endoscope 50*a* and/or sheath 80, such as to facilitate their advancement through the stomach and into the duodenum. In some embodiments, shaft 110 comprises at least a braided portion. In some embodiments, shaft 110 comprises a tapered portion, such as is described herebelow in reference to FIG. 27.

Console 200 can be constructed and arranged in a similar fashion to console 200 of FIG. 1 described hereabove. Console 200 can comprise an operator (e.g. clinician) accessible user interface 205. User interface 205 can comprise one or more user output and/or user input components, such as a component selected from the group consisting of: screen; touchscreen; light; audible transducer such as a beeper or speaker; tactical transducer such as a vibratory motor assembly; a keyboard; a membrane keypad; a switch; safety-switch 206 such as a foot-activated switch; a mouse; a microphone; and combinations of one or more of these.

Console 200 can comprise a controller, such as controller 250. Controller 250 can comprise one or more components or assemblies selected from the group consisting of: an electronics module; a power supply; memory (e.g. volatile or non-volatile memory circuitry); a microcontroller; a microprocessor; a signal analyzer; an analog to digital converter; a digital to analog converter; a sensor interface; transducer drive circuitry; software; and combinations of one or more of these. Controller 250 can comprise one or more algorithms 251, which can be constructed and arranged to automatically and/or manually control and/or monitor one or more devices, assemblies and/or components of system 10. Algorithm 251 of controller 250 can be configured to determine one or more tissue expansion and/or tissue treatment parameters. In some embodiments, algorithm 251 processes one or more sensor signals (e.g. signals from functional elements 139, 29, 39 and/or 49 described herebelow) to modify one or more of: volume of tissue expansion fluid delivered; rate of tissue expansion fluid delivery; temperature of tissue expansion fluid delivery; amount of ablative fluid delivered; rate of ablative fluid delivery; energy delivered; power of energy delivered; voltage of energy delivered; current of energy delivered; temperature of ablative fluid or energy delivered; device and/or treatment element location within the GI tract; functional assembly pressure (e.g. balloon pressure); and combinations of one or more of these. Treatment element 135 can deliver energy to a surface of tissue, a delivery zone as described hereabove, which is a subset of the target tissue treated by that energy delivery (e.g. due to the conduction of heat or other energy to neighboring tissue). Algorithm 251 can comprise an algorithm configured to determine a delivery zone parameter such as a delivery zone parameter selected from the group consisting of: anatomical location of a delivery zone; size of delivery zone; percentage of delivery zone to receive energy; type of energy to be delivered to a delivery zone; amount of energy to be delivered to a delivery zone; and combinations of one or more of these. Information regarding the delivery zone parameter can be provided to an operator of system 10 (e.g. a clinician), such as via user interface 205. This information can be employed to set a delivery zone parameter, assist the operator in determining the completion status of the procedure (e.g. determining when the procedure is sufficiently complete) and/or to advise the operator to continue to complete a pre-specified area or volume of target tissue. The total area of treatment or number of delivery zones or number of treatments during a particular procedure (any of which can be employed in algorithm 251) can be defined by clinical and/or demographic data of the patient.

Console 200 can comprise one or more reservoirs or other sources of fluid, such as reservoir 220. Reservoir 220 can be configured to provide fluid at an ablative temperature (e.g. sufficiently hot or cold to ablate tissue), a treatment neutralizing (e.g. warming or cooling) fluid configured to reduce ablative effects, an insufflation fluid, injectate 221 (e.g. similar to injectate 221 described hereabove in reference to FIG. 1), an agent (e.g. agent 420 described hereabove in reference to FIG. 1), and/or another fluid. Console 200 can comprise an energy delivery unit, such as EDU 260, configured to deliver energy to treatment element 135 and/or one or more other components of system 10, such as one or more components of devices 100, 20, 30 and/or 40. Controller 250, reservoir 220 and/or EDU 260 can be of similar construction and arrangement as controller 250, reservoir 220 and/or EDU 260, respectively, of FIG. 1 described hereabove.

Console 200 can comprise a pressure or other fluid pumping assembly, such as pumping assembly 225 constructed and arranged to deliver positive pressure or vacuum pressure (e.g. any pressure below another pressure) to one or more fluid delivery elements or fluid pathways (e.g. lumens) of system 10. Pumping assembly 225 can be constructed and arranged to provide and/or extract fluid to radially expand and/or radially compact, respectively, one or more expandable assemblies, such as functional assemblies 130, 25, 35 and/or 45. Pumping assembly 225 can comprise one or more pumps or other fluid delivery mechanisms, and/or other pressure or vacuum generators. In some embodiments, pumping assembly 225 is constructed and arranged to provide a recirculating ablative fluid (e.g. hot or cold) to catheter 100 and/or catheter 40. In these embodiments, pumping assembly 225 can be constructed and arranged to further provide a recirculating "neutralizing fluid" (e.g. a cooling or warming fluid, respectively, to counteract the ablative effects of the previously circulated ablative fluid) to balloon 36 and/or 46, respectively. Pumping assembly 225 can be of similar construction and arrangement as pumping assembly 225 of FIG. 1 described hereabove. In some embodiments, pumping assembly 225 is constructed and arranged to deliver injectate 221 to a functional assembly 130, 25, 35 and/or 45, such as an injectate configured to expand tissue and/or to create a therapeutic restriction, as described herein, such as an injectate similar to injectate 221 described hereabove in reference to FIG. 1.

Console 200 includes port 203, which is operably attached to one or more of: user interface 205 (e.g. safety-switch 206 or another component of user interface 205), controller 250, reservoir 220 and/or pumping assembly 225. Port 203 is constructed and arranged to operably attach (e.g. fluidly, electrically, optically, acoustically, mechanically and/or otherwise operably attach) to one or more of ports 103, 23, 33 and 43 of devices 100, 20, 30 and 40, respectively. Console 200 can be constructed and arranged to deliver fluids and/or energy via port 203 to one or more of devices 100, 20, 30 and 40. In some embodiments, an inflation fluid and/or a fluid at an ablative temperature is provided and/or recovered by console 200, such as a fluid at an ablative temperature delivered to functional assembly 130 of catheter 100 and/or functional assembly 45 of catheter 40. In some embodiments, insufflation, pneumatic and/or hydraulic fluids are delivered and/or recovered by console 200 via port 203. In some embodiments, an injectate 221 is delivered by console 200, such as is described herebelow in reference to tissue expansion catheter 20 and multi-function catheter 40. In some embodiments, one or more control rods (not shown) are translated (e.g. advanced and/or retracted) within one or more lumens or other openings of catheter 100, 20, 30 and/or 40, such as to expand a cage, deploy a radially deployable arm, change the shape of an assembly, translate an assembly, rotate an assembly and/or otherwise control the position, shape and/or configuration of an assembly of system 10.

Console 200 can provide energy to, send information to and/or record and/or receive a signal from one or more other elements of catheter 100, such as functional elements 139, 29, 39 and/or 49 described herebelow.

Catheter 100 can be constructed and arranged to treat target tissue of a patient. In some embodiments, catheter 100 is of similar construction and arrangement as catheter 100 of FIG. 1 described hereabove. Catheter 100 comprises handle 102 which attaches to a proximal end of shaft 110 and includes port 103 for operable attachment to console 200. Positioned on the distal end or on a distal portion of shaft 110 is functional assembly 130. Functional assembly 130 can comprise an expandable element selected from the group consisting of: an inflatable balloon such as balloon 136 shown; a radially expandable cage or stent; one or more radially deployable arms; an expandable helix; an unfurlable compacted coiled structure; an unfurlable sheet; an unfoldable compacted structure; and combinations of one or more of these. Functional assembly 130 can comprise an energy delivery element or other tissue treatment element 135, such as an energy delivery element configured to deliver thermal, electrical, light, sound and/or ablative chemical energy to target tissue. In some embodiments, treatment element 135 comprises a mechanical abrader configured to treat tissue through abrasion. In some embodiments, functional assembly 130 comprises a balloon 136 which can be configured to receive one or more expansion and/or ablative fluids. Balloon 136 can comprise a compliant balloon, a non-compliant balloon, a pressure-thresholded balloon and/or otherwise be constructed and arranged as described in detail hereabove. Functional assembly 130 can be configured to both ablate (e.g. via a hot or cold ablative fluid) and neutralize the ablation (e.g. via a cooling or warming fluid, respectively), prior to and/or after the ablation, as described herein.

Via port 103, console 200 can provide and/or extract one or more fluids to and/or from one or more lumens or other flow pathways of catheter 100, such as fluid provided by reservoir 220 and/or propelled by (i.e. delivered and/or extracted by) pumping assembly 225. Console 200, via EDU 260, can be configured to provide energy to one or more treatment elements 135 of catheter 100, such as energy contained in fluid at an ablative temperature (hot and/or cold), electrical energy (e.g. RF or microwave energy), light energy (e.g. laser light energy), or sound energy (e.g. subsonic or ultrasonic sound energy). In some embodiments, console 200 provides a fluid configured to treat target tissue with direct contact, such as an ablating agent (e.g. a sclerosant or other chemically ablative agent) and/or a fluid at an ablative temperature, either or both delivered directly to a target tissue surface.

In some embodiments, treatment element 135 comprises a fluid at an ablative temperature provided by console 200. In these embodiments, treatment element 135 can comprise a sufficiently hot fluid that is introduced into balloon 136 for a first time period to ablate target tissue, after which a cooling fluid is introduced into balloon 136, for a second time period, to extract heat from tissue (e.g. extract heat from target tissue and/or non-target tissue to reduce the ablation effect). Alternatively or additionally, a cooling fluid can be introduced into balloon 136 prior to the delivery of the hot fluid (e.g. for a third time period). In some embodiments, treatment element 135 comprises a sufficiently cold fluid that is introduced into balloon 136 for a first time period to ablate target tissue, after which a higher temperature fluid is introduced into balloon 136, for a second time period, to warm tissue (e.g. warm target tissue and/or non-target tissue to reduce the ablation effect). Alternatively or additionally, a warming fluid can be introduced into balloon 136 prior to the delivery of the cold fluid (e.g. for a third time period). Both the ablative and ablation-reducing fluids can be provided by console 200. These fluids can be provided in a recirculating manner as described in applicant's co-pending application U.S. patent application Ser. No. 14/470,503, entitled "Heat Ablation Systems, Devices and Methods for the Treatment of Tissue", filed Aug. 27, 2014, the content of which is incorporated herein by reference in its entirety for all purposes. Alternatively or additionally, these fluids can be provided in a single bolus manner as described in applicant's co-pending U.S. patent application Ser. No. 14/917,243, entitled "Systems, Method and Devices for Treatment of Target Tissue", filed Mar. 7, 2016, the content of which is incorporated herein by reference in its entirety for all purposes. In some embodiments, thermal ablation is performed using system 10 as described herein.

In some embodiments, target tissue and/or tissue proximate the target tissue is cooled, heated and subsequently cooled again. In these embodiments, target tissue and/or tissue proximate the target tissue can be cooled during at least a portion of a first step, such as a first step including supplying a first fluid (e.g. a recirculating fluid) to functional assembly 130 for a first time period (e.g. a duration of at least 10 seconds or approximately between 15-30 seconds), wherein the first fluid is supplied at a cooling temperature (e.g. continuously supplied by reservoir 220 at a temperature of approximately 10° C.-25° C.). In a subsequent second step, target tissue and/or tissue proximate the target tissue can be heated (e.g. ablated) during at least a portion of the second step, such as a second step including supplying a second fluid (e.g. a recirculating fluid) to functional assembly 130 for a second time period (e.g. a duration of at least 5 seconds or approximately between 8-15 seconds), wherein the second fluid is supplied at a heat ablating temperature (e.g. continuously supplied by reservoir 220 at a temperature of approximately 85° C.-95° C.). In a subsequent third step, target tissue and/or tissue proximate the target tissue can be cooled during at least a portion of the third step, such as a third step including supplying a third fluid (e.g. a recirculating fluid) to functional assembly 130 for a third time period (e.g. a duration of at least 10 seconds or approximately between 15-30 seconds), wherein the second fluid is supplied at a cooling temperature (e.g. continuously supplied by reservoir 220 at a temperature of approximately 10° C.-25° C.). In some embodiments, other temperatures and/or durations for each heating or cooling cycle are used. In some embodiments, the second time period in which a hot fluid is supplied to functional assembly 130 comprises a time less than the first time period and/or the third time period. In some embodiments, the temperature of the fluid supplied to functional assembly 130 during the first time period and/or the third time period is at least 18° C. less and/or at least 60° C. less than the temperature of the fluid supplied to functional assembly 130 during the second time period. In some embodiments, the first temperature and the third temperature comprise a similar temperature. In some embodiments, a cooling fluid at approximately 10° C. is delivered to functional assembly 130 for approximately 30 seconds, after which an ablative fluid at approximately 95° C. is delivered to functional assembly 130 for approximately 12 seconds, after which a cooling fluid at approximately 10° C. is delivered to functional assembly 130 for approximately 30 seconds. Alternatively, a warming fluid can be delivered to functional assembly 130 prior to and/or after the delivery of a cryogenically ablative fluid (e.g. for the similar time periods as described herein in reference to heat ablation). In some embodiments, the volume, temperature and/or duration of fluid delivered to functional assembly 130 is automatically and/or dynamically adjusted, such as an adjustment performed based on a signal provided by one or more sensors as described herein. For example, a temperature and/or duration can be adjusted during a first ablation of an axial segment of intestine and/or during a subsequent second ablation of the same or different axial segment of intestine. In some embodiments, a pre-cooling and/or post-cooling step is used to avoid the need for a tissue expansion step (e.g. tissue expansion proximate tissue to be ablated in a heat ablation step). In other embodiments, a tissue expansion step is included.

In some embodiments, a first axial segment of tubular tissue is cooled (e.g. non-ablatively cooled), via functional assembly 130, for a first time period $TP_1$, and subsequently heat ablated for a second time period $TP_2$. A first reservoir $220_A$ includes the cooling fluid at a temperature $T_A$, (e.g. fluid continuously maintained or at least initially provided at temperature $T_A$) and a second reservoir $220_B$ includes the (heat) ablative fluid at a temperature $T_B$ (e.g. fluid continuously maintained or at least initially provided at temperature $T_B$). In some embodiments, after the heat ablation during time period $TP_2$, an additional tissue cooling step is performed via functional assembly 130, for a third time period $TP_3$. Additionally axial segments of tubular tissue can subsequently be treated (e.g. additional axial segments treated via tissue cooling and subsequent heat ablation, with or without a subsequent tissue cooling step). $T_A$ can comprise a temperature at or below approximately 25° C., such as a temperature at or below approximately 20° C. and/or 15° C., and $T_B$ can comprise a temperature at or above approximately 65° C., such as a temperature at or above approximately 75° C., 85° C. and/or 95° C. $TP_1$ can comprise a time duration of between 3 seconds and 60 seconds (e.g. between 20 seconds and 40 seconds); $TP_2$ can comprise a time duration of between 1 seconds and 30 seconds (e.g. between 5 seconds and 15 seconds); and $TP_3$ can comprise a time duration of between 3 seconds and 60 seconds (e.g. between 20 seconds and 40 seconds). In these embodiments, $T_A$, $T_B$, $TP_1$, $TP_2$ and/or $TP_3$ can be varied (e.g. automatically by system 10), based on information recorded by a sensor of the present inventive concepts (e.g. a sensor measuring temperature, pressure, flow rate and/or other parameter at one or more locations of catheter 100, console 200 or other component of system 10). One or more of $T_A$, $T_B$, $TP_1$, $TP_2$ and/or $TP_3$ can be held relatively constant or unchanged, during one or more axial tissue segment ablations. However, one or more of $T_A$, $T_B$, $TP_1$, $TP_2$ and/or $TP_3$ can vary (e.g. be allowed to vary), such as when $T_A$ increases during an extraction of cooling fluid from catheter 100 (e.g. the recovered fluid warms the cooling fluid in the first reservoir $220_A$). These variations (e.g. as measured by one or more sensors of system 10) can result in an adjustment (e.g. an automatic adjustment) to another parameter (e.g. $T_A$, $T_B$, $TP_1$, $TP_2$ and/or $TP_3$), such as an adjustment made by algorithm 251 (e.g. an algorithm comprising a lookup table including reservoir temperatures and corresponding treatment durations) based on a signal produced by one or more functional elements 109, 119, 139, 209, 229 and/or 309 described hereabove in reference to FIG. 1, that have been configured as a sensor. In some embodiments, $T_A$, $T_B$ $TP_1$, $TP_2$ and/or $TP_3$ are varied based on the value of $T_A$ and/or $T_B$. For example, if the temperature $T_A$ of the cooling fluid were to increase during a multi-ablation procedure, the time period $TP_2$ and/or temperature $T_B$ could be compensatingly adjusted (e.g. decreased). In some embodiments, time period $TP_2$ is decreased by up to 2 seconds (e.g. from an initial time period of approximately 11 to 13 seconds, in one or more decrements), as the temperature $T_A$ increases by up to 16° C. (e.g. from a starting temperature of approximately 9° C.), such as during an clinical procedure comprising ablation of two or more axial segments (e.g. ablation of between two and six axial segments). While the previous embodiments have been described in reference to a cooling of tissue followed by a heat ablation of tissue (which may also include a subsequent tissue cooling step), alternatively, system 10 can be configured to (non-ablatively) warm tissue, followed by cryogenic ablation of tissue (which can also include a subsequent tissue warming step).

In some embodiments, treatment element 135 comprises one or more energy or other tissue treatment elements positioned in, on and/or within functional assembly 130. Treatment element 135 can comprise one or more energy delivery elements configured to deliver energy to target tissue, such as an energy delivery element selected from the group consisting of: a fixed or recirculating volume of fluid at a high enough temperature to ablate tissue; a fixed or recirculating volume of fluid at a low enough temperature to ablate tissue; one or more thermal energy delivery elements such as one or more elements configured to deliver heat energy or cryogenic energy; an array of electrodes such as an array of electrodes configured to deliver radiofrequency (RF) energy; one or more electromagnetic energy delivery elements such as one or more elements configured to deliver microwave energy; one or more optical elements configured to deliver light energy such as laser light energy; one or more sound energy delivery elements such as one or more elements configured to deliver subsonic and/or ultrasonic sound energy; one or more chemical or other agent delivery elements; and combinations of one or more of these. In some embodiments, catheter 100 is constructed and arranged to deliver RF energy, such as is described in applicant's co-pending U.S. patent application Ser. No. 14/609,332, entitled "Electrical Energy Ablation Systems, Devices and Methods for the Treatment of Tissue", filed Jan. 29, 2015; and/or to deliver ablative fluid directly to tissue, such as is described in applicant's co-pending U.S. patent application Ser. No. 14/609,334, entitled "Ablation Systems, Devices and Methods for the Treatment of Tissue", filed Jan. 29, 2015; the content of each of which is incorporated herein by reference in its entirety for all purposes.

In some embodiments, catheter 100 is further constructed and arranged to provide geometric information (e.g. diameter information) of a luminal structure such as the duodenum. In these embodiments, catheter 100 and functional assembly 130 can be of similar construction and arrangement as functional assembly 35 and lumen diameter sizing catheter 30 described herebelow.

In some embodiments, system 10 comprises one or more devices for expanding target tissue or tissue proximate target tissue, such as tissue expansion catheter 20. In some embodiments, target tissue to be treated comprises mucosal tissue and the tissue to be expanded comprises submucosal tissue proximate the mucosal tissue to be treated. In some embodiments, tissue expansion catheter 20 is of similar construction and arrangement as catheter 100 described hereabove in reference to FIG. 1. In some embodiments, tissue expansion catheter 20 is of similar construction and arrangement as a tissue expansion device described in applicant's co-pending International PCT Patent Application Serial Number PCT/US2015/022293, entitled "Injectate Delivery Devices, Systems and Methods", filed Mar. 24, 2015, the content of which is incorporated herein by reference in its entirety for all purposes. Tissue expansion catheter 20 can be configured to expand a full or partial circumferential segment of luminal wall tissue, such as to expand one or more layers of submucosal tissue in one or more axial segments of the duodenum or other portion of the GI tract. Tissue expansion catheter 20 can be configured to expand multiple segments of GI tract tissue, such as multiple relatively contiguous segments of submucosal tissue expanded as described in detail herein.

Tissue expansion catheter 20 comprises handle 22 which attaches to a proximal end of shaft 21 and includes port 23 for operable attachment to console 200. Positioned on the distal end of shaft 21 or on a distal portion of catheter 20 is functional assembly 25. Functional assembly 25 can comprise an expandable element selected from the group consisting of: an inflatable balloon such as balloon 26 shown; a radially expandable cage or stent; one or more radially deployable arms; an expandable helix; an unfurlable compacted coiled structure; an unfurlable sheet; an unfoldable compacted structure; and combinations of one or more of these. Balloon 26 can comprise a compliant balloon, a non-compliant balloon, a pressure-thresholded balloon and/or otherwise it can be constructed and arranged as described in detail hereabove. Balloon 26 can comprise a tissue-contacting length of between 20 mm and 26 mm, such as a tissue-contacting length of approximately 23 mm Balloon 26 can comprise a wall thickness of between 0.0002" and 0.0010", such as a wall thickness of approximately 0.0005". Functional assembly 25 can be configured to expand to a diameter between 27.5 mm and 37.5 mm, such as a diameter of approximately 32.5 mm. Functional assembly 25 can be configured to be expanded via control 24 and/or via user interface 205 of console 200 (e.g. inflated and deflated by delivery and extraction, respectively, of air, water and/or other fluids by console 200).

Functional assembly 25 comprises one or more fluid delivery elements 28. The one or more fluid delivery elements 28 can each comprise an element selected from the group consisting of: needle such as a straight needle or a curved needle; nozzle; fluid jet; iontophoretic fluid delivery element; and combinations of one or more of these. The one or more fluid delivery elements 28 are configured to deliver injectate 221 and/or another fluid to tissue when functional assembly 25 is expanded (e.g. at least partially expanded with inflation fluid provided by console 200), positioning the fluid delivery elements 28 proximate (e.g. in contact with or close to) tissue to be expanded, such as luminal wall tissue of the GI tract.

The one or more fluid delivery elements 28 can be configured to be advanced (e.g. advanced into tissue) and retracted via control 24 of catheter 20. The one or more fluid delivery elements 28 can be positioned in one or more ports 27, as shown in FIG. 2. In some embodiments, a vacuum provided by console 200 causes tissue to tend toward and/or enter each port 27, such that each fluid delivery element 28 can inject fluid (e.g. injectate 221) into the engaged and/or captured tissue without having to extend significantly beyond the associated port 27 (e.g. fluid delivery element 28 can be configured to remain within port 27 during delivery of fluid into tissue captured within port 27). By limiting excursion of fluid delivery element 28 out of port 27, risk of fluid delivery element 28 and/or injectate 221 penetrating through the outer surface of the GI tract is prevented or at least significantly reduced. In some embodiments, fluid can be delivered into tissue by fluid delivery element 28 with or without advancement of fluid delivery element 28 into the captured tissue (e.g. tissue is drawn into a port 27 via an applied vacuum such that fluid delivery element 28 penetrates or otherwise engages the tissue for fluid delivery without advancement of the fluid delivery element 28). In some embodiments, fluid delivery elements 28, ports 27 and/or other portions of tissue expansion catheter 20 are of similar construction and arrangement as a tissue expansion device described in applicant's co-pending International PCT Patent Application Serial Number PCT/US2015/022293, entitled "Injectate Delivery Devices, Systems and Methods", filed Mar. 24, 2015, the content of which is incorporated herein by reference in its entirety for all purposes.

In some embodiments, functional assembly 25 comprises three or more fluid delivery elements 28 arranged in a circumferential pattern, such as three fluid delivery elements 28 arranged along a circumference and separated by approximately 120°. The multiple fluid delivery elements 28 can be configured to be advanced individually (e.g. via multiple controls 24), or simultaneously (e.g. via a single control 24). In some embodiments, two fluid delivery elements 28 are separated by approximately 180°. In some embodiments, four fluid delivery elements 28 are separated by approximately 90°.

In some embodiments, system 10 includes injectate 221 which can be provided by console 200 to catheter 20, and delivered into tissue by the one or more fluid delivery elements 28. Injectate 221 can comprise one or more materials as described hereabove in reference to injectate 221 of FIG. 1.

In some embodiments, catheter 20 and/or console 200 are configured to reduce a volume of fluid (e.g. liquid or gas) within functional assembly 25 (e.g. within balloon 26) as injectate 221 is delivered into tissue (e.g. submucosal tissue), such as to prevent excessive force being applied by functional assembly 25 to tissue proximate the expanding tissue (i.e. due to the decreasing luminal diameter proximate the expanding tissue in contact with functional assembly 25). In some embodiments, system 10 is constructed and arranged to inflate or otherwise expand functional assembly 25 (e.g. balloon 26) to a first target pressure, such as a pressure of approximately 0.7 psi. Injectate 221 is delivered via one or more fluid delivery elements 28 into submucosal tissue (e.g. simultaneously or sequentially). Fluid contained within functional assembly 25 (e.g. within balloon 26) can be reduced or increased to maintain the pressure at a second target pressure, for example a pressure higher than the first target pressure such as a pressure between 0.8 psi and 0.9 psi. Fluid of up to 10 ml can be injected while maintaining the second target pressure in functional assembly 25 (e.g. by decreasing the amount of fluid in functional assembly 25 to cause 1 mm steps of diameter decrease of functional assembly 25).

In some embodiments, tissue expansion catheter 20 is further constructed and arranged to provide geometric information (e.g. diameter information) of a luminal structure such as the duodenum or other intestinal location. In these embodiments, catheter 20 and functional assembly 25 can be of similar construction and arrangement as lumen diameter sizing catheter 30 and functional assembly 35, respectively, described herebelow.

In some embodiments, system 10 comprises one or more separate devices for estimating or otherwise measuring (e.g. "sizing") the diameter, average diameter, equivalent diameter, minimum diameter, cross sectional area and/or other geometric measure (herein "diameter") of luminal tissue, such as lumen diameter sizing catheter 30. Sizing catheter 30 is constructed and arranged to be placed into one or more locations of the GI tract or other internal location of the patient and measure the diameter or other geometric parameter of tissue. In some embodiments, sizing catheter 30 is of similar construction and arrangement as catheter 100 described hereabove in reference to FIG. 1. Sizing catheter 30 can be configured to measure the diameter of multiple segments of intestinal or other GI tract tissue, such as to measure multiple diameters along the length of the duodenum.

Catheter 30 comprises handle 32 which attaches to a proximal end of shaft 31 and includes port 33 for operable attachment to console 200. Positioned on the distal end of shaft 31 or on a distal portion of catheter 30 is functional assembly 35. Functional assembly 35 can comprise an expandable cage, balloon 36, or other expandable element as described herein, constructed and arranged to measure the inner surface diameter of tubular tissue (e.g. average diameter, equivalent diameter, minimum diameter, cross sectional area and/or other geometric measure of the inner surface of tubular tissue), such as a diameter of the duodenum or jejunum. Balloon 36 can comprise a compliant balloon, a non-compliant balloon, a pressure-thresholded balloon and/or otherwise be constructed and arranged as described in detail hereabove. Functional assembly 35 can be configured to be expanded via control 34 and/or via user interface 205 of console 200 (e.g. inflated and deflated by delivery and extraction, respectively, of fluids by console 200).

Fluids delivered by console 200 to functional assembly 35 (e.g. fluids supplied by reservoir 220) can be provided at one or more predetermined pressures, or pressure profiles. Diameter measurements can be accomplished by performing a visualization procedure (manual or automated) that assesses functional assembly 35 diameter. Alternatively or additionally, functional assembly 35 can be controllably filled with a fluid, and controller 250 can include an algorithm (e.g. algorithm 251 described hereabove in reference to FIG. 1) that correlates the fluid volume and/or fluid pressure to the diameter of tubular tissue in contact with functional assembly 35. In some embodiments, subsequent selection (e.g. device model or size selection) and/or expansion diameter (e.g. inflated diameter chosen for sufficient apposition) of functional assemblies 130, 25 and/or 45 of devices 100, 20 and/or 40, respectively, can be determined using the information provided by sizing catheter 30 and/or console 200. In some embodiments, catheter 30 performs one or more sizing procedures as described herein.

In some embodiments, functional assembly 35 comprises a balloon, expandable cage and/or other expandable element that includes two or more electrodes configured to provide a tissue impedance measurement whose value can be correlated to a level of apposition of functional assembly 35, and whose expanded diameter (e.g. visually or otherwise measured) correlates to a diameter of tubular tissue in contact with the expandable element. Alternatively or additionally, functional assembly 130 of catheter 100, functional assembly 25 of catheter 20 and/or functional assembly 45 of catheter 40 can be used to measure a diameter of the inner surface of tubular tissue, such as has been described hereabove in reference to functional assembly 35 and catheter 30.

In some embodiments, system 10 comprises one or more devices, such as multi-function catheter 40 shown, that are constructed and arranged to perform two or more functions selected from the group consisting of: treat target tissue such as to deliver energy or otherwise ablate target tissue; expand tissue such as to expand one or more layers of submucosal tissue (e.g. proximate to and/or including target tissue); and determine or estimate a diameter (e.g. an average diameter, equivalent diameter, minimum diameter, cross sectional area and/or other geometric measure) of a lumen of tubular tissue; and combinations of one or more of these. Multi-function catheter 40 is constructed and arranged to be placed into one or more locations of the GI tract or other internal location of the patient and perform two or more of the functions listed above. In some embodiments, multi-function catheter 40 is of similar construction and arrangement as catheter 100 described hereabove in reference to FIG. 1. Multi-function catheter 40 can be configured to perform the multiple functions at multiple segments of GI tract, such as multiple relatively contiguous axial segments of the duodenum or other intestinal location as is described herein.

Catheter 40 comprises handle 42 which attaches to a proximal end of shaft 41 and includes port 43 for operable attachment to console 200. Positioned on the distal end of shaft 41 or on a distal portion of catheter 40 is functional assembly 45. Functional assembly 45 can comprise an expandable cage, balloon 46, or other expandable element constructed and arranged to be positioned in apposition with and/or in close proximity to the inner wall of tubular tissue, such as tissue of the duodenum, jejunum and/or other intestinal location. Balloon 46 can comprise a compliant balloon, a non-compliant balloon, a pressure-thresholded balloon and/or otherwise be constructed and arranged as described in detail hereabove. Functional assembly 45 can be configured to be expanded via control 44 and/or via user interface 205 of console 200 (e.g. inflated and deflated by delivery and extraction, respectively, of fluids by console 200).

Functional assembly 45 can comprise treatment element 135', which can comprise a fluid at an ablative temperature delivered into functional assembly 45 by console 200 and/or an energy delivery element permanently positioned on, in and/or within functional assembly 45 (e.g. an energy delivery element configured to deliver thermal energy, electrical energy, light energy, sound energy and/or chemical energy as described herein). In some embodiments, treatment element 135' comprises a mechanical abrader configured to treat tissue through abrasion. In some embodiments, treatment element 135' is of similar construction and arrangement as functional element 139a of catheter 100 of FIG. 1. Functional assembly 45 can be configured to both ablate (e.g. via a hot or cold ablative fluid) and neutralize (e.g. via a cooling or warming fluid, respectively), prior to and/or after the ablation, as described herein.

Alternatively or additionally, functional assembly 45 can comprise one or more elements configured to expand tissue, such as fluid delivery elements 48. Fluid delivery elements 48 can each be positioned within one or more ports 47 as shown. Fluid delivery elements 48 and ports 47 can be constructed and arranged as described hereabove in reference to fluid delivery element 139c and ports 137, respectively, of catheter 100 of FIG. 1.

Devices 100, 20, 30 and/or 40 can comprise one or more functional elements, such as functional elements 139, 29, 39 and/or 49, respectively, shown positioned in, on and/or within functional assemblies 130, 25, 35 and 45, respectively. Alternatively or additionally, one or more functional elements 139, 29, 39 and/or 49 can be located at a different location of the associated device, such as in, on and/or within the associated shaft and/or handle of the device. In some embodiments, one or more functional elements 139, 29, 39 and/or 49 comprise a sensor, such as a sensor selected from the group consisting of: physiologic sensor; blood glucose sensor; blood gas sensor; blood sensor; respiration sensor; EKG sensor; EEG sensor; neuronal activity sensor; blood pressure sensor; flow sensor such as a flow rate sensor; volume sensor; pressure sensor; force sensor; sound sensor such as an ultrasound sensor; electromagnetic sensor such as an electromagnetic field sensor or an electrode; gas bubble detector such as an ultrasonic gas bubble detector; strain gauge; magnetic sensor; ultrasonic sensor; optical sensor such as a light sensor; chemical sensor; visual sensor such as a camera; temperature sensor such as a thermocouple, thermistor, resistance temperature detector or optical temperature sensor; impedance sensor such as a tissue impedance sensor; and combinations of one or more of these. Alternatively or additionally, one or more functional elements 139, 29, 39 and/or 49 comprise a transducer, such as a transducer selected from the group consisting of: an energy converting transducer; a heating element; a cooling element such as a Peltier cooling element; a drug delivery element such as an iontophoretic drug delivery element; a magnetic transducer; a magnetic field generator; an ultrasound wave generator such as a piezo crystal; a light producing element such as a visible and/or infrared light emitting diode; a motor; a pressure transducer; a vibrational transducer; a solenoid; a fluid agitating element; and combinations of one or more of these. Functional elements 139, 29, 39 and/or 49 can be electrically connected to EDU 260 (e.g. to receive power, send signals and/or receive signals), such as via an electrical connection provided by port 203. Functional elements 139, 29, 39 and/or 49 can send or receive signals from controller 250 of console 200, such as one or more sensor signals used to control ablation energy provided by console 200. Functional elements 139, 29, 39 and/or 49 can be activated and/or otherwise controlled via controls 104, 24, 34 and/or 44, respectively. Alternatively or additionally, user interface 205 of console 200 can be configured to allow operator control of functional elements 139, 29, 39 and/or 49.

In some embodiments, console 200 comprises one or more functional elements 209, comprising a sensor or transducer as described hereabove. Functional element 209 can comprise one or more pressure sensors, such as one or more pressure sensors configured to provide a signal used to regulate fluid delivery provided to one or more of devices 100, 20, 30 and/or 40. Functional element 209 can comprise one or more temperature sensors, such as one or more temperature sensors that provide a signal used to regulate temperature of one or more fluids of console 200. Functional element 209 can be positioned to measure a parameter (e.g. temperature or pressure) of fluid within reservoir 220, within pumping assembly 225 and/or within a fluid conduit of console 200.

In some embodiments, system 10 comprises one or more agents configured to be delivered to the patient, such as agent 420. Agent 420 can be delivered by one or more of devices 100, 20, 30, 40 and/or 50, or by a separate device such as a syringe or other medication delivery device. In some embodiments, injectate 221 comprises agent 420, such as when agent 420 is delivered by one or more fluid delivery elements 139c as described herein. In some embodiments, agent 420 comprises an anti-peristaltic agent, such as L-menthol (i.e. oil of peppermint). Alternatively or additionally, agent 420 can comprise glucagon, buscopan, hycosine, somatostatin, an opiod agent and/or any anti-peristaltic agent. Agent 420 can be delivered into the GI tract, such as via endoscope 50a, sheath 80 and/or devices 100, 20, 30 and/or 40. Agent 420 can be delivered systemically, such as via an intravenous or intra-arterial access line, or injected directly into tissue. Agent 420 can comprise a drug or other agent as described hereabove in reference to agent 420 of FIG. 1.

As described above, user interface 205 can comprise safety-switch 206 such as a foot-activated switch. Safety-switch 206 can be configured to allow a clinician to activate or modify one or more processes of system 10 without having to use his or her hands (e.g. without having to use a digit of the hand). In some embodiments, system 10 is constructed and arranged to perform a function selected from the group consisting of: automatic contraction (e.g. deflation) of functional assembly 130 if safety-switch 206 is not activated (e.g. continuously or semi-continuously pushed, pressed or otherwise activated, such as by a foot or digit of an operator); automatic replacement of ablative fluid (e.g. hot fluid) with neutralizing fluid (e.g. cold fluid) if safety-switch 206 is not activated; initiate introduction of ablative fluid (e.g. hot fluid) into functional assembly 130 by activation of safety-switch 206 (e.g. after functional assembly 130 has been pre-expanded with cold fluid and an operator has confirmed proper position for treatment); allow hands-free activation (e.g. initiation) of a treatment step such that one or more operators can maintain their hands on one or more of endoscope 50a and/or devices 100, 20, 30 and/or 40; allow hands-free activation (e.g. initiation) of a treatment step such that the required number of operators is reduced; and combinations of one or more of these.

Each of devices 100, 20, 30 and/or 40 can be provided in one or more sizes, such as one or more lengths of the associated shaft 110, 21, 31 and/or 41, respectively, and/or one or more diameters (e.g. expanded diameter) of the associated functional assembly 130, 25, 35 and/or 45, respectively. Luminal sizing as described herein or other anatomical information can be used to select the appropriately sized device to treat the patient.

In some embodiments, system 10 of FIG. 2 comprises one or more sensors, such as one or more functional elements 109, 119, 139, 209, 229 and/or 309 described hereabove in reference to FIG. 1, that comprise a sensor. These one or more sensors can be configured to provide a signal, such as a signal used to adjust one or more console 200 settings (e.g. console settings 201) of the present inventive concepts.

Applicant has conducted human studies with the systems, methods and devices of the present inventive concepts. Included below are results of early human clinical studies conducted by the applicant, and associated data collected.

Some patients received treatment of approximately 9 cm of relatively full-circumferential axial length of duodenal mucosa (via three approximately 3 cm hot fluid balloon-based ablations), and some patients received treatment of less than or equal to 6 cm of relatively full-circumferential axial length of duodenal mucosa (via two or less approximately 3 cm hot fluid balloon-based ablations).

Early results showed: baseline HbA1c was 9.2% and FPG was 187 mg/dl. 1 month post-procedure, HbA1c was reduced by 1.1% in LS-DMR patients (patients receiving duodenal mucosa treatments of approximately 9 cm (e.g. 9.3 cm) of duodenal tissue) but only 0.1% in SS-DMR patients (patients receiving duodenal mucosa treatment of approximately 3 cm (e.g. 3.4 cm) of duodenal tissue, the data representing 12 LS-DMR patients vs 7 SS-DMR patients, each group at 1 month (p=0.058). By 3 months, HbA1c was reduced by approximately 2% in LS-DMR patients but was unchanged in SS-DMR patients (N=5 in each group at 3 months). FPG reductions in LS-DMR patients were −64 mg/dl and −67 mg/dl at 1 and 3 months.

Table A below shows a breakdown of a number of patients who received various quantities of duodenal axial segment treatments comprising delivery of heat from an ablative fluid delivered to a balloon-based treatment assembly. Thirty five patients were treated in a dosimetric evaluation of the systems, methods and devices described herein. In the study, an ablation is defined as an axial length of circumferentially ablated tissue, ablated with a single positioning of the balloon and subsequent hot fluid delivery to the balloon. Ablation dose is defined as the total length of circumferentially ablated tissue on a single procedural day. A single patient received 5 ablations (the highest dose administered), and duodenal stenosis presented as food intolerance and epigastric discomfort. After endoscopic balloon dilation, the patient recovered without further issue. This patient with the duodenal stenosis lost a substantial amount of weight in the 2 weeks after the development of stenosis (nearly 10 kilograms). Controlled duodenal stenosis may be an effective means of achieving substantial weight loss with its attendant benefits on metabolic or obesity-related ailments. Creation of a therapeutic restriction can be performed as described in co-pending International Patent Application Serial Number PCT/US2014/066829, titled "Systems, Devices and Methods for the Creation of a Therapeutic Restriction in the Gastrointestinal Tract", filed Nov. 21, 2014, the content of which is incorporated herein by reference in its entirety for all purposes.

TABLE A

| Number of Duodenal Ablations | Number of Patients |
|---|---|
| 0 | 2 |
| 1 | 6 |
| 2 | 4 |
| 3 | 22 |
| 4 | 0 |
| 5 | 1 |

In some embodiments, the systems, devices and methods of the present inventive concepts can be configured to deliver at least two ablations to target tissue (e.g. at least two sequential deliveries of energy or other treatments to different axial segments of GI mucosa), such as to deliver at least three ablations to target tissue. In some embodiments, a minimum and/or maximum amount of duodenal mucosa is treated, such as has been described hereabove.

Table B is a table of cumulative demographic information for the first 21 patients of the applicant's studies. These baseline characteristics are generalizable and relevant to the Type 2 diabetes population.

TABLE B

| Characteristic | Value (N = 32) | N in calc |
|---|---|---|
| Duration diabetes—yr | 5.1 +/− 2.9 | 27 |
| Age—yr | 52.9 +/− 7.6 | 26 |
| Female sex—N (%) | 12 (46.2) | 26 |
| Weight—kg | 86.7 +/− 13.2 | 26 |
| Height—cm | 165.7 +/− 10.2 | 26 |
| BMI—kg/m$^2$ | 31.6 +/− 4.0 | 26 |
| BP Systolic—mmHg | 122.5 +/− 16.2 | 26 |
| BP Diastolic—mmHg | 77.2 +/− 8.0 | 26 |
| Medications | 1.7 +/− 0.6 | 19 |

In some embodiments, the systems, devices and methods of the present inventive concepts can be configured to treat patients with a characteristic selected from the group consisting of: duration of diabetes less than 10 years; age between 18 yrs and 75 yrs; BMI between 20 and 60, such as a BMI between 24 and 40; and combinations thereof.

Table C is a table of results of applicant's studies, detailing recorded dose dependent improvements in glycemic control. Applicant measured three validated measures of glycemic control, Hemoglobin A1c (HbA1c), fasting plasma glucose (FPG), and two hour post-prandial glucose (2hPG).

TABLE C

| | | Baseline | | 1 month | | | 3 months | | |
|---|---|---|---|---|---|---|---|---|---|
| | | N | Value | N | Value | Delta | N | Value | Delta |
| HbA1c | All subjects | 26 | 9.22 | 23 | 8.25 | −0.97 | 14 | 7.99 | −1.23 |
| | ≥3 ablations | 16 | 9.42 | 15 | 7.91 | −1.51 | 8 | 7.08 | −2.34 |
| | <3 ablations | 10 | 8.91 | 8 | 8.90 | −0.01 | 6 | 9.22 | 0.31 |
| FPG | All subjects | 26 | 187.6 | 23 | 141.7 | −45.8 | 14 | 160.1 | −27.4 |
| | ≥3 ablations | 16 | 186.7 | 15 | 123.1 | −63.6 | 8 | 129.8 | −56.9 |
| | <3 ablations | 10 | 189.0 | 8 | 176.6 | −12.4 | 6 | 200.7 | 11.7 |
| 2hPG | All subjects | 26 | 263.1 | 20 | 199.3 | −63.9 | 14 | 207.1 | −56.0 |
| | ≥ablations | 16 | 268.9 | 13 | 183.6 | −85.3 | 8 | 163.8 | −105.1 |
| | <ablations | 10 | 253.9 | 7 | 228.3 | −25.6 | 6 | 264.8 | 10.9 |

In some embodiments, the systems, devices and methods of the present inventive concepts can be configured to provide a therapeutic benefit selected from the group consisting of: a reduction in HbA1c of at least 0.7%, 1.0% or 1.5% at three months, such as a reduction of approximately 2.18 at three months; an FPG of no more than 150 mg/dl, 126 mg/dl or 100 mg/dl, such as an FPG that can result with a reduction of approximately 63.5 mg/dl; a 2hPG of no more than 250, 200 or 175, such as an 2hPG that can result with a reduction of approximately 103.7; and combinations thereof.

In some embodiments, an absolute change of at least 0.7%, 1.0%, 1.5% and/or 2.0% in HbA1c is expected. In some embodiments, a relative change above an HbA1c target is expected, such as a relative change of at least 50%, 75% or 100%, such as when the target HbA1c is an HbA1c of approximately 6.5%, 7.0% or 7.5%. It has been reported that a 1% absolute change in HbA1c correlates to a 40% reduction in risk of microvascular complication due to diabetes.

Figure 44:
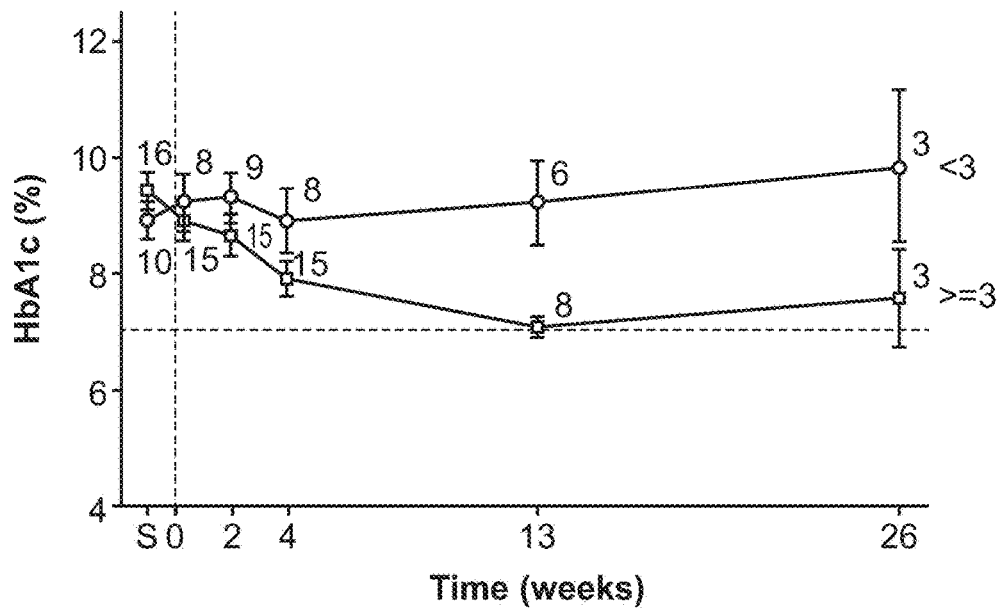
FIGS. 44-62 are graphs representing the results of early human clinical studies conducted by the applicant, and associated data collected, consistent with the present inventive concepts.

FIG. 44 is a graph illustrating an approximately 2% HbA1c reduction in patients receiving three or more ablations compared with no change in those receiving fewer than 3 ablations.

In some embodiments, the systems, devices and methods of the present inventive concepts can be configured to achieve an HbA1c level at or below 7.5%, or 7.0% or 6.5%, such as at a time period of 3 months or more, such as by ablating a cumulative length of duodenal mucosa greater than 6 cm, greater than 7 cm, greater than 8 cm or greater than 9 cm (e.g. via 2, 3 or more ablations as described herein).

Figure 45:
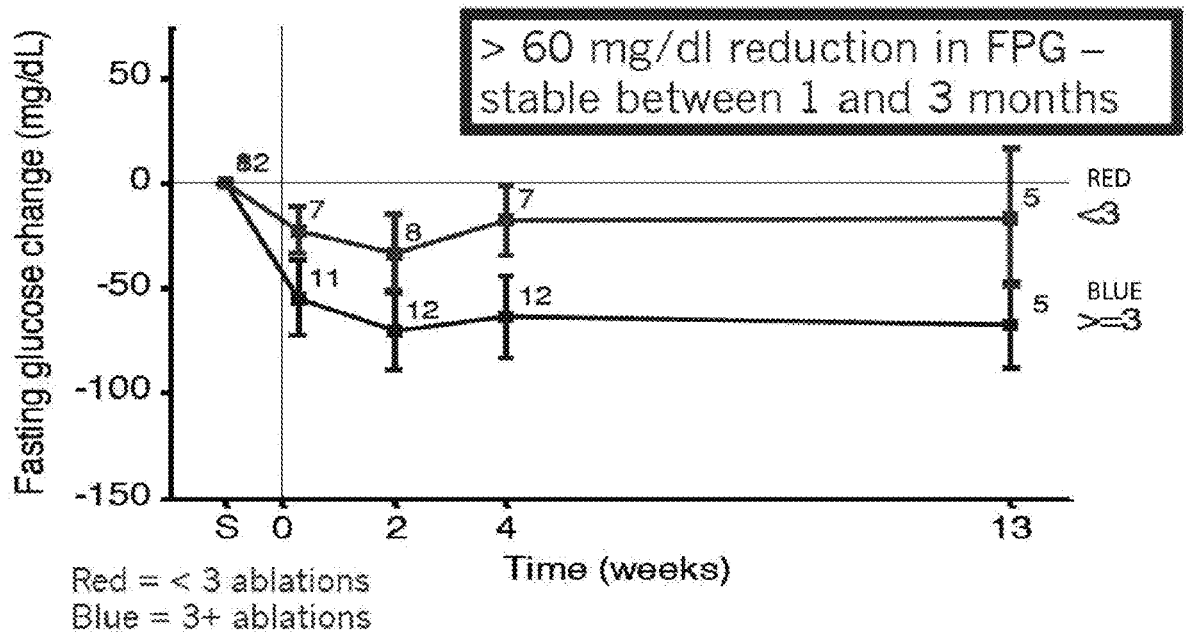

FIG. 45 is a graph illustrating a similar reduction in FPG levels, which remain stable between one and three month post procedure.

Figure 46:
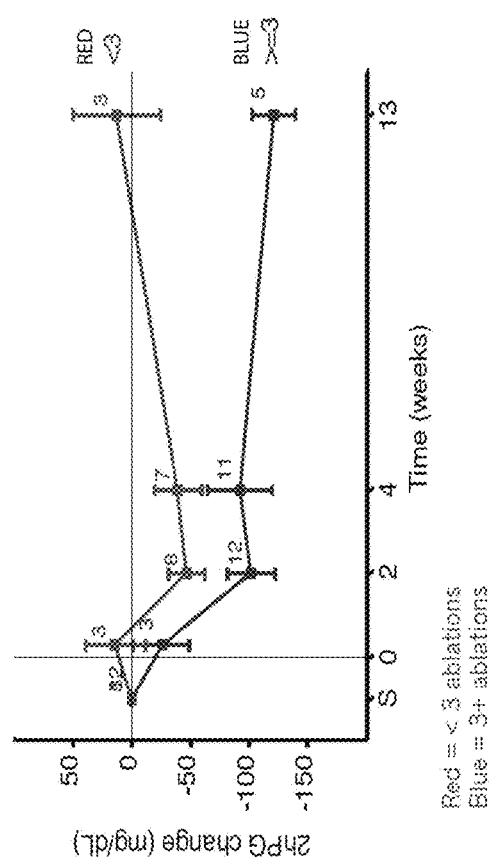

FIG. 46 is a graph illustrating similar improvement in 2hPG measurements.

Figure 47:
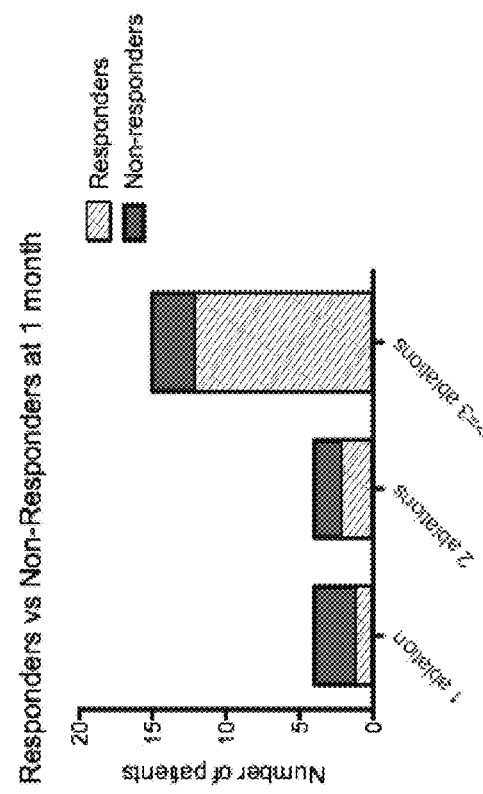

FIG. 47 is a graph of treatment response rates, showing that more ablations correlate to a higher percentage of positive patient outcomes. Responders, or patients with positive clinical results, are defined as having an HbA1c reduction of at least 0.7% at 1 month.

Figure 48:
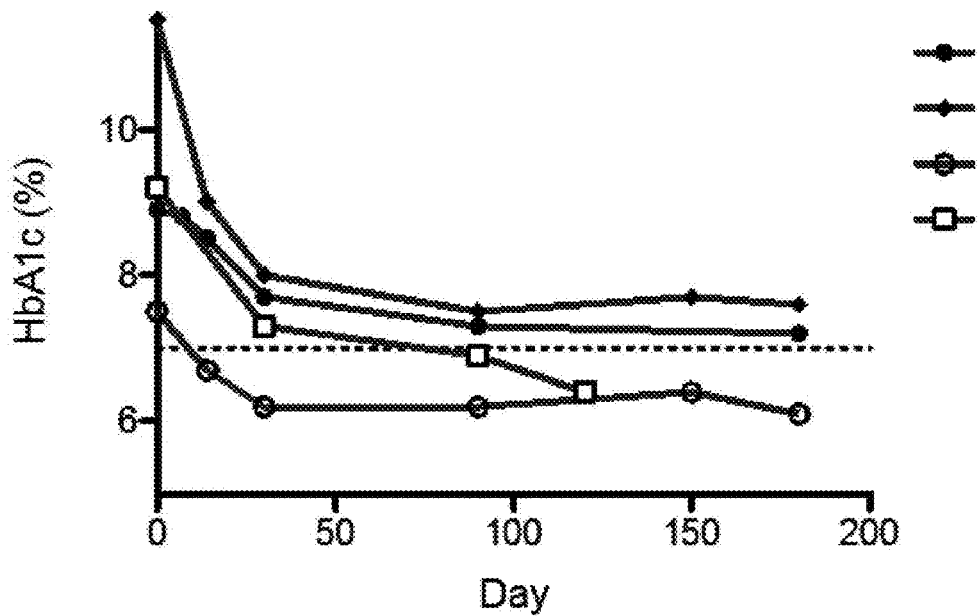

FIG. 48 is a graph of HbA1c percentages, measured for at least 120 days post treatment, showing a durable treatment effect in four out of five patients.

In some embodiments, the systems, devices and methods of the present inventive concepts can be configured to maintain HbA1c below 7.5% at 150 days. Note that 3 out of 4 patients are also on lower levels of medications than were being administered prior to the tissue treatment procedure.

Figure 49:
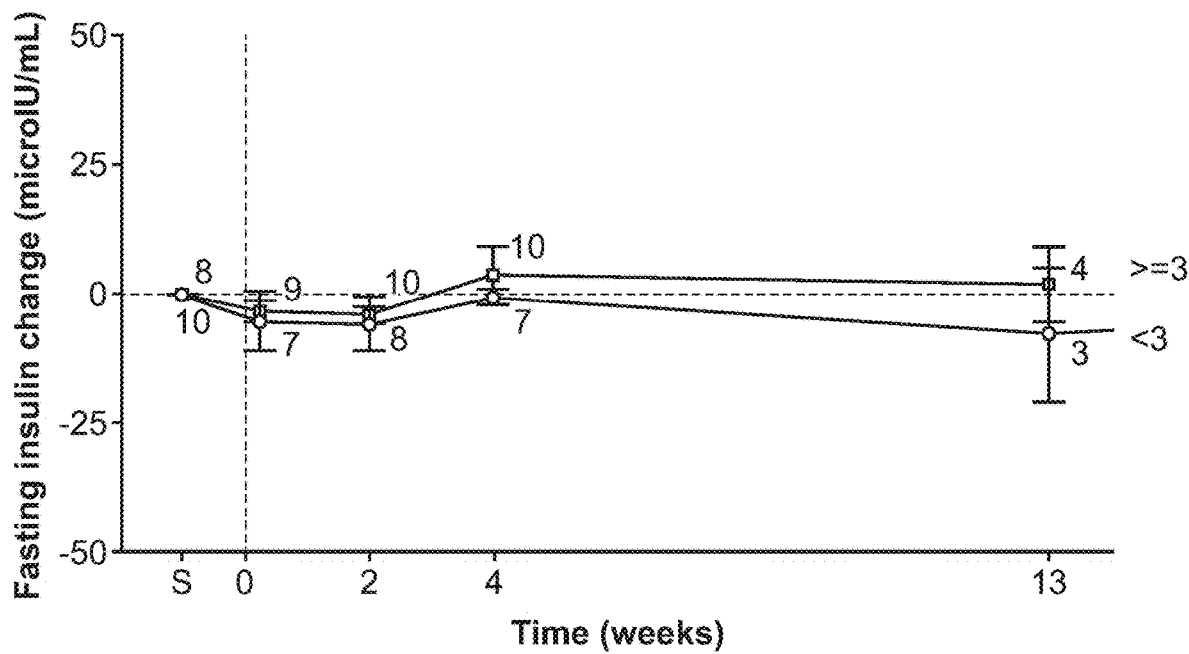

FIG. 49 is a graph of fasting insulin change data, over 3 months, showing an improvement in the health of the beta cell.

Figure 50:
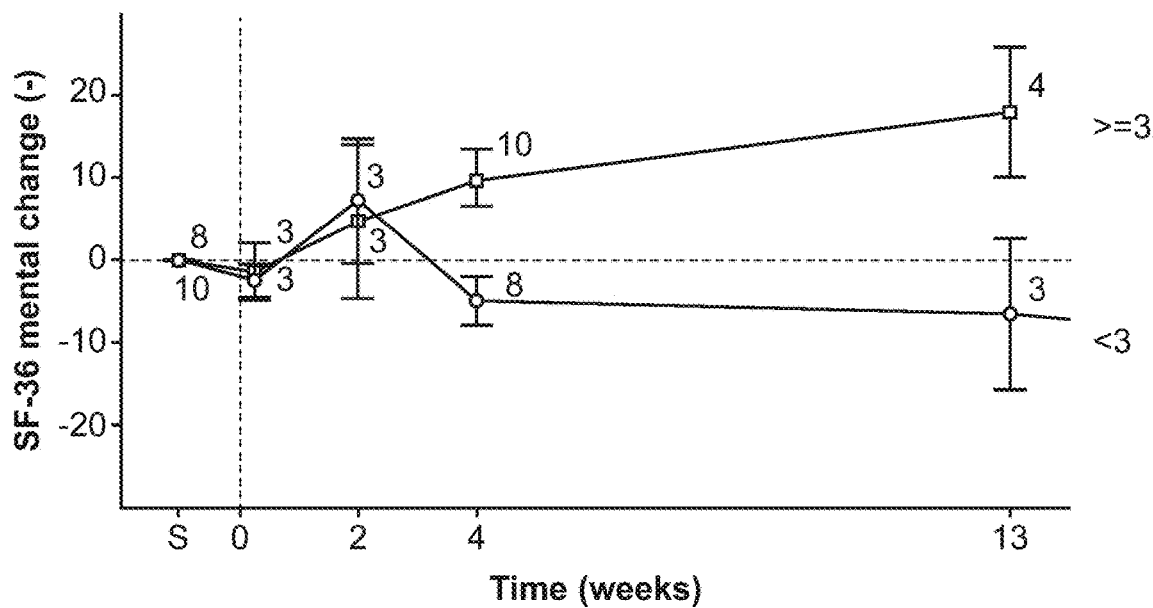

FIG. 50 is a graph of SF-36 Mental value changes, showing improved patient satisfaction through better glycemic control.

In some embodiments, the systems, devices and methods of the present inventive concepts can be configured to cause an improvement in a patient condition as measured by the clinical standard SF-36 Health Survey, such as an improvement in the SF-36 Mental Change score of at least 3 points, at least 5 points or at least 10 points.

Figure 51:
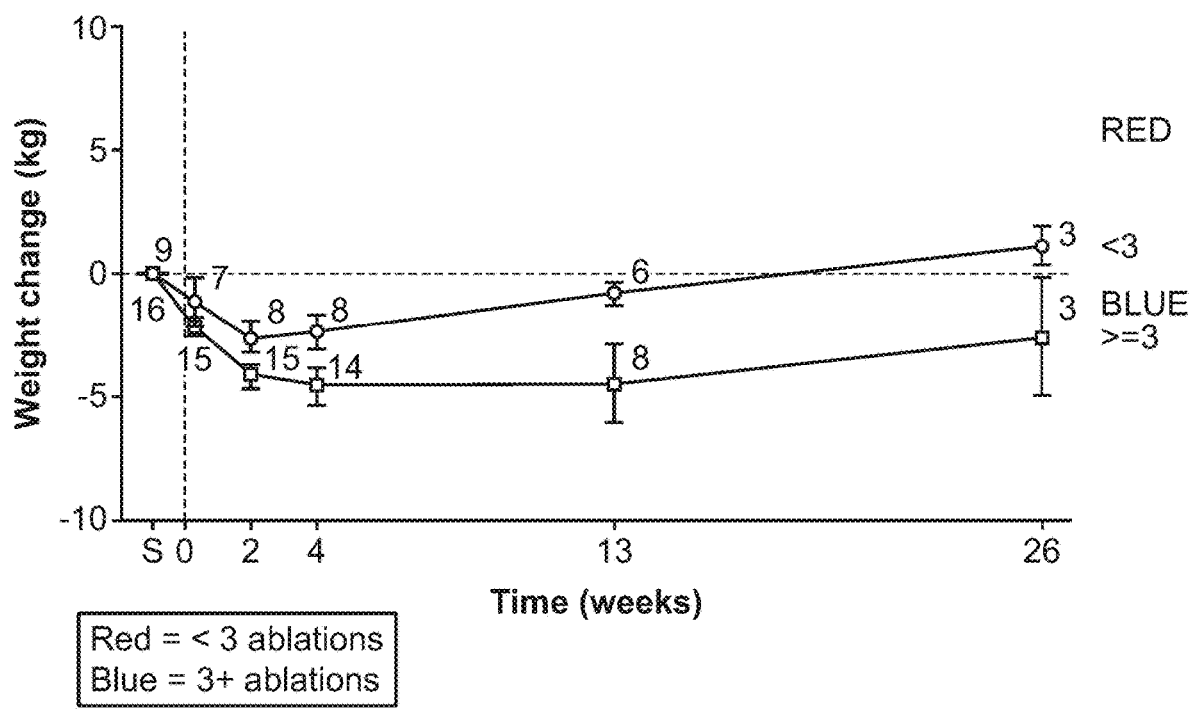

FIG. 51 is a graph of weight change in study patients, showing that weight loss was also noticed in a dose dependent manner.

In some embodiments, the systems, devices and methods of the present inventive concepts can be configured to achieve at least 3 kg or at least 4 kg of weight loss.

Figure 52:
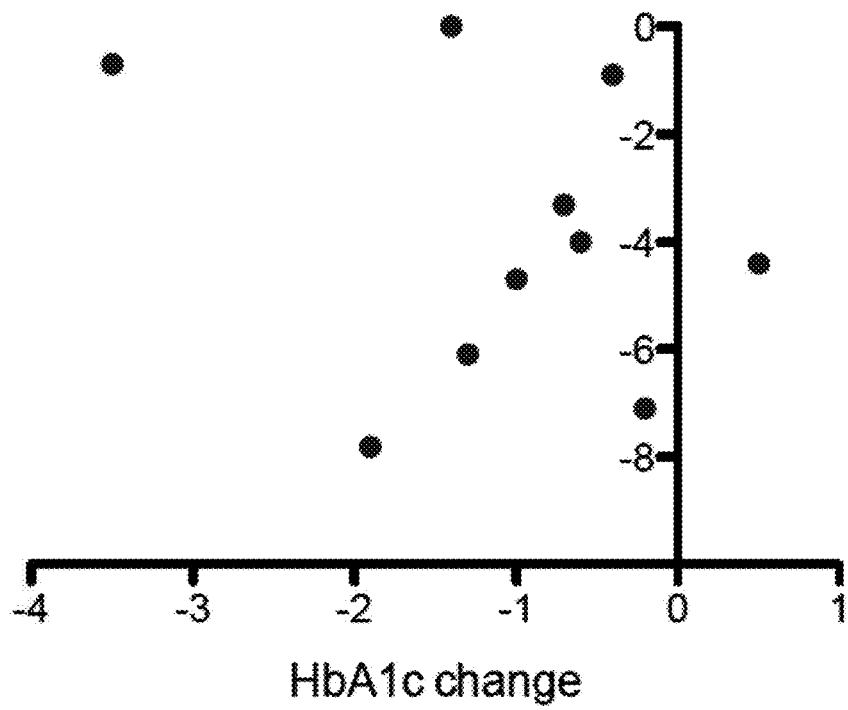

FIG. 52 is a graph suggesting that weight loss and HbA1c are not well correlated based on 30 day post treatment data.

Figure 53:
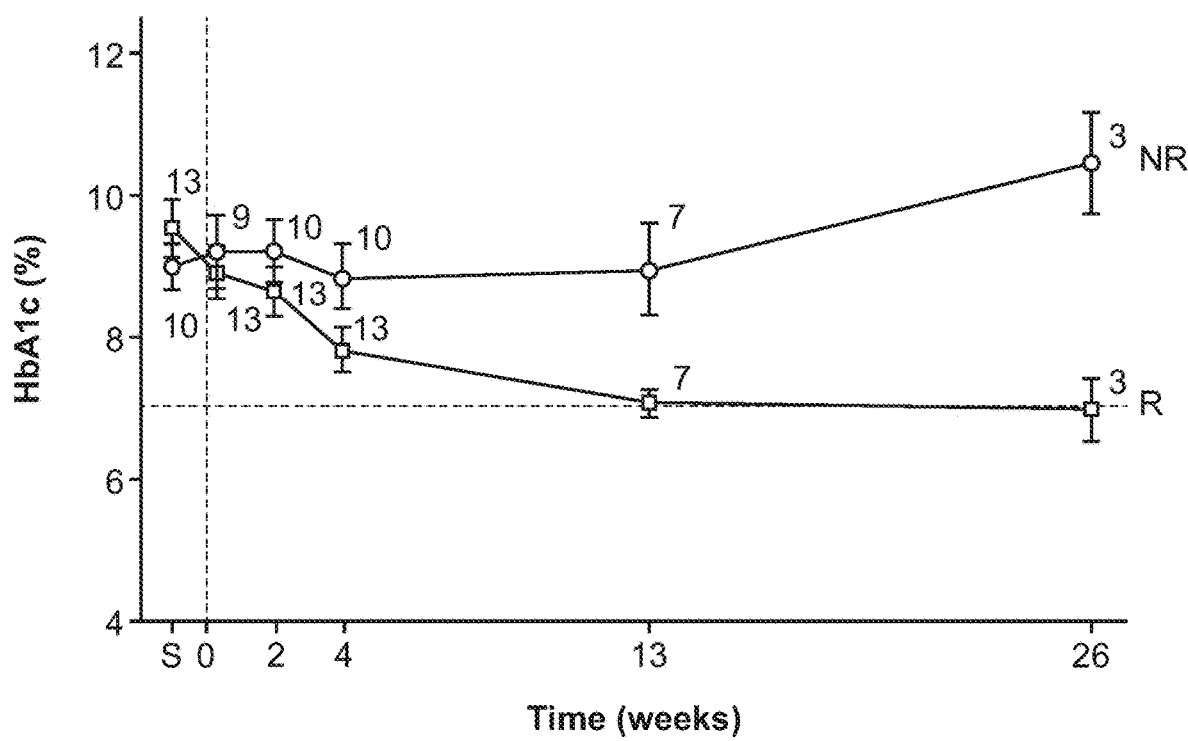

FIG. 53 is a graph of HbA1c percentage over a twenty six week period, comparing responders R and non-responders NR.

Figure 54:
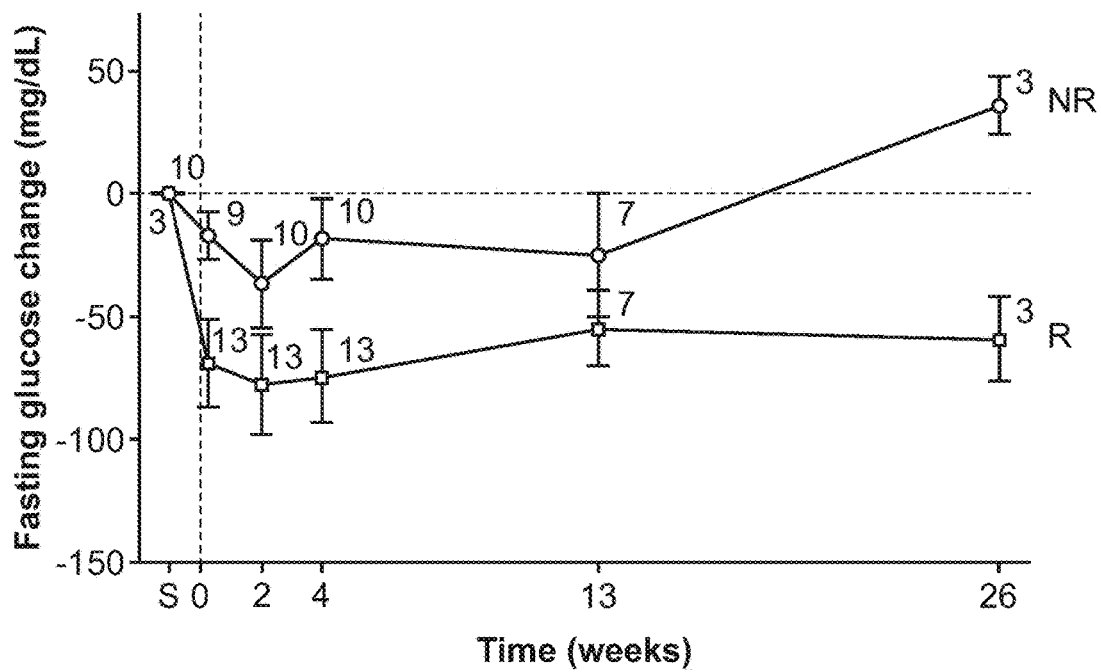

FIG. 54 is a graph of Fasting glucose change (mg/dL) over a twenty six week period, comparing responders R and non-responders NR.

Figure 55:
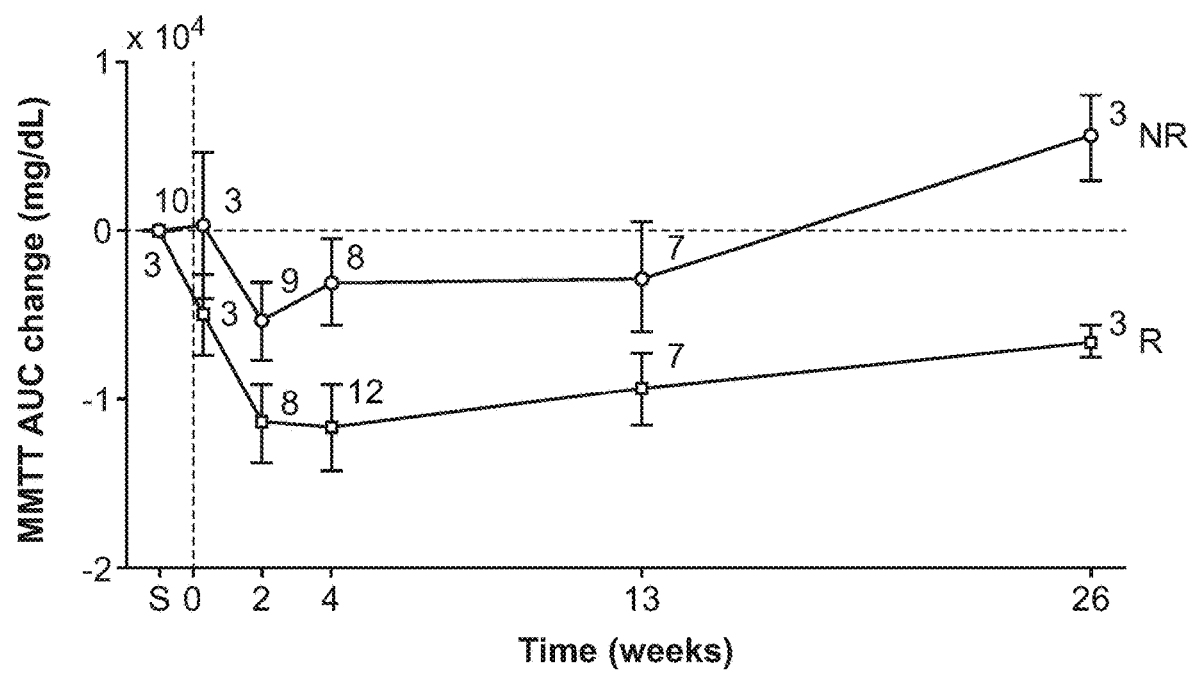

FIG. 55 is a graph of the change in the area under the curve of a mixed meal tolerance test.

Figure 56:
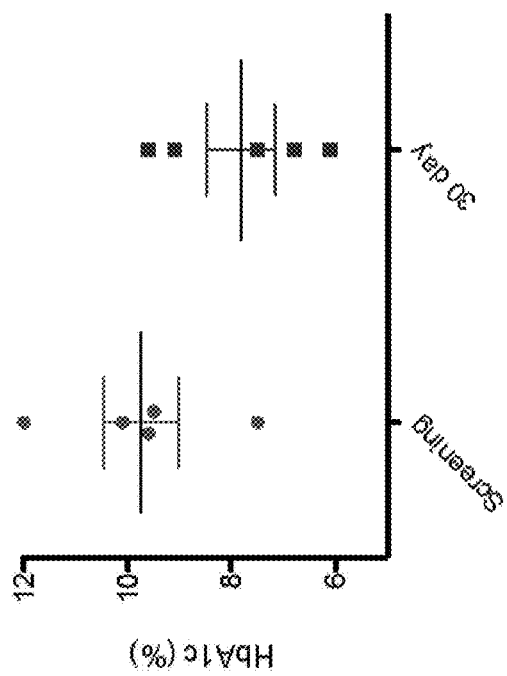

FIG. 56 is a graph of three patients exhibiting a large treatment effect, a 1.9% HbA1c improvement at 30 days.

Table D is a table presenting the large effect size of high dose cohort being statistically significantly better than low dose cohort.

TABLE D

| Characteristic | 3 or more | less than 3 | p-value |
|---|---|---|---|
| 1 MONTH | | | |
| Number subjects | 15 | 8 | |
| Baseline HbA1c—% | 9.39 +/− 1.42 | 9.08 +/− 1.03 | 0.58 |
| HbA1c Change—% | −1.49 +/− 0.92 | −0.18 +/− 1.00 | 0.0047 |
| Baseline FPG—mg/dL | 187 +/− 68 | 202 +/− 45 | 0.61 |
| FPG Change—mg/dL | −64 +/− 74 | −25 +/− 44 | 0.19 |
| 3 MONTH | | | |
| Number subjects | 8 | 6 | |
| Baseline HbA1c—% | 9.36 +/− 1.48 | 9.30 +/− 1.11 | 0.93 |
| HbA1c Change—% | −2.29 +/− 1.24 | −0.08 +/− 1.61 | 0.013 |
| Baseline FPG—mg/dL | 187 +/− 55 | 218 +/− 33 | 0.25 |
| FPG Change—mg/dL | −57 +/− 46 | −18 +/− 64 | 0.20 |

Human studies using the systems, devices and methods of the present inventive concepts have demonstrated significant effectiveness, such as at least a 2% HbA1c reduction in numerous patients at 3 months, a strong indication of clinical value for patients with poorly controlled glucose levels. The studies demonstrated excellent concordance between HbA1c and other surrogate markers such as fasting glucose and post-prandial glucose. The studies also demonstrated clinically meaningful weight loss. In some embodiments, the systems, devices and methods of the present inventive concepts can be used to treat naïve patients with an HbA1c of more than 6%, 6.5%, or 7%. The treatment could further include the administration of metformin. The treatment of the present inventive concepts (with or without the administration of metformin or other single drug) could provide a therapeutic benefit to the patient better than a treatment comprising drug therapy alone (e.g. metformin and/or another single drug therapy). In some embodiments, metformin and a second-line drug can be included in the treatment of the present inventive concepts. Treatment outcomes would include improvement in HbA1c, such as patients who achieve an improvement (i.e. reduction) of at least 1% in HbA1c and/or patients who achieve a target HbA1c of less than or equal to 6.0%, 6.5%, 7.0%, or 7.5%. Treatment can also include reduction in hypoglycemic events, improved quality of life, weight loss, and combinations of the above.

Included below are results of continued studies and associated data collected through Jul. 8, 2015.

Applicant's continued studies included the recording of various patient parameters affected by the treatment of the present inventive concepts, these parameters including but not limited to: HbA1c, fasting blood glucose and post prandial glucose. Patients received between one and five ablations (e.g. two to five sequential ablations performed along two to five axial segments of the duodenum distal to the ampulla of Vater) on a single procedural day. The ablations were delivered by an expandable balloon filled with hot fluid at an ablative temperature, as described in detail herein. The data below in Table E were collected from 39 patients with the following patient demographics:

TABLE E

| Characteristic | Value (N = 39) |
|---|---|
| Duration diabetes—yr | 5.9 +/− 2.2 |
| Age—yr | 53.7 +/− 7.3 |
| Female sex—N (%) | 14 (35.9) |
| Weight—kg | 85.1 +/− 12.0 |
| Height—cm | 165.5 +/− 8.8 |
| BMI—kg/m$^2$ | 31.0 +/− 3.4 |

Procedures were completed using general anesthesia. All patients were discharged on either the day of procedure (19/39) or after an overnight stay (20/39). The number of patients available (included) for each follow-up study described in FIGS. 57-61 and Table F, has the following distribution:

| | Elapsed Time since Procedure | | | | | |
|---|---|---|---|---|---|---|
| 2 Day | 14 Day | 1 Month | 3 Months | 6 Months | 9 Months | 12 Months |
| # of Pts at Follow-up 39 | 39 | 39 | 38 | 34 | 21 | 21 |

The average baseline HbA1c was 9.5% (SD 1.3%) in 39 patients treated between August 2013 and December 2014. HbA1c was 8.1% (SD 1.3%) 1 month post-procedure, 7.3% (SD 1.2%) 3 months post-procedure, and 8.1% (SD 1.6%) 6 months post-procedure. These HbA1c improvements in the entire cohort are seen despite substantial masking of treatment effect due to medication reductions in highly responsive patients in the months immediately after the procedure. The average HbA1c improvement in 21 patients at a 1 year follow-up is 0.5% (despite the fact that 9 out of these 21 patients were on reduced glycemic medicines compared to before their procedure).

Figure 57:
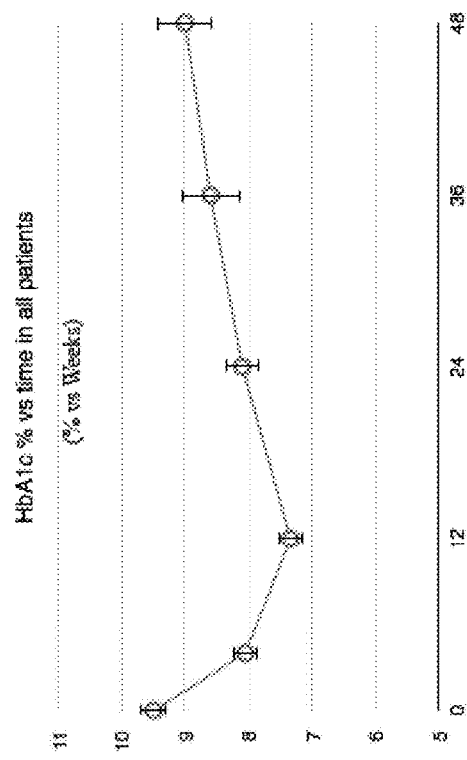

FIG. 57 represents the average HbA1c (%) in all available (at the time of follow-up) subjects treated by the systems, devices and methods of the present inventive concepts.

The magnitude of the treatment effect was analyzed as a function of treated dose (i.e. a dosimetric analysis was performed). Patients who had approximately 9 cm (e.g. 9.3 cm) of duodenal tissue treated (e.g. in at least three applications of thermal energy to duodenal tissue) were labeled to have received a "Long Segment DMR" ("LS-DMR"). Patients who had approximately 3 cm (e.g. 3.4 cm) of duodenal tissue treated (e.g. in two or less applications of thermal energy to duodenal tissue) were labeled as "Short Segment DMR" ("SS-DMR"). At 1 month follow up, HbA1c was reduced by an average of 1.7% (SD 1.0%) in LS-DMR and by 0.7% (SD 1.2%) in the SS-DMR (n=28 vs 11 at 1 months). At 3 months follow up, HbA1c was reduced by an average of 2.5% (SD 1.3%) in LS-DMR and by 1.2% (SD 1.8%) in SS-DMR (n=28 vs 10 at 3 months, p<0.05 for LS vs SS).

Figure 58:
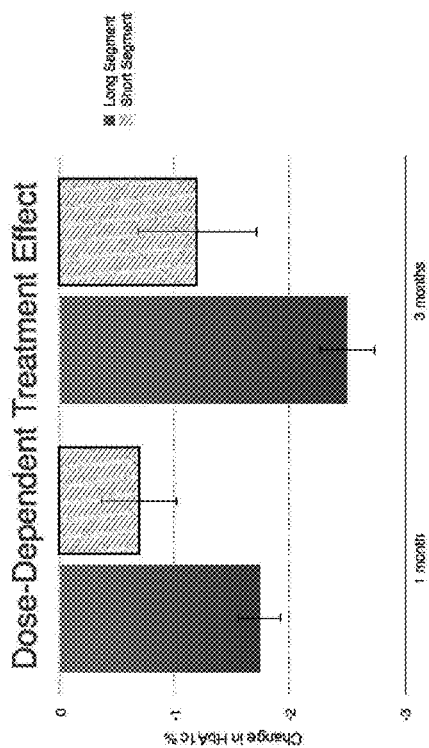

FIG. 58 represents the average change in HbA1c (%) from baseline in patients with LS-DMR and SS-DMR (p<0.05 for the difference at 3 months).

These clinical studies did not specify a medication treatment algorithm for the treating diabetologist to prescribe. Note that the treating diabetologist was not made aware of the patients' treatment allocation when determining the appropriate post-procedure management strategy. As such, clinical decisions with respect to medication adjustments in individual patients were made but these adjustments were not well controlled with respect to a rigorous efficacy evaluation. By the time of the six month post-procedure follow up visit, several patients experienced changes to their glycemic medications that would be expected to confound efficacy analysis at later time points (see Table F below). In particular, 13 out of 26 LS-DMR patients experienced reductions in medications and 1 patient experienced an increase in medication prescription, compared to 4 with reductions and 3 with increases among the SS-DMR patients.

TABLE F

| Treatment Received | Patients with reduction in glycemic meds | Patients with no med changes | Patients with increases in glycemic meds |
|---|---|---|---|
| LS-DMR | 13 | 12 | 1 |
| SS-DMR | 4 | 3 | 3 |

Table F represents the number of patients in each treatment arm with medication changes preceding the six month post-procedure follow-up visit.

At 6 months, LS-DMR patients experienced a decline in HbA1c of 1.6% (SD 1.6%) on average (n=26) despite the fact that 13 of 26 patients had reductions in glycemic medicines that would be expected to mask the magnitude of the procedure's treatment effect. The impact of medication reductions is evident in the analysis of fasting plasma glucose (FPG) in LS-DMR patients whose baseline HbA1c was between 7.5% and 10%. Patients whose meds were unchanged after the procedure ("stable meds" group in left graph below) retain stable FPG between week 12 and week 24. Patients, whose medicines were reduced, however, experienced a decay in treatment effect, the timing of which is coincident with the timing of prescribed medication reductions.

Figure 59:
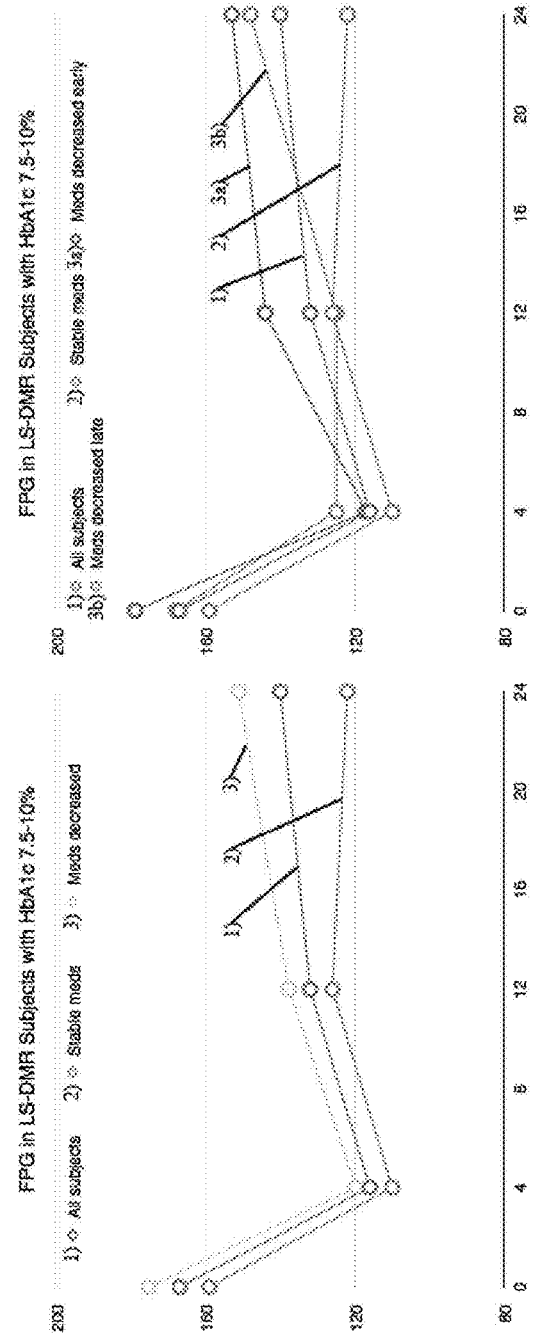

FIG. 59 represents the average fasting plasma glucose in LS-DMR patients with baseline HbA1c between 7.5% and 10%. The graph on the left shows FPG in all patients ("all patients"), the subset who experienced medication reductions ("meds decreased") and those whose medications were held constant through 24 week follow up ("stable meds"). The graph on the right shows the effect of medication reductions within the first 12 weeks ("meds decreased early") compared to those with medication reductions between week 12 and week 24 ("meds decreased late"). The timing of medication reductions corresponds to the timing of worsening FPG measurements.

Analysis of patients on consistent medications with a baseline HbA1c of between 7.5% and 10% revealed a mean HbA1c of 8.6 (SD 0.9; n=7) at baseline, 6.6 (SD 0.8; n=7) at 3 months, 7.2 (SD 0.6; n=6) at 6 months, and 7.3 (SD 0.3; n=4) at 12 months post procedure. These patients also experienced a reduction of fasting plasma glucose of 32 mg/dl (SD 21) at 3 months, 36 mg/dl (SD 24) at 6 months, and 20 mg/dl (SD 15) at 12 months.

Figure 60:
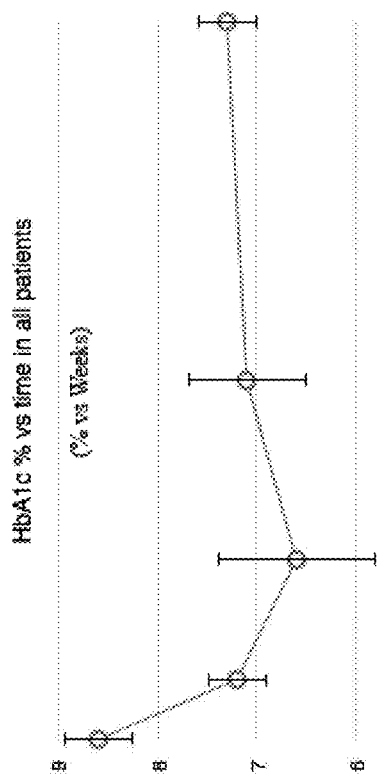

FIG. 60 represents mean HbA1c in LS-DMR patients with baseline HbA1c between 7.5% and 10% and consistent antidiabetic medications. Taken together, HbA1c measurements and fasting plasma glucose levels in LS-DMR patients with a baseline HbA1c level between 7.5% and 10% suggest durability of treatment response through 12 months of follow up.

Patient quality of life was assessed using the SF-36 standardized questionnaire. At screening, LS-DMR patients had a physical composite score (PCS) of 47 (SD 9) and a mental composite score of 46 (SD 11). At 6 months, patients in the LS-DMR group saw an increase in PCS of 3.1 points (SD 10; n=22) and MCS of 3.4 points (SD 14; n=22; p<0.05). The data suggest an improvement in the mental quality of life for poorly controlled diabetic patients who received LS-DMR.

Patients received a follow-up endoscopy at 1 month and/or 3 months post-procedure per protocol. Of the 19 patients who have received a follow-up endoscopy at 1 month, 4 patients had a reduction in height and/or width of plicae in the duodenum near the treatment area but otherwise the mucosa appeared to be healing normally with no scarring. No luminal narrowing indicative of stenosis was present in any of the 1 month endoscopies. Of the 37 patients who have received a follow-up endoscopy at 3 months, two patients had an endoscopically apparent reduction in height and/or width of plicae in the duodenum near the treatment area. All other patients had normal endoscopies with the mucosa fully healed and no evidence of scarring. No luminal narrowing was observed in any of the 3 month endoscopies. These results indicate that the treatment can effectively ablate the mucosa without damage to the duodenal structure and that the mucosa regrows quickly within the ablated region. The reduction in height and width of the plicae may be indicative of a reduction in the mucosal redundancy as part of the normal healing process.

A second procedure of the present inventive concepts was performed in 3 previously treated patients. There were no particular procedural challenges or significant adverse events associated with the second procedure in these three patients. Two patients had been non-responders to initial procedure, and their second procedure did not successfully improve glycemic control. A third patient had an improvement in glycemic control through 3 months after the first procedure, but this benefit was not fully sustained through the 6 month follow up visit. A repeat procedure was performed in month 8, and the patient has since been followed for six months after the second procedure. 14 months after the first procedure, therefore, the patient has an HbA1c of 7.3% (reduction of at least 2%) and a FPG of 100 mg/dl.

Figure 61:
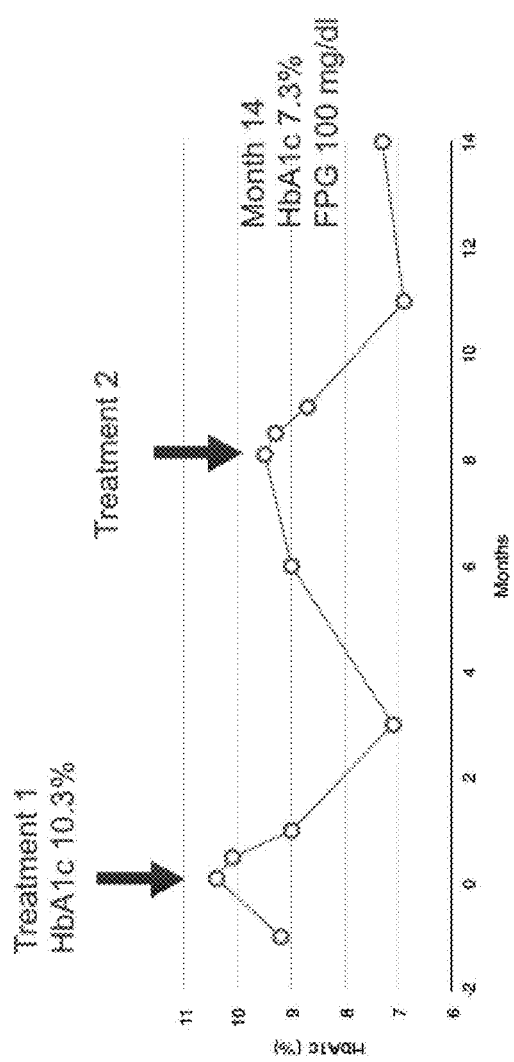

FIG. 61 represents HbA1c over time in a single patient receiving two treatments (at month 0 and month 8, respectively).

The above summary provides clinical data on 39 patients enrolled and treated in an initial study focused on procedural and patient safety and clinical effectiveness. The results demonstrate that the procedure can be safely completed with devices performing as intended, that the procedure can be well tolerated by patients, and that there exists a strong suggestion of significant clinical effectiveness. The limited number and transient nature of adverse events suggest that the safety profile of the technology and procedure is favorable. Although there were three adverse events of duodenal stenosis formation, all were endoscopically treated with non-emergent endoscopic balloon dilation using techniques familiar to operators and resolved with no long-term sequelae. Other significant potential risks, including pancreatitis, perforation, bleeding, infection, or ulcer, have not been observed. No evidence for malabsorption, severe hypoglycemia, or late complications was found. The experience thus far indicates a safe procedure that can be well tolerated by patients. Mean HbA1c is reduced in treated patients despite net medication reductions in the patient cohort. In addition, a statistically significant dosimetric treatment response is also observed, with LS-DMR patients responding more effectively than SS-DMR patients. In addition, LS-DMR patients experienced more medication reductions (to prophylactically avoid hypoglycemia) than SS-DMR patients. This observation was made despite the fact that neither patients nor the treating endocrinologist was aware of the length of treated tissue in individual patients. Furthermore, 23/27 LS-DMR patients experienced an HbA1c reduction of at least 1% at 3 months of follow up, compared to 6/10 SS-DMR patients. Patients on consistent medications with a baseline HbA1c of between 7.5% and 10% showed evidence of a durable response to treatment, with persistent reductions in HbA1c and fasting glucose through 12 months of treatment follow up. This durable treatment response is observed even without aggressive diabetes management on the part of the treating physician, such as may be achieved through education, lifestyle recommendations, or aggressive pharmacotherapy. The treatment of the present inventive concepts may offer an even more significant and durable clinical effect when coupled with intensive medical management. The treatment effect does not appear to be weight dependent. Patients did not report any food intolerance or change in food preference that might explain this HbA1c reduction. While patients lost a small amount of weight, the magnitude of weight loss is likely not enough to explain the degree of HbA1c improvement. Furthermore, there did not appear to be any correlation between the magnitude of HbA1c reduction and weight loss.

In some embodiments, the systems, device and methods of the present inventive concepts can reduce the need for insulin therapy in a larger proportion of patients, such as to provide durable glycemic control with or without the therapies administered to the patient prior to the treatment of the present inventive concepts, or with a decrease in dosage of one or more previously administered medications.

The systems, devices and methods of the present inventive concepts can be configured to treat patients with microvascular disease or patients with a high risk of microvascular disease, such as to improve patient health and/or eliminate or otherwise reduce the need for one or more medications (e.g. one or more insulin medications). The treatment can be configured to reduce diabetic retinopathy (e.g. as shown in a reduction in diabetic retinopathy score), proteinuria and/or peripheral neuropathy severity. Additionally or alternatively, the treatment can be configured to reduce the effects of macrovascular disease such as myocardial infarction, stroke, peripheral vascular disease, CV death, and combinations of one or more of these.

The systems, devices and methods of the present inventive concepts can be configured to treat patients with a disease or disorder of the liver, such as non-alcoholic fatty liver disease (NAFLD) and/or non-alcoholic steatohepatitis (NASH). For example, treatment element 135 of device 100 and/or treatment element 135' of device 40 can be configured to modify one or more axial segments of the intestine (e.g. ablate a full circumferential or partial circumferential axial segment of duodenal mucosal and/or submucosal tissue). In some embodiments, intestinal submucosal tissue of an axial segment of intestine is expanded (e.g. by device 30 or device 40 as described hereabove), prior to ablation of at least the mucosal layer relatively within the expanded submucosal tissue. In some embodiments, the mucosal tissue is ablated by introducing hot fluid into balloon 136 of device 100 or balloon 46 of device 40. In some embodiments, tissue treatment element 135 of device 100 or tissue treatment element 135' of device 40 comprises an element selected from the group consisting of: an ablative fluid delivered to a balloon or other expandable fluid reservoir; a tissue treatment element comprising an energy delivery element mounted to an expandable assembly such as an electrode or other energy delivery element configured to deliver radiofrequency (RF) energy and/or microwave energy; a light delivery element configured to deliver laser or other light energy; a fluid delivery element (e.g. a sponge or a nozzle) configured to deliver ablative fluid directly onto tissue; a sound delivery element such as a ultrasonic and/or subsonic sound delivery element; and combinations thereof, as described in detail herein. In some embodiments, a patient with NAFLD and/or NASH is selected and treated as described herebelow in reference to FIG. 7.

Figure 62:
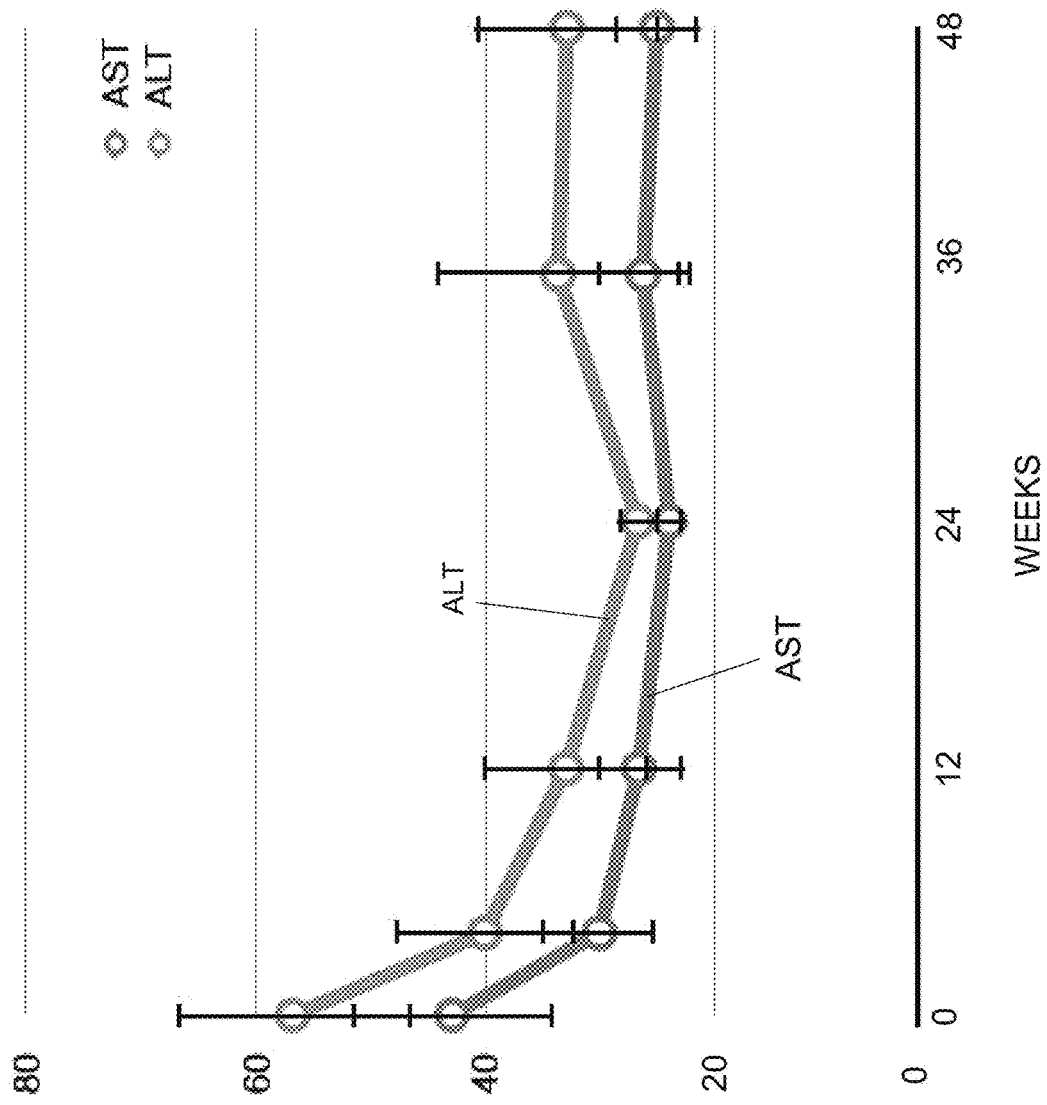

Applicant's clinical studies described hereabove have demonstrated potential benefit to patients with a liver disease or disorder such as NAFLD and/or NASH. FIG. 62 exhibits an improvement (reduction) in the level of liver transaminases found in the treated patients.

FIG. 62 represents an improvement (reduction) in the level (expressed in mg/dL) of two liver transaminases, aspartate transaminase (AST) and alanine transaminase (ALT), that resulted after a mucosal treatment of the present inventive concepts. The data presented in FIG. 62 represents 13 patients through week 24, and 8 (of the 13) patients through week 48. The data presented is representative of patients that had at least 3 cm of duodenal mucosa treated, such as when two or more axial segments of duodenal mucosa were treated to achieve a cumulative treated length of at least 6 cm or at least 9 cm. Pre-procedure, each patient had elevated baseline levels of AST and ALT as shown, which is indicative of inflammation of the liver. The AST and ALT levels were sustainably reduced after treatment of multiple segments of duodenal mucosa using the systems, devices and methods of the present inventive concepts. These reductions correlate to one or more of: improvement in steatosis, reduced inflammation of the liver and/or reduced fibrosis of the liver. In some embodiments, the methods of the present inventive concepts are configured to improve steatosis, reduce cirrhosis, reduce inflammation of the liver, reduce fibrosis of the liver and/or reduce liver failure.

FIGS. 3-33 described herebelow illustrate various configurations for the systems and catheters of the present inventive concepts, such as system 10 and catheter 100 described hereabove in reference to FIG. 1, and system 10 and catheters 100, 20, 30 and/or 40 described hereabove in reference to FIG. 2. In the below figures, each system 10 and catheter 100 can comprise one or more components of similar construction and arrangement to system 10 and catheters 100, 20, 30 and/or 40 of FIG. 1 and/or FIG. 2, whether shown in the associated figure or not. In some of the figures, one or more conduits 111 have been removed for illustrative clarity, such as one or more fluid, translatable rod, signal and/or power transporting conduits attached to one or more functional elements, inflatable balloons or other expandable elements and/or other components of the system 10 and/or catheter 100 illustrated in the associated figure. Each of the functional assemblies 130 can be constructed and arranged to perform a first step of a medical procedure (e.g. a tissue ablation procedure, a tissue expansion procedure and/or a tissue diagnostic procedure) at a first axial segment of the intestine, and subsequently perform at least a second step of the medical procedure at a second axial segment of the intestine, at a location proximal or distal to the first axial segment of the intestine. In some embodiments, a sequence of three or more steps at three or more axial segments can be performed. In some embodiments, both a tissue expansion and a tissue ablation are performed at each selected axial segment of the intestine.

Each functional assembly 130 can comprise a balloon 136 or other expandable element, such as: a radially expandable cage or stent; one or more radially deployable arms; an expandable helix; an unfurlable compacted coiled structure; an unfurlable sheet; and/or an unfoldable compacted structure.

Figure 3A:
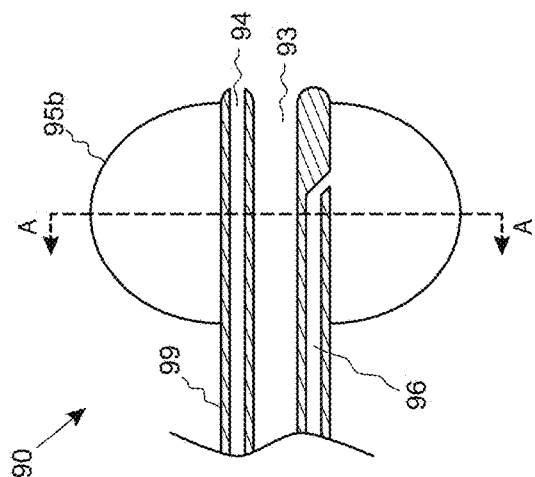
FIGS. 3A and 3B are side sectional and end sectional views, respectively, of the distal portion of a sheath, without an inserted catheter or guidewire, consistent with the present inventive concepts.
Figure 3B:
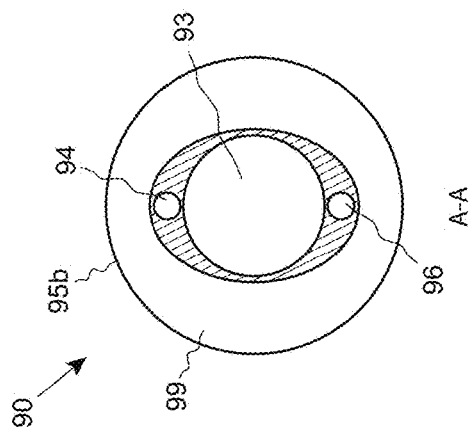
Figure 3:
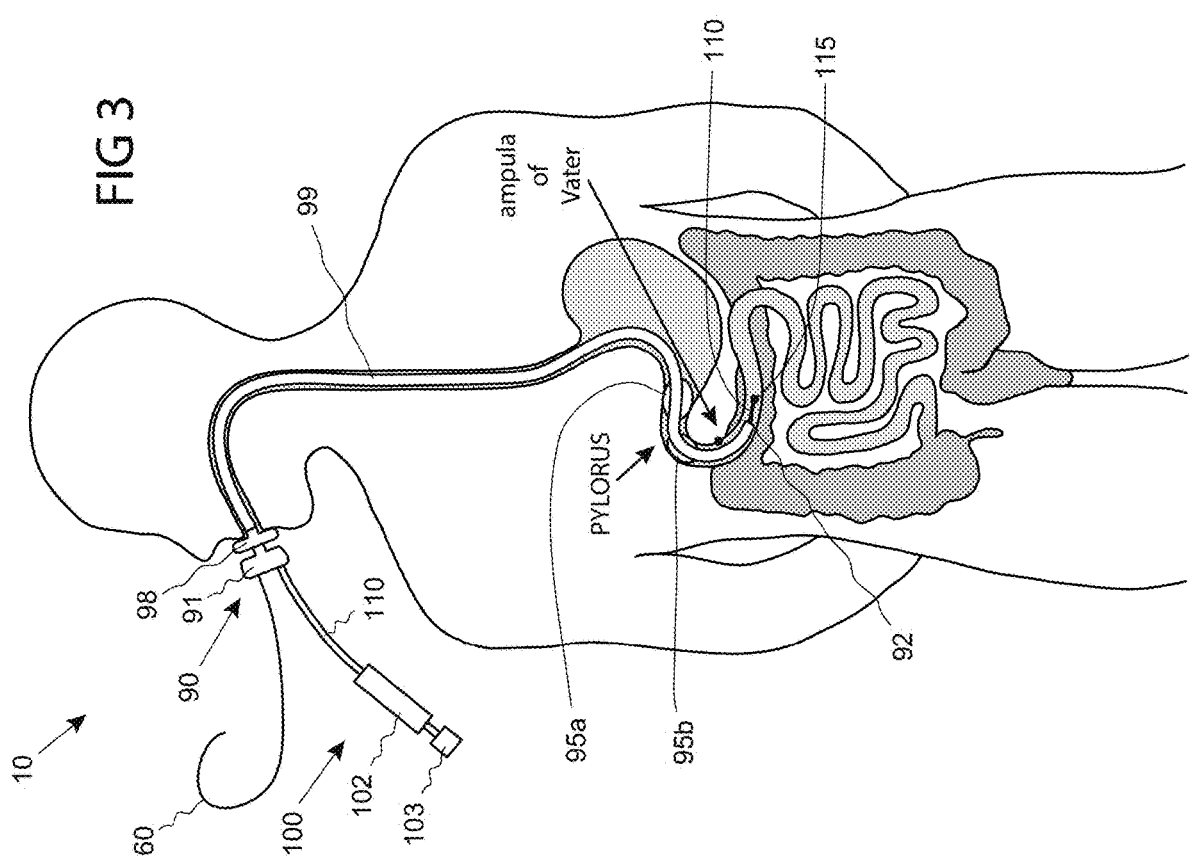
FIG. 3 is an anatomic view of a system for performing a medical procedure comprising a catheter and a sheath for inserting the catheter into the intestine of the patient, consistent with the present inventive concepts.

Referring now to FIG. 3, an anatomic view of a system for performing a medical procedure comprising a catheter and a sheath for inserting the catheter into the intestine of the patient is illustrated, consistent with the present inventive concepts. System 10 comprises catheter 100 and sheath 90 (e.g. an introducer sheath), each of which has been inserted through the mouth of the patient and advanced through the stomach to a location distal to the patient's pylorus. System 10 can further comprise guidewire 60. System 10 can comprise one or more other components, such as console 200 and other components not shown, but similar to those described hereabove in reference to system 10 of FIG. 1 or system 10 of FIG. 2. Catheter 100 comprises port 103, handle 102, shaft 110, bulbous tip 115 and other components, such as those described hereabove in reference to catheter 100 of FIG. 1, or catheters 100, 20, 30 and/or 40 of FIG. 2.

Sheath 90 comprises an elongate, flexible tube, shaft 99, and an input port 91 on the proximal end of shaft 99. Input port 91 can include a funnel-shaped or other opening configured to assist in the introduction of catheter 100 or other devices into a lumen of sheath 90. Input port 91, or another proximal portion of sheath 90, can be configured to attach sheath 90 to an endoscope or other body introduction device (e.g. device 50 described herein). In some embodiments, input port 91 comprises a strain relief configured to attach sheath 90 to a body introduction device. Bite block 98 can be positioned about shaft 99 at a location relatively proximate to input port 91. Positioned along a distal portion of shaft 99 are one or more anchor elements, such as anchor elements 95a and 95b shown. Anchor elements 95a and 95b can comprise a radially expandable structure, such as an expandable structure selected from the group consisting of: an inflatable balloon; a radially expandable cage or stent; one or more radially deployable arms; an expandable helix; an unfurlable compacted coiled structure; an unfurlable sheet; an unfoldable compacted structure; and combinations of one or more of these. Anchor elements 95a and 95b have been positioned at locations proximal and distal, respectively, to the pylorus, and subsequently radially expanded, such as to anchor distal end 92 of shaft 99 at a location distal to the ampulla of Vater (e.g. to avoid inadvertently treating or otherwise adversely affecting the ampulla of Vater and/or tissue proximate the ampulla of Vater). In some embodiments, anchor element 95a and/or 95b can be configured to be inflated within the duodenal bulb of the patient.

In some embodiments, shaft 99 comprises a variable stiffness along its length, such as a more flexible distal portion constructed and arranged to be positioned distal to the pylorus, than a portion that would be positioned proximal to the pylorus (e.g. to avoid a "slack" segment in the stomach when advancing catheter 100 through shaft 99). In some embodiments, shaft 99 comprises a variable stiffness as described herebelow in reference to shafts 110' and 110" of FIGS. 27 and 28, respectively. In some embodiments, shaft 99 comprises a shaft including a braided portion. In some embodiments, sheath 90 comprises a non-circular cross-section (e.g. as described herebelow in reference to FIG. 32 or 33), such as to efficiently couple with an endoscope or other body introduction device (e.g. device 50 described herein), such as a non-circular cross-section selected from the group consisting of: oval; kidney shape; and combinations thereof.

FIGS. 3A and 3B illustrate side sectional and end sectional views, respectively, of the distal portion of sheath 90, without an inserted catheter 100 nor an inserted guidewire 60. Shaft 99 includes a lumen 94, such as a lumen constructed and arranged to slidingly receive a guidewire, such as guidewire 60, to permit over-the-wire advancement and retraction of sheath 90. Shaft 99 further includes working channel 93, such as a lumen constructed and arranged to slidingly receive a treatment or diagnostic device, such as catheter 100 as described herein. In some embodiments, working channel 93 comprises a diameter greater than or equal to 10 mm, or 20 mm. In some embodiments, sheath 90 is advanced to a desired location (e.g. with or without catheter 100 residing within working channel 93), and subsequently bulbous tip 115 of catheter 100 is advanced out of distal end 92 of sheath 90. Shaft 99 can further comprise a lumen 96, which can be configured as an inflation lumen when one or more of anchor elements 95a or 95b comprise a balloon or other inflatable structure. Alternatively, lumen 96 can be constructed and arranged to receive a translatable rod or other filament, such as when anchor element 95a and/or 95b comprise an expandable scaffold, radially deployable arm or other structure whose expansion and contraction is controlled by the translation of the filament. Working channel 93 and/or lumen 94 can be configured as a port for delivering and/or extracting fluids from the intestine (e.g. to insufflate and/or desufflate, respectively, a segment of the intestine).

In some embodiments, system 10 of FIG. 3 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIGS. 4A, 4B and 4C, anatomical, side sectional views of a series of steps for performing a medical procedure are illustrated, consistent with the present inventive concepts. System 10 comprises catheter 100, a body introducer such as endoscope 50a, and a tool for extracting fluid, fluid transport tool 71. System 10, catheter 100 and endoscope 50a can be of similar construction and arrangement to the similar components described hereabove in reference to FIG. 1 or FIG. 2. Endoscope 50a comprises one or more working channels, such as lumens 51 and 54 shown. The distal portion of catheter 100 (including the distal portion of shaft 110) has been inserted through and out of lumen 51, and functional assembly 130 has been radially expanded, such as to perform a diagnostic or therapeutic procedure on an axial segment of intestinal tissue in contact with functional assembly 130. Functional assembly 130 can be configured to perform one or more medical procedures as described herein (e.g. a therapeutic procedure such as a tissue ablation procedure and/or a tissue expansion procedure, and/or a diagnostic procedure). Functional assembly 130 can comprise an extending shaft, such as an extending shaft with a bulbous tip such as bulbous tip 115 described hereabove in reference to FIG. 1 or FIG. 2.

Tool 71 has been advanced through lumen 54 of endoscope 50a and can be positioned proximate functional assembly 130 as shown in FIG. 4A, distal to functional assembly 130 as shown in FIG. 4B, and positioned alongside functional assembly 130 (i.e. between the proximal and distal ends of functional assembly 130) as shown in FIG. 4C. Tool 71 can be activated (e.g. via a control on a proximal end of tool 71 or via a control of an attached console such as console 200 described hereabove), such as to extract fluids (e.g. liquids or gases) from within an intestinal segment proximate functional assembly 130, such as to cause the wall of the intestine to make contact and/or increase contact with functional assembly 130. Alternatively or additionally, extraction of fluids (e.g. desufflation) can be performed with one or more lumens of endoscope 50a and/or one or more lumens or ports of catheter 100 (e.g. as described herebelow in reference to FIGS. 5A and 5B).

In some embodiments, tool 71 is alternatively or additionally constructed and arranged to deliver fluids (e.g. a gas) into an intestinal segment proximate (e.g. proximal to and/or distal to) functional assembly 130, such as to insufflate the intestine, such as to decrease contact between functional assembly 130 and the intestinal wall.

In some embodiments, tool 71 is alternatively or additionally constructed and arranged to produce a patient image, such as when tool 71 comprises a camera device (e.g. a visible light camera or infrared camera). In some embodiments, tool 71 alternatively or additionally comprises a tool selected from the group consisting of: a fluid injection device such a tool comprising a needle; a heating tool; a cooling tool (e.g. a tool comprising a Peltier element); a light; a vibrational tool, an agitating tool; and combinations of one or more of these.

In some embodiments, system 10 of FIGS. 4A-C comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIGS. 5A and 5B, end and side views of the distal portion of a catheter including recessed ports, shaft-located vacuum ports, and an inflatable distal tip are illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (three conduits 111 shown in FIG. 5B). In some embodiments, bulbous tip 115 is positioned on the distal end of catheter 100 as shown. Functional assembly 130 is configured to radially expand and contract, and can comprise an expandable element selected from the group consisting of: an inflatable balloon such as balloon 136 shown; a radially expandable cage or stent; one or more radially deployable arms; an expandable helix; an unfurlable compacted coiled structure; an unfurlable sheet; an unfoldable compacted structure; and combinations of one or more of these as described herein. Functional assembly 130 is shown in a radially expanded state in FIGS. 5A and 5B.

In some embodiments, functional assembly 130 includes one or more recesses, such as the three recesses 133 (e.g. a recess of balloon 136) shown in FIG. 5A. Positioned within each recess 133 is a port 137, configured to capture or at least engage tissue when a vacuum is applied to each port 137, such as via one or more conduits such as conduits 111 described hereabove.

Recesses 133 can be sized such that port 137 is relatively flush with the surface of an expanded functional assembly 130 or is otherwise constructed and arranged to limit the radial extension of each port 137 from the outer surface of an expanded functional assembly 130, such as to allow the surface of functional assembly 130 proximate each port 137 to sufficiently contact intestinal wall tissue (e.g. to avoid "tenting" of the tissue around each port 137), and/or to avoid trauma to intestinal wall tissue proximate each port 137.

In some embodiments, catheter 100 comprises one or more ports configured to deliver and/or extract fluids, such as to perform an insufflation or desufflation step, such as to change the level of contact between functional assembly 130 and the intestinal wall (e.g. desufflation to achieve sufficient apposition between functional assembly 130 and the intestinal wall to ablate target tissue), as described herein. Catheter 100 of FIG. 5B comprises port 112a positioned on shaft 110 proximal to functional assembly 130 and port 112b positioned distal to functional assembly 130. Ports 112a and 112b are fluidly connected to conduits 111a and 111b, respectively, such that fluid can be extracted (e.g. liquids or gases extracted by console 200 described hereabove) from within the intestine by ports 112a and/or 112b, such as to desufflate the intestine proximal and/or distal to functional assembly 130. Alternatively or additionally, fluid can be delivered to the intestine by ports 112a and/or 112b, such as to insufflate and/or desufflate the associated segment of the intestine. Catheter 100 can comprise one or more ports positioned along functional assembly 130, such as ports 137 which include openings 138 shown in FIG. 5B. Fluid can be delivered or extracted, such as to insufflate or desufflate, respectively, as described hereabove in reference to ports 112a and 112b. Alternatively or additionally, ports 137 including openings 138 can be configured to capture or at least frictionally engage tissue (e.g. wall tissue of the intestine), such as to complete a tissue expansion procedure and/or to anchor the distal portion of catheter 100, each as described herein. In some embodiments, functional assembly 130 of FIGS. 5A-B is configured to both expand one or more tissue portions and ablate one or more tissue portions. In some embodiments, ports 112a, 112b or another component of catheter 100 or system 10 (e.g. a working channel of introduction device 50) is configured to automatically insufflate and/or desufflate, such as an insufflation and/or desufflation triggered by a recording by a sensor of system 10 (e.g. a sensor as described herein, and whose signal is processed by algorithm 251 to automatically initiate the delivery and/or extraction of fluids from the intestine).

In some embodiments, catheter 100 comprises a bulbous distal tip, such as a tip configured to be inflated or otherwise expanded, such as inflatable tip 115' shown in FIG. 5A-B which can comprise a balloon or other expandable structure. Inflatable tip 115' can be fluidly attached to conduit 111c which can travel proximally to be attached to an inflation source, such as a pumping assembly 225 and reservoir 220 of console 200 described hereabove in reference to FIG. 1. Inflatable tip 115' can be configured to expand to a diameter of at least 4 mm and/or a diameter of no more than 15 mm, such as an inflation that occurs after inflatable tip 115' exits a lumen (e.g. a lumen of an introduction device such as endoscope 50a or sheath 90 described hereabove in reference to FIG. 1).

In some embodiments, catheter 100 comprises functional element 119 positioned in, on and/or within shaft 110. Functional element 119 can comprise a heating or cooling element configured to modify and/or control the temperature of fluid entering balloon 136.

In some embodiments, catheter 100 of FIGS. 5A-B comprises one or more sensors, such as one or more functional elements 109, 119 and/or 139 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIGS. 6A and 6B, anatomical, side sectional views of the distal end of a catheter comprising a functional assembly configured to expand to multiple geometric configurations are illustrated, consistent with the present inventive concepts. Catheter 100 comprises shaft 110, functional assembly 130, and other components, such as one or more components of similar construction and arrangement to those described hereabove in reference to catheter 100 of FIG. 1 or FIG. 2, such as one or more conduits 111 which have been removed for illustrative clarity. Functional assembly 130 can comprise balloon 136 and can be configured to radially expand and contract, such as radial expansion that is limited or is otherwise reduced at a mid-portion (e.g. tissue contacting portion) of balloon 136. Balloon 136 comprises proximal wall 131 and distal wall 132. In FIG. 6A, functional assembly 130 has been expanded (i.e. balloon 136 has been inflated with a first volume of fluid) to a first level of expansion, and proximal wall 131 and distal wall 132 each relatively remain within a single plane. Balloon 136 can be constructed and arranged such that proximal wall 131 and/or distal wall 132 deflect (as shown in FIG. 6B) when additional fluid is delivered into balloon 136, such as to prevent further expansion of portions of balloon 136 in contact with the intestinal wall (e.g. to prevent additional force on the intestinal wall and/or uneven apposition of balloon 136 with the intestinal wall).

In some embodiments, balloon 136 further comprises a radial expansion limiting element, such as restrictor 134, which can comprise a tubular restrictor (e.g. circumferential mesh) positioned on an inner surface of, outer surface of and/or within the wall of balloon 136.

In some embodiments, catheter 100 of FIGS. 6A-B and/or one or more components attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Referring now to FIG. 7, an anatomical, side sectional view of the distal end of a catheter comprising a functional assembly including a balloon with varied wall thickness is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity. Functional assembly 130 can comprise balloon 136 and can be configured to radially expand and contract. Balloon 136 comprises one or more thick wall portions 134*a*, each of which can comprise a portion of the wall of balloon 136 that is thicker than one or more other wall portions of balloon 136. Thick wall portion 134*a* can comprise one or more thick wall portions positioned at a proximal and/or distal location of the tissue-contacting portion of balloon 136 (e.g. one or more wall portions thicker than the wall at a mid-portion of balloon 136). Thick wall portion 134*a* can function as an insulating portion constructed and arranged to limit transfer of energy (e.g. heat energy or cryogenic energy) between functional assembly 130 and intestinal wall tissue at one or more locations of functional assembly 130 (e.g. at the proximal and distal tissue-contacting portions of balloon 136).

In some embodiments, catheter 100 of FIG. 7 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Referring now to FIG. 8, an anatomical, side sectional view of the distal end of a catheter comprising a functional assembly including an insulating element is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity. Functional assembly 130 can comprise balloon 136 and can be configured to radially expand and contract. Functional assembly 130 comprises one or more insulating elements 134*b*, positioned on the inner surface, outer surface and/or within the wall of balloon 136. Insulating elements 134*b* can be positioned at a proximal and/or distal location of the tissue-contacting portion of balloon 136. Insulating element 134*b* can be constructed and arranged to limit transfer of energy (e.g. heat energy or cryogenic energy) between functional assembly 130 and intestinal wall tissue at one or more locations of functional assembly 130 (e.g. at the proximal and distal tissue-contacting portions of balloon 136).

In some embodiments, catheter 100 of FIG. 8 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Referring now to FIG. 9, a side view of a catheter comprising a tissue dissecting assembly is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity. Shaft 110 comprises shaft 110*a*, 110*b* and 110*d*. Shaft 110 can comprise additional shafts, such as a shaft 110*c* not shown but constructed and arranged such that shafts 110*a*, 110*b* and 110*c* are separated by approximately 120°. Catheter 100 can comprise bulbous tip 115 as shown. Functional assembly 130 can comprise an inflatable balloon, balloon 136. Catheter 100 comprises one or more tools 141 (two shown in FIG. 9), each of which is slidingly received by a shaft (e.g. shafts 110*a* and 110*b* shown). Each tool 141 can be operably connected to a translatable shaft or other translatable conduit, such as a conduit 111 comprising a translatable shaft as described hereabove in reference to FIG. 1.

FIG. 9A illustrates a magnified view of one of the tools 141 of catheter 100 of FIG. 9. The distal portions of shafts 110*a* and 110*b* are attached along functional assembly 130 (e.g. attached along balloon 136) and the distal end of each shaft 110*a* and 110*b* is positioned near the distal end of functional assembly 130.

In some embodiments, tools 141 comprise a sharp instrument (e.g. blade, needle or other cutting element) configured to dissect tissue, such as a dissection that occurs when functional assembly 130 is advanced within a lumen of the intestine while tools 141 are engaged (e.g. extended distally). In some embodiments, tool 141 comprises a tissue dissection element selected from the group consisting of: blunt dissector; needle; needle knife; fluid delivery element; and combinations of one or more of these. In some embodiments, tool 141 comprises a vacuum port, such as port 137 described herein. In some embodiments, tools 141 are alternatively or additionally configured to deliver an agent to tissue and/or to deliver energy to tissue, such as an agent selected from the group consisting of: EtOH; hypertonic saline; Sotradecol; and combinations of one or more of these. Tools 141 can be configured to remove and/or treat a full or partial circumferential axial segment of intestinal tissue, such as to remove the mucosal tissue along one or more axial segments of intestine (e.g. duodenum) to provide a therapeutic benefit (e.g. to treat a disease or disorder such as diabetes).

In some embodiments, catheter 100 of FIG. 9 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIGS. 10A-D, side views of a distal portion of a system 10 including a sheath with a sealing distal end are illustrated, consistent with the present inventive concepts. System 10 comprises sheath 90 and catheter 100. System 10 can comprise one or more other components, such as console 200 and other components not shown, but similar to those described hereabove in reference to system 10 of FIG. 1 or FIG. 2. Catheter 100 comprises shaft 110, functional assembly 130 (shown in its compacted state in FIGS. 10A-C, and in its expanded state in FIG. 10D), and other components, such as one or more components of similar construction and arrangement to those described hereabove in reference to catheter 100 of FIG. 1 or FIG. 2, such as one or more conduits 111 which have been removed for illustrative clarity. Catheter 100 can comprise bulbous tip 115 positioned on the distal end of shaft 110. Sheath 90 comprises distal end 92 and sealing element 97 positioned on or about distal end 92. Sealing element 97 comprises one or more elastic or otherwise resilient materials constructed and arranged to tend to close upon itself, such as to seal (e.g. partially seal and/or reduce tissue or fluid ingress into sheath 90) one or more openings on the distal end of sheath 90. Sealing element 97 can be further constructed and arranged to stretch or otherwise open, such as to allow a device to pass therethrough, such as the distal portion of catheter 100, and form a seal (e.g. form a partial seal and/or reduce tissue or fluid ingress between sheath 90 and an inserted device) around the portion of the device passing through sealing element 97.

Figure 10A:
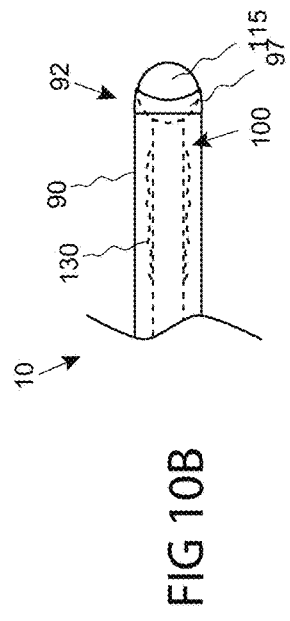
FIGS. 10A-D are side views of a distal portion of a system including a sheath with a sealing distal end, consistent with the present inventive concepts.
Figure 10B:
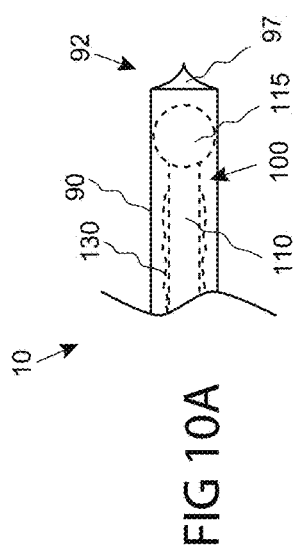
Figure 10C:
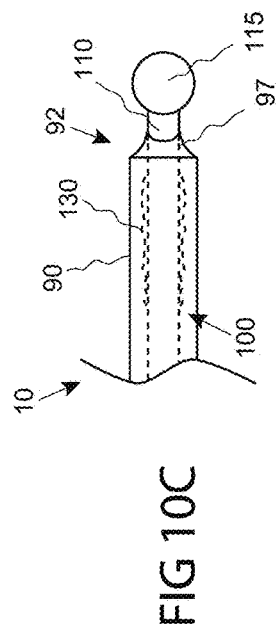
Figure 10D:
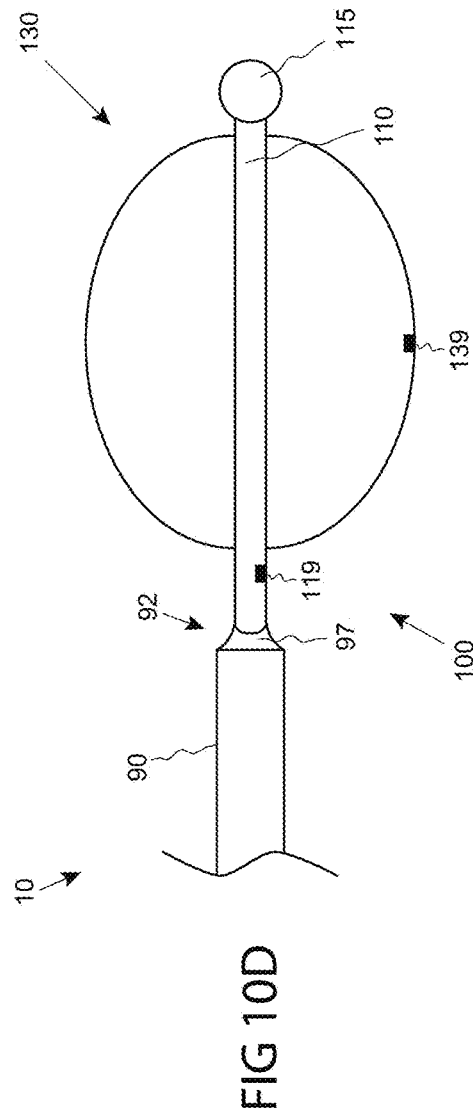

In FIG. 10A, bulbous tip 115 of catheter 100 remains within a lumen of sheath 90, and sealing element 97 is in a resiliently biased position (e.g. closed or partially closed). In FIG. 10B, catheter 100 has been advanced such that bulbous tip 115 extends partially through sealing element 97, which has resiliently expanded to accommodate bulbous tip 115. In FIG. 10C, catheter 100 has been further advanced such that bulbous tip 115 has fully passed through sealing element 97, and sealing element 97 has partially collapsed to surround shaft 110 (e.g. to form a seal or partial seal and/or to limit tissue or fluid ingress between shaft 110 and sealing element 97). In FIG. 10D, catheter 100 has been further advanced such that functional assembly 130 has passed through sealing element 97, and functional assembly 130 has been radially expanded.

Sealing element 97 can be constructed and arranged to provide a seal or near-seal (generally "seal") around one or more device components positioned within sealing element 97, such as to prevent capture of tissue between sealing element 97 and the inserted component, and/or limit fluids passing therebetween. Sealing element 97 can comprise one or more materials, such as metals (e.g. superelastic metals, metal coils or metal cages), plastic, elastomers, and the like. In some embodiments, sealing element 97 is connected to one or more controls on the proximal end of sheath 90, such as to control the orifice or other shape of sealing element 97, such as when sealing element 97 comprises a mechanically-actuated valve actuated by a control rod, or when sealing element 97 comprises an electrically-actuated valve connected to an electrical wire (e.g. a solenoid valve or a valve comprising heat activated shape memory metal such as heat-activated nickel titanium alloy).

In some embodiments, system 10 of FIGS. 10A-D comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIG. 11, a side view of the distal portion of a catheter including multiple shafts arranged in a spiraled configuration is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (three conduits 111 shown in FIG. 11). Functional assembly 130 can comprise an inflatable balloon, balloon 136. Shaft 110 of FIG. 11 comprises multiple shafts, such as shafts 110a, 110b, 110c, and 110d shown. Shafts 110a-c are each arranged in a helical, spiral and/or otherwise twisted-shaft geometry (hereinafter spiraled, helix or helical configuration) about shaft 110d. Shaft 110d comprises one or more lumens or tubes, such as a lumen constructed and arranged to inflate or otherwise expand functional assembly 130. Ports 137a, 137b, and 137c (singly or collectively port 137) are attached to functional assembly 130, such as with equal 120° spacing along a circumference of balloon 136 and positioned at a relative mid-portion of balloon 136. Shafts 110a-c are operably attached to ports 137a-c, respectively. Shafts 110a-c can each comprise one or more lumens or tubes, such as a vacuum lumen configured to deliver a vacuum to an attached port 137 and a lumen configured to slidingly receive a conduit 111 which includes a fluid delivery element 139c (for example a needle, not shown) at its distal end, such as is described hereabove in reference to FIG. 1 or FIG. 2.

As described above, in the embodiment of FIG. 6, shafts 110a-c are arranged in a helical arrangement along at least a portion of the length of shaft 110. In this helical arrangement, relatively similar advancement of the proximal ends of multiple conduits 111 causes relatively similar advancement of the distal ends of multiple conduits 111 (i.e. relatively similar advancement of multiple fluid delivery elements 139c), even when shaft 110 is in a curvilinear geometry. This equilibration is due to the helix causing each shaft 110a-c to transition between the inner and outer radii of one or more curves when catheter 100 has been inserted through tortuous or otherwise curvilinear anatomy. If the shafts 110a-c were arranged in a relatively co-linear, non-helical arrangement, a lumen on the inside of a curve would traverse a shorter path length than a lumen on the outside of the curve. The helical arrangement of shafts 110a-c ensures that no tube or lumen (or filament within the tube or lumen) is consistently on either the inside or outside of a curved portion of shaft 110.

Shafts 110a-c can be arranged in a helix with a uniform or non-uniform pitch. In some embodiments, shafts 110a-c are arranged with a pitch such that each shaft spirals (e.g. rotates or helically traverses) between 360° (1 turn) and 1440° (4 turns) about a central axis (e.g. shaft 110d) along at least a portion of the length of shaft 110. In some embodiments, one or more continuous segments of shaft 110 comprise a helical portion. In some embodiments, shaft 110 comprises an arrangement of shafts 110a-c which spiral approximately 540° (1.5 turns) about shaft 110d along at least a portion of the length of shaft 110. In some embodiments, the helical portion of shaft 110 is a segment proximate functional assembly 130 (e.g. in a distal portion of shaft 110). This helical arrangement of shafts 110a-c ensures that if shaft 110 is coiled in one or more directions, none of the lumens of shafts 110a-c are always on the inside or outside of a curved portion of shaft 110, minimizing differences in the lumen path lengths caused by shortening of a lumen in compression (inside of a curve) and/or extending of a lumen in tension (outside of a curve). Similar lumen path lengths result in similar travel distances in one or more filaments within shafts 110a-c, such as similar travel distances of conduits 111 during advancement and/or retraction of the associated fluid delivery element 139c into and/or out of ports 137. The one or more helical portions of shaft 110 described hereabove enable the translation provided by a control on a proximal handle (e.g. handle 102 of FIG. 1 or FIG. 2) to accommodate shaft 110a-c lumen path length variations that result when shaft 110 is in a curved geometry.

In some embodiments, catheter 100 of FIG. 11 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIG. 12, a side view of a distal portion of a catheter comprising ports mounted on a tapered proximal portion of a functional assembly is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (two conduits 111 shown in FIG. 12). Catheter 100 can comprise bulbous tip 115 on its distal end. Shaft 110 comprises shafts 110a, 110b and 110d shown. Shaft 110 can comprise additional shafts, such as a shaft 110c not shown but constructed and arranged such that shafts 110a, 110b and 110c are separated by approximately 120°. In some embodiments, shafts 110a, 110b and/or 110d are constructed and arranged to allow an imaging device such as an endoscope as described herein to be positioned proximate functional assembly 130, such as to be in between portions of one or more shafts 110a, 110b and/or 110d. For example, shafts 110a and/or 110b can begin to diverge (e.g. when functional assembly 130 is in an expanded or partially expanded state) away from a central shaft 110d and toward a tissue contacting portion of functional assembly 130, the divergence positioned at least 3 cm, 6 cm or 9 cm from the proximal end of functional assembly 130, such as to create space for positioning the distal end of an endoscope relatively proximate functional assembly 130. Functional assembly 130 can comprise an inflatable balloon, balloon 136, which can be connected to an inflation lumen or tube, conduit 111a.

Functional assembly 130 of FIG. 12 comprises one or more ports 137 that are mounted to a proximal portion of functional assembly 130, such as on a tapered proximal wall 131 of balloon 136. Positioning of ports 137 on wall 131 avoid ports 137 being on a tissue contacting surface of balloon 136 (e.g. to avoid an uneven or undesired transfer of energy from balloon 136 to tissue, such as when balloon 136 is configured to receive fluid at an ablative temperature). In some embodiments, the proximal portion of functional assembly 130 comprises a taper angle TA between 80° and 10°, such as a taper angle TA between 60° and 20°. In some embodiments, the distal portion of functional assembly 130 comprises a tapered portion (as shown), such as a tapered portion with a taper angle TA between 80° and 10°, such as between 60° and 20°. Each port 137 comprises an opening 138, such as an opening sized to capture or otherwise engage tissue against and/or within port 137 when vacuum is applied to port 137, such as a vacuum applied via one or more attached vacuum delivery conduits 111 (not shown but such as those described herein). In some embodiments, shafts 110a and 110b and one or more other shafts comprise a lumen configured to slidingly receive a separate tube, (e.g. conduit 111b within shaft 110b) such as a translatable tube with a fluid delivery element 139c positioned on the distal end of the tube. In some embodiments, each fluid delivery element 139c is of similar construction and arrangement to fluid delivery element 139c of FIG. 1, such as to deliver fluid into tissue engaged and/or captured against and/or within port 137. Positioning of ports 137 on the proximal end (e.g. proximal taper) of functional assembly 130 can be configured to limit the depth of a needle or other fluid delivery element 139c into the wall of the intestine.

In some embodiments, catheter 100 of FIG. 12 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 13:
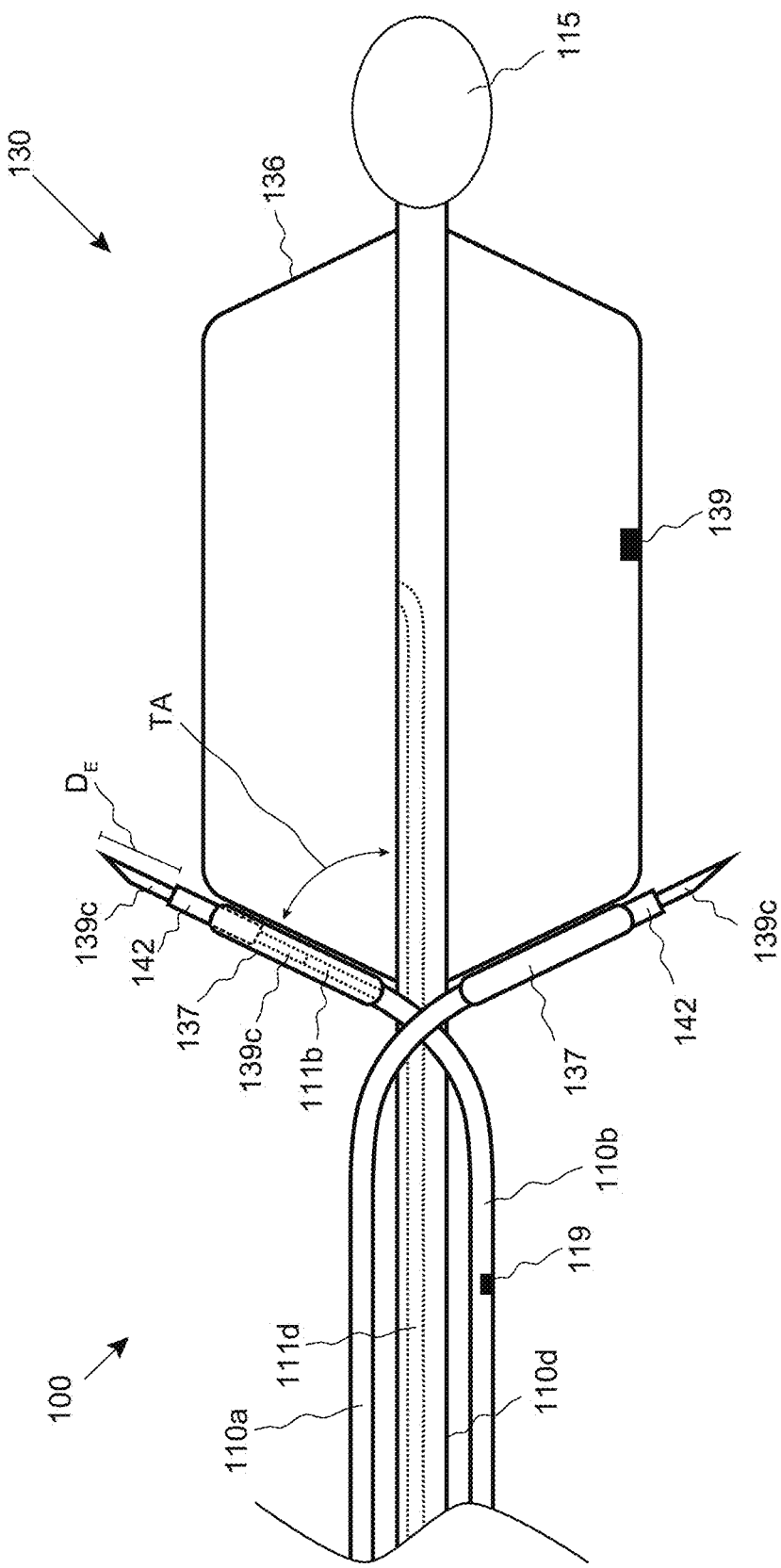
FIG. 13 is a side view of a distal portion of a catheter comprising needle-directing ports mounted on a proximal end of a functional assembly, consistent with the present inventive concepts.

Referring now to FIG. 13, a side view of a distal portion of a catheter comprising needle-directing ports mounted on a proximal end of a functional assembly is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (two conduits 111 shown in FIG. 13). Catheter 100 can comprise bulbous tip 115 on its distal end. Shaft 110 comprises multiple shafts, such as shafts 110*a*, 110*b* and 110*d* shown. Shaft 110 can comprise additional shafts, such as a shaft 110*c* not shown but constructed and arranged such that shafts 110*a*, 110*b* and 110*c* are separated by approximately 120°. Functional assembly 130 can comprise an inflatable balloon, balloon 136, such as a balloon which can be inflated by fluid delivered by an inflation tube, conduit 111*d* shown. Functional assembly 130 of FIG. 13 comprises one or more needle trajectory-directing ports 137 that are mounted to a proximal end of functional assembly 130, such as on a tapered proximal portion of balloon 136. In some embodiments, functional assembly 130 comprises a taper angle TA between 80° and 10°, such as a taper angle TA between 60° and 20°. Each port 137 is configured to slidingly receive a fluid delivery element 139*c* (e.g. a needle), as well as a tissue stop 142 and a translatable tube (e.g. conduit 111*b* shown within shaft 110*b*) fluidly attached to fluid delivery element 139*c*. Conduit 111*b*, tissue stop 142 and fluid delivery element 139*c* are configured to translate within port 137 (e.g. port 137 slidingly receives fluid delivery element 139*c*), such as when the proximal end of fluid delivery conduit 111*b* is advanced and/or retracted (e.g. via a control on a proximal handle as described herein). Fluid delivery element 139*c* is shown in an advanced state in FIG. 13, and retraction of conduit 111*b* can position the distal end of fluid delivery element 139 within port 137 or at a location more proximal than port 137.

Each tissue stop 142 can comprise a travel limiting element (e.g. a donut-shaped or c-shaped element) that at least partially circumferentially surrounds fluid delivery element 139*c*. Tissue stop 142 can be mechanically fixed to fluid delivery element 139*c*, such as via a crimp, swage, weld or adhesive. Each tissue stop 142 comprises a diameter or other sufficient surface area configured to limit travel of the surrounded fluid delivery element 139*c* into tissue (e.g. to prevent extension beyond submucosal tissue or beyond an outer layer of the intestine). Each fluid delivery element 139*c* extends a distance $D_E$ beyond the attached tissue stop 142. Distance $D_E$ can be chosen such as to inject fluid a predetermined depth beyond the inner wall of the intestine during each injection, such as to prevent fluid delivery too deep and/or too shallow into the intestinal wall. In some embodiments, distance $D_E$ comprises a distance of less than or equal to 8 mm, such as less than or equal to 6 mm, 5 mm, 4 mm, 3 mm or 2 mm In some embodiments, catheter 100 of FIG. 13 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Figure 14:
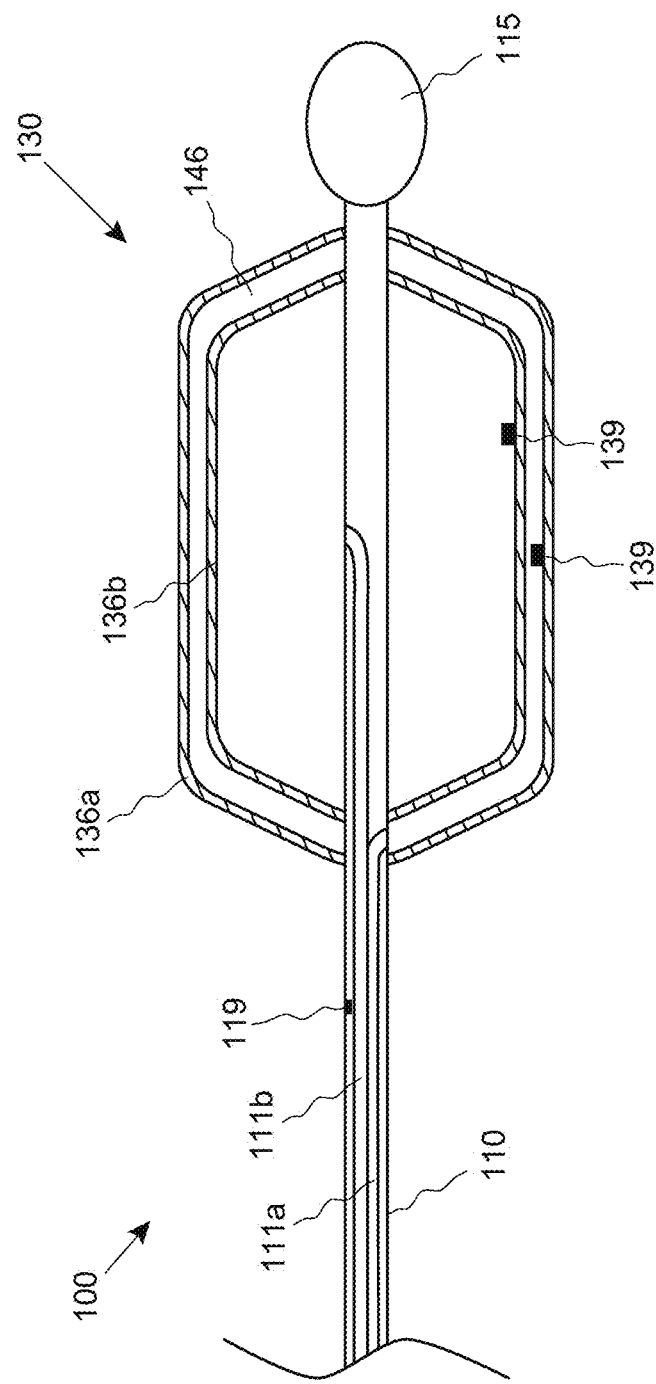
FIG. 14 is a side sectional view of a distal portion of a catheter comprising a functional assembly including an inner and outer balloon, consistent with the present inventive concepts.

Referring now to FIG. 14, a side sectional view of a distal portion of a catheter comprising a functional assembly including an inner and outer balloon is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (two conduits 111 shown in FIG. 14). Catheter 100 can comprise bulbous tip 115 on its distal end. Functional assembly 130 of FIG. 14 comprises an outer balloon 136*a* and an inner balloon 136*b*. Catheter 100 can be constructed and arranged such as to fill balloon 136*b* with a first fluid (e.g. a non-ablative gas) and fill the space between balloon 136*a* and 136*b*, space 146, with a second fluid (e.g. an ablative fluid such as a fluid at an ablative temperature). Balloon 136*b* can be filled via conduit 111*b* (partially expanding balloon 136*a*), and space 146 can be filled via conduit 111*a* (fully expanding balloon 136*a*). Filling of either or both balloons can be accomplished with a console, such as console 200 described hereabove in reference to FIG. 1 or FIG. 2.

In some embodiments, balloon 136*b* is configured to inflate rapidly with a gas, and space 146 is configured to inflate with a fluid such as a liquid or a gas. In these embodiments, a first fluid can be introduced into space 146, such as a fluid at a cooling, warming or other non-ablative temperature. In a second step, a fluid at an ablative temperature is delivered into space 146, such as an ablative fluid that is recirculated within space 146. In the dual-balloon configuration of FIG. 14, the volume of ablative fluid is reduced (e.g. reduced by the volume of balloon 136*a* as compared to single balloon 136 embodiments described herein). In addition to rapid expansion, rapid radial contraction of functional assembly 130 can be accomplished by rapidly withdrawing gas from balloon 136*a*, such as in an emergency situation.

In some embodiments, catheter 100 of FIG. 14 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Figure 15:
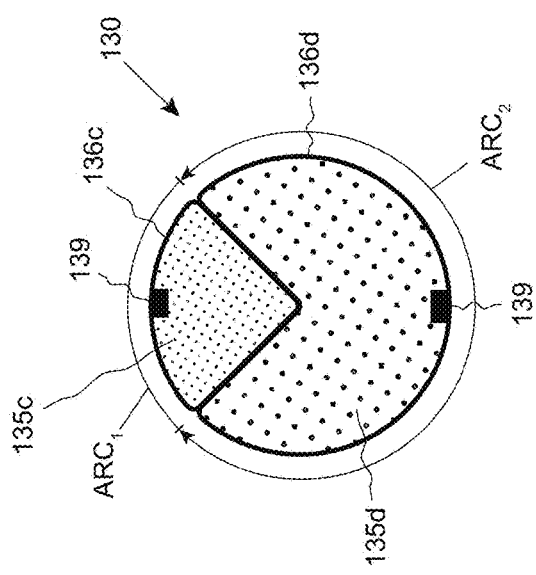
FIG. 15 is an end sectional view of a distal portion of a catheter comprising a functional assembly including two partial circumferential balloons, consistent with the present inventive concepts.

Referring now to FIG. 15, an end sectional view of a distal portion of a catheter comprising a functional assembly including two partial circumferential balloons is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity. Catheter 100 can comprise bulbous tip 115 on its distal end (not shown). Functional assembly 130 of FIG. 15 comprises a treatment balloon 136*c* configured to treat target tissue, and a positioning balloon 136*d* configured to position treatment balloon 136*c* against tissue. Catheter 100 can be constructed and arranged such as to fill balloon 136*c* with a first fluid 135*c* (e.g. an ablative fluid such as a fluid at an ablative temperature), and fill balloon 136*d* with a second fluid 135*d*

(e.g. a non-ablative fluid such as a non-ablative gas). When both balloons 136c and 136d are fully inflated, functional assembly 130 is fully expanded such as to contact intestinal wall tissue.

When inflated, both balloon 136c and balloon 136d comprise complementary partial circumferential shapes, with a collective cross section comprising a full or nearly-full circle. The outer surface of balloon 136c traverses arc ARC1 and the outer surface of balloon 136d traverses arc ARC2, such that arc ARC1 and arc ARC2 collectively traverse approximately 360°. In some embodiments, arc ARC1 of treatment balloon 136c traverses between 10° and 350° (i.e. balloon 136d correspondingly traverses between 350° and 10°). Arc ARC1 of balloon 136c can be constructed and arranged to determine the circumferential portion of an axial segment of intestinal tissue to be treated, such as when balloon 136c is filled with ablative fluid. In these embodiments, balloon 136c can be filled with neutralizing fluid prior to and/or after being filled with ablative fluid, as described herein.

In some embodiments, functional assembly 130 comprises one or more functional elements, such as functional element 139 positioned in, on and/or within balloon 136c and functional element 139 positioned in, on and/or within balloon 136d. One or more functional elements 139 of FIG. 15 can comprise a sensor, such as a sensor configured to produce a signal related to a condition of functional assembly 130 (e.g. temperature or pressure within one or more of balloons 136c and/or 136d).

In some embodiments, catheter 100 of FIG. 15 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 16:
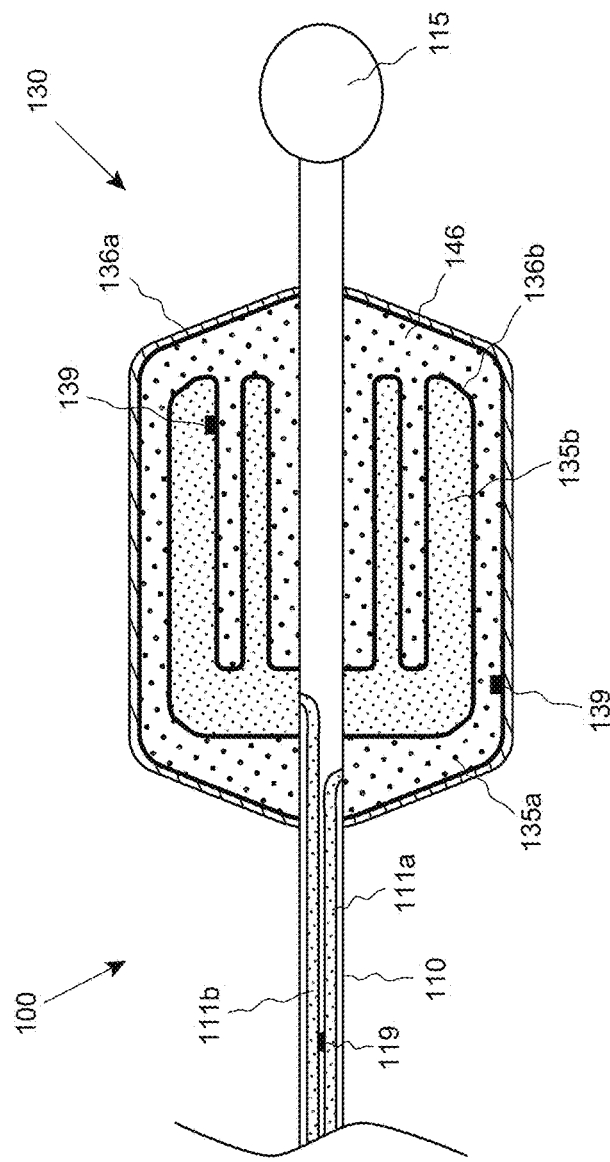
FIG. 16 is a side sectional view of a distal portion of a catheter comprising a functional assembly including an inner chamber and an outer balloon, consistent with the present inventive concepts.

Referring now to FIG. 16, a side sectional view of a distal portion of a catheter comprising a functional assembly including an inner chamber and an outer balloon is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity (two conduits 111 shown in FIG. 16). Catheter 100 can comprise bulbous tip 115 on its distal end. Functional assembly 130 of FIG. 16 comprises an inflatable balloon, outer balloon 136a which surrounds an inner chamber 136b. Inner chamber 136b can comprise an inflatable balloon as well. Catheter 100 can comprise functional element 119 positioned in, on and/or within shaft 110 (e.g. proximate and/or within conduits 111a or 111b), a functional element 139 positioned in, on and/or within balloon 136a, and/or a functional element 139 positioned in, on and/or within inner chamber 136b. Functional elements 119 and/or 139 can each comprise one or more valves, such as a pressure-regulated valve, electronic valve, duckbill valve or other valve configured to modify flow of fluid entering, exiting and/or within conduit 111a, conduit 111b, balloon 136a and/or inner chamber 136b.

Catheter 100 can be constructed and arranged to fill inner chamber 136b with a fluid 135b, and fill the space between balloon 136a and inner chamber 136b, space 146, with a fluid 135a. Inner chamber 136b can be filled via a lumen of shaft 110, conduit 111b (partially expanding balloon 136a), and space 146 can be filled via a separate lumen of shaft 110, conduit 111a (fully expanding balloon 136a). Filling of either or both balloons can be accomplished with a console, such as console 200 described hereabove in reference to FIG. 1 or FIG. 2.

In some embodiments, fluid 135b (which fills inner chamber 136b) comprises a fluid at an ablative temperature (i.e. a liquid or gas at a temperature sufficiently hot or sufficiently cold to ablate tissue). Fluid 135a, which fills space 146 between balloon 136a and inner chamber 136b, can comprise fluid at a neutralizing temperature, room temperature, or other temperature. Fluid 135a, once in place within space 146, can be heated or cryogenically chilled by fluid 135b contained within inner chamber 136b (i.e. in a heat exchange arrangement), such that when balloon 136a is in contact with tissue, ablation of target tissue can be performed, as described herein. Inner chamber 136b can comprise a balloon with a convoluted, complex, radiator-like and/or other shape configured to increase the area of the outer surface of inner chamber 136b in contact with space 146, such as to enhance heat exchange between the two (e.g. a shape similar to the shape shown in FIG. 16). Fluid 135a in space 146 and/or fluid 135b within balloon 136 can be recirculated prior to and/or during ablation of tissue, such as via one or more pumps of an attached console, such as via one or more pumping assemblies 225 of console 200 described hereabove in reference to FIG. 1.

In other embodiments, inner chamber 136b is filled with fluid 135b or another material at a non-ablative temperature and/or inner chamber 136b otherwise simply occupies space (e.g. with or without inflation of inner chamber 136b) within balloon 136a. In these embodiments, inner chamber 136b can be configured such that ablative energy is not delivered from inner chamber 136b to space 146. In these embodiments, inner chamber 136b can be constructed and arranged to significantly reduce the amount of an ablative fluid 135a that otherwise would be required to fully expand balloon 136a, such as when inner chamber 136b comprises a volume of at least 30%, 40% or 50% of the volume defined by the outer surface of a fully expanded balloon 136a. Alternatively or additionally, inner chamber 136b can comprise a volume and/or a shape configured to improve flow dynamics of fluid 135b within space 146, such as when space 146 is filled with a recirculating ablative fluid 135b. Fluid 135a in space 146 and/or fluid 135b within balloon 136 can be recirculated prior to and/or during ablation of tissue, such as via one or more pumps of an attached console, such as via one or more pumping assemblies 225 of console 200 described hereabove in reference to FIG. 1.

In some embodiments, catheter 100 of FIG. 16 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIGS. 17A-B, two anatomical, side sectional views of a distal portion of a catheter comprising a functional assembly and at least one stabilizing assembly are illustrated, consistent with the present inventive concepts. Catheter 100 comprises shaft 110, functional assembly 130 (shown in its compacted state in FIG. 17A and in its expanded state in FIG. 17B), and other components, such as one or more components of similar construction and arrangement to those described hereabove in reference to catheter 100 of FIG. 1 or FIG. 2, such as one or more conduits 111, some of which have been removed for illustrative clarity (three conduits 111 shown in FIGS. 17A-B). Catheter 100 can comprise bulbous tip 115 on its distal end. Functional assembly 130 can comprise an inflatable balloon, balloon 136, which can be fluidly attached to an inflation lumen or tube, such as the attached conduit 111c shown. Catheter 100 further comprises one or more stabilizing assemblies, such as the two stabilizing assemblies 143a and 143b shown in FIG. 17. Stabilizing assemblies 143a and/or 143b (singly or collectively stabilizing assembly 143), can each comprise an expandable assembly positioned proximate functional assembly 130, such as at or within 0.5 cm, 1.0 cm, 2.0 cm, 3.0 cm or 5.0 cm of either end of functional assembly 130. In some embodiments, a first stabilizing assembly 143 (e.g. stabilizing assembly 143a as shown) is positioned proximal to functional assembly 130 and a second stabilizing assembly 143 (e.g. stabilizing assembly 143b as shown) is positioned distal to functional assembly 130. In some embodiments, functional assembly 130 comprises a length between 1 cm and 4 cm, such as a length between 2 cm and 3 cm. In some embodiments, one or more stabilizing assemblies 143 comprise a length between 0.5 cm and 6.0 cm, such as a length between 1.0 cm and 4.0 cm.

Each stabilizing assembly 143 can comprise a radially expandable element such as a radially expanding element selected from the group consisting of: an inflatable balloon; a radially expandable cage or stent; one or more radially deployable arms; an expandable helix; an unfurlable compacted coiled structure; an unfurlable sheet; an unfoldable compacted structure; and combinations of one or more of these. Each stabilizing assembly 143 can be operably attached to a conduit, such as conduits 111a and 111b shown, each comprising a lumen configured to inflate a stabilizing assembly 143 with a fluid (e.g. a liquid or a gas), or a lumen that slidingly receives a control rod configured to expand the associated stabilizing assembly 143. Each stabilizing assembly 143 can comprise one or more functional elements, such as functional elements 139 shown.

In some embodiments, catheter 100 is constructed and arranged to first expand one or more stabilizing assemblies 143, such as to center functional assembly 130 within a lumen of the intestine while functional assembly 130 is in a compacted or partially expanded state (e.g. to relatively center functional assembly 130 within a lumen of the intestine to avoid undesired contact of functional assembly 130 with the inner wall of the intestine), as is shown in FIG. 17A. In these embodiments, a pre-centered functional assembly 130 can subsequently expand to make contact with the wall of the intestine, as shown in FIG. 17B. The filling of a pre-centered functional assembly 130 can avoid undesired partial-contact ablations, undesired partial fluid delivery element insertion tissue expansions, and/or other undesired energy or fluid transfer that might occur in a partially expanded state of functional assembly 130.

Conduit 111c can be constructed and arranged to provide and/or modify (e.g. reduce) ablative energy from functional assembly 130, such as a conduit configured to provide to, modify and/or extract from functional assembly 130 one or more of: fluid at an ablative temperature; RF energy; sound energy such as ultrasound energy; light energy such as laser light energy; and combinations of one or more of these. In FIG. 17A, stabilizing assemblies 143a and 143b have been expanded, while functional assembly 130 remains radially compacted. Functional assembly 130 is positioned at an axial segment of the intestine in which a medical procedure is to be performed (e.g. a tissue expansion procedure and/or a tissue ablation procedure). In FIG. 17B, functional assembly 130 has been radially expanded to contact the intestinal wall at the desired location. A subsequent tissue expansion, tissue ablation or other step can be performed using functional assembly 130. In some embodiments, confirmation of proper location of functional assembly 130 is performed (e.g. via a visualization device as described herein) prior to expansion and/or ablation of tissue.

In some embodiments, stabilizing assembly 143a and/or 143b comprise an anchor element configured to be translated independent of functional assembly 130. In some embodiments, stabilizing assemblies 143a and 143b are expanded to anchor within intestinal tissue, and stabilizing assembly 143a and/or 143b are translated to stretch a segment of intestine (e.g. place an axial segment of the intestine in tension after which functional assembly 130 can be used to treat and/or diagnose tissue between stabilizing assemblies 143a and 143b). In some embodiments, one or more stabilizing assemblies 143 are configured to treat tissue and/or diagnose tissue, such as to deliver fluid to expand tissue and/or to deliver energy to tissue (e.g. when a stabilizing assembly 143 is filled with ablative fluid).

In some embodiments, catheter 100 of FIG. 17 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIG. 18, an anatomical, side sectional view of a distal portion of a catheter comprising a functional assembly configured to avoid unintended translation within the intestine is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (two conduits 111 shown in FIG. 18). Catheter 100 can comprise bulbous tip 115 (not shown, but such as is described herein) on its distal end. Functional assembly 130 can comprise an inflatable balloon, balloon 136. Functional assembly 130 can be constructed and arranged to avoid unintended translation, such as to avoid translation between a first procedural step and a second procedural step that are intended to be performed at the same location (e.g. a tissue expansion procedure and a tissue ablation procedure that should be performed at the same relative axial segment of the intestine).

In some embodiments, functional assembly 130 (e.g. balloon 136) comprises a shape constructed and arranged to anchor functional assembly 130 to prevent or otherwise reduce (herein "prevent") unintended translation of functional assembly 130 within the intestine, such as the dogbone shape shown in FIG. 18. Other non-tubular shapes and/or other multi-diameter shapes can be employed to avoid unintended translation, such as a shape comprising two or more trapezoidal cross sections. During intended translation, functional assembly 130 can be fully or partially compacted as described herein.

Alternatively or additionally, functional assembly 130 can comprise a port 137 positioned on an outer surface of functional assembly 130 and constructed and arranged to anchor functional assembly 130 to prevent unintended translation of functional assembly 130 within the intestine (e.g. anchor functional assembly 130). Each port 137 can be fluidly attached to a conduit 111e, which can be configured to apply a vacuum to port 137, such as to engage with intestinal wall tissue to prevent or otherwise limit translation. During intended translation, vacuum can be removed from the one or more ports 137.

Alternatively or additionally, functional assembly 130 can comprise one or more extending anchors, such as the two extending anchors 144a shown. Anchors 144a can be configured to frictionally engage intestinal tissue when functional assembly 130 is expanded. Anchors 144a can comprise a barb-like geometry that can be oriented to prevent translation in one or more directions, such as to prevent movement of functional assembly 130 proximally (i.e. to the left of the page), as shown in FIG. 18.

Alternatively or additionally, functional assembly 130 can comprise a tethered anchor, such as anchor 144b shown in FIG. 18. Anchor 144b can be deployed, such as via one or more conduits 111, not shown. Anchor 144b can comprise a grasping structure configured to provide sufficient retention force to prevent unintended translation of functional assembly 130, but still be intentionally disengaged by an operator of catheter 100. Anchor 144b can be attached to distal end 132 of functional assembly 130 as shown, such as to prevent migration of functional assembly 130 proximally (i.e. to the left of the page). In some embodiments, anchor 144b or a separate anchor is attached to the proximal end 131 of functional assembly 130, such as to prevent migration of functional assembly 130 distally (i.e. to the right of the page).

Alternatively or additionally, functional assembly 130 can comprise a coating configured to anchor prevent or otherwise reduce unintended translation of functional assembly 130. Functional assembly 130 can comprise coating 147 positioned on at least a portion of the tissue-contacting surfaces of functional assembly 130. Coating 147 can comprise a coating and/or a surface treatment configured to enhance frictional engagement of functional assembly 130 with tissue.

In some embodiments, catheter 100 of FIG. 18 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts.

In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 19:
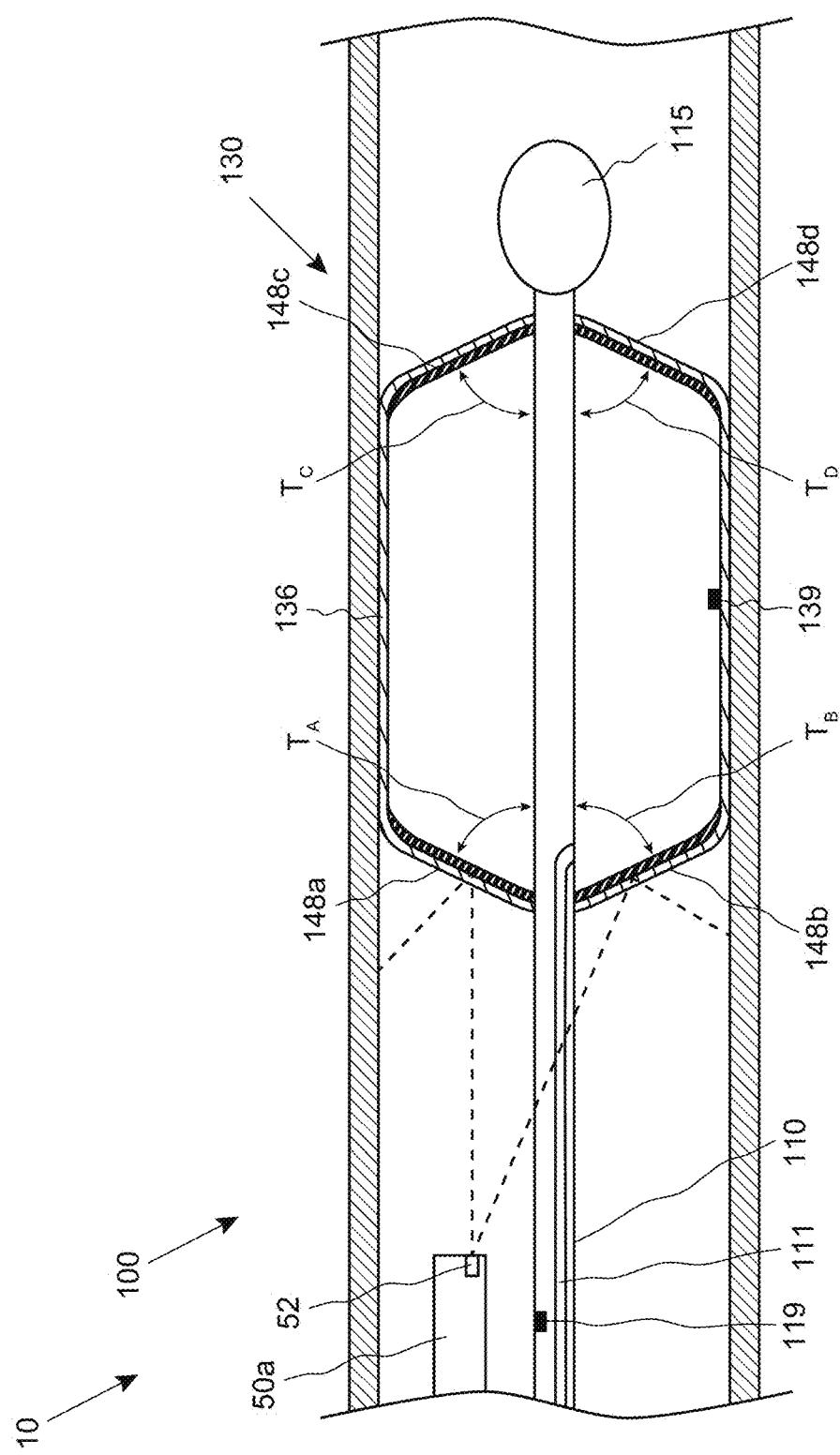
FIG. 19 is an anatomical, side sectional view of a distal portion of a system and catheter comprising a functional assembly including one or more reflective surfaces, consistent with the present inventive concepts.

Referring now to FIG. 19, an anatomical, side sectional view of a distal portion of a system and catheter comprising a functional assembly including one or more reflective surfaces is illustrated, consistent with the present inventive concepts. System 10 comprises catheter 100 and a camera device, such as endoscope 50a comprising camera 52. Catheter 100 has been advanced into an intestine, alongside endoscope 50a, to a desired axial segment of the intestine, to perform a medical procedure. In some embodiments, catheter 100 is introduced through a working channel of endoscope 50a, through a sheath and/or over a guidewire, as has been described herein. System 10 can comprise one or more other components, such as console 200 and other components not shown, but similar to those described hereabove in reference to system 10 of FIG. 1 or system 10 of FIG. 2. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (one conduit 111 shown in FIG. 19). Catheter 100 can comprise bulbous tip 115 on its distal end. Functional assembly 130 can comprise an inflatable balloon, balloon 136, which can be fluidly attached to an inflation lumen, such as conduit 111 shown.

Endoscope 50a comprises camera 52 which provides a view distal to and along the axis of the distal portion of endoscope 50a. Catheter 100 can comprise one or more reflectors, such as a reflector comprising a reflective fluid (e.g. a reflective fluid positioned within balloon 136) and/or a reflective surface. Functional assembly 130 and/or another portion of catheter 100 can comprise a reflector selected from the group consisting of: mirror; folding mirror; foil-coated mylar portion; chrome tape; acrylic mirror; and combinations of one or more of these. For example, functional assembly 130 can comprise one or more reflective surfaces, such as one or more of reflective surfaces 148a, 148b, 148c and/or 148d (singly or collectively reflective surface 148). Each reflective surface 148 can comprise a flexible portion and/or a rigid portion, such as a reflective surface 148 comprising at least a flexible portion positioned on, in and/or within functional assembly 130. Each reflective surface 148 is positioned to be viewed by camera 52, and provide a reflective image of intestinal tissue or a portion of system 10 that otherwise might not be viewed by camera 52. Each reflective surface 148 can be positioned on a tapered portion of functional assembly 130, such as at taper angles $T_A$, $T_B$, $T_C$ and/or $T_D$, respectively. Each reflective surface 148 can comprise a portion of balloon 136. A reflective surface 148 can be positioned on a proximal portion of functional assembly 130, such as when the proximal portion of functional assembly 130 comprises a geometry selected from the group consisting of: flat surface; convex surface; pyramid shaped surface; and combinations of one or more of these. Reflective surfaces 148a and 148b can be configured to provide an image of tissue or objects proximal to the proximal end of functional assembly 130, such as tissue or objects proximal to camera 52 and/or otherwise are outside of the field of view of camera 52. Reflective surfaces 148c and 148d can be configured to provide an image of tissue or objects proximal to the distal end of functional assembly 130, or any tissue or objects proximal to the distal end of functional assembly 130. Functional assembly 130 can be configured to expand tissue and/or ablate tissue, such as a tissue expansion or ablation involving use of an image provided by a reflective surface 148.

In some embodiments, one or more reflective surfaces 148 are positioned such that camera 52 views non-target tissue, such as viewing of non-target tissue such as the ampulla of Vater or other non-target tissue as described herein, that is viewed prior to and/or during an ablation step.

In some embodiments, system 10 of FIG. 19 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 20:
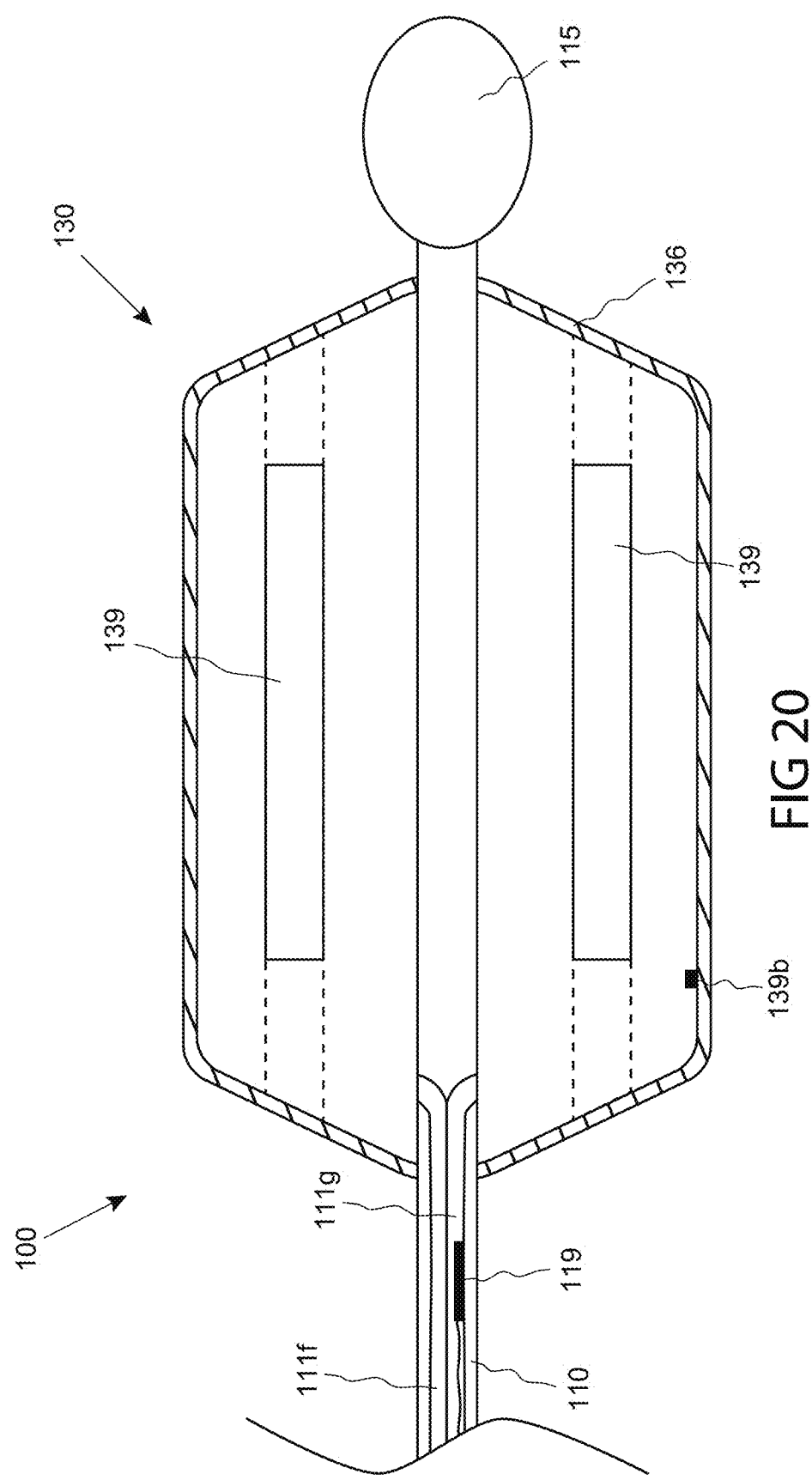
FIG. 20 is a side sectional view of a distal portion of a catheter comprising a functional assembly attached to at least two fluid conduits, consistent with the present inventive concepts.

Referring now to FIG. 20, a side sectional view of a distal portion of a catheter comprising a functional assembly attached to at least two fluid conduits is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (two conduits 111 shown in FIG. 20). Catheter 100 can comprise bulbous tip 115 on its distal end. Functional assembly 130 can comprise an inflatable balloon, balloon 136 shown. Balloon 136 is fluidly attached to a first fluid handling conduit, conduit 111f, and a second fluid handling conduit, conduit 111g. Catheter 100 can be constructed and arranged to fill balloon 136 with fluid and/or evacuate balloon 136 of fluid with both conduit 111f and conduit 111g, fills and/or evacuations with each conduit performed sequentially and/or simultaneously, singly and/or collectively.

In some embodiments, catheter 100 is constructed and arranged to fill and/or evacuate balloon 136 with conduits 111f and conduit 111g simultaneously to reduce the fill and/or evacuation time that would result with a single conduit 111. In some embodiments, catheter 100 is constructed and arranged to switch from filling or evacuating with a single conduit 111 to filling or evacuating, respectively, using at least two conduits 111, when an undesired condition occurs (e.g. when an undesired condition is detected by an operator and/or automatically by system 10). In these embodiments, functional element 139b can comprise a sensor configured to detect the undesired condition, such as a sensor configured to detect an occlusion (e.g. a pressure sensor or a flow sensor), a sensor configured to detect a leak (e.g. a fluid detector or a pressure sensor), a sensor configured to detect gas (e.g. undesired gas) in a conduit 111, or combinations of one or more of these. Information from the sensor-based functional element 139b can be used to adjust flow of fluid, such as to modify (e.g. stop and/or reverse) flow of fluid after detection of a leak or occlusion, and/or to begin delivery of a second fluid (e.g. a neutralizing fluid) after detection of a leak. In some embodiments, after detection of a leak or occlusion by a functional element 139b, fluid can be delivered and/or extracted by two conduits 111 simultaneously.

In some embodiments, functional element 119 comprises a heating or cooling element configured to modify and/or control the temperature of fluid entering balloon 136 via conduit 111g. In these embodiments, one or more conduits 111 can be fluidly connected to balloon 136, such as one or both of conduits 111f and/or 111g.

In some embodiments, functional assembly 130 further comprises one or more functional elements 139 positioned on, in and/or within balloon 136, such as multiple functional elements 139 equally separated along a circumference of balloon 136 (e.g. three elements spaced approximately 120° apart). Each functional element 139 can span a length of balloon 136 (e.g. as shown with dotted lines), or a portion of the length of balloon 136. In some embodiments, functional element 139 can comprise an insulating element configured to prevent or at least limit a transfer of energy (e.g. thermal energy) from functional assembly 130 to tissue locations proximate each functional element 139. Treatment of an axial segment of tissue that is less than 360° can be accomplished, for example a near 360° segment of treated tissue with one or more axial lines of non-ablated tissue corresponding to the position of one or more functional elements 139. In some embodiments, treatment of less than 360° of an axial segment is performed to reduce adverse effects, such as to reduce the likelihood of stricture formation. In some embodiments, functional element 139 is both an insulator as well as a fluid delivery element (e.g. fluid delivery element 139c described herein). In these embodiments, functional element 139 can comprise a port (e.g. port 137 or other vacuum port), through which a needle or other fluid delivery element 139c can translate or otherwise engage tissue for fluid delivery into the tissue.

In some embodiments, catheter 100 of FIG. 20 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 21:
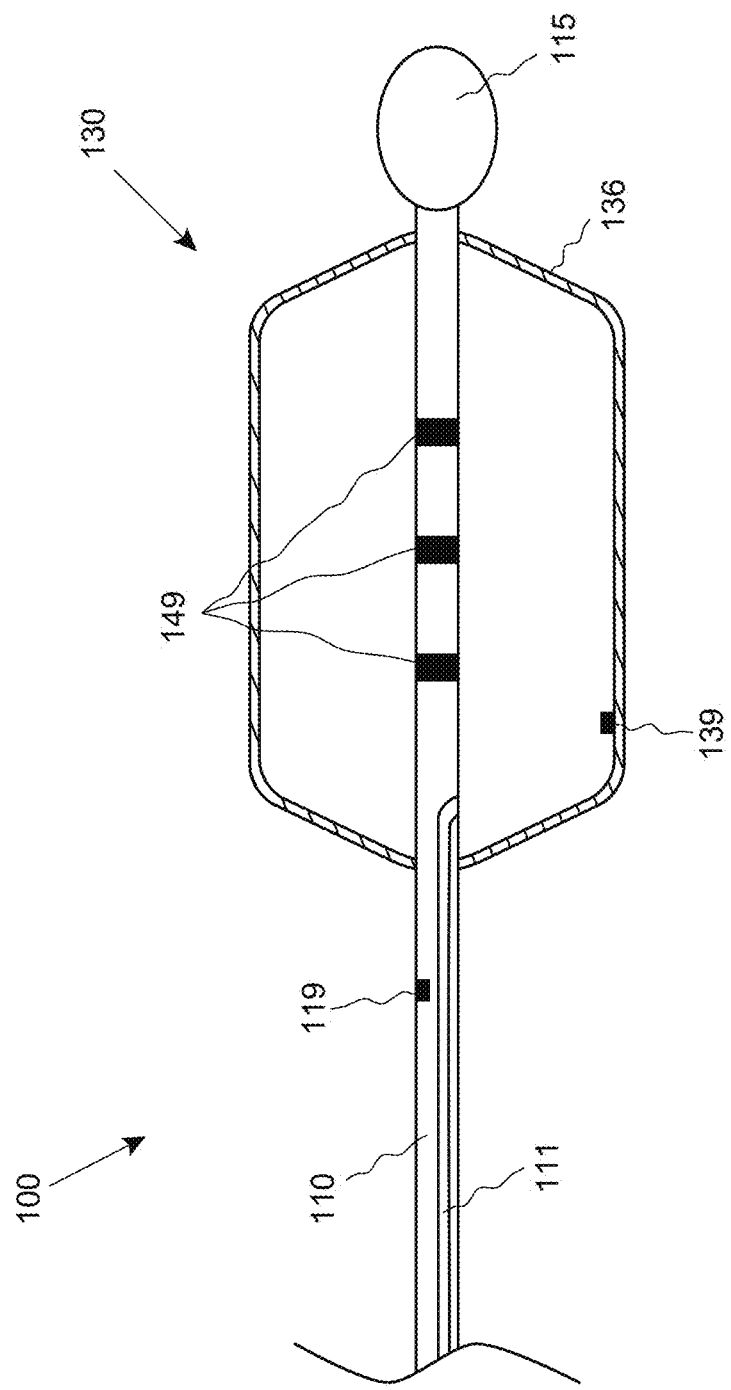
FIG. 21 is a side sectional view of a distal portion of a catheter comprising a functional assembly including one or more light delivery elements, consistent with the present inventive concepts.

Referring now to FIG. 21, a side sectional view of a distal portion of a catheter comprising a functional assembly including one or more light delivery elements is illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (one conduit 111 shown in FIG. 21). Catheter 100 can comprise bulbous tip 115 on its distal end. Functional assembly 130 can comprise an inflatable balloon, balloon 136, which can be fluidly attached to an inflation lumen, such as conduit 111 shown.

Functional assembly 130 can comprise one or more light delivery elements, such as the three light delivery elements 149 shown in FIG. 21. Light delivery elements 149 can be positioned anywhere on, in and/or within functional assembly 130, such as on a shaft 110 that passes through functional assembly 130 (also as shown). Functional assembly 130 and light delivery elements 149 can be constructed and arranged to assist in the visualization of functional assembly 130, such as when viewed by a camera device and/or simply viewed by an unassisted eye of an operator of catheter 100. In some embodiments, light delivery elements 149 deliver high intensity visible light which allows direct visualization of functional assembly 130 through the patient's skin (e.g. skin surrounding the abdominal wall). In some embodiments, one or more light delivery elements 149 deliver non-visible light, such as infrared light which can be visualized by an infrared (e.g. near infrared) or other non-visible light imaging device, such as imaging device 55 described hereabove in reference to FIG. 1. Alternatively or additionally, light delivery element 149 can provide non-light energy, such as an element configured to produce a magnetic or electromagnetic field that can be detected by an external device to locate functional assembly 130. Light delivery elements 149 can comprise one or more light delivery elements selected from the group consisting of: light; LED; optical component such as a lens, mirror or prism; a fluorescent agent (e.g. a fluorescent agent within and/or on functional assembly 130); and combinations of one or more of these. Light delivery elements 149 can be operably attached (e.g. electrically or optically) attached to a conduit (not shown but such as one or more conduits 111 described herein) which is in turn attached to a source of power (e.g. one or more wires attached to power of console 200) and/or light (e.g. one or more light guides such as optical fibers attached to a light source of console 200).

In some embodiments, catheter 100 of FIG. 21 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Figure 22:
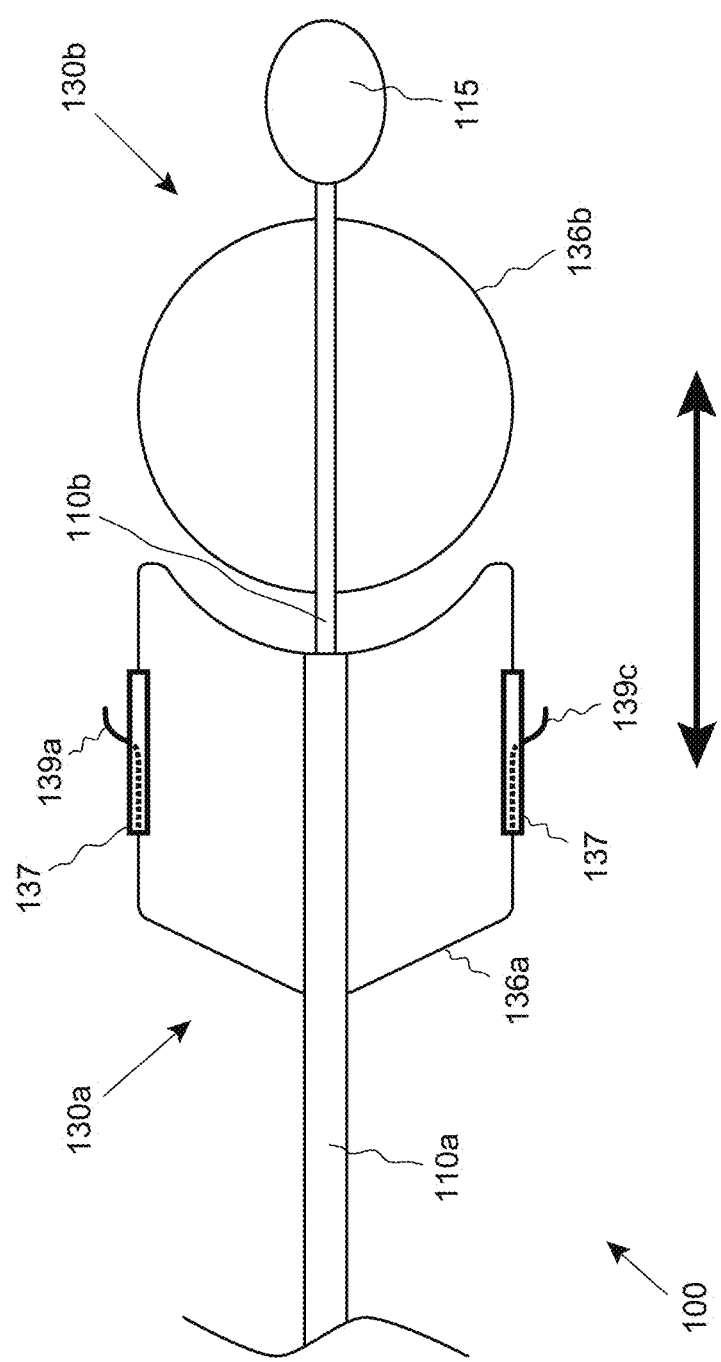
FIG. 22 is a side view of a distal portion of a catheter comprising a functional assembly comprising a first expanding element and a second expanding element, consistent with the present inventive concepts.

Referring now to FIG. 22, a side view of a distal portion of a catheter comprising a functional assembly comprising a first expanding element and a second expanding element is illustrated, consistent with the present inventive concepts. Catheter 100 can comprise one or more components of similar construction and arrangement to those described hereabove in reference to catheter 100 of FIG. 1 or FIG. 2, such as one or more conduits 111 which have been removed for illustrative clarity. Catheter 100 can comprise a shaft comprising an outer shaft 110a and an inner shaft 110b. Shaft 110a comprises a lumen configured to slidingly receive shaft 110b. Catheter 100 comprises a first functional assembly 130a mounted about a distal portion of shaft 110a. Catheter 100 further comprises a second functional assembly 130b, positioned distal to functional assembly 130a and mounted about a distal portion of shaft 110b. Functional assembly 130a and/or functional assembly 130b can each be of similar construction and arrangement to functional assembly 130 of FIG. 1, or functional assemblies 130, 25, 35 and/or 45 of FIG. 2. Catheter 100 can comprise bulbous tip 115 on its distal end.

Shaft 110a and/or shaft 110b can be operably attached to one or more translational controls (e g manual and/or mechanized controls on a proximal handle such as handle 102 of FIG. 1 or FIG. 2), such as to telescopically translate shaft 110a relative to shaft 110b. This translation will accordingly change the distance between functional assembly 130a and functional assembly 130b.

Functional assembly 130a can comprise balloon 136a and functional assembly 130b can comprise balloon 136b. Each of functional assemblies 130a and 130b can be configured to be radially expanded (each shown in FIG. 22 in an expanded state), such as via the delivery of one or more fluids into balloons 136a and 136b, respectively, such as via one or more fluidly attached conduits 111 configured to deliver and withdraw inflation fluids, as described herein.

In some embodiments, functional assembly 130a is constructed and arranged to expand tissue (e.g. one or more layers of tissue such as submucosal tissue), such as when functional assembly 130a comprises one or more ports 137 and fluid delivery element 139c (e.g. a curved needle as shown in FIG. 22 that can be fluidly attached to one or more conduits supplying one or more injectates). In these embodiments, functional assembly 130a can be constructed and arranged as described hereabove in reference to functional assembly 130 of FIG. 1 or functional assembly 25 of FIG. 2. Ports 137 can comprise two or more ports 137, such as three ports 137 distributed approximately 120° around a circumference of functional assembly 130a. Each port 137 can comprise a fluid delivery element 139c configured to exit port 137 (as shown in FIG. 22), and/or remain within the associated port 137. Port 137 can be fluidly attached to a vacuum source, such as via one or more fluidly attached conduits 111, as described herein. In some embodiments, ports 137 and/or the associated fluid delivery elements 139c (e.g. a curved needle as shown, a straight needle, a nozzle, a fluid jet and the like), comprise a trajectory and/or are otherwise configured to deliver fluid and expand tissue distal to functional assembly 130a, such as in a direction towards functional assembly 130b.

In some embodiments, functional assembly 130b is constructed and arranged to ablate or otherwise treat target tissue, such as when functional assembly 130b is attached to a source of ablative energy as described herein, such as one or more ablative fluids which are delivered to and/or recirculated within functional assembly 130b (e.g. via one or more fluidly attached conduits 111 configured to deliver and withdraw ablative fluids, as described herein).

Functional assembly 130a and functional assembly 130b can comprise expanded geometries configured to nest or otherwise mate with each other, such as the concave shaped distal end of functional assembly 130a that comprises a size and shape configured to nest with the convex shaped proximal end of functional assembly 130b.

In some embodiments, the distal portion of catheter 100 is positioned in an axial segment of intestinal tissue, and a tissue expansion (e.g. submucosal tissue expansion) is performed with balloon 136a frictionally engaging tissue. Subsequently, a tissue ablation is performed using functional assembly 130b, such as by first retracting or otherwise assuring that functional assembly 130b is nested or otherwise in relative proximity to functional assembly 130a, after which the ablation energy can be delivered to tissue (e.g. balloon 136b filled with ablative fluid). In some embodiments, a tissue cooling or warming procedure is performed prior to the delivery of the fluid at an ablative temperature, as described herein.

In some embodiments, catheter 100 of FIG. 22 and/or a component attached to catheter 100 comprises one or more sensors, such as functional elements 119, 139a (of functional assembly 130a) and/or 139b (of functional assembly 130b), that have been configured as a sensor. In some embodiments, catheter 100 of FIG. 22 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts.

Figure 23:
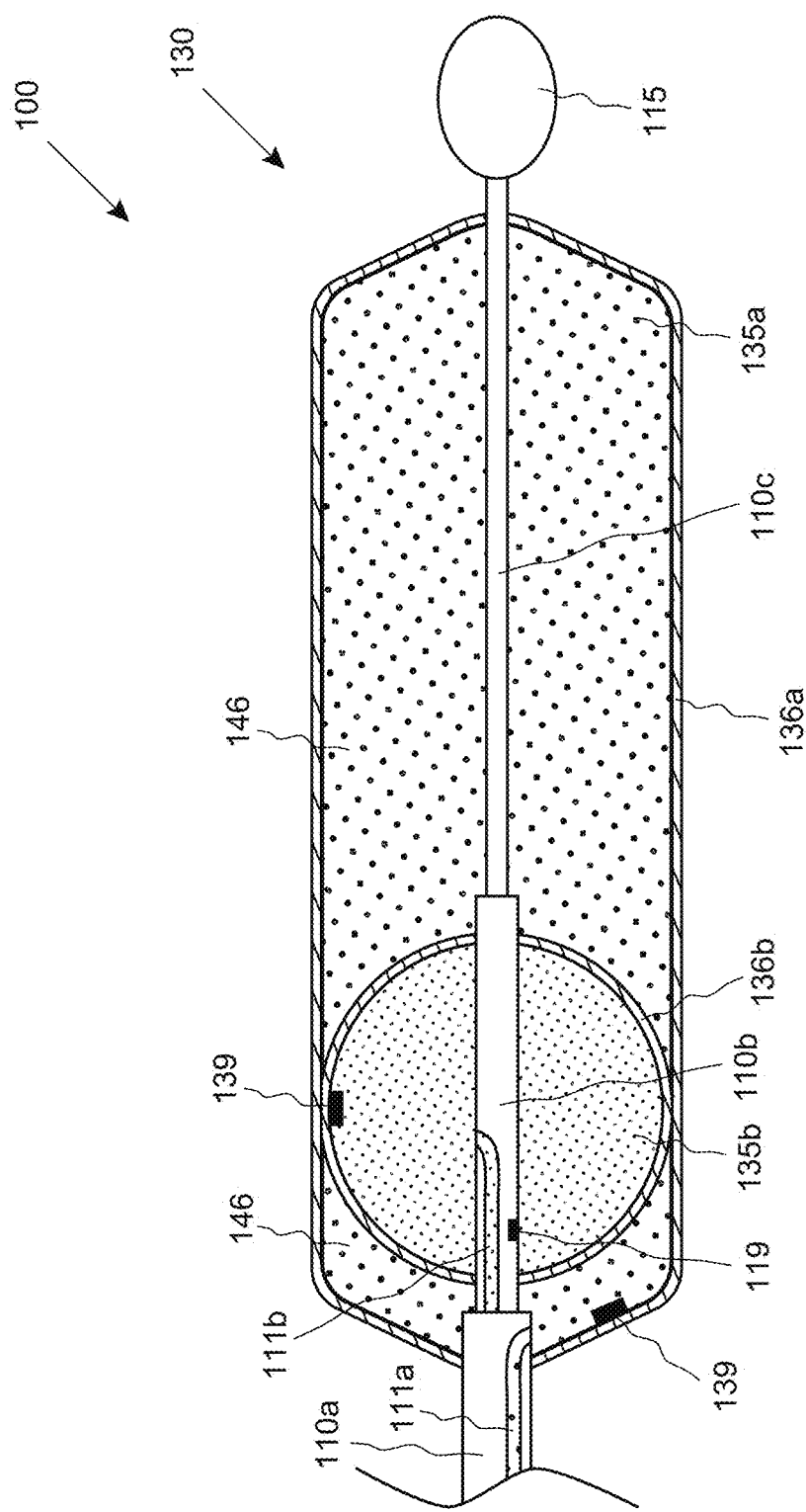
FIG. 23 is a side sectional view of a distal portion of a catheter comprising an inner balloon configured to ablate and an outer balloon configured to position, consistent with the present inventive concepts.

Referring now to FIG. 23, a side sectional view of a distal portion of a catheter comprising an inner balloon configured to ablate and an outer balloon configured to position is illustrated, consistent with the present inventive concepts. Catheter 100 can comprise one or more components of similar construction and arrangement to those described hereabove in reference to catheter 100 of FIG. 1 or FIG. 2, such as one or more conduits 111, some of which have been removed for illustrative clarity (two conduits 111 shown in FIG. 23). Catheter 100 can comprise a shaft 110 comprising an outer shaft 110a, an inner shaft 110b and an extending shaft 110c. Shaft 110a comprises a lumen configured to slidingly receive shaft 110b, and shaft 110b comprises a lumen to slidingly receive shaft 110c. Functional assembly 130 comprises outer balloon 136a which is mounted about shaft 110a and configured to position (e.g. anchorably position) functional assembly 130 at a desired axial segment of intestinal tissue. Functional assembly 130 further comprises inner balloon 136b, positioned within outer balloon 136a, and mounted about shaft 110b. Catheter 100 can comprise bulbous tip 115 on its distal end. Catheter 100 can comprise functional element 119 positioned in, on and/or within shaft 110 (e.g. proximate and/or within conduits 111a or 111b), a functional element 139 positioned in, on and/or within outer balloon 136a, and/or a functional element 139 positioned in, on and/or within inner balloon 136b. Functional elements 119 and/or 139 can each comprise one or more valves, such as a pressure-regulated valve, electronic valve, duckbill valve or other valve configured to modify flow of fluid entering, exiting and/or within conduit 111a, conduit 111b, outer balloon 136a and/or inner balloon 136b.

Catheter 100 can be constructed and arranged to fill inner balloon 136b with a fluid 135b, and fill outer balloon 136a (e.g. fill the space between outer balloon 136a and inner balloon 136b, space 146) with fluid 135a. Inner balloon 136b can be filled via a lumen of shaft 110b, conduit 111b, and outer balloon 136a can be filled via a lumen of shaft 110a, conduit 111a. Filling of either or both balloons can be accomplished with a console, such as console 200 described hereabove in reference to FIG. 1 or FIG. 2.

In some embodiments, fluid 135b (which fills inner balloon 136b) comprises a fluid at an ablative temperature (i.e. a liquid or gas at a temperature sufficiently hot or sufficiently cold to ablate tissue). Fluid 135a which fills space 146 between outer balloon 136a and inner balloon 136b can comprise fluid at a neutralizing temperature, room temperature, or other temperature. In some embodiments, fluid 135a comprises a gas.

Fluid 135a in space 146 and/or fluid 135b within inner balloon 136b can be recirculated prior to and/or during ablation of tissue, such as via one or more pumps of an attached console, such as via one or more pumping assemblies 225 of console 200 described hereabove in reference to FIG. 1.

Shaft 110a, shaft 110b and/or shaft 110c can be operably attached to one or more translational controls or mechanical linkage assembly (e.g. a control on a proximal handle such as handle 102 of FIG. 1 or FIG. 2 or a mechanical linkage assembly of console 200), such as to telescopically translate shaft 110a relative to shaft 110b, translate shaft 110a relative to shaft 110c, and/or translate shaft 110b relative to shaft 110c. The position of inner balloon 136b within outer balloon 136a can be changed by translating inner shaft 110b along shaft 110c.

In some embodiments, outer balloon 136a is inflated with fluid 135a such that outer balloon 136a contacts the inner wall of an axial segment of intestinal tissue. Subsequently, inner balloon 136b is filled with fluid 135b (e.g. with fluid at a cooling or warming temperature, or fluid at an ablative temperature), expanding inner balloon 136b to sufficiently contact the inner surface of outer balloon 136a, such that thermal energy can be transferred between inner balloon 136b and tissue proximate inner balloon 136b (e.g. energy transferred through the contacting portion of outer balloon 136a). In some embodiments, inner balloon 136b is first filled with fluid at a non-ablative temperature (e.g. a cooled fluid configured to extract heat from tissue) and subsequently filled with fluid at an ablative temperature (e.g. a heated fluid configured to ablate tissue). In some embodiments, after an ablative fluid is delivered to inner balloon 136b (whether or not a non-ablative fluid was first delivered to inner balloon 136b), a non-ablative fluid is subsequently delivered to inner balloon 136b (e.g. to neutralize the effects of tissue ablation). In these various embodiments, neutralizing fluid, ablative fluid and/or other fluid can be recirculated within inner balloon 136b, as described herein.

As described above, inner balloon 136b can be translated within outer balloon 136a, such as by advancing and/or retracting shaft 110b. In some embodiments, outer balloon 136a is inflated to frictionally engage an axial segment of intestinal tissue. Subsequently, inner balloon 136b is positioned at a first location within outer balloon 136a, and a first ablation step is performed. Subsequently, inner balloon 136b is positioned at a second location within outer balloon 136a (e.g. without repositioning outer balloon 136a), and a second ablation step is performed. Additional similar repositioning and ablating steps can be repeated, such as to treat all or a portion of the length of the intestine contacted by outer balloon 136a. In addition to introducing fluid at an ablative temperature to inner balloon 136b, each ablation step can include introducing a non-ablative fluid (e.g. a cooling fluid) prior to and/or after the delivery of the ablative fluid.

Alternative to the step-wise placement of inner balloon 136b followed by a period of ablation, which can be repeated, catheter 100 can be configured to deliver ablative fluid into inner balloon 136b and to treat target tissue while translating (continuously or intermittently) inner balloon 136b within outer balloon 136a, such as translation performed at a rate sufficiently slow to ablate target tissue, but sufficiently fast to avoid adversely affecting non-target tissue. In some embodiments, inner balloon 136b is manually or automatically advanced at an average rate of at least 1 mm/minute, such as a rate of at least 2 mm/minute or 3 mm/minute. In some embodiments, inner balloon 136b is manually or automatically advanced at an average rate of less than 3 mm/second, such as a rate of less than 2 mm/second or 1 mm/second.

In some embodiments, inner balloon 136b treats target tissue without ablative fluid, such as by delivering RF energy, light energy and/or other energy as described herein.

In some embodiments, outer balloon 136a can comprise a fluid delivery element (such as fluid delivery element 139c described hereabove in reference to FIG. 1), which can be constructed and arranged to expand tissue proximate outer balloon 136a, such as during a tissue expansion procedure that occurs prior to one or more ablation steps performed by inner balloon 136b. In some embodiments, outer balloon 136a comprises a length of at least 3 cm, at least 4 cm, at least 5 cm, or at least 6 cm. In these embodiments, inner balloon 136b can comprise a length of at least 0.5 cm, such as at least 1.0 cm, 1.5 cm, 2.0 cm, 2.5 cm or 3.0 cm.

In some embodiments, catheter 100 of FIG. 23 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein, as described herein.

Figure 24:
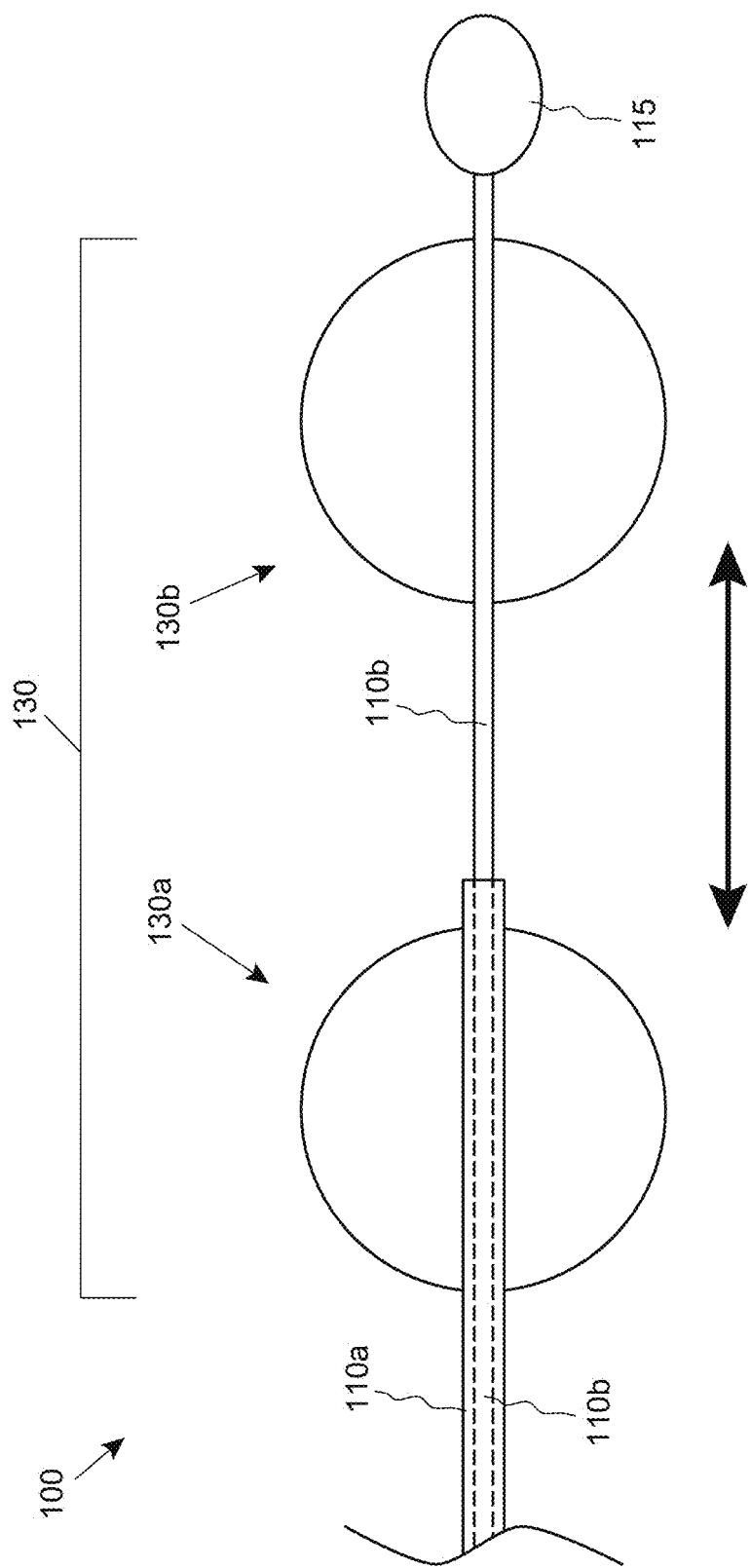
FIG. 24 is a side view of a distal portion of a catheter comprising a functional assembly including a first expanding element and a second expanding element, consistent with the present inventive concepts.

Referring now to FIG. 24, a side view of a distal portion of a catheter comprising a functional assembly including a first expanding element and a second expanding element is illustrated, consistent with the present inventive concepts. Catheter 100 can comprise one or more components of similar construction and arrangement to those described hereabove in reference to catheter 100 of FIG. 1 or FIG. 2, such as one or more conduits 111 which have been removed for illustrative clarity. Catheter 100 can comprise a shaft comprising an outer shaft 110a and an inner shaft 110b. Shaft 110a comprises a lumen configured to slidingly receive shaft 110b. Catheter 100 can comprise bulbous tip 115 on its distal end.

Catheter 100 of FIG. 24 comprises a first functional assembly 130a mounted about a distal portion of shaft 110a. Catheter 100 further comprises a second functional assembly 130b, positioned distal to functional assembly 130a and mounted about a distal portion of shaft 110b. Functional assembly 130a and/or functional assembly 130b can each be of similar construction and arrangement to functional assembly 130 of FIG. 1, or functional assemblies 130, 25, 35 and/or 45 of FIG. 2. In some embodiments, one of functional assembly 130a or 130b comprises an expandable element, such as an expandable element selected from the group consisting of: an inflatable balloon (e.g. inflatable balloon 136 described herein); a radially expandable cage or stent; one or more radially deployable arms; an expandable helix; an unfurlable compacted coiled structure; an unfurlable sheet; an unfoldable compacted structure; and combinations of one or more of these. In these embodiments, relative translation of functional assemblies 130a and 130b can be used to manipulate tissue, such as to place an axial segment of intestinal tissue in tension.

Shaft 110a and/or shaft 110b can be operably attached to one or more translational controls or mechanical linkage assemblies (e.g. on a proximal handle such as handle 102 of FIG. 1 or FIG. 2 or a mechanical linkage assembly of console 200), such as to telescopically translate shaft 110a relative to shaft 110b. This translation will accordingly change the distance between functional assembly 130a and functional assembly 130b.

Each of functional assemblies 130a and 130b can be configured to be radially expanded (each shown in FIG. 24 in an expanded state), such as via the delivery of one or more fluids into functional assemblies 130a and 130b, such as via one or more fluidly attached conduits 111, not shown but configured to deliver and withdraw inflation fluids, as described herein. Functional assembly 130a and/or 130b can comprise one or more functional elements 139 configured to perform a medical procedure, such as to deliver energy and/or fluid to tissue in a therapeutic medical procedure, as described herein.

In some embodiments, functional assembly 130a and/or 130b is constructed and arranged to expand tissue, such as when the functional assembly 130 comprises one or more fluid delivery elements (e.g. fluid delivery element 139c of FIG. 1) and optionally a tissue-engaging port (e.g. port 137 of FIG. 1) surrounding each fluid delivery element 139c as described herein. In these embodiments, functional assembly 130a can be constructed and arranged as described hereabove in reference to functional assembly 130 of FIG. 1 or functional assembly 25 of FIG. 2. Alternatively or additionally, functional assembly 130a and/or 130b can be constructed and arranged to deliver energy to tissue, such as when the functional assembly 130 is configured to receive ablative fluid or to deliver RF, light energy, sound energy and/or other energy to tissue. In some embodiments, one of functional assembly 130a or 130b is configured to perform a tissue expansion step and the other functional assembly 130 is configured to perform a tissue ablation step. In other embodiments, a first functional assembly 130 comprising functional assembly 130a or 130b is configured to perform a tissue expansion and/or ablation step and a second functional assembly 130 comprising the other functional assembly is configured to provide an anchoring function, such as to stabilize the first functional assembly 130.

In some embodiments, catheter 100 comprises one or more sensors, such as functional elements 119, 139a (of functional assembly 130a) and/or 139b (of functional assembly 130b), that have been configured as a sensor. In some embodiments, catheter 100 of FIG. 24 and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts.

Referring now to FIGS. 25A-C, anatomical, side sectional views of the distal portion of a multiple expandable assembly catheter in a series of steps are illustrated, consistent with the present inventive concepts. Catheter 100 comprises shaft 110 and other components, such as one or more components of similar construction and arrangement to those described hereabove in reference to catheter 100 of FIG. 1 or FIG. 2, such as one or more conduits 111 which have been removed for illustrative clarity. Catheter 100 can comprise bulbous tip 115 on its distal end. Catheter 100 comprises a functional assembly 130, positioned on a distal portion of catheter 100 (e.g. positioned on a distal portion of shaft 110), and comprising multiple expandable functional assemblies, such as two or more functional assemblies, such as the six functional assemblies 130a, 130b, 130c, 130d, 130e and 130f shown (singly or collectively functional assembly 130). Each functional assembly 130 can be configured to radially expand and contract, such as a functional assembly comprising an expandable element, such as an element selected from the group consisting of: an inflatable balloon (e.g. inflatable balloon 136 as described herein); a radially expandable cage or stent; one or more radially deployable arms; an expandable helix; an unfurlable compacted coiled structure; an unfurlable sheet; an unfoldable compacted structure; and combinations of one or more of these. In some embodiments, a first functional assembly 130 comprises a first type of expandable element such as a balloon configured to be filled with fluid, and a second functional assembly 130 comprises a different type of expandable element, such as an expandable cage or stent. In some embodiments, each functional assembly 130 is operably attached to a different conduit 111, not shown but configured to allow independent radial expansion and contraction of each functional assembly 130 (e.g. individual conduits 111 comprising individual inflation lumens and/or individual expansion control rods). Alternatively or additionally, two or more functional assemblies 130 can be operably attached to a single conduit 111, such as two or more functional assemblies 130 comprising a balloon connected to a single inflation lumen configured to expand (e.g. inflate) and/or compact (e.g. deflate) the two or more functional assemblies 130 relatively simultaneously or at least in a manner dependent on the other.

Each functional assembly 130 can comprise a functional element 139, such as a functional element comprising one or more of: a sensor; a transducer; a tissue treatment element; a fluid delivery element such as a needle; and combinations of one or more of these.

In some embodiments, one or more functional assemblies 130 is configured to treat and/or diagnose tissue, such as a functional assembly 130 configured to expand tissue and/or ablate tissue. In these embodiments, one or more different functional assemblies 130 can be configured to provide an anchoring force configured to prevent unintended translation of the distal portion of catheter 100. For example, a series of functional assemblies 130 can comprise alternating tissue treatment functional assemblies 130 and/or tissue diagnosis functional assemblies 130 and anchoring functional assemblies 130.

One or more of functional assemblies 130*a-f* can be configured to treat and/or diagnose tissue simultaneously or sequentially. As shown in FIG. 25A, all functional assemblies 130*a-f* can be in an expanded state simultaneously (e.g. via a simultaneous or non-simultaneous expansion). Each functional assembly 130 can be configured to ablate or expand tissue simultaneously with one or more other functional assemblies 130. In some embodiments, a first set of functional assemblies 130 can be configured to receive ablative fluid to ablate tissue (e.g. a hot fluid), and a different set of functional assemblies 130 (e.g. positioned in between the ablating functional elements in an alternating pattern) configured to receive a neutralizing fluid (e.g. a cooling fluid) to limit or otherwise control the amount of tissue ablated by the ablating functional assemblies 130.

In some embodiments, one set of functional assemblies (e.g. functional assemblies 130*a*, 130*c* and 130*e* as shown) are expanded, and a second set of functional assemblies (e.g. functional assemblies 130*b*, 130*d* and 130*f*) are unexpanded or partially expanded (as shown). Any combination of functional assemblies 130 can be operated in fully expanded, partially expanded or contracted states, in any configuration, such as is shown in FIG. 25C in which a series of three bordering functional assemblies, 130*a*, 130*b* and 130*c*, are expanded, and a series of three bordering functional assemblies, 130*d*, 130*e* and 130*f* are partially expanded.

In some embodiments, a first set of one or more functional assemblies 130 are expanded to anchor the distal portion of catheter 100, while a second set of one or more functional assemblies 130 remain partially expanded or contracted. In these embodiments, the expanded set of functional assemblies 130 can be configured to perform a medical procedure such as a tissue expansion and/or ablation procedure. Alternatively, the set of unexpanded functional assemblies 130 can be expanded (e.g. to contact the intestinal wall), and one or more functional assemblies 130 of either set used to perform the medical procedure.

Figure 26:
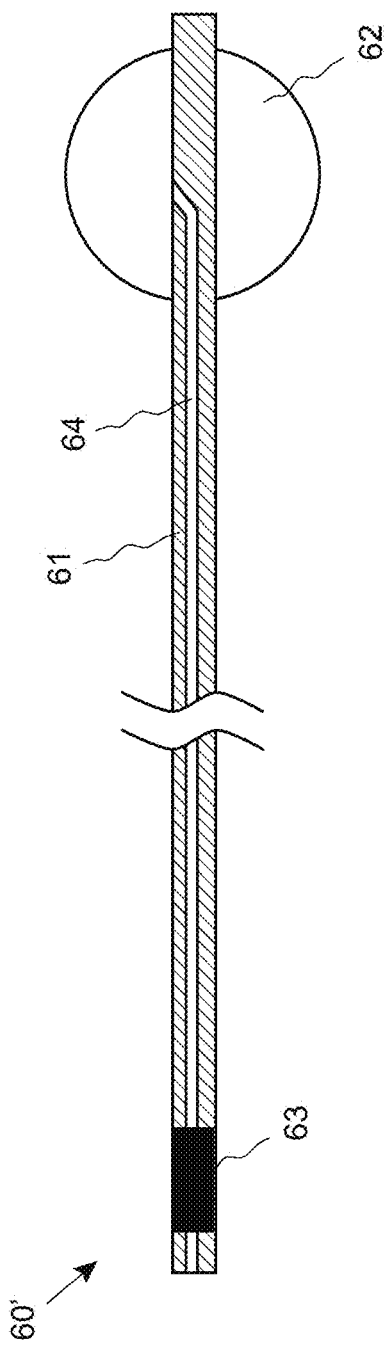
FIG. 26 is a side sectional view of an anchorable guidewire, consistent with the present inventive concepts.

Referring now to FIG. 26, a side sectional view of an anchorable guidewire is illustrated, consistent with the present inventive concepts. Guidewire 60' comprises shaft 61 and expandable element 62 positioned on the distal end or a distal portion of shaft 61. Expandable element 62 is constructed and arranged to frictionally engage the inner walls of a segment of the intestine, such as to provide an anchoring force when one or more devices, such as the catheter of the present inventive concepts (e.g. catheter 100 of FIG. 1 or catheters 100, 20, 30 and/or 40 of FIG. 2) is advanced over guidewire 60'. In some embodiments, expandable element 62 is configured to expand to a diameter between 1.0 cm and 10.0 cm. Expandable element 62 can comprise an expandable element selected from the group consisting of: an inflatable balloon; a radially expandable cage or stent; one or more radially deployable arms; an expandable helix; an unfurlable compacted coiled structure; an unfurlable sheet; an unfoldable compacted structure; and combinations of one or more of these. Shaft 61 and expandable element 62 (in its radially compacted state) comprise a diameter configured to be slidingly received by one or more guidewire lumens, such as lumen 116 of catheter 100 described hereabove in reference to FIG. 1.

Guidewire 60' comprises an assembly configured to expand and contract expandable element 62, such as valve assembly 63. Valve assembly 63 comprises a diameter configured to be slidingly received by one or more guidewire lumens, such as lumen 116 of catheter 100 described hereabove in reference to FIG. 1. In some embodiments, valve assembly 63 is positioned within the walls of shaft 61 or valve assembly 63 comprises a similar diameter to shaft 61, such as to allow guidewire 60' to pass through an appropriate lumen of a device without excessive translation force being required. In some embodiments, valve assembly 63 is of similar construction and arrangement to that described in U.S. Pat. No. 6,325,777.

In some embodiments, expandable element 62 comprises an inflatable structure, such as an inflatable balloon (e.g. a compliant balloon or a non-compliant balloon) which is fluidly attached to valve assembly 63 by lumen 64 which travels between expandable element 62 and the proximal end of shaft 61. Valve assembly 63 is configured to allow a fluid such as a gas (e.g. air) or a liquid (e.g. saline) to be introduced into expandable element 62 via valve assembly 63 and lumen 64. Valve assembly 63 can be further configured to maintain expandable element 62 in an inflated state (inflated state shown in FIG. 26).

Figure 26A:
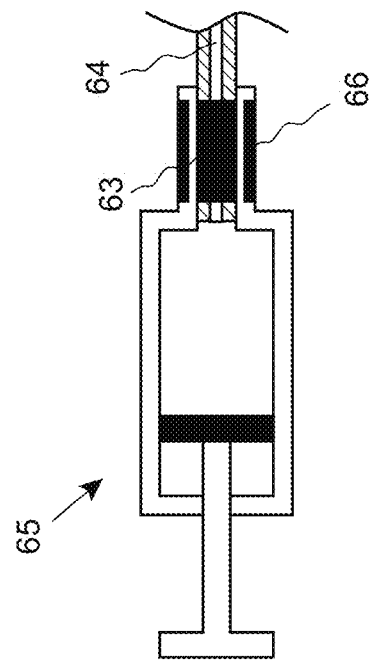
FIG. 26A is a side sectional view of the proximal portion of a guidewire, with an expansion tool attached about the valve assembly, consistent with the present inventive concepts.

Referring additionally to FIG. 26A, a side sectional view of the proximal portion of guidewire 60' is illustrated, with expansion tool 65 attached about valve assembly 63, consistent with the present inventive concepts. Expansion tool 65 is configured to slidingly engage valve assembly 63, and to cause expandable element 62 to expand (e.g. to expand to frictionally engage an inner wall portion of the intestine) and/or to contract (e.g. to disengage from an inner wall portion of the intestine). In some embodiments, expansion tool 65 comprises a mechanism activation element, such as coil 66 which can be attached to electrical power (not shown but such as a battery of expansion tool 65) to create a magnetic field which opens a magnetically activated valve assembly 63, such that fluid can be delivered into and/or extracted from expansion element 62. When tool 65 is removed from guidewire 60' (i.e. moved away from valve assembly 63), valve assembly 63 can close, maintaining expandable element 62 in the expanded or compacted state it was in prior to the removal of tool 65.

Referring now to FIG. 27, a medical device shaft comprising a tapered profile is illustrated, consistent with the present inventive concepts. Shaft 110' comprises a tapered outer wall whose wall thickness decreases along its length, such as to be more flexible as it approaches its distal end (e.g. to the right of the page). One or more conduits 111 of the present inventive concepts are positioned in, on and/or within shaft 110' (three shown in FIG. 27). Alternatively or additionally, shaft 110' can comprise multiple materials whose combination within an inner and/or outer wall changes along its length, such as to create a variable stiffness along its length, such as to be more flexible on a distal portion. Shaft 110' can comprise a stiffness that changes relatively continuously, or in one or more discrete steps. Shaft 110' can comprise a stiffness that changes along the majority of its length, or along one or more discrete portions (e.g. at a distal portion or at a mid-portion).

Shaft 110' can comprise one or more functional elements 119, such as a functional element 119 described hereabove in reference to FIG. 1 that has been configured as a sensor. These one or more sensors can be configured to provide a signal, such as a signal used to adjust one or more console 200 settings (e.g. console settings 201) of the present inventive concepts.

Referring now to FIG. 28, a medical device shaft comprising a varied pitch braid is illustrated, consistent with the present inventive concepts. Shaft 110" comprises a braided shaft, including braid filament 117 within its outer wall. One or more conduits 111 of the present inventive concepts are positioned in, on and/or within shaft 110" (three shown in FIG. 28). Braid filament 117 can comprise a metal filament (e.g. stainless steel filament) or a non-metal filament, (e.g. a plastic filament). Shaft 110" can comprise a braid whose pitch varies along its length, such that the stiffness of shaft 110" changes along its length, such as to become more flexible towards its distal end by decreasing the pitch (i.e. less turns per length) of braid filament 117, as shown in FIG. 28. Alternatively or additionally, one or more parameters of braid filament 117 can be varied along the length of shaft 110", such as its material, diameter or other parameter that would influence the stiffness imparted by braid filament 117 upon shaft 110". Shaft 110" can comprise a stiffness that changes relatively continuously, or in one or more discrete steps. Shaft 110" can comprise a stiffness that changes along the majority of its length, or along one or more discrete portions (e.g. at a distal portion or at a mid-portion).

Shaft 110" can comprise one or more functional elements 119, such as a functional element 119 described hereabove in reference to FIG. 1 that has been configured as a sensor. These one or more sensors can be configured to provide a signal, such as a signal used to adjust one or more console 200 settings (e.g. console settings 201) of the present inventive concepts.

Referring now to FIGS. 29A-D, a camera view of a series of steps for expanding tissue and treating target tissue at a single axial segment of intestine are illustrated, consistent with the present inventive concepts. A distal portion of catheter 100 is being viewed by a camera device (e.g. configured as a sensor of the present inventive concepts), such as an endoscopic camera such as a camera of endoscope 50a described hereabove in reference to FIGS. 1, 2 and 19, and/or camera 52 of FIG. 19. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111 which have been removed for illustrative clarity. Functional assembly 130 can comprise an expandable element, such as balloon 136 shown. Functional assembly 130 of catheter 100 has been introduced into the intestine, such as by being inserted via one or more of: through a working channel of an endoscope (e.g. the endoscope producing the camera view); over a guidewire; inserted alongside an endoscope (e.g. over a guidewire); through a sheath attached to or independent of an endoscope (e.g. over a guidewire); through a laparoscopic port (e.g. over a guidewire); and/or through any body introduction device.

Functional assembly 130 comprises a distal wall (e.g. distal wall 132 shown in the camera view), and a proximal wall (e.g. proximal wall 131 described hereabove in reference to FIGS. 6A, 6B and 18), and a side-wall portion therebetween. Functional assembly 130 of catheter 100 has been inserted into an axial segment of the intestine, and inflated such that a tissue-contacting portion of balloon 136 is in substantial contact with the inner wall of the axial segment of the intestine (i.e. all portions of functional assembly 130 shown in the camera view of FIGS. 29A-D except for distal wall 132). The image provided by the camera is looking through at least a portion of the proximal wall of functional assembly 130 (e.g. an endoscope or other camera device has been advanced to a location relatively proximate the proximal wall of functional assembly 130). At least the proximal wall of functional assembly 130 is constructed of materials to be transparent, or at least relatively transparent (hereinafter "transparent") to the camera view, such as a clear material transparent with respect to the camera being used (e.g. transparent to visible light used by a visible light camera, transparent to infrared light used by an infrared camera, transparent to ultrasound waves as used by an ultrasound imager and/or transparent to radiation used by a radiation-based camera). At least one or more portions of the tissue-contacting surfaces (e.g. portions of the side-wall) of functional assembly 130 can also be transparent to the camera view, such as is shown in FIG. 29D, such as to view the tissue in contact with functional assembly 130 during a therapeutic or diagnostic procedure. In some embodiments, at least a portion of the distal wall is transparent. For example, system 10 can be configured to detect a change of the tissue (e.g. a color change) and/or a change to a material delivered into the tissue, such as injectate 221 described herein, and to adjust one or more console settings 201 based on the color change or other image information (e.g. a console setting related to an injectate delivery parameter during tissue expansion and/or an energy delivery parameter during tissue ablation).

In some embodiments, functional assembly 130 is configured to both expand tissue and ablate tissue, such that a single functional assembly 130 can be positioned, anchored, and complete the tissue expansion steps described herebelow in reference to FIGS. 29A-B, and subsequently (while remaining anchored in the same axial location of intestine) complete the tissue ablation steps described herebelow in reference to FIGS. 29C-D. Functional assembly 130 can be anchored throughout the tissue expansion and tissue treatment steps by maintaining sufficient force against the lumen wall, such as by sufficient expansion of functional assembly 130 and/or by other anchoring means as described herein.

In other embodiments, a first functional assembly 130 is configured to expand tissue, and a second functional assembly 130 is configured to treat tissue. In these embodiments, the first functional assembly is positioned, anchored, and used to complete the tissue expansion steps described herebelow in reference to FIGS. 29A-B. Subsequently, the first functional assembly 130 is moved away from the axial segment, and a second functional assembly 130 (e.g. positioned on the same catheter 100 or a second catheter 100) is positioned in the same axial segment, anchored, and used to complete the tissue ablation steps described herebelow in reference to FIGS. 29C-D.

In FIG. 29A, a tissue expansion step has been initiated, such as a tissue expansion step in which one or more needles or other fluid delivery elements (e.g. three equally spaced fluid delivery elements 139c of FIG. 1) are delivering fluid into tissue (e.g. submucosal tissue of the intestine). As shown in FIG. 29A, certain areas of tissue have been expanded, areas of tissue $T_{EXP}$, while other areas in contact with the tissue-contacting portions (e.g. sidewalls) of functional assembly 130, $T_{NOT\,EXP}$ are unexpanded (e.g. yet to be expanded). In some embodiments, the visual feedback of the camera view of FIG. 29A is provided to an operator (e.g. via a display of console 200 or endoscope 50a described hereabove in reference to FIG. 1), such that the operator can continue fluid delivery until all desired tissue is expanded. Alternatively or additionally, system 10 can be configured to assess completeness of tissue expansion, such as to continue or otherwise adjust fluid delivery (e.g. automatically), and/or notify the operator of a desire to continue fluid delivery, based on the visual feedback. In some embodiments, the fluid delivered (e.g. injectate 221 of FIG. 1) comprises visualizable material configured to be visualized, to enhance visualization of expanded tissue and/or to identify an adverse situation such as delivered fluid leaking into the intestinal lumen (e.g. versus a submucosal layer of tissue).

In FIG. 29B, relatively all of the tissue desired to be expanded by functional assembly 130 has been expanded. In some embodiments, sufficient expansion of tissue is visually confirmed (e.g. an operator manually confirms that all, a majority, or any sufficient amount of the tissue in contact with functional assembly 130 and potentially beyond functional assembly 130 has been expanded). This confirmation can be performed prior to performing a subsequent step, such as an ablation step. In some embodiments, system 10 is configured to confirm sufficient tissue expansion has been completed (e.g. automatically or semi-automatically), such as via an image analysis algorithm, such as algorithm 251 of controller 250 described hereabove in reference to FIG. 1. In some embodiments, visualizable or other material of injectate 221 is detected by the camera device or one or more other sensors of system 10, and algorithm 251 correlates the amount and/or location of the detected material to a level of tissue expansion.

In FIG. 29C, a target tissue ablation step has been subsequently initiated, such as a target tissue ablation step in which energy is delivered to tissue (e.g. via ablative fluid being introduced into functional assembly 130 and/or by delivery of RF of other energy into tissue by functional assembly 130). In some embodiments, the target tissue treated comprises mucosal tissue of the duodenum or other intestinal mucosal tissue, such as to treat diabetes, hypercholesterolemia, and/or another patient disease or disorder. As shown in FIG. 29C, certain areas of tissue have been treated, areas of tissue $T_{TRTD}$, while other areas in contact with the tissue-contacting portions (e.g. sidewalls) of functional assembly 130 are simply expanded ($T_{EXP}$ shown in FIG. 29C). In some embodiments, system 10 is configured to provide visual feedback of the camera view of FIG. 29C to an operator (e.g. via a display of console 200 or endoscope 50a described hereabove in reference to FIG. 1), such that the operator can continue tissue ablation until all desired tissue is treated. Alternatively or additionally, system 10 can be configured to assess completeness of tissue ablation and to adjust tissue ablation console setting (e.g. automatically), based on the visual feedback. In some embodiments, ablated tissue is identified by a color change that occurs during ablation. Alternatively or additionally, system 10 can be configured to further differentiate ablated tissue, such as by detecting a color or other change to injectate 221 delivered in the tissue expansion steps.

In FIG. 29D, relatively all of the tissue desired to be ablated by functional assembly 130 has been treated. In some embodiments, sufficient treatment of tissue is visually confirmed (e.g. an operator manually confirms that all, a majority, or any sufficient amount of the tissue in contact with functional assembly 130 has been ablated or otherwise treated). This confirmation is performed prior to removing functional assembly 130 and/or repositioning functional assembly 130 at a different axial segment (e.g. when a medical procedure comprises ablating multiple axial segments, as described herein). In some embodiments, system 10 is configured to confirm sufficient tissue ablation or other treatment has been completed (e.g. automatically or semi-automatically), such as via an image analysis algorithm, such as algorithm 251 of controller 250 described hereabove in reference to FIG. 1. In some embodiments, visualizable changes or other changes to injectate 221 within tissue is detected by the camera device or one or more other sensors of system 10, and algorithm 251 correlates the amount and/or location of the changed injectate 221 to a level of tissue ablation.

Referring now to FIGS. 30A-B, side sectional views of a distal portion of a catheter comprising a tissue-engaging fluid delivery element are illustrated, consistent with the present inventive concepts. Catheter 100 comprises shaft 110, functional assembly 130 (shown in its expanded state), and other components, such as one or more components of similar construction and arrangement to those described hereabove in reference to catheter 100 of FIG. 1 or FIG. 2, such as one or more conduits 111, some of which have been removed for illustrative clarity (three conduits 111 shown in FIGS. 30A-B). Catheter 100 can comprise bulbous tip 115 on its distal end. Shaft 110 of FIGS. 30A-B comprises at least shafts 110a, 110b and 110d shown. Shaft 110 can comprise additional shafts, such as a shaft 110c not shown but constructed and arranged such that shafts 110a, 110b and 110c are separated by approximately 120°. Functional assembly 130 can comprise an inflatable balloon, balloon 136, such as a balloon configured to expand upon receiving inflation fluid via a lumen or tube such as conduit 111d positioned within shaft 110d. Shafts 110a and 110b each comprise a conduit 111a and 111b, respectively, such as translatable hollow tubes configured to advance and retract and allow delivery and/or extraction of fluid (e.g. simultaneously or sequentially). Functional assembly 130 comprises one or more guiding elements 137' that are positioned on a tissue-contacting portion of functional assembly 130, such as three ports 137 distributed 120° apart along a circumference of balloon 136 (two shown in FIGS. 30A-B).

Each guiding element 137' comprises a channel configured to slidingly receive a fluid delivery element 139c' and guide the associated fluid delivery element 139c' into tissue at a particular trajectory. Each guiding element 137' is attached to a translatable conduit (e.g. conduits 111a and 111b shown), which is configured to provide fluid to each fluid delivery element 139c' (e.g. injectate 221 as described hereabove in reference to FIG. 1), as well as advance and retract fluid delivery element 139c' in and out of guiding element 137', as has been described herein. Each fluid delivery element 139c' can be configured to deliver fluid to expand tissue (e.g. submucosal tissue of the duodenum or other intestinal submucosa).

Fluid delivery element 139c' can comprise a tissue-engaging geometry, such as the spiraled (e.g. cork-screw) geometry shown in FIG. 30B. For example, fluid delivery element 139c' can be resiliently biased in a cork-screw, helical, zig-zag or other tissue-engaging geometry that can be straightened, for example when constrained within a channel of guiding element 137' as shown in FIG. 30A, and transition to a non-linear, tissue-engaging geometry when unconstrained, for example when exiting guiding element 137'. The tissue-engaging geometry shown in FIG. 30B can be used to provide a tissue retention force when fluid delivery element 139c' is positioned into tissue, such as to prevent undesired or unintended movement of fluid delivery element 139c' during fluid delivery and/or between fluid delivery steps. The tissue-engaging geometry shown in FIG. 30B can avoid a separate tissue retention element, such as vacuum-assisted port such as a vacuum-assisted port 137 described hereabove in reference to FIG. 1.

In some embodiments, catheter 100 of FIGS. 30A-B and/or a component attached to catheter 100 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein, as described herein.

Referring now to FIG. 31, a medical device shaft comprising one or more insulating elements is illustrated, consistent with the present inventive concepts. Shaft 110''' comprises at least one insulating element, such as the two insulating elements 152 shown. One or more conduits 111 of the present inventive concepts are positioned in, on and/or within shaft 110'''. Each insulating element 152 can comprise an element configured to insulate one or more internal portions of shaft 110''' from the outer surface of shaft 110'''. In some embodiments, one or more conduits 111 can include fluid at an ablative temperature, and one or more insulating elements 152 comprise a thermally insulating layer of shaft 110''' configured to prevent the outer wall of shaft 110''' from undesirably damaging intestinal wall tissue and/or a separate device in contact with and/or otherwise in proximity to the outer surface of shaft 110'''. In some embodiments, one or more insulating elements 152 comprise one or more materials that have low thermal conductivity, such as a material with a lower thermal conductivity than the outer wall of shaft 110''' and/or lower than the thermal conductivity of an outer wall of a conduit 111. In some embodiments, one or more insulating elements 152 comprise a thermos construction including a reflective surface and a gap (e.g. air gap) configured to provide insulation. In some embodiments, two or more insulating elements 152 transport a recirculating fluid configured to prevent the outer surface of shaft 110''' from reaching an undesired temperature.

Shaft 110''' can comprise one or more functional elements 119, such as a functional element 119 described hereabove in reference to FIG. 1 that has been configured as a sensor. These one or more sensors can be configured to provide a signal, such as a signal used to adjust one or more console 200 settings (e.g. console settings 201) of the present inventive concepts.

Referring now to FIG. 32, an end sectional view of a system comprising a catheter with a non-circular cross section and a body introduction device with a circular cross section is illustrated, consistent with the present inventive concepts. System 10 comprises catheter 100 and a body introduction device 50, such as endoscope 50a described herein. Body introduction device 50 can comprise one or more working channels, such as lumens 51 and 54 shown, and/or it can include an imaging device, such as camera 52 shown. System 10 can comprise one or more other components, such as console 200 and other components not shown, but similar to those described hereabove in reference to system 10 of FIG. 1 or system 10 of FIG. 2. Catheter 100 comprises functional assembly 130 (not shown), and other components, such as one or more components of similar construction and arrangement to those described hereabove in reference to catheter 100 of FIG. 1 or FIG. 2, such as one or more conduits 111, some of which have been removed for illustrative clarity (three conduits 111 shown in FIG. 32). Catheter 100 can comprise bulbous tip 115 on its distal end.

Catheter 100 comprises shaft 110'''', which comprises an oval, kidney-shape or other non-circular cross sectional geometry (e.g. the kidney-shaped geometry shown in FIG. 32) configured to partially surround body introduction device 50, such that when shaft 110'''' is nested against body introduction device 50, the cumulative periphery defined by both shaft 110'''' and body introduction device 50 can be inserted into a tube (e.g. an intestinal or other GI lumen) with a smaller diameter than would be possible with a circular geometry shaft of catheter 100 of the same cross sectional area as shaft 110''''.

In some embodiments, system 10 of FIG. 32 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139a, 139b and/or 139c described hereabove in reference to FIG. 1, such as a functional element constructed and arranged to perform a therapeutic and/or diagnostic medical procedure, as described herein.

Referring now to FIG. 33, an end sectional view of a system comprising a catheter with a functional assembly comprising a non-circular unexpanded cross section and a body introduction device with a circular cross section is illustrated, consistent with the present inventive concepts. System 10 comprises catheter 100 and a body introduction device 50, such as endoscope 50a described herein. Body introduction device 50 can comprise one or more working channels, such as lumens 51 and 54 shown, and/or it can include an imaging device, such as camera 52 shown. System 10 can comprise one or more other components, such as console 200 and other components not shown, but similar to those described hereabove in reference to system 10 of FIG. 1 or system 10 of FIG. 2. Catheter 100 can comprise one or more components of similar construction and arrangement to those described hereabove in reference to catheter 100 of FIG. 1 or FIG. 2, such as one or more conduits 111, some of which have been removed for illustrative clarity (three conduits 111 shown in FIG. 33). Catheter 100 can comprise bulbous tip 115 on its distal end.

Catheter 100 comprises shaft 110, upon which functional assembly 130' is mounted (e.g. on a distal portion of shaft 110). When radially collapsed, functional assembly 130' comprises an oval, kidney-shape or other non-circular cross sectional geometry (e.g. the kidney-shaped geometry shown in FIG. 33) configured to partially surround body introduction device 50, such that when shaft 110 and a radially collapsed functional assembly 130' are nested against body introduction device 50. The cumulative periphery defined by radially collapsed functional assembly 130', shaft 110 and body introduction device 50 can be inserted into a tube (e.g. an intestinal or other GI lumen) with a smaller diameter than would be possible with a radially compacted functional assembly 130 with a circular geometry and the same cross sectional area as functional assembly 130'.

In some embodiments, system 10 of FIG. 33 comprises one or more sensors, such as one or more functional elements 109, 119, 139, 209, 229 and/or 309 described hereabove in reference to FIG. 1, that have been configured as a sensor. These one or more sensors can be configured to provide a signal, such as a signal used to adjust one or more console 200 settings (e.g. console settings 201) of the present inventive concepts. In some embodiments, functional assembly 130 comprises one or more functional elements, such as functional element 139*a*, 139*b* and/or 139*c* described hereabove in reference to FIG. 1, such as a functional element constructed and arranged to perform a therapeutic and/or diagnostic medical procedure, as described herein.

Referring now to FIG. 34, a method of performing a medical procedure including gathering sensor information is illustrated, consistent with the present inventive concepts. The method of FIG. 34 will be described using the devices and components of system 10 and one or more catheters 100 described hereabove in reference to one or more of FIGS. 1-25. In Step 3410, the distal portion of a catheter 100, including a functional assembly 130, is inserted into the intestine of a patient, such as an insertion through a body introduction device 50, such as an endoscope or sheath, or an insertion alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

In Step 3420, functional assembly 130 is positioned at an axial segment of the intestine. Sensor information can be gathered and the intestinal location selected to position functional assembly 130 can be based on the sensor information. Sensor information can be gathered by one or more sensors of system 10, such as one or more functional elements 109, 119, 139, 209, 229 and/or 309 described hereabove that have been configured as a sensor.

In Step 3430, functional assembly 130 is activated and/or adjusted. Sensor information can be gathered, and functional assembly 130 can be activated and/or adjusted based on the gathered sensor information. Sensor information can be gathered by one or more sensors of system 10, such as one or more functional elements 109, 119, 139, 209, 229 and/or 309 described hereabove that have been configured as a sensor. In some embodiments, catheter 100 is activated and/or adjusted based on the sensor information. In some embodiments, activation of functional assembly 130 comprises initiation of a function selected from the group consisting of: delivering fluid to tissue (e.g. delivering injectate 221 to submucosal tissue or other tissue); delivering energy to tissue (e.g. delivering thermal energy to tissue from an ablative fluid or delivering electromagnetic energy such as RF energy to tissue) to treat target tissue; cooling and/or warming tissue (e.g. cooling and/or warming performed prior to and/or after a heat ablation or cryogenic ablation, respectively); performing a therapeutic procedure on tissue; performing a diagnostic procedure on tissue; and combinations of one or more of these. After initial activation, adjustment of functional assembly 130 can comprise a modification selected from the group consisting of: adjustment of fluid delivery to tissue (e.g. adjustment of fluid delivery rate from fluid delivery element 139*c* or adjustment of pressure within functional assembly 130); adjustment of energy delivery to tissue (adjustment of temperature of ablative fluid within functional assembly 130, adjustment of flow rate of fluid being delivered to and/or extracted from functional assembly 130, adjustment of pressure within functional assembly 130, and/or adjustment of contact of functional assembly 130 with tissue); adjustment of a therapeutic procedure parameter; adjustment of a diagnostic procedure parameter; adjustment of fluid withdrawn from functional assembly 130; and combinations of one or more of these.

In Step 3440, a check of procedure completeness is performed, either manually by an operator of system 10 and/or automatically or semi-automatically by system 10 (e.g. via algorithm 251 of console 200). If incomplete, Step 3420 can be performed again, such as to reposition functional assembly 130 in a different (e.g. second) axial segment, after which Step 3430 can be performed in the different axial segment. Alternatively, if the procedure is determined to be incomplete, Step 3430 can be repeated in the same axial segment (e.g. without the repositioning of Step 3420). If during Step 3440 it is determined the procedure is complete, Step 3450 can be performed in which catheter 100 is removed from the patient.

In some embodiments, Step 3430 comprises the performance of two medical steps, such as a first step involving tissue expansion and a second step involving tissue ablation. In these embodiments, the first and second steps can be performed by a single functional assembly 130, such as a functional assembly 130 configured to expand tissue (e.g. via a fluid delivery element 139*c*) and ablate tissue (e.g. via a functional element 139*a*). Alternatively, the first step can be performed by a first functional assembly 130 and the second step performed by a second functional assembly 130. The first and second functional assemblies can be included in a single catheter 100, or on separate catheters 100. In these two functional assembly 130 embodiments, STEP 3420 (positioning of functional assembly 130) can be repeated for each functional assembly 130. Each functional assembly 130 and catheter 100 can comprise one or more sensors configured to provide a signal to perform the positioning of Step 3420 and/or the activation and/or adjustment of Step 3430.

In some embodiments, Steps 3420 and 3430 are repeated two or more times, such as to treat a cumulative axial length of intestinal tissue of at least 6 cm, such as at least 9 cm, such as when performing a duodenal mucosal ablation procedure of the present inventive concepts to treat diabetes. In these embodiments, functional assembly 130 can be constructed and arranged to treat a near full circumferential (e.g. between 320° and 360°) axial segment of mucosal tissue in each ablation step. In these embodiments, each ablation step can be preceded by a tissue expansion step (e.g. a submucosal tissue expansion step), such as to expand a near full circumferential (e.g. between 320° and 360°) axial segment of submucosal tissue, such as to create a safety margin of tissue for the subsequent ablation step.

Figure 35:
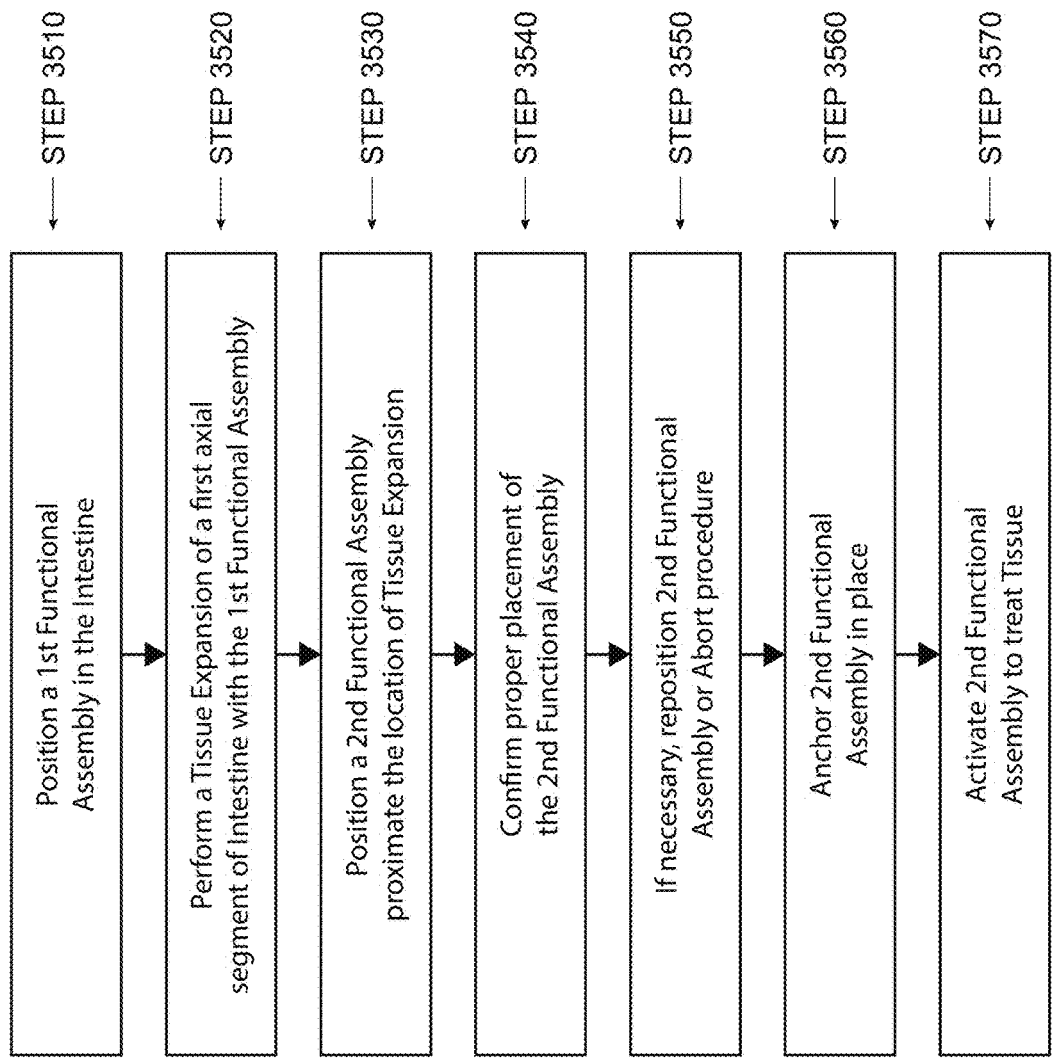
FIG. 35 is a flowchart of a method of performing a medical procedure including performing a tissue expansion with a functional assembly, and treating target tissue with the same or a different functional assembly, consistent with the present inventive concepts.

Referring now to FIG. 35, a method of performing a medical procedure including performing a tissue expansion with a functional assembly, and treating target tissue with the same or a different functional assembly is illustrated, consistent with the present inventive concepts. The method of FIG. 35 will be described using the devices and components of system 10 and one or more catheters 100 described hereabove in reference to one or more of FIGS. 1-25. In Step 3510, the distal portion of a catheter 100, including a functional assembly 130, is inserted into the intestine of a patient, such as an insertion through a body introduction device 50, such as an endoscope or sheath, or an insertion alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

In Step 3520, a first functional assembly 130 is positioned in the intestine (e.g. in the duodenum), and one or more layers of a first axial segment of intestinal tissue (e.g. submucosal tissue) is expanded. Tissue expansion can comprise expansion of a near full circumferential (e.g. between 320° and 360°) layer of tissue, and can be accomplished by one or more fluid delivery elements 139*c* delivering injectate 221 supplied by console 200 into one or more tissue locations (e.g. 3 tissue locations simultaneously or sequentially without repositioning functional assembly 130).

In Step 3530, a second functional assembly 130 is positioned in a location similar to (e.g. within) the first axial segment of expanded tissue. The first and second functional assemblies 130 can be included on a single catheter 100 (e.g. in two different locations on shaft 110), or on two different catheters 100.

In Step 3540, a confirmation of proper placement can be performed (e.g. a visual examination that all sufficient tissue in contact with the second functional assembly 130 has been expanded). If improper placement is identified, the second functional assembly 130 can be repositioned in Step 3550 and/or the procedure can be aborted.

In Step 3560, the second functional assembly 130 is anchored in place, such as by expanding second functional assembly 130, and/or deploying one or more anchoring mechanisms as described herein.

In Step 3570, the second functional assembly 130 is activated to treat (e.g. ablate tissue) proximate second functional assembly 130. The anchoring previously performed ensures that the treatment is performed in an area of expanded tissue (e.g. expanded submucosal tissue), such as to create a safety margin of tissue in all locations receiving energy or other treatment from second functional assembly 130 during the entire treatment. For example, the anchoring performed prevents unknown or otherwise unintended translation of the second functional assembly 130 prior to and/or during the treatment of Step 3570. Anchoring of functional assembly 130 can be performed a single time or multiple times, and can be maintained during any or all of the Steps 3510 through 3570.

While the embodiment of FIG. 35 describes use of a first and second functional assembly 130, a single functional assembly 130 can be used as well. In a single functional assembly 130, the anchoring performed in Step 3560 can be performed during Step 3520 and/or during Step 3530, and maintained through Step 3570. The method of FIG. 35 can be included in any treatment and/or diagnostic procedure as described herein.

Figure 36:
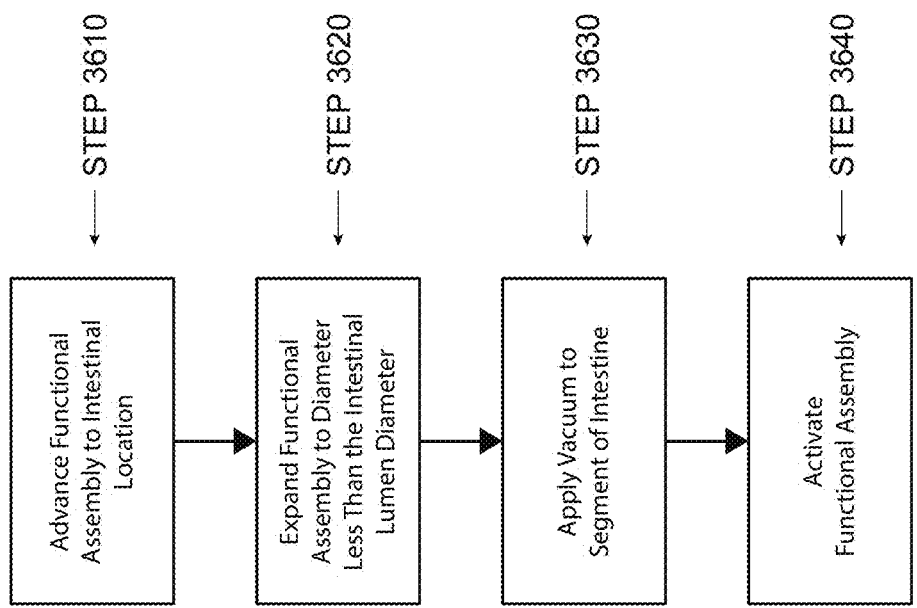
FIG. 36 is a flowchart of a method of performing a medical procedure including expanding a functional assembly to a non-contacting configuration, and subsequently collapsing the intestine around the functional assembly, consistent with the present inventive concepts.

Referring now to FIG. 36, a method of performing a medical procedure including expanding a functional assembly to a non-contacting configuration, and subsequently collapsing the intestine around the functional assembly is illustrated, consistent with the present inventive concepts. The method of FIG. 36 will be described using the devices and components of system 10 and one or more catheters 100 described hereabove in reference to one or more of FIGS. 1-25. In Step 3610, the distal portion of a catheter 100, including a functional assembly 130, is inserted into the intestine of a patient, such as an insertion through a body introduction device 50, such as an endoscope or sheath, or an insertion alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

In Step 3620, functional assembly 130 is expanded to a diameter such that there are gaps between the tissue contacting surface of functional assembly 130 and the intestinal wall (e.g. the effective diameter of functional assembly is less than the effective diameter of the lumen of the intestine at that location).

In Step 3630, the intestinal wall is caused to collapse around functional assembly 130, such as by applying a vacuum to a segment of the intestine (e.g. a segment just proximal and/or just distal to functional assembly 130), such as by using desufflation techniques described herein (e.g. via a port 112 or 137 of catheter 100 described hereabove, or via a working channel of an endoscope).

In Step 3640, functional assembly 130 is activated and/or adjusted, such as to perform a medical therapeutic and/or diagnostic procedure as described herein.

The method of FIG. 36 can be constructed and arranged such that a reduced number of sizes (e.g. diameters) of functional assemblies 130 can be provided by system 10 to an operator (e.g. a clinician), since sufficient contact is achieved between the intestinal wall and functional assembly 130 via desufflation versus expansion of functional assembly 130. In some embodiments, system 10 comprises a kit of one or more catheters 100, collectively comprising two or less different diameter functional assemblies 130, such as a single catheter 100 comprising a single diameter functional assembly 130. The method of FIG. 36 can be included in any treatment and/or diagnostic procedure as described herein.

Figure 37:
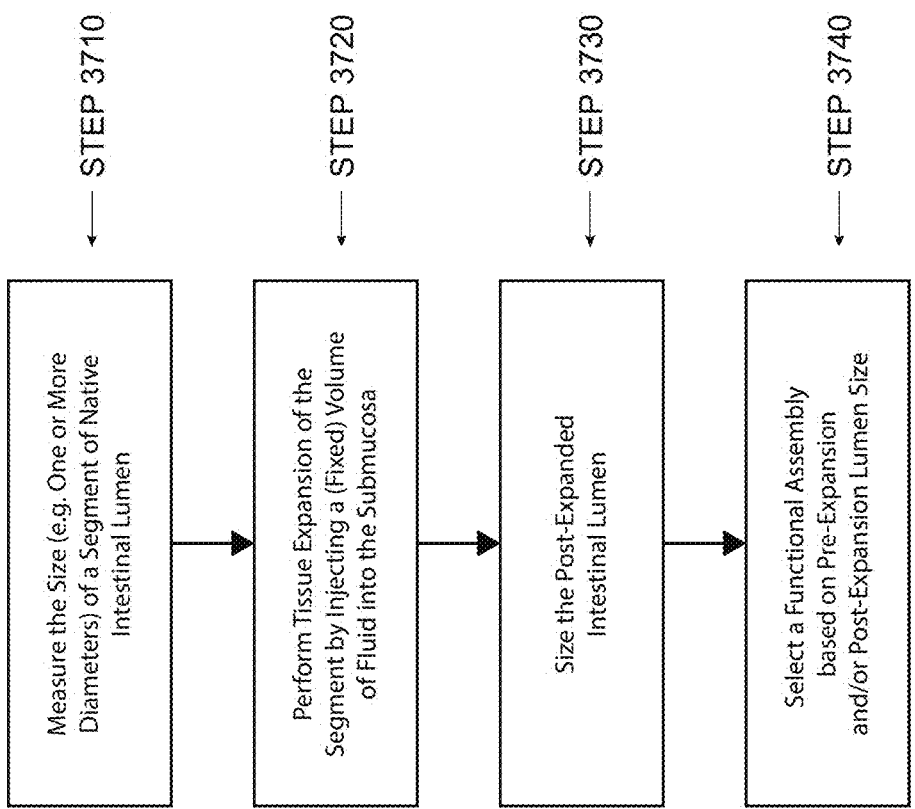
FIG. 37 is a flowchart of a method of performing a medical procedure including ablating tubular tissue proximate expanded tissue, including performing the ablation based on one or more pre-tissue-expansion diameters and/or one or more post-tissue-expansion diameters, consistent with the present inventive concepts.

Referring now to FIG. 37, a method of performing a medical procedure including ablating tubular tissue proximate expanded tissue is illustrated, including performing the ablation based on one or more pre-tissue-expansion diameters and/or one or more post-tissue-expansion diameters, consistent with the present inventive concepts. The method of FIG. 37 will be described using the devices and components of system 10 and one or more catheters 100 described hereabove in reference to one or more of FIGS. 1-25. In Step 3710, the distal portion of a catheter 100, including a functional assembly 130, is inserted into the intestine of a patient, such as an insertion through a body introduction device 50, such as an endoscope or sheath, or an insertion alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

Also in Step 3710, functional assembly 130 of catheter 100 is used to measure the size (e.g. one or more diameters) of a segment of intestine (e.g. an axial segment of the duodenum), such as is described herein.

In Step 3720, catheter 100 (or a second catheter 100 inserted after the catheter of Step 3710 is removed) is used to perform tissue expansion, such as a full or near-full circumferential expansion (as described herein) of the axial segment measured in Step 3710. The tissue expansion can comprise injection of a fixed volume of fluid into tissue (e.g. submucosal tissue to be expanded), such as via one or more functional elements 139 configured as needles or other fluid delivery elements configured to deliver injectate 221 into tissue.

In Step 3730, catheter 100 of Step 3710 and/or 3720 is used to measure the post-expansion size (e.g. one or more diameters) of the segment of intestine expanded in Step 3720.

In Step 3740, catheter 100 of Step 3710, 3720, 3730 and/or a different catheter is used to ablate tissue (e.g. mucosal tissue) of the segment of intestine expanded in Step 3720. In some embodiments, a catheter 100 is selected based on a pre-determined diameter of an expandable functional assembly 130, such as a functional assembly 130 comprising an expandable balloon 136. The selection of the diameter of the functional assembly 130 can be based on one or more of: the diameter(s) of the intestinal segment measured in Step 3710 (pre-expansion); the diameter(s) of the intestinal segment measured in Step 3730 (post-expansion); and/or both the diameter(s) measured in Step 3710 and the diameter(s) measured in Step 3730 (e.g. based on the difference in the two diameters). Alternatively or in addition to the selection of a functional assembly 130 diameter based on the above, volume of fluid delivered to functional assembly 130, pressure of fluid maintained within functional assembly 130 and/or another functional assembly 130 expansion parameter can be selected based on one or more of the measured luminal diameters. For example, a volume and/or pressure of ablative fluid introduced into functional assembly 130 can be selected based on one or more of the measured luminal diameters.

Steps 3710-3740 can be repeated, such as to treat multiple axial segments of intestinal tissue (e.g. multiple segments of the duodenum). The method of FIG. 37 can be included in any treatment and/or diagnostic procedure as described herein.

Figure 38:
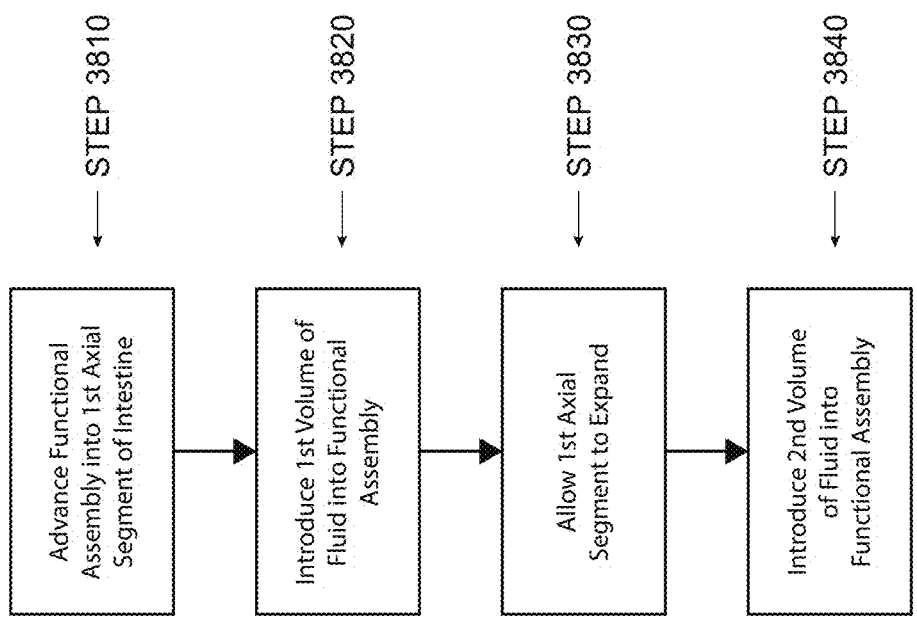
FIG. 38 is a flowchart of a method of expanding a functional assembly in two discrete steps, consistent with the present inventive concepts.

Referring now to FIG. 38, a method of expanding a functional assembly in two discrete steps is illustrated, consistent with the present inventive concepts. The method of FIG. 38 will be described using the devices and components of system 10 and one or more catheters 100 described hereabove in reference to one or more of FIGS. 1-25. Pressure, volume and/or other system parameters can be measured by one or more sensor-based functional elements of the present inventive concepts, such as those described hereabove. In Step 3810, the distal portion of a catheter 100, including a functional assembly 130, is inserted into the intestine of a patient such that functional assembly 130 is positioned at a first axial segment of the intestine. Catheter 100 can be inserted through a body introduction device 50, such as an endoscope or sheath, or inserted alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10 (e.g. via algorithm 251).

In Step 3820, a first volume of fluid is introduced into functional assembly 130. The first volume can be a pre-determined volume and/or mass of fluid, or it can be a volume which is determined based on a first threshold, such as a pressure or volume threshold, such as a threshold for the pressure generated within functional assembly 130 (e.g. a pressure measured within functional assembly 130, shaft 110, connecting assembly 300 and/or console 200 by a sensor-based functional element of the present inventive concepts). In some embodiments, the first threshold comprises a pressure threshold between 0.4 psi and 1.2 psi, such as between 0.6 psi and 1.0 psi.

In Step 3830, the axial segment of the intestine surrounding functional assembly 130 is allowed to expand (e.g. a physiologic response to the presence of functional assembly 130 and other portions of catheter 100).

In Step 3840, a second volume of fluid is introduced into functional assembly 130, such as after a fixed time period of Step 3830 and/or after a physiologic change in intestinal diameter occurs (e.g. expansion of the axial segment is observed for example after a time period of at least 15 seconds, at least 30 seconds, at least 1 minute, or at least 2 minutes).

The method of FIG. 38 can be performed prior to a luminal sizing procedure, a tissue expansion procedure and/or a tissue ablation procedure as described herein. In some embodiments, a luminal sizing procedure is performed to determine any of the thresholds described hereabove. Steps 3810-3840 can be repeated, such as to treat and/or diagnose multiple axial segments of intestinal tissue (e.g. multiple segments of the duodenum).

Figure 39:
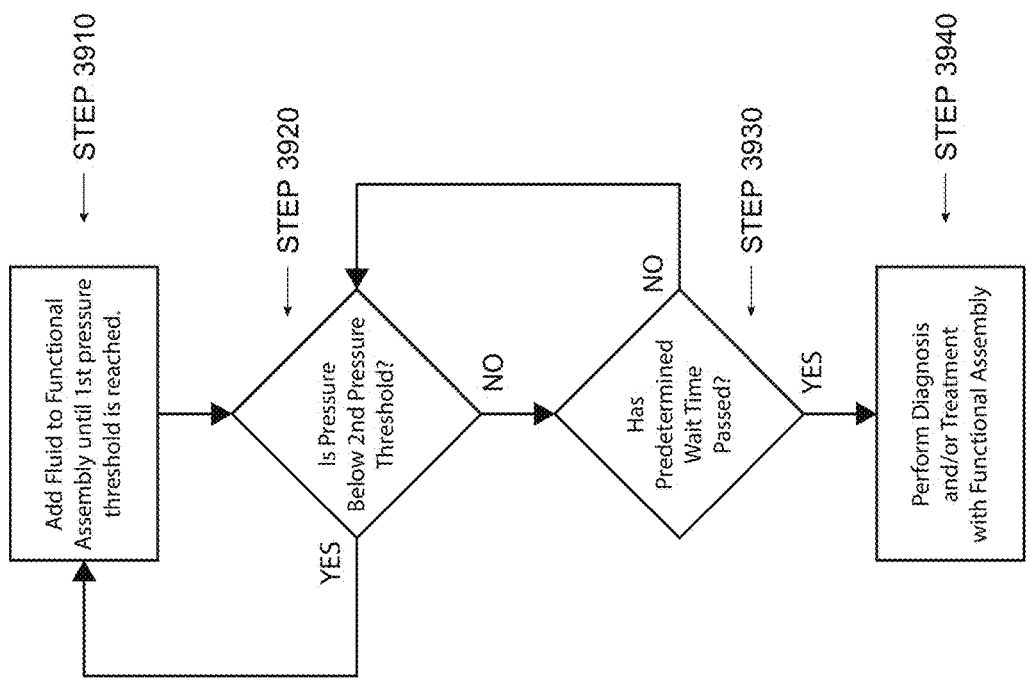
FIG. 39 is a flowchart of a method of expanding a functional assembly based on two pressure thresholds, consistent with the present inventive concepts.

Referring now to FIG. 39, a method of expanding a functional assembly based on two pressure thresholds is illustrated, consistent with the present inventive concepts. The method of FIG. 39 will be described using the devices and components of system 10 and one or more catheters 100 described hereabove in reference to one or more of FIGS. 1-25. In Step 3910, the distal portion of a catheter 100, including a functional assembly 130, is inserted into the intestine of a patient such that functional assembly 130 is positioned at a first axial segment of the intestine. Catheter 100 can be inserted through a body introduction device 50, such as an endoscope or sheath, or inserted alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

Also in Step 3910, fluid is introduced into functional assembly 130 until a first threshold is reached (e.g. a first pressure threshold related to pressure measured within functional assembly 130, shaft 110, connecting assembly 300 and/or console 200).

In Step 3920, pressure within functional assembly 130 is measured and compared to a second threshold (e.g. a second pressure threshold less than the first pressure threshold). Alternatively or additionally, pressure of a different portion of system 10 can be measured, such as a pressure of a fluid line or reservoir in fluid communication with functional assembly 130 (e.g. a pressure within shaft 110, connecting assembly 300 and/or console 200).

If the measured pressure falls below the second pressure threshold, Step 3910 is repeated, introducing more fluid into functional assembly 130 until a third pressure threshold is reached (e.g. a third pressure threshold of similar pressure level to the first pressure threshold).

If the pressure measured in Step 3920 does not fall below the second pressure threshold, Step 3930 is performed, In Step 3930, completion of a first time period is checked, such as the time since initially introducing fluid into functional assembly 130, the time since first achieving the first pressure threshold, or other time period. If the time period is not completed, Step 3920 is performed again. If the time period is completed, Step 3940 is performed.

In Step 3940, functional assembly 130, in its expanded state that results from Steps 3910-3930, is used to perform a diagnostic procedure (e.g. luminal diameter measurement procedure) and/or a treatment procedure (e.g. a tissue expansion procedure and/or a tissue ablation procedure).

Steps 3910-3940 can be repeated, such as to treat and/or diagnose multiple axial segments of intestinal tissue (e.g. multiple segments of the duodenum). In some embodiments, functional assembly 130, Step 3920 is repeated and pressure is monitored (e.g. for a second time period). If pressure falls below a fourth pressure threshold (e.g. a fourth pressure threshold similar to the second pressure threshold), a third volume of fluid can be introduced into functional assembly 130. The third volume of fluid can be delivered until a fifth pressure threshold is reached, such as a fifth pressure threshold similar to the first pressure threshold and/or the third pressure threshold.

Figure 40:
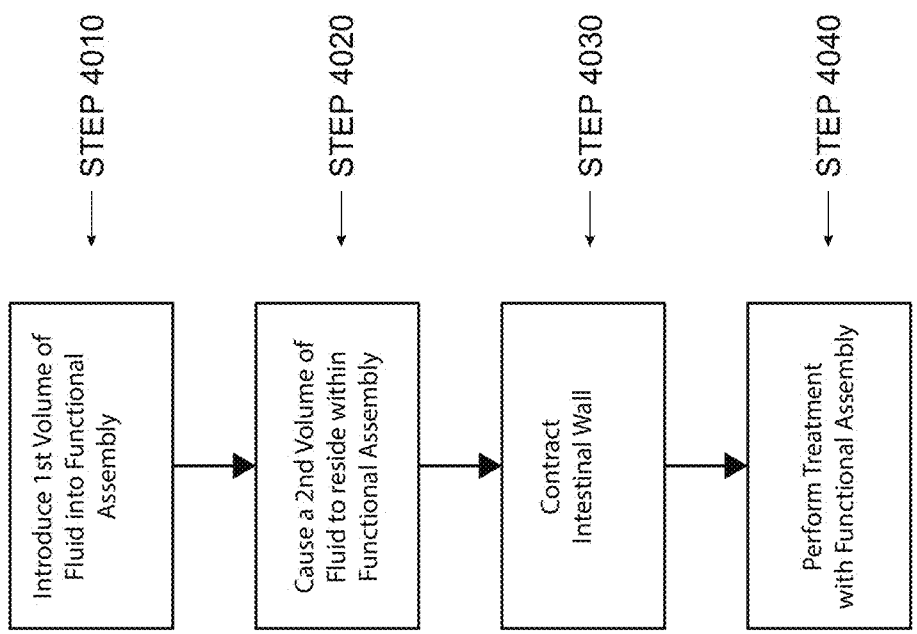
FIG. 40 is a flowchart of a method of causing a functional assembly to contact wall tissue of a segment of the intestine, consistent with the present inventive concepts.

Referring now to FIG. 40, a method of causing a functional assembly to contact wall tissue of a segment of the intestine is illustrated, consistent with the present inventive concepts. The method of FIG. 40 will be described using the devices and components of system 10 and one or more catheters 100 described hereabove in reference to one or more of FIGS. 1-25. In Step 4010, the distal portion of a catheter 100, including an expandable functional assembly 130, is inserted into the intestine of a patient such that functional assembly 130 is positioned at a first axial segment of the intestine. Catheter 100 can be inserted through a body introduction device 50, such as an endoscope or sheath, or inserted alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10 (e.g. via algorithm 251).

Also in Step 4010, a first volume of fluid is introduced into functional assembly 130. For example, the first volume of fluid can be a fluid volume that causes a sufficient or otherwise pre-determined level of apposition between a balloon 136 of functional assembly 130 and the luminal wall of the axial segment of the intestine. The first volume of fluid can be a fluid volume that causes the pressure within functional assembly 130 to reach a threshold.

In Step 4020, the volume of fluid in functional assembly 130 is changed to a second volume, different than the first volume. In some embodiments, the second volume is less than the first volume (i.e. fluid is extracted from functional assembly 130 in Step 4020). In other embodiments, the second volume is greater than the first volume (i.e. fluid is added to functional assembly 130).

In Step 4030, the intestinal wall is contracted, such as by using one or more desufflation techniques as described herein. In some embodiments, such as when fluid is extracted from functional assembly 130 in Step 4020, contraction of the intestinal wall causes the intestinal wall to make contact with functional assembly 130. In other embodiments, such as when fluid is added to functional assembly 130 in Step 4030, contraction of the intestinal wall causes increased contact between the intestinal wall and functional assembly 130.

In Step 4040, a treatment (e.g. an ablation treatment or other treatment as described herein) is performed upon the axial segment of the intestinal wall in contact with functional assembly 130 (and neighboring tissue as described herein).

The method of FIG. 40 can be used to accurately control the amount of contact between functional assembly 130 and the luminal wall of an axial segment of the intestine and/or to precisely control the timing of contact between functional assembly 130 and the luminal wall.

Steps 4010-4040 can be repeated, such as to treat and/or diagnose multiple axial segments of intestinal tissue (e.g. multiple segments of the duodenum).

Figure 41:
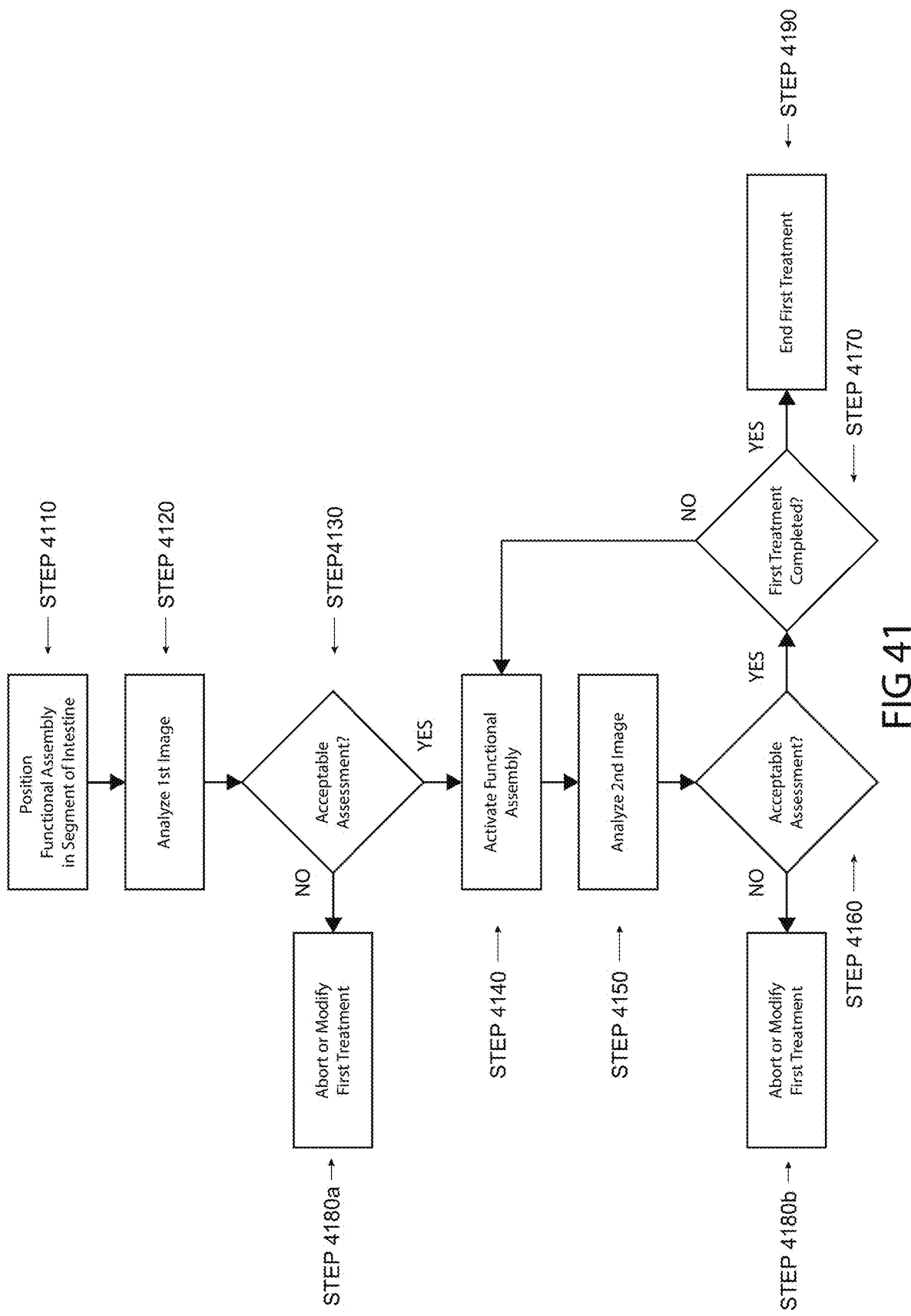
FIG. 41 is a flowchart of a method of performing a tissue treatment that includes activating a functional assembly based on an image, consistent with the present inventive concepts.

Referring now to FIG. 41, a method of performing a tissue treatment that includes activating a functional assembly based on an image is illustrated, consistent with the present inventive concepts. The method of FIG. 41 will be described using the devices and components of system 10 and one or more catheters 100 described hereabove in reference to one or more of FIGS. 1-25. In Step 4110, the distal portion of a catheter 100, including a functional assembly 130, is inserted into the intestine of a patient such that functional assembly 130 is positioned at a first axial segment of the intestine. Catheter 100 can be inserted through a body introduction device 50, such as an endoscope or sheath, or inserted alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

In some embodiments, functional assembly 130 is at least partially expanded (e.g. via a fluid introduced into a balloon of functional assembly 130 or via a mechanical linkage configured to radially deploy a portion of functional assembly 130) within the first axial segment of the intestine in Step 4110.

In Step 4120, one or more images are captured, such as by camera 52 of introduction device 50 (e.g. a camera of an endoscope), by imaging device 55 and/or another imaging device of system 10. The one or more images can comprise an image including patient tissue, functional assembly 130 and/or another component of system 10. The one or more captured images are analyzed, such as an analysis performed manually (e.g. by a clinician) and/or automatically (e.g. by one or more image processing algorithms of system 10, such as algorithm 251). In some embodiments, the image capture by camera 52 and/or imaging device 55 (e.g. and analyzed by algorithm 251) comprises an image selected from the group consisting of: a spectroscopy image, such as a Raman spectroscopy or other image configured to identify denatured proteins; a fluorescence image, such as a time-resolved fluorescence image; optical coherence tomography (OCT) image; ultrasound image; ultrasonic elastography image; colorimetry image; confocal endomicroscopy image; and combinations of one or more of these. In some embodiments, injectate 221 is present in tissue, and a color change or fluorescence is detected when injectate 221 is heated.

In Step 4130, the results of the image analysis performed in Step 4120 are compared to a level of acceptability. If an acceptable level is achieved, the method of FIG. 41 continues in Step 4140. If an acceptable level is not achieved, Step 4180a is performed in which the first treatment is aborted or modified. Unacceptable levels of acceptability can include images which identify: improper positioning of functional assembly 130 such as positioning of functional assembly proximate non-target tissue (e.g. the ampulla of Vater); improper expansion of functional assembly 130; improper position of one or more fluid delivery elements 139c; presence of diseased tissue proximate functional assembly 130 or otherwise; presence of infected tissue proximate functional assembly 130 or otherwise; and combinations of one or more of these.

Aborting the first treatment in Step 4180a can comprise removing catheter 100 (and potentially one or more of devices of system 10) from the patient.

Modifying the first treatment in Step 4180a can comprise returning to step 4110 in which functional assembly 130 is repositioned in the intestine and/or another adjustment is made based on the unacceptable results of the image analysis of Step 4130.

In Step 4140, functional assembly 130 is activated (e.g. energy is delivered to tissue such as heat delivered from hot fluid, RF energy is delivered by one or more electrode-based functional elements 139, light energy is delivered by one or more optical component-based functional elements 139, and/or other energy is delivered as described herein).

In Step 4150, one or more images are captured, such as by camera 52 of introduction device 50 (e.g. a camera of an endoscope), by imaging device 55 and/or another imaging device of system 10. The one or more images can comprise an image including patient tissue, functional assembly 130 and/or another component of system 10. The one or more captured images are analyzed, such as an analysis performed manually (e.g. by a clinician) and/or automatically (e.g. by one or more image processing algorithms of system 10, such as algorithm 251).

In Step 4160, the results of the image analysis performed in Step 4150 are compared to a level of acceptability. If an acceptable level is achieved, the method of FIG. 41 continues in Step 4170. If an acceptable level is not achieved, Step 4180b is performed in which the first treatment is aborted or modified. Unacceptable levels of acceptability can include images which identify: inadequate expansion of tissue; inadequate treatment of target tissue; undesired treatment of target tissue; adverse effects upon non-target tissue; improper positioning of functional assembly 130 such as positioning of functional assembly proximate non-target tissue (e.g. the ampulla of Vater); improper expansion of functional assembly 130; improper position of one or more fluid delivery elements 139c; presence of diseased tissue proximate functional assembly 130 or otherwise; presence of infected tissue proximate functional assembly 130 or otherwise; and combinations of one or more of these.

Aborting the first treatment in Step 4180b can comprise removing catheter 100 (and potentially one or more of devices of system 10) from the patient.

Modifying the first treatment in Step 4180b can comprise returning to Step 4110 in which functional assembly 130 is repositioned in the intestine and/or another adjustment is made based on the unacceptable results of the image analysis of Step 4130.

Alternatively, modifying the first treatment in Step 4180b can comprise returning to Step 4140 (as shown in FIG. 41), in which functional assembly 130 is reactivated, to deliver additional (similar or dissimilar) energy to tissue.

In Step 4170, an assessment of first treatment completeness is performed. The assessment can be performed manually (e.g. by a clinician) and/or automatically (e.g. by one or more algorithms of system 10, such as via one or more images produced as described herein). If it is determined that the first treatment is not complete, Step 4140 and subsequent steps are repeated, such as to deliver additional energy to tissue. If it is determined that the first treatment is complete, Step 4190 is performed in which the first treatment is ended. In some embodiments, Step 4190 comprises overall completion of a patient procedure, such as when catheter 100 and/or other components of system 10 are removed from the patient. In other embodiments, the steps of the method of FIG. 41 are repeated for a second treatment, such as by repeating Step 4110 at a second axial segment of intestinal tissue and continuing with the subsequent steps. In some embodiments, at least 2 or at least 3 axial segments of axial segments of duodenal tissue are treated, such as is described herein to treat diabetes.

Figure 42:
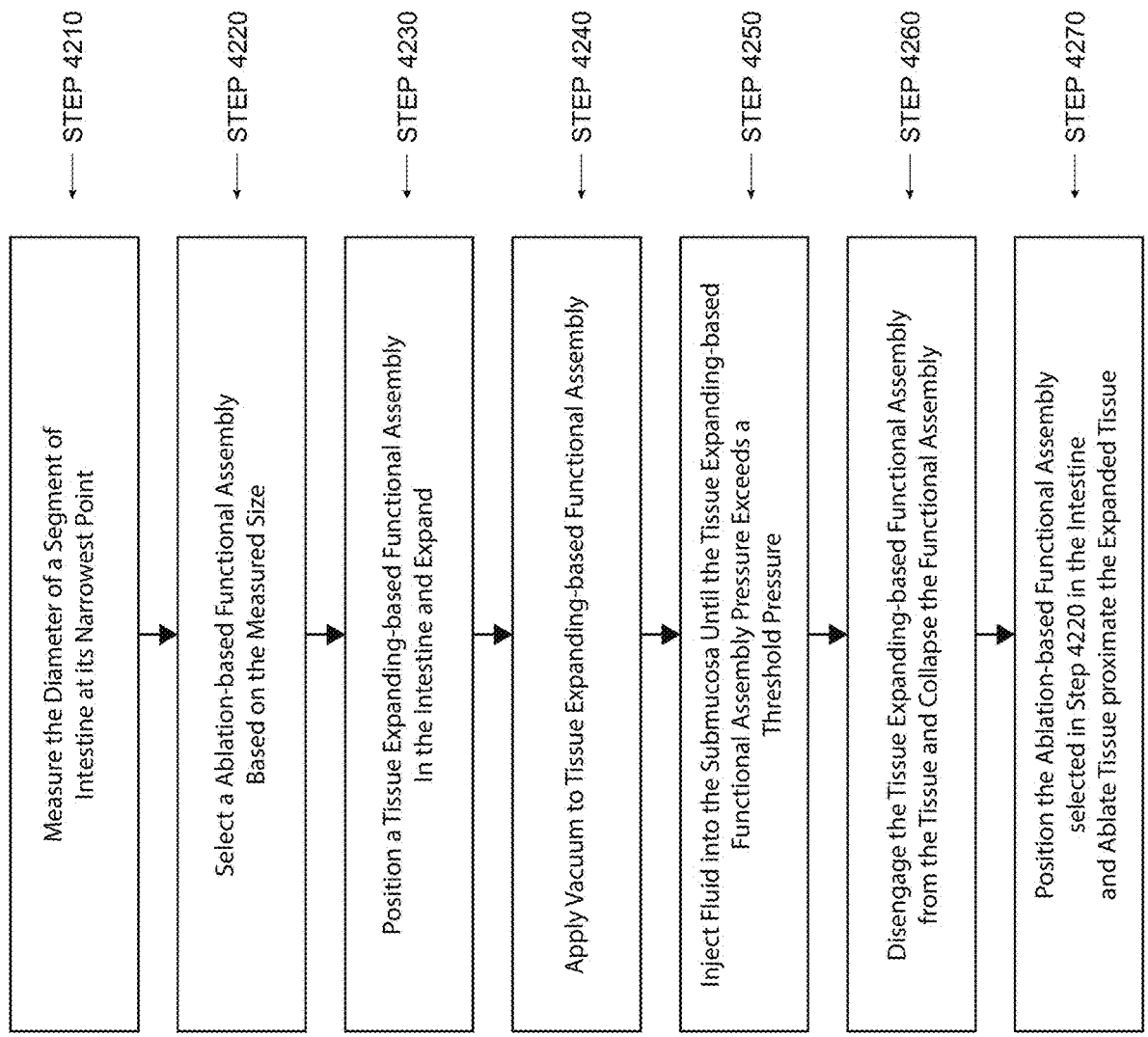
FIG. 42 is a flowchart of a method of performing a tissue treatment based on the geometry of the intestine, consistent with the present inventive concepts.

Referring now to FIG. 42, a method of performing a tissue treatment based on the geometry of the intestine is illustrated, consistent with the present inventive concepts. The method of FIG. 42 will be described using the devices and components of system 10 and one or more catheters 100 described hereabove in reference to one or more of FIGS. 1-25. In Step 4210, the narrowest segment of a portion of the intestine (e.g. the narrowest portion of a duodenal or other intestinal segment to be treated) is identified, and one or more diameters (e.g. the narrowest diameter) are measured. The identification of the narrowest segment and/or the diameters can be measured by a component of system 10, such as catheter 100, camera 52 of introduction device 50, and/or imaging device 55. In some embodiments, the identification and measurement are performed in the same clinical procedure as the tissue expansion and ablation performed subsequently in Steps 4220 through 4270. Alternatively, the identification and measurement are performed in a separate procedure, such as an imaging procedure (e.g. an ultrasound, Ct scan or MRI procedure), which can be performed at an earlier date.

In Step 4220, a first catheter 100a is selected based on an ablation-based functional assembly 130a that is appropriate for the (narrowest) diameters measured in Step 4210. For example, system 10 can include multiple catheters 100 each with a functional assembly 130a with a different expanded diameter. The selection performed in Step 4220 provides a functional assembly 130a with an appropriate diameter to avoid excessive force being exerted between functional assembly 130a and the narrowest segment of the intestine being treated (e.g. during an energy delivery or other ablation step). The diameter of the ablation-based functional assembly 130a selected can be approximately equal to, slightly larger than or slightly smaller than the narrowest diameter measured, such as to provide adequate ablation (e.g. in Step 4270 described hereinbelow) of one or more inner layers of the intestine (e.g. all of the mucosal layer and a partial inner sublayer of the submucosal layer), without damaging outer layers of the intestine (e.g. the serosal layer).

In Step 4230, a second catheter 100b comprising a functional assembly 130b configured for tissue expansion is selected. In some embodiments, the second catheter 100b is the same catheter as first catheter 100a (e.g. its functional assembly 130b is configured to both ablate tissue and expand tissue or the catheter 100a comprises two separate functional assemblies 130a and 130b, such as are described herein). In some embodiments, the second catheter 100b comprises a functional assembly 130b that is selected based on the diameter measurements performed in Step 4210 (e.g. to be compatible with the narrowest diameter of the intestinal segment to be treated).

The second catheter 100b is inserted into the intestine of a patient such that its functional assembly 130b is positioned at a first axial segment of the intestine. Second catheter 100b can be inserted through a body introduction device 50, such as an endoscope or sheath, or inserted alongside a body introduction device 50. In some embodiments, second catheter 100b is inserted over a guidewire 60. Second catheter 100b can be attached to console 200 of system 10. System 10 and/or second catheter 100b can comprise one or more sensors configured to produce a signal, such as a signal used to set and/or change one or more console settings 201 of system 10. In some embodiments, the first catheter 100a and/or second catheter 100b are used to measure the intestinal lumen diameters in step 4210 or otherwise.

Also in Step 4230, functional assembly 130b is expanded, such as by delivering gas or another fluid into functional assembly 130b until its diameter achieves a predetermined size and/or until a sufficient apposition with tissue is achieved (e.g. as determined by a pressure measurement and/or direct visualization as described herein).

In Step 4240, vacuum can be applied to the second catheter 100b, such as a vacuum delivered to one or more ports 137 of functional assembly 130b. The applied vacuum can engage each port 137 with tissue or at least bring tissue into proximity with each port 137. In some embodiments, the applied vacuum causes tissue to enter the associated port 137. In some embodiments, the applied vacuum is configured to cause one or more fluid delivery elements 139c to move closer to, engage with and/or penetrate tissue (e.g. tissue captured within a port 137).

In Step 4250, injectate 221 is delivered into tissue (e.g. submucosal tissue), such as until the pressure within functional assembly 130b reaches a threshold. Alternatively, a fixed amount of injectate 221 is delivered into tissue, or injectate 221 is delivered into tissue until an acceptable image of tissue expansion is visualized (e.g. via camera 52 of introduction device 50 and/or imaging device 55 as described herein). In some embodiments, the volume of air or other fluid delivered into functional assembly 130b during Step 4230 (to expand functional assembly 130b), is adjusted (e.g. decreased) during the delivery of injectate 221 into tissue. The adjustment of the fluid within functional assembly 130 can be based on a measured pressure (e.g. that increases as tissue expands) and/or the amount of injectate delivered into tissue. Adjustment (e.g. decrease) of fluid within functional assembly 130b can be performed to avoid excessive force being applied to tissue and/or to allow proper tissue expansion (e.g. proper expansion of one or more layers of submucosal tissue).

In Step 4260, functional assembly 130b is disengaged from tissue (e.g. vacuum is removed from one or more ports 137 and/or one or more fluid delivery elements 139c are retracted or otherwise disengaged from tissue), and functional assembly 130b is radially collapsed. Second catheter 100b can be removed from the patient, repositioned, and/or remain in place (e.g. when first catheter 100a and second catheter 100b comprise the same catheter).

In Step 4270, a functional assembly 130a of catheter 100a is positioned at or near the first axial segment of intestine (herein "at the first axial segment of intestine") and tissue of the first axial segment is ablated (i.e. tissue proximate the tissue expanded in Step 4250). First catheter 100a can be inserted through a body introduction device 50, such as an endoscope or sheath, or inserted alongside a body introduction device 50. In some embodiments, first catheter 100a is inserted over a guidewire 60. As described above, catheter 100a and catheter 100b can comprise the same catheter, avoiding the need to position a second catheter at the first axial segment. First catheter 100a can be attached to console 200 of system 10. System 10 and/or first catheter 100a can comprise one or more sensors configured to produce a signal, such as a signal used to set and/or change one or more console settings 201 of system 10.

Also in Step 4270, functional assembly 130a is activated to ablate tissue of the first axial segment of intestine, such as by delivering thermal or other energy provided by console 200 to tissue, as described herein.

The tissue expansion procedure performed in steps 4230 through 4260 can be repeated at multiple axial segments of intestine. In some embodiments, a series of multiple tissue expansions are followed by a corresponding series of ablation steps of Step 4270 (e.g. ablating the same or a different quantity of axial segments of intestine). Alternatively, a single tissue expansion (Steps 4230 through 4260) at a first segment of intestine is followed by a single ablation Step 4270 performed at the same first segment. Subsequently, similar tissue expansion can be performed at one or more additional segments of the intestine (e.g. a second, third, etc). Ablation of Step 4270 can be performed soon after each tissue expansion of Steps 4230 through 4260 (e.g. in an alternating fashion of tissue expansion of a segment followed by ablation of that segment).

Figure 43:
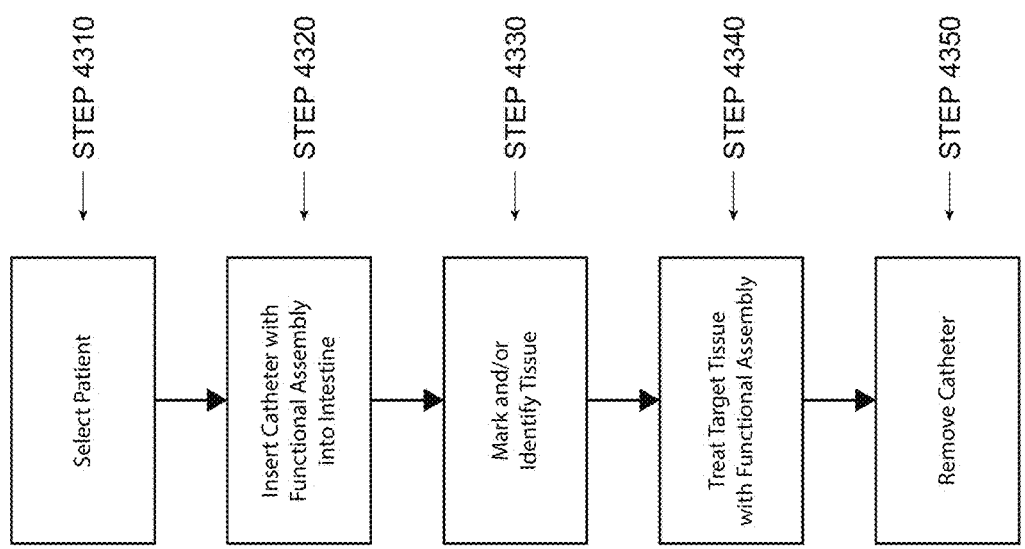
FIG. 43 is a flowchart of a method of marking tissue and performing a tissue treatment based on the tissue marking, consistent with the present inventive concepts.

Referring now to FIG. 43, a method of marking tissue and performing a tissue treatment based on the tissue marking is illustrated, consistent with the present inventive concepts. The method of FIG. 43 will be described using the devices and components of system 10 and one or more catheters 100 described hereabove in reference to one or more of FIGS. 1-25. In Step 4310, a patient is selected for treatment by the systems, methods and devices of the present inventive concepts, such as a diabetic patient selected for ablation of duodenal mucosa.

In Step 4320, the distal portion of a catheter 100, including a functional assembly 130, is inserted into the intestine of a patient such that functional assembly 130 is positioned at a first axial segment of the intestine. Catheter 100 can be inserted through a body introduction device 50, such as an endoscope or sheath, or inserted alongside a body introduction device 50. In some embodiments, catheter 100 is inserted over a guidewire 60. Catheter 100 can be attached to console 200 of system 10. System 10 and/or catheter 100 can comprise one or more sensors configured to produce a signal, such as a signal used to set and/or change one or more console settings 201 of system 10.

In Step 4330, one or more portions of tissue are marked and/or identified. In some embodiments, Step 4330 is performed prior to Step 4320. In some embodiments, the tissue marking and/or identification of Step 4330 is performed with catheter 100 and/or another component of system 10, such as tool 500 as described hereabove. Tissue marking can comprise implantation of a temporary marker, or marking of tissue with a tattoo or other tissue dyeing procedure, such as using marker 430, also described hereabove. In some embodiments, marked tissue comprises tissue selected from the group consisting of: target tissue; non-target tissue; tissue proximate non-target tissue (e.g. tissue proximate the ampulla of Vater or tissue proximate the pylorus); safety margin tissue; diseased tissue; healthy tissue; and combinations of one or more of these.

In Step 4340, target tissue is treated (e.g. target tissue comprising diseased tissue or otherwise adversely functioning tissue) with functional assembly 130 of catheter 100, such as a target tissue treatment comprising tissue ablation; tissue expansion; tissue expansion and ablation; and combinations of one or more of these. The treatment of target tissue is performed at a location selected based on the tissue identification and/or marking performed in Step 4330.

For example, in procedures treating mucosa of the duodenum, one or more markings can be made to prevent adversely affecting the ampulla of Vater (e.g. by preventing energy deliver to tissue within 1.5 cm, 1.0 cm or 0.5 cm of the ampulla of Vater) and/or to ensure treatment of tissue (e.g. mucosal tissue) within 5 cm, within 10 cm or within 15 cm of the ampulla of Vater.

In Step 4350, catheter 100 is removed. The markers may be removed, or left in place (e.g. when a dye is used or when a deployed marker is constructed and arranged to pass through the GI system naturally).

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth below not be construed as being order-specific unless such order specificity is expressly stated in the claim.

What is claimed is:

1. A method for performing a medical procedure in an intestine of a patient, comprising:
   providing a system comprising:
   a catheter for insertion into the intestine, the catheter comprising:
   an elongate shaft comprising a distal portion; and
   a functional assembly positioned on the shaft distal portion and comprising at least one treatment element;
   introducing the catheter into the patient; and
   treating target tissue with the at least one treatment element, wherein the target tissue comprises mucosal tissue of the small intestine and treating comprises ablating at least a portion of the mucosal tissue of the small intestine;
   wherein the medical procedure is configured to treat at least one of non-alcoholic fatty liver disease (NAFLD) or non-alcoholic steatohepatitis (NASH); and
   wherein the patient has elevated baseline levels of aspartate transaminase (AST) and alanine transaminase (ALT) before treatment and achieves sustainable reductions in AST and ALT levels after treatment using the system.

2. The method according to claim 1, wherein the medical procedure is further configured to treat insulin resistance.

3. The method according to claim 1, wherein the medical procedure is further configured to treat a disease or disorder selected from the group consisting of: Type 2 diabetes; Type 1 diabetes; "Double diabetes"; gestational diabetes; hyperglycemia; pre-diabetes; impaired glucose tolerance; insulin resistance; and combinations thereof.

4. The method according to claim 1, wherein the system further comprises a console operably attached to the functional assembly, and wherein the console comprises one or more variable console parameters used to control the functional assembly.

5. The method according to claim 4, wherein the system further comprises at least one sensor constructed and arranged to produce a sensor signal, and wherein the method further comprises adjusting at least one variable console parameter based on the sensor signal.

6. The method according to claim 5, wherein the console is configured to perform closed-loop energy delivery to the functional assembly based on the sensor signal.

7. The method according to claim 1, wherein treating target tissue modifies at least one of (1) nutrient absorption by the target tissue, (2) hormonal signaling from the target tissue, or (3) secretions of the target tissue.

8. The method according to claim 1, wherein the treating target tissue comprises treating mucosal tissue within 15 cm of the ampulla of Vater.

9. The method according to claim 1, wherein the method comprises avoiding treating tissue between a first location proximate the ampulla of Vater and a second location 0.5 cm distal to the ampulla of Vater.

10. The method according to claim 1, wherein at least 6 cm of length of duodenum are treated.

11. The method according to claim 10, wherein at least 9 cm of length of duodenum are treated.

12. The method according to claim 1, wherein the treating target tissue comprises treating at least a first axial segment and a second axial segment of the intestine.

13. The method according to claim 12, wherein the treating target tissue comprises treating between two and six axial segments of the intestine to treat at least 6 cm of axial length of intestine.

14. The method according to claim 1, wherein the treating target tissue comprises treating an amount of tissue that is based on the severity of the patient's NAFLD and/or NASH.

15. The method according to claim 1, further comprising identifying non-target tissue, wherein the non-target tissue is identified by marking tissue selected from the group consisting of: ampulla of Vater; tissue proximate the ampulla of Vater; pylorus; tissue proximate the pylorus; and combinations thereof.

16. The method according to claim 1, wherein the treating target tissue comprises a series of tissue ablation steps, each comprising ablation of an axial length of intestinal tissue, wherein each ablation step is preceded by a tissue expansion step.

17. The method according to claim 16, further comprising preventing axial motion of the functional assembly between each of the tissue expansion steps and each of the tissue ablation steps.

18. The method according to claim 16, further comprising applying vacuum to tissue during each of the tissue expansion steps.

19. The method according to claim 1, wherein the treating target tissue comprises a series of tissue ablation steps, each ablation step comprising ablation of an axial length of intestinal tissue, wherein each ablation step is followed by a tissue neutralizing step.

20. The method according to claim 19, wherein each ablation step comprises a heat ablation of tissue and each neutralizing step comprises a cooling of tissue.

21. The method according to claim 19, further comprising performing a separate tissue neutralizing step prior to each ablation step.

22. The method according to claim 21, wherein each ablation step comprises a heat ablation of tissue and each separate neutralizing step comprises a cooling of tissue.

23. The method according to claim 1, further comprising maintaining the functional assembly at or below a target diameter.

24. The method according to claim 1, further comprising maintaining the functional assembly at or below a target pressure.

25. The method according to claim 1, further comprising maintaining the functional assembly at or below a target volume.

26. The method according to claim 1, further comprising delivering an anti-peristaltic agent.

27. The method according to claim 1, further comprising modifying the pressure of a segment of intestine that is proximate the target tissue being treated.

28. The method according to claim 1, wherein the functional assembly includes a tissue contacting portion comprising a surface area between 500 $mm^2$ and 3500 $mm^2$.

29. The method according to claim 1, where the functional assembly comprises an expanded diameter between 19 mm and 28 mm.

30. The method according to claim 1, wherein the catheter further comprises a fluid removal port configured to remove fluid from a segment of the intestine.

* * * * *